United States Patent
Kim et al.

(10) Patent No.: US 10,749,119 B2
(45) Date of Patent: Aug. 18, 2020

(54) PLURALITY OF HOST MATERIALS AND ORGANIC ELECTROLUMINESCENT DEVICE COMPRISING THE SAME

(71) Applicant: Rohm and Haas Electronic Materials Korea Ltd., Cheonan (KR)

(72) Inventors: Bitnari Kim, Anyang (KR); Sang-Hee Cho, Suwon (KR); Hee-Ryong Kang, Seoul (KR); Jin-Ri Hong, Bucheon (KR)

(73) Assignee: Rohm and Haas Electronic Materials Korea Ltd, Seoul (KR)

( * ) Notice: Subject to any disclaimer, the term of this patent is extended or adjusted under 35 U.S.C. 154(b) by 132 days.

(21) Appl. No.: 15/551,951

(22) PCT Filed: Feb. 2, 2016

(86) PCT No.: PCT/KR2016/001102
§ 371 (c)(1),
(2) Date: Aug. 18, 2017

(87) PCT Pub. No.: WO2016/148390
PCT Pub. Date: Sep. 22, 2016

(65) Prior Publication Data
US 2018/0033975 A1    Feb. 1, 2018

(30) Foreign Application Priority Data

Mar. 13, 2015  (KR) .................. 10-2015-0035281
Jan. 19, 2016  (KR) .................. 10-2016-0006579

(51) Int. Cl.
| | | |
|---|---|---|
| *H01L 51/00* | (2006.01) | |
| *C09K 11/06* | (2006.01) | |
| *C07D 209/80* | (2006.01) | |
| *C07D 209/86* | (2006.01) | |
| *C07D 403/10* | (2006.01) | |
| *C07D 487/04* | (2006.01) | |
| *C07D 487/06* | (2006.01) | |
| *C09K 11/02* | (2006.01) | |
| *H01L 51/50* | (2006.01) | |

(52) U.S. Cl.
CPC ........ *H01L 51/0072* (2013.01); *C07D 209/80* (2013.01); *C07D 209/86* (2013.01); *C07D 403/10* (2013.01); *C07D 487/04* (2013.01); *C07D 487/06* (2013.01); *C09K 11/025* (2013.01); *C09K 11/06* (2013.01); *H01L 51/001* (2013.01); *H01L 51/0052* (2013.01); *H01L 51/0058* (2013.01); *H01L 51/0067* (2013.01); *H01L 51/0074* (2013.01); *C09K 2211/1007* (2013.01); *C09K 2211/1029* (2013.01); *C09K 2211/1088* (2013.01); *C09K 2211/1092* (2013.01); *C09K 2211/185* (2013.01); *H01L 51/0085* (2013.01); *H01L 51/5016* (2013.01); *H01L 2251/5384* (2013.01)

(58) Field of Classification Search
CPC .................................................. H01L 51/0072
See application file for complete search history.

(56) References Cited

U.S. PATENT DOCUMENTS

| | | | | |
|---|---|---|---|---|
| 2014/0374711 | A1* | 12/2014 | Cho | .............. H01L 51/0072 257/40 |
| 2015/0243905 | A1 | 8/2015 | Yamamoto et al. | |
| 2017/0117488 | A1* | 4/2017 | Ahn | .............. H01L 51/0073 |

FOREIGN PATENT DOCUMENTS

| | | |
|---|---|---|
| JP | 3139321 | 2/2001 |
| KR | 2008-0047210 | 5/2008 |
| KR | 2010-0015581 | 2/2010 |
| KR | 20130139412 A | 12/2013 |
| WO | 2013/105747 A1 | 7/2013 |
| WO | 2013109045 A1 | 7/2013 |
| WO | 2013/157886 A1 | 10/2013 |
| WO | 2014/092354 A1 | 6/2014 |
| WO | 2015/156587 A1 | 10/2015 |
| WO | 2015/174738 A1 | 11/2015 |

OTHER PUBLICATIONS

Park et al., English machine translation of Intl. Pub. No. WO 2013/105747 A1 (Year: 2013).*

* cited by examiner

Primary Examiner — Peter F Godenschwager
(74) Attorney, Agent, or Firm — S. Matthew Cairns

(57) ABSTRACT

The present disclosure relates to a plurality of host materials and organic electroluminescent device comprising the same. By comprising a specific combination of a plurality of host materials, the organic electroluminescent device of the present disclosure can show long lifespan while maintaining high luminous efficiency.

6 Claims, No Drawings

PLURALITY OF HOST MATERIALS AND ORGANIC ELECTROLUMINESCENT DEVICE COMPRISING THE SAME

TECHNICAL FIELD

The present disclosure relates to a plurality of host materials and organic electroluminescent device comprising the same.

BACKGROUND ART

An electroluminescent (EL) device is a self-light-emitting device which has advantages in that it provides a wider viewing angle, a greater contrast ratio, and a faster response time. An organic EL device was first developed by Eastman Kodak, by using small aromatic diamine molecules and aluminum complexes as materials to form a light-emitting layer [Appl. Phys. Lett. 51, 913, 1987].

In an organic electroluminescent device (OLED), electricity is applied to an organic light-emitting material which converts electric energy to light. Generally, OLED has a structure comprising an anode, a cathode, and an organic layer disposed between the two electrodes. The organic layer of OLED may comprise a hole injection layer, a hole transport layer, an electron blocking layer, a light-emitting layer (comprising a host and dopant materials), an electron buffering layer, a hole blocking layer, an electron transport layer, an electron injection layer, etc. A material for preparing the organic layer can be classified according to its function, as a hole injection material, a hole transport material, an electron blocking material, a light-emitting material, an electron buffering material, a hole blocking material, an electron transport material, an electron injection material, etc. Holes and electrons are injected from an anode and a cathode, respectively, to the light-emitting layer by applying electricity to OLED; excitons having high energy are formed by recombinations between the holes and the electrons, which make organic light-emitting compounds be in an excited state, and the decay of the excited state results in a relaxation of the energy into a ground state, accompanied by light-emission.

The most important factor determining luminous efficiency in OLED is a light-emitting material. The light-emitting material needs to have high quantum efficiency, high electron mobility, and high hole mobility. Furthermore, the light-emitting layer formed by the light-emitting material needs to be uniform and stable. According to colors visualized by light-emission, the light-emitting material can be classified as a blue-, green-, or red-emitting material, and a yellow- or orange-emitting material can be additionally included therein. Furthermore, the light-emitting material can be classified according to its function, as a host material and a dopant material. Recently, the development of OLED providing high efficiency and long lifespan is urgent. In particular, considering EL requirements for a middle or large-sized OLED panel, materials showing better performances than conventional ones must be urgently developed. In order to achieve the development, a host material which plays a role as a solvent in a solid state and transfers energy, should have high purity, and an appropriate molecular weight for being deposited under vacuum. In addition, a host material should have high glass transition temperature and high thermal decomposition temperature to ensure thermal stability; high electrochemical stability to have long lifespan; ease of preparation for amorphous thin film; and good adhesion to materials of adjacent layers. Furthermore, a host material should not move to an adjacent layer.

The light-emitting material can be prepared by combining a host with a dopant to improve color purity, luminous efficiency, and stability. Generally, a device showing good EL performances comprises a light-emitting layer prepared by combining a host with a dopant. The host material greatly influences the efficiency and lifespan of the EL device when using a host/dopant system, and thus its selection is important.

Korean Patent Application Laid-open No. 2008-0047210 discloses an organic light emitting device comprising a carbazole derivative compound as a dopant material. Also, Korean Patent Application Laid-open No. 2010-0015581 discloses an organic electroluminescent device comprising the triazine compound linked with carbazole, etc., directly as a host material. Further, Japanese Patent No. 3139321 discloses an organic emitting device comprising a biscarbazole derivative as a hole transport material. However, the above publications do not specifically disclose an organic electroluminescent device using a plurality of host materials of a combination of 7H-dibenzo[c,g]carbazole having linker triazine with a carbazole derivative.

In this regard, the present inventors have tried to find an organic electroluminescent device that can provide superior efficiency and long lifespan, and have found that it could be using a plurality of host materials comprising 7H-dibenzo[c,g]carbazole having linker triazine, and a carbazole derivative compared to using the conventional sole host material for a light-emitting layer.

DISCLOSURE OF THE INVENTION

Problems to be Solved

The objective of the present disclosure is to provide an organic electroluminescent device having long lifespan while maintaining high luminous efficiency.

Solution to Problems

The present inventors found that the above objective can be achieved by an organic electroluminescent device comprising at least one light-emitting layer disposed between an anode and a cathode, wherein the light-emitting layer comprises a host and a phosphorescent dopant, wherein the host comprises a plurality of host compounds, wherein at least a first host compound of a plurality of host compounds is represented by the carbazole derivative of the following formula 1:

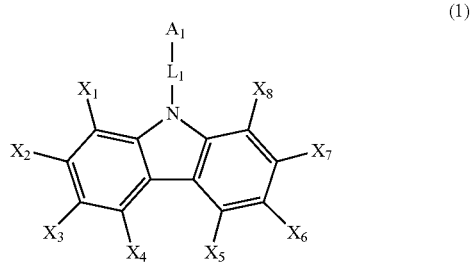

wherein $A_1$ represents a substituted or unsubstituted (C6-C30)aryl group, or a substituted or unsubstituted (5- to 30-membered) heteroaryl group, and $A_1$ may be linked to $X_1$ or $X_8$;

$L_1$ represents a single bond, or a substituted or unsubstituted (C6-C30)arylene group;

$X_1$ to $X_8$, each independently, represent hydrogen, deuterium, a halogen, a cyano group, a carboxyl group, a nitro group, a hydroxyl group, a substituted or unsubstituted (C1-C30)alkyl group, a substituted or unsubstituted (C3-C30)cycloalkyl group, a substituted or unsubstituted (C3-C30)cycloalkenyl group, a substituted or unsubstituted (3- to 7-membered)heterocycloalkyl group, a substituted or unsubstituted (C6-C30)aryl group, a substituted or unsubstituted (3- to 30-membered)heteroaryl group, —$NR_5R_6$, or —$SiR_7R_8R_9$; or may be linked to an adjacent substituent(s) to form a substituted or unsubstituted mono- or polycyclic (C3-C30), alicyclic or aromatic ring, whose carbon atom(s) may be replaced with at least one hetero atom selected from nitrogen, oxygen, and sulfur; and $R_5$ to $R_9$, each independently, represent hydrogen, deuterium, a halogen, a cyano group, a carboxyl group, a nitro group, a hydroxyl group, a substituted or unsubstituted (C1-C30)alkyl group, a substituted or unsubstituted (C3-C30)cycloalkyl group, a substituted or unsubstituted (C3-C30)cycloalkenyl group, a substituted or unsubstituted (3- to 7-membered)heterocycloalkyl group, a substituted or unsubstituted (C6-C30)aryl group, or a substituted or unsubstituted (3- to 30-membered)heteroaryl group; or may be linked to an adjacent substituent(s) to form a substituted or unsubstituted mono- or polycyclic (C3-C30), alicyclic or aromatic ring, whose carbon atom(s) may be replaced with at least one hetero atom selected from nitrogen, oxygen, and sulfur;

and a second host compound of a plurality of host compounds is represented by the 7H-dibenzo[c,g]carbazole having linker triazine of the following formula 2:

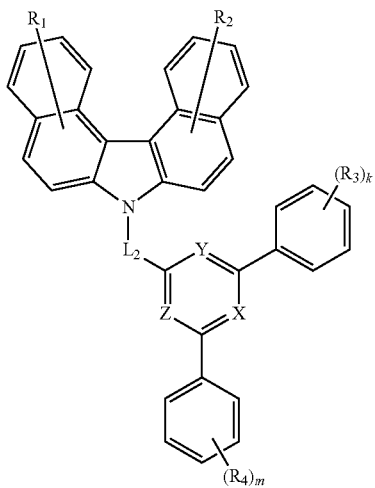

(2)

wherein

X, Y and Z, each independently, represent N or $CR_{10}$; provided that at least one of X, Y and Z represent N;

$L_2$ represents a substituted or unsubstituted (C6-C30) arylene group;

$R_1$ to $R_4$, each independently, represent hydrogen, deuterium, a halogen, a cyano group, a carboxyl group, a nitro group, a hydroxyl group, a substituted or unsubstituted (C1-C30)alkyl group, a substituted or unsubstituted (C3-C30)cycloalkyl group, a substituted or unsubstituted (C3-C30)cycloalkenyl group, a substituted or unsubstituted (3- to 7-membered)heterocycloalkyl group, a substituted or unsubstituted (C6-C30)aryl group, a substituted or unsubstituted (3- to 30-membered)heteroaryl group, —$NR_{11}R_{12}$, or —$SiR_{13}R_{14}R_{15}$; or may be linked to an adjacent substituent(s) to form a substituted or unsubstituted mono- or polycyclic (C3-C30), alicyclic or aromatic ring, whose carbon atom(s) may be replaced with at least one hetero atom selected from nitrogen, oxygen, and sulfur;

$R_{10}$ to $R_{15}$, each independently, represent hydrogen, deuterium, a halogen, a cyano group, a carboxyl group, a nitro group, a hydroxyl group, a substituted or unsubstituted (C1-C30)alkyl group, a substituted or unsubstituted (C3-C30)cycloalkyl group, a substituted or unsubstituted (C3-C30)cycloalkenyl group, a substituted or unsubstituted (3- to 7-membered)heterocycloalkyl group, a substituted or unsubstituted (C6-C30)aryl group, or a substituted or unsubstituted (3- to 30-membered)heteroaryl group;

k and m, each independently, represent an inter of 1 to 5; and where k or m represents an integer of 2 or more, each of $R_3$ or $R_4$ may be the same or different; and the heteroaryl and the heterocycloalkyl, each independently, contain at least one hetero atom selected from B, N, O, S, Si, and P.

Effects of the Invention

According to the present disclosure, an organic electroluminescent device having high efficiency and long lifespan is provided. In addition, the organic electroluminescent device of the present disclosure can be used for the manufacture of a display system or a lighting system.

EMBODIMENTS OF THE INVENTION

Hereinafter, the present disclosure will be described in detail. However, the following description is intended to explain the present disclosure, and is not meant in any way to restrict the scope of the present disclosure.

The organic electroluminescent device comprising the compounds of formulae 1 and 2 will be described in detail.

In formula 1, $A_1$ represents a substituted or unsubstituted (C6-C30)aryl group, or a substituted or unsubstituted (5- to 30-membered)heteroaryl group; preferably, a substituted or unsubstituted (C6-C25)aryl group, or a substituted or unsubstituted (6- to 25-membered)heteroaryl group; and more preferably, a substituted or unsubstituted (C6-C25)aryl group, or a substituted or unsubstituted (6- to 20-membered) heteroaryl group. For example, $A_1$ may be selected from the group consisting of a substituted or unsubstituted phenyl, an unsubstituted biphenyl, an unsubstituted terphenyl, an unsubstituted naphthyl, a substituted fluorenyl, an unsubstituted spirofluorenyl, an unsubstituted fluoranthenyl, an unsubstituted phenanthrenyl, a substituted triazinyl, a substituted quinoxalinyl, a substituted quinazolinyl, an unsubstituted triphenylsilyl, an unsubstituted triphenylaminyl, an unsubstituted triphenylenyl, an unsubstituted dibenzothiophenyl, an unsubstituted benzonaphthothiophenyl, a substituted or unsubstituted dibenzofuranyl, a substituted carbazolyl, a substituted benzocarbazolyl, and a substituted dibenzocarbazolyl. The substituent of $A_1$ may not be a nitrogen-containing heteroaryl. The substituent of the substituted aryl or the substituted heteroaryl may be at least one of (C1-C30)alkyl, (C6-C30)aryl, (5- to 30-membered)heteroaryl, and mono- or di-(C1-C30)alkyl(C6-C30)aryl; preferably, at least one of (C1-C6)alkyl, (C6-C18)aryl, and di(C1-C6)alkyl(C6-C18)aryl; and for example, at least one of methyl, phenyl, biphenyl, naphthyl, naphthylphenyl, and fluorenyl substituted with dimethyl. Also, $A_1$ may be linked to $X_1$ or $X_8$; and the linkage is preferably a single bond.

In formula 1, $L_1$ represents a single bond, or a substituted or unsubstituted (C6-C30)arylene group; preferably, a single bond, or a substituted or unsubstituted (C6-C18)arylene group; and more preferably, a single bond, or a substituted or unsubstituted (C6-C12)arylene group. For example, $L_1$ may be a single bond, a substituted or unsubstituted phenyl, or an unsubstituted naphthyl, wherein the substituent of a substituted phenyl may be a carbazolyl substituted with phenyl.

In formula 1, $X_1$ to $X_8$, each independently, represent hydrogen, deuterium, a halogen, a cyano group, a carboxyl group, a nitro group, a hydroxyl group, a substituted or unsubstituted (C1-C30)alkyl group, a substituted or unsubstituted (C3-C30)cycloalkyl group, a substituted or unsubstituted (C3-C30)cycloalkenyl group, a substituted or unsubstituted (3- to 7-membered)heterocycloalkyl group, a substituted or unsubstituted (C6-C30)aryl group, a substituted or unsubstituted (3- to 30-membered)heteroaryl group, —$NR_5R_6$, or —$SiR_7R_8R_9$; or may be linked to an adjacent substituent(s) to form a substituted or unsubstituted mono- or polycyclic (C3-C30), alicyclic or aromatic ring, whose carbon atom(s) may be replaced with at least one hetero atom selected from nitrogen, oxygen, and sulfur; preferably, each independently, hydrogen, a substituted or unsubstituted (C6-C25)aryl group, a substituted or unsubstituted (5- to 30-membered)heteroaryl group, —$NR_5R_6$, or —$SiR_7R_8R_9$; or may be linked to an adjacent substituent(s) to form a substituted or unsubstituted mono- or polycyclic (C5-C25), alicyclic or aromatic ring, whose carbon atom(s) may be replaced with at least one hetero atom selected from nitrogen, oxygen, and sulfur; and more preferably, each independently, hydrogen, a substituted or unsubstituted (C6-C18)aryl group, a substituted or unsubstituted (6- to 30-membered)heteroaryl group, —$NR_5R_6$, or —$SiR_7R_8R_9$; or may be linked to an adjacent substituent(s) to form a substituted or unsubstituted mono- or polycyclic (C6-C18) aromatic ring, whose carbon atom(s) may be replaced with at least one nitrogen atom. For example, $X_1$ to $X_8$, each independently, may be hydrogen, a substituted or unsubstituted phenyl, a substituted biphenyl, a substituted naphthyl, a substituted fluorenyl, an unsubstituted triphenylaminyl, an unsubstituted dibenzothiophenyl, an unsubstituted dibenzofuranyl, a substituted carbazolyl, a substituted benzocarbazolyl, an unsubstituted dibenzocarbazolyl, a substituted pyrimidinyl, a substituted or unsubstituted 25-membered heteroaryl, an unsubstituted 29-membered heteroaryl, $NR_5R_6$, or —$SiR_7R_8R_9$; or may be linked to an adjacent substituent(s) to form an unsubstituted benzene ring, a substituted indole ring, or a substituted benzoindole ring, wherein the substituent of the substituted phenyl, the substituted biphenyl, the substituted naphthyl, the substituted fluorenyl, the substituted carbazolyl, the substituted benzocarbazolyl, the substituted pyrimidinyl, the substituted 25-membered heteroaryl, the substituted indole ring, or the substituted benzoindole ring may be at least one of an unsubstituted (C6-C30)aryl, a tri(C6-C30)arylsilyl, a mono- or di-(C6-C30)arylamino, a mono- or di-(C1-C30)alkyl(C6-C30)aryl, and a (3- to 30-membered)heteroaryl unsubstituted or substituted with (C6-C30)aryl; preferably, at least one of an unsubstituted (C6-C18)aryl, a tri(C6-C18)arylsilyl, a di(C6-C18)arylamino, a di(C1-C10)alkyl(C6-C18)aryl, and a (6- to 25-membered)heteroaryl unsubstituted or substituted with a (C6-C18)aryl; and for example, at least one of phenyl, biphenyl, naphthyl, naphthylphenyl, diphenylamine, triphenylsilyl, fluorenyl substituted with dimethyl, dibenzofuranyl, dibenzocarbazolyl, benzocarbazolyl substituted with phenyl, carbazolyl substituted with phenyl, naphthyl or biphenyl, and 25-membered heteroaryl.

In formula 1, $R_5$ to $R_9$, each independently, represent hydrogen, deuterium, a halogen, a cyano group, a carboxyl group, a nitro group, a hydroxyl group, a substituted or unsubstituted (C1-C30)alkyl group, a substituted or unsubstituted (C3-C30)cycloalkyl group, a substituted or unsubstituted (C3-C30)cycloalkenyl group, a substituted or unsubstituted (3- to 7-membered)heterocycloalkyl group, a substituted or unsubstituted (C6-C30)aryl group, or a substituted or unsubstituted (3- to 30-membered)heteroaryl group; or may be linked to an adjacent substituent(s) to form a substituted or unsubstituted mono- or polycyclic (C3-C30), alicyclic or aromatic ring, whose carbon atom(s) may be replaced with at least one hetero atom selected from nitrogen, oxygen, and sulfur; preferably, each independently, hydrogen, or a substituted or unsubstituted (C6-C25) aryl group; more preferably, each independently, a substituted or unsubstituted (C6-C18)aryl group; and for example, an unsubstituted phenyl, an unsubstituted biphenyl, or a fluoreneyl substituted with dimethyl.

The compound of formula 1 may be represented by any one of the following formulae 3 to 5:

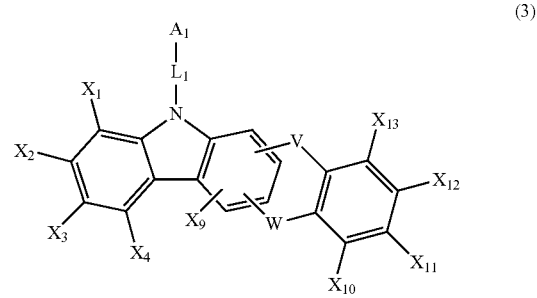

(3)

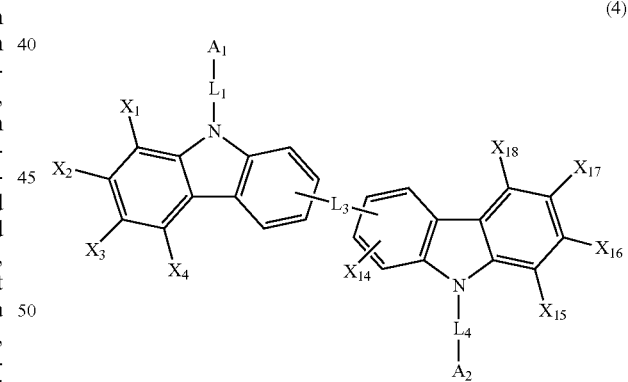

(4)

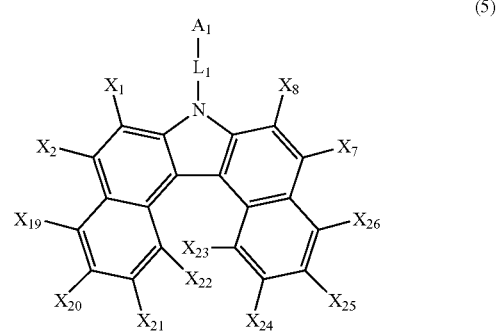

(5)

In formula 3, V and W represent a single bond or $NR_{16}$; provided that both V and W are not a single bond or $NR_{16}$; wherein $R_{16}$ represents hydrogen, deuterium, a halogen, a cyano group, a carboxyl group, a nitro group, a hydroxyl group, a substituted or unsubstituted (C1-C30)alkyl group, a substituted or unsubstituted (C3-C30)cycloalkyl group, a substituted or unsubstituted (C3-C30)cycloalkenyl group, a substituted or unsubstituted (3- to 7-membered)heterocycloalkyl group, a substituted or unsubstituted (C6-C30)aryl group, or a substituted or unsubstituted (3- to 30-membered) heteroaryl group; preferably, a substituted or unsubstituted (C6-C25)aryl group; more preferably, a substituted or unsubstituted (C6-C18)aryl group; and for example, an unsubstituted phenyl, an unsubstituted biphenyl, an unsubstituted naphthylphenyl, an unsubstituted naphthyl, or a fluorenyl substituted with dimethyl.

In formula 4, $A_2$ represents a substituted or unsubstituted (C6-C30)aryl group; preferably, an unsubstituted (C6-C25) aryl group; more preferably, an unsubstituted (C6-C18)aryl group; and for example, an unsubstituted phenyl, an unsubstituted biphenyl, or an unsubstituted naphthyl. Also, $A_2$ may be linked to $X_{14}$ or $X_{15}$; and the linkage is preferably a single bond.

In formula 4, $L_3$ and $L_4$, each independently, represent a single bond, or a substituted or unsubstituted (C6-C30) arylene group; preferably, each independently, a single bond, or an unsubstituted (C6-C25)arylene group; more preferably, each independently, a single bond, or an unsubstituted (C6-C18)arylene group; and for example, each independently, a single bond, an unsubstituted phenylene, an unsubstituted biphenylene, or an unsubstituted naphthylene.

In formulae 3 to 5, $X_9$ to $X_{26}$, each independently, represent hydrogen, deuterium, a halogen, a cyano group, a carboxyl group, a nitro group, a hydroxyl group, a substituted or unsubstituted (C1-C30)alkyl group, a substituted or unsubstituted (C3-C30)cycloalkyl group, a substituted or unsubstituted (C3-C30)cycloalkenyl group, a substituted or unsubstituted (3- to 7-membered)heterocycloalkyl group, a substituted or unsubstituted (C6-C30)aryl group, a substituted or unsubstituted (3- to 30-membered)heteroaryl group, $-NR_5R_6$, or $-SiR_7R_8R_9$; or may be linked to an adjacent substituent(s) to form a substituted or unsubstituted mono- or polycyclic (C3-C30), alicyclic or aromatic ring, whose carbon atom(s) may be replaced with at least one hetero atom selected from nitrogen, oxygen, and sulfur; preferably, each independently, hydrogen, a substituted or unsubstituted (C6-C25)aryl group, a substituted or unsubstituted (5- to 25-membered)heteroaryl group, $-NR_5R_6$, or $-SiR_7R_8R_9$; or may be linked to an adjacent substituent(s) to form a substituted or unsubstituted mono- or polycyclic (C5-C25), alicyclic or aromatic ring, whose carbon atom(s) may be replaced with at least one hetero atom selected from nitrogen, oxygen, and sulfur; more preferably, each independently, hydrogen, an unsubstituted (C6-C18)aryl group, an unsubstituted (6- to 18-membered)heteroaryl group, $-NR_5R_6$, or $-SiR_7R_8R_9$; or may be linked to an adjacent substituent(s) to form an unsubstituted mono- or polycyclic (C5-C18) aromatic ring; and for example, each independently, hydrogen, an unsubstituted phenyl, an unsubstituted naphthyl, an unsubstituted dibenzothiophenyl, $-NR_5R_6$, or $-SiR_7R_8R_9$; or may be linked to an adjacent substituent(s) to form an unsubstituted benzene ring.

In formulae 3 to 5, $A_1$, $L_1$, $X_1$ to $X_4$, $X_7$, $X_8$, and $R_5$ to $R_9$ are as defined in formula 1.

In formula 2, X, Y and Z, each independently, represent N or $CR_{10}$; provided that at least one of X, Y and Z represent N; In formula 2, $L_2$ represents a substituted or unsubstituted (C6-C30)arylene group; preferably, a substituted or unsubstituted (C6-C18)arylene group; more preferably, an unsubstituted (C6-C12)arylene group; and for example, phenylene, naphthylene, or biphenylene.

In formula 2, $R_1$ to $R_4$, each independently, represent hydrogen, deuterium, a halogen, a cyano group, a carboxyl group, a nitro group, a hydroxyl group, a substituted or unsubstituted (C1-C30)alkyl group, a substituted or unsubstituted (C3-C30)cycloalkyl group, a substituted or unsubstituted (C3-C30)cycloalkenyl group, a substituted or unsubstituted (3- to 7-membered)heterocycloalkyl group, a substituted or unsubstituted (C6-C30)aryl group, a substituted or unsubstituted (3- to 30-membered)heteroaryl group, $-NR_{11}R_{12}$, or $-SiR_{13}R_{14}R_{15}$; or may be linked to an adjacent substituent(s) to form a substituted or unsubstituted mono- or polycyclic (C3-C30), alicyclic or aromatic ring, whose carbon atom(s) may be replaced with at least one hetero atom selected from nitrogen, oxygen, and sulfur; preferably, each independently, hydrogen, a substituted or unsubstituted (C6-C25)aryl group, or a substituted or unsubstituted (3- to 25-membered)heteroaryl group; or may be linked to an adjacent substituent(s) to form a substituted or unsubstituted mono- or polycyclic (C3-C25), alicyclic or aromatic ring, whose carbon atom(s) may be replaced with at least one hetero atom selected from nitrogen, oxygen, and sulfur; more preferably, each independently, hydrogen, a substituted or unsubstituted (C6-C18)aryl group, or a substituted or unsubstituted (5- to 18-membered)heteroaryl group; or may be linked to an adjacent substituent(s) to form a substituted or unsubstituted mono- or polycyclic (C5-C18), alicyclic or aromatic ring, whose carbon atom(s) may be replaced with at least one hetero atom selected from nitrogen, oxygen, and sulfur; and for example, hydrogen, an unsubstituted phenyl, an unsubstituted naphthyl, a fluorenyl substituted with dimethyl, a carbazolyl substituted with phenyl, an unsubstituted dibenzofuranyl, or an unsubstituted dibenzothiophenyl; or may be linked to an adjacent substituent(s) to form an unsubstituted benzene ring, an indene ring substituted with dimethyl, an indole ring substituted with phenyl, an unsubstituted benzothiophene ring, or an unsubstituted benzofuran ring.

In formula 2, $R_{10}$ to $R_{15}$, each independently, represent hydrogen, deuterium, a halogen, a cyano group, a carboxyl group, a nitro group, a hydroxyl group, a substituted or unsubstituted (C1-C30)alkyl group, a substituted or unsubstituted (C3-C30)cycloalkyl group, a substituted or unsubstituted (C3-C30)cycloalkenyl group, a substituted or unsubstituted (3- to 7-membered)heterocycloalkyl group, a substituted or unsubstituted (C6-C30)aryl group, or a substituted or unsubstituted (3- to 30-membered)heteroaryl group; preferably, each independently, hydrogen, or a substituted or unsubstituted (C6-C25)aryl group; more preferably, each independently, hydrogen, or a substituted or unsubstituted (C6-C18)aryl group; and for example, hydrogen, a substituted or unsubstituted phenyl, an unsubstituted biphenyl, an unsubstituted naphthyl, or a fluorenyl substituted with dimethyl.

In formula 2, k and m, each independently, represent an inter of 0 to 5; and preferably, each independently, an inter of 0 to 2, and where k or m represents an integer of 2 or more, each of $R_3$ or $R_4$ may be the same or different.

In formulae 1 and 2, the heteroaryl and the heterocycloalkyl, each independently, contain at least one hetero atom selected from B, N, O, S, Si, and P; and preferably, contain at least one hetero atom selected from N, O, S and Si.

In formula 2, $L_2$ may be represented by any one of the following formulae 7 to 19:
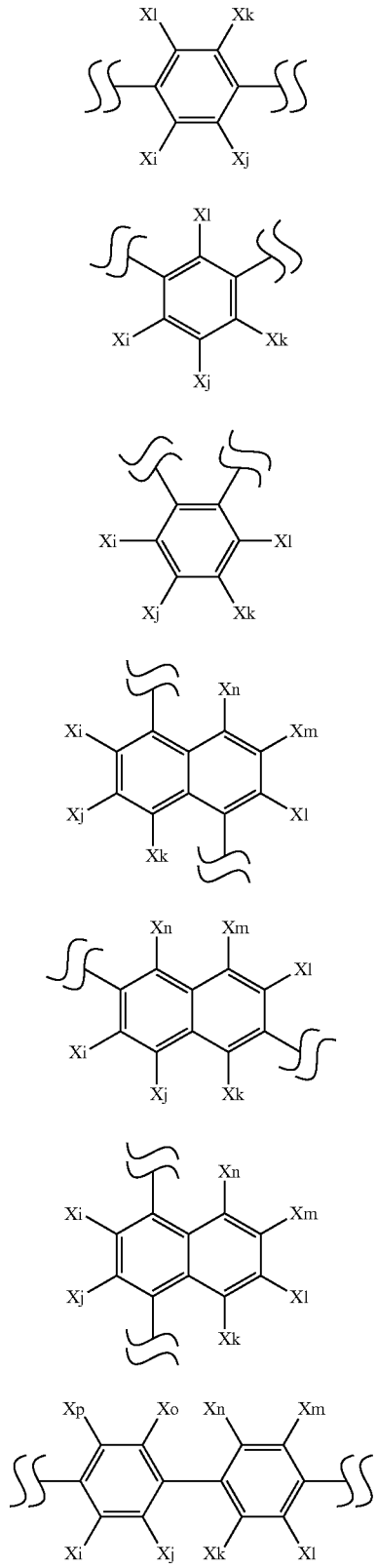
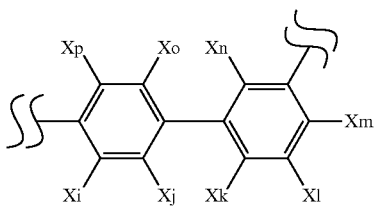
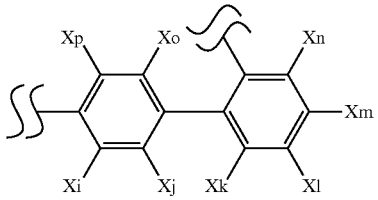
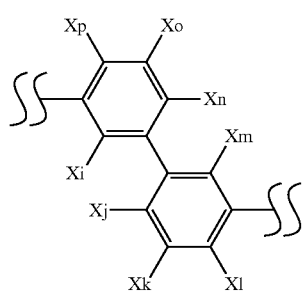
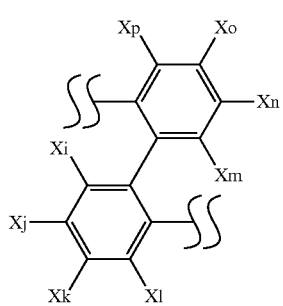
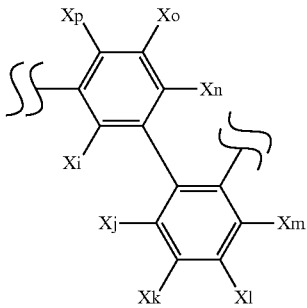

-continued

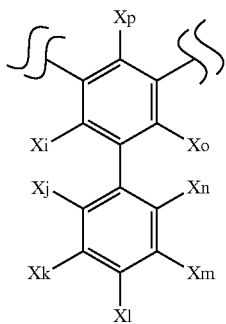

(19)

wherein

Xi to Xp, each independently, represent hydrogen, deuterium, a halogen, a cyano group, a substituted or unsubstituted (C1-C30)alkyl group, a substituted or unsubstituted (C2-C30)alkenyl group, a substituted or unsubstituted (C2-C30)alkynyl group, a substituted or unsubstituted (C3-C30)cycloalkyl group, a substituted or unsubstituted (C6-C60) aryl group, a substituted or unsubstituted (3- to 30-membered)heteroaryl group, a substituted or unsubstituted tri(C1-C30)alkylsilyl group, a substituted or unsubstituted tri(C6-C30)arylsilyl group, a substituted or unsubstituted di(C1-C30)alkyl(C6-C30)arylsilyl group, a substituted or unsubstituted (C1-C30)alkyldi(C6-C30)arylsilyl group, or a substituted or unsubstituted mono- or di-(C6-C30) arylamino group; or may be linked to an adjacent substituent (s) to form a substituted or unsubstituted mono- or polycyclic (C3-C30), alicyclic or aromatic ring, whose carbon atom(s) may be replaced with at least one hetero atom selected from nitrogen, oxygen, and sulfur; preferably, each independently, hydrogen, a halogen, a cyano group, a substituted or unsubstituted (C1-C10)alkyl group, a substituted or unsubstituted (C3-C20)cycloalkyl group, a substituted or unsubstituted (C6-C12)aryl group, a substituted or unsubstituted (C1-C6)alkyldi(C6-C12)arylsilyl group, or a substituted or unsubstituted tri(C6-C20)arylsilyl group; more preferably, hydrogen.

Herein, "(C1-C30)alkyl" is meant to be a linear or branched alkyl having 1 to 30 carbon atoms constituting the chain, in which the number of carbon atoms is preferably 1 to 20, more preferably 1 to 10, and includes methyl, ethyl, n-propyl, isopropyl, n-butyl, isobutyl, tert-butyl, etc.; "(C2-C30)alkenyl" is meant to be a linear or branched alkenyl having 2 to 30 carbon atoms constituting the chain, in which the number of carbon atoms is preferably 2 to 20, more preferably 2 to 10, and includes vinyl, 1-propenyl, 2-propenyl, 1-butenyl, 2-butenyl, 3-butenyl, 2-methylbut-2-enyl, etc.; "(C2-C30)alkynyl" is meant to be a linear or branched alkynyl having 2 to 30 carbon atoms constituting the chain, in which the number of carbon atoms is preferably 2 to 20, more preferably 2 to 10, and includes ethynyl, 1-propynyl, 2-propynyl, 1-butynyl, 2-butynyl, 3-butynyl, 1-methylpent-2-ynyl, etc.; "(C3-C30)cycloalkyl" is a mono- or polycyclic hydrocarbon having 3 to 30 ring backbone carbon atoms, in which the number of carbon atoms is preferably 3 to 20, more preferably 3 to 7, and includes cyclopropyl, cyclobutyl, cyclopentyl, cyclohexyl, etc.; "3- to 7-membered heterocycloalkyl" is a cycloalkyl having 3 to 7, preferably 5 to 7, ring backbone atoms, including at least one heteroatom selected from B, N, O, S, Si, and P, preferably O, S, and N, and includes tetrahydrofuran, pyrrolidine, thiolan, tetrahydropyran, etc.; "(C6-C30)aryl(ene)" is a monocyclic or fused ring derived from an aromatic hydrocarbon having 6 to 30 ring backbone carbon atoms, in which the number of carbon atoms is preferably 6 to 20, more preferably 6 to 15, and includes phenyl, biphenyl, terphenyl, naphthyl, binaphthyl, phenylnaphthyl, naphthylphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, etc.; "3- to 30-membered heteroaryl" is an aryl having 3 to 30 ring backbone atoms including at least one, preferably 1 to 4 heteroatoms selected from the group consisting of B, N, O, S, Si, and P; is a monocyclic ring, or a fused ring condensed with at least one benzene ring; may be partially saturated; may be one formed by linking at least one heteroaryl or aryl group to a heteroaryl group via a single bond(s); and includes a monocyclic ring-type heteroaryl including furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl including benzofuranyl, benzothiophenyl, isobenzofuranyl, dibenzofuranyl, dibenzothiophenyl, benzimidazolyl, benzothiazolyl, benzoisothiazolyl, benzoisoxazolyl, benzoxazolyl, isoindolyl, indolyl, benzoindolyl, indazolyl, benzothiadiazolyl, quinolyl, isoquinolyl, cinnolinyl, quinazolinyl, quinoxalinyl, carbazolyl, phenoxazinyl, phenanthridinyl, benzodioxolyl, etc.; "nitrogen-containing (5- to 30-membered) heteroaryl" indicates an aryl group having 5 to 30 ring backbone atoms, preferably 5 to 20 ring backbone atoms, more preferably 5 to 15 ring backbone atoms, containing at least one, preferably 1 to 4, nitrogen as the hetero atom, may be a monocyclic ring, or a fused ring condensed with at least one benzene ring; may be partially saturated; may be one formed by linking at least one heteroaryl or aryl group to a heteroaryl group via a single bond(s); and includes a monocyclic ring-type heteroaryl such as pyrrolyl, imidazolyl, pyrazolyl, triazinyl, tetrazinyl, triazolyl, tetrazolyl, pyridyl, pyrazinyl, pyrimidinyl, pyridazinyl, etc. and a fused ring-type heteroaryl such as benzoimidazolyl, isoindolyl, indolyl, indazolyl, benzothiadiazolyl, quinolyl, isoquinolyl, cinnolinyl, quinazolinyl, quinoxalinyl, carbazolyl, benzocarbazolyl, dibenzocarbazolyl, phenanthridinyl, etc. Furthermore, "halogen" includes F, Cl, Br, and I.

Herein, "substituted" in the expression "substituted or unsubstituted" means that a hydrogen atom in a certain functional group is replaced with another atom or group, i.e. a substituent. The substituents of the substituted alkyl group, the substituted cycloalkyl group, the substituted cycloalkenyl group, the substituted heterocycloalkyl group, the substituted aryl(ene) group, the substituted heteroaryl group, and the substituted mono- or polycyclic, alicyclic or aromatic ring in $A_1$, $A_2$, $L_1$ to $L_4$, $X_1$ to $X_{26}$, and $R_1$ to $R_{16}$ of formulae 1 to 5, each independently, are at least one selected from the group consisting of deuterium; a halogen; a cyano; a carboxyl; a nitro; a hydroxyl; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (3- to 30-membered)heteroaryl unsubstituted or substituted with a (C6-C30)aryl; a (C6-C30)aryl unsubstituted or substituted with a cyano, a (3- to 30-membered)heteroaryl or a tri(C6-C30)arylsilyl; a tri(C1-C30)alkylsilyl; a tri(C6-C30)arylsilyl; a di(C1-C30)alkyl(C6-C30)arylsilyl; a (C1-C30)alkyldi(C6-C30)arylsilyl; an amino; a mono- or di-(C1-C30) alkylamino; a mono- or di-(C6-C30)arylamino; a (C1-C30)

alkyl(C6-C30)arylamino; a (C1-C30)alkylcarbonyl; a (C1-C30)alkoxycarbonyl; a (C6-C30)arylcarbonyl; a di(C6-C30)arylboronyl; a di(C1-C30)alkylboronyl; a (C1-C30)alkyl(C6-C30)arylboronyl; a (C6-C30)aryl(C1-C30)alkyl; and a mono- or di-(C1-C30)alkyl(C6-C30)aryl; preferably, each independently, at least one selected from the group consisting of a (C1-C15)alkyl; a (5- to 30-membered)heteroaryl unsubstituted or substituted with a (C6-C25)aryl; an unsubstituted (C6-C25)aryl; a tri(C6-C18)arylsilyl; a di(C6-C18)arylamino; and a di(C1-C15)alkyl(C6-C18)aryl; more preferably, each independently, at least one selected from the group consisting of a (C1-C6)alkyl; a (6- to 25-membered)heteroaryl unsubstituted or substituted with a (C6-C12)aryl; an unsubstituted (C6-C18)aryl; a tri(C6-C12)arylsilyl; a di(C6-C12)arylamino; and a di(C1-C6)alkyl(C6-C18)aryl; and for example, at least one selected from the group consisting of methyl, phenyl, biphenyl, naphthyl, naphthylphenyl, fluorenyl substituted with dimethyl, dibenzofuranyl, triphenylsilyl, diphenylamino, dibenzothiophenyl, dibenzocarbazolyl, benzocarbazolyl substituted with phenyl, carbazolyl substituted with phenyl, biphenyl or naphthyl, and 25-membered heteroaryl.

According to one embodiment of the present invention, in formula 1, $A_1$ represents a substituted or unsubstituted (C6-C25)aryl group, or a substituted or unsubstituted (6- to 25-membered)heteroaryl group; $L_1$ represents a single bond, or a substituted or unsubstituted (C6-C18)arylene group; $X_1$ to $X_8$, each independently, represent hydrogen, a substituted or unsubstituted (C6-C25)aryl group, a substituted or unsubstituted (5- to 30-membered)heteroaryl group, —$NR_5R_6$, or —$SiR_7R_8R_9$; or may be linked to an adjacent substituent(s) to form a substituted or unsubstituted mono- or polycyclic (C5-C25), alicyclic or aromatic ring, whose carbon atom(s) may be replaced with at least one hetero atom selected from nitrogen, oxygen, and sulfur; and $R_5$ to $R_9$, each independently, represent hydrogen, or a substituted or unsubstituted (C6-C25)aryl group.

According to another embodiment of the present invention, in formula 1, $A_1$ represents a substituted or unsubstituted (C6-C25)aryl group, or a substituted or unsubstituted (6- to 20-membered)heteroaryl group; $L_1$ represents a single bond, or a substituted or unsubstituted (C6-C12)arylene group; $X_1$ to $X_8$, each independently, represent hydrogen, a substituted or unsubstituted (C6-C18)aryl group, a substituted or unsubstituted (6- to 30-membered)heteroaryl group, —$NR_5R_6$, or —$SiR_7R_8R_9$; or may be linked to an adjacent substituent(s) to form a substituted or unsubstituted mono- or polycyclic (C6-C18) aromatic ring, whose carbon atom(s) may be replaced with at least one nitrogen atom; and $R_5$ to $R_9$, each independently, represent a substituted or unsubstituted (C6-C18)aryl group.

According to one embodiment of the present invention, in formula 2, $L_2$ represents a substituted or unsubstituted (C6-C18)arylene group; $R_1$ to $R_4$, each independently, represent hydrogen, a substituted or unsubstituted (C6-C25)aryl group, or a substituted or unsubstituted (3- to 25-membered) heteroaryl group; or may be linked to an adjacent substituent (s) to form a substituted or unsubstituted mono- or polycyclic (C3-C25), alicyclic or aromatic ring, whose carbon atom(s) may be replaced with at least one hetero atom selected from nitrogen, oxygen, and sulfur; and k and m, each independently, represent an inter of 0 to 2.

According to another embodiment of the present invention, in formula 2, $L_2$ represents an unsubstituted (C6-C12) arylene group; $R_1$ to $R_4$, each independently, represent hydrogen, a substituted or unsubstituted (C6-C18)aryl group, or a substituted or unsubstituted (5- to 18-membered) heteroaryl group; or may be linked to an adjacent substituent (s) to form a substituted or unsubstituted mono- or polycyclic (C5-C18), alicyclic or aromatic ring, whose carbon atom(s) may be replaced with at least one hetero atom selected from nitrogen, oxygen, and sulfur; and k and m, each independently, represent an inter of 0 to 2.

The first host compound of formula 1 may be selected from the group consisting of the following compounds, but is not limited thereto:

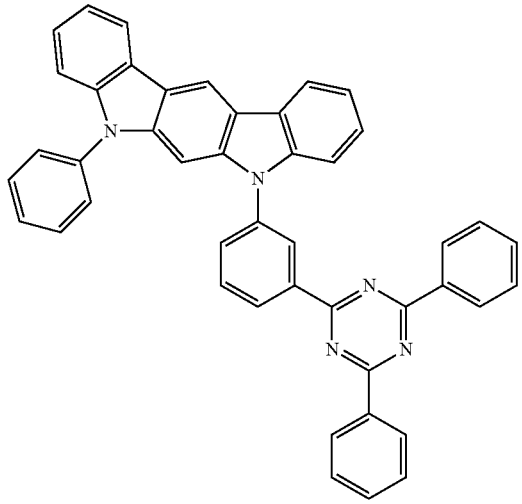

H-1

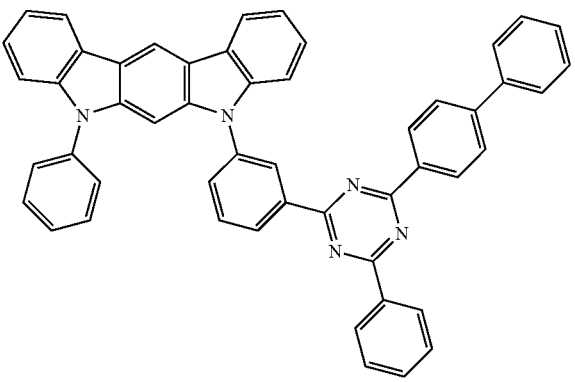

H-2

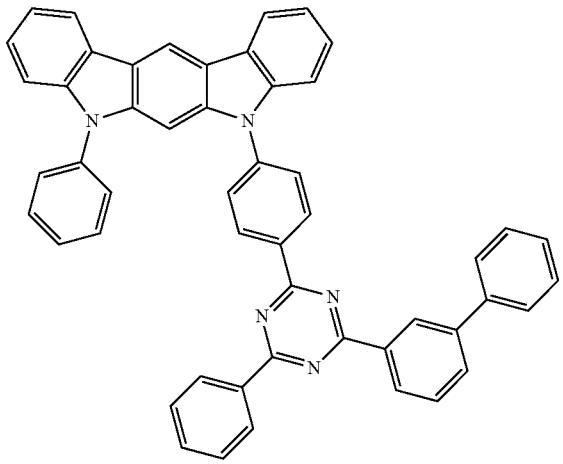

H-3

-continued
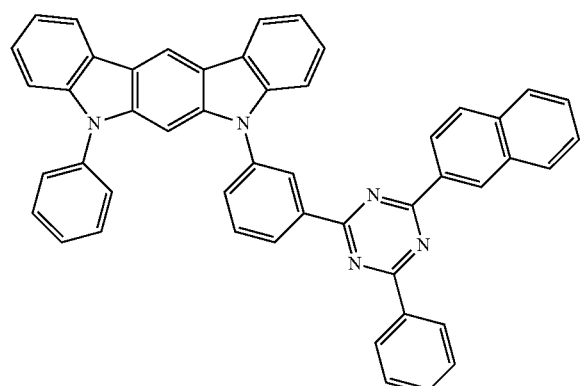
H-4
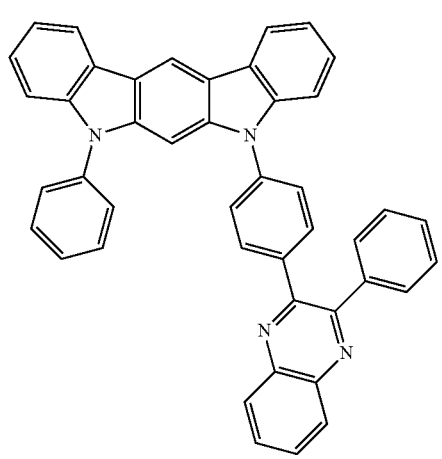
H-5
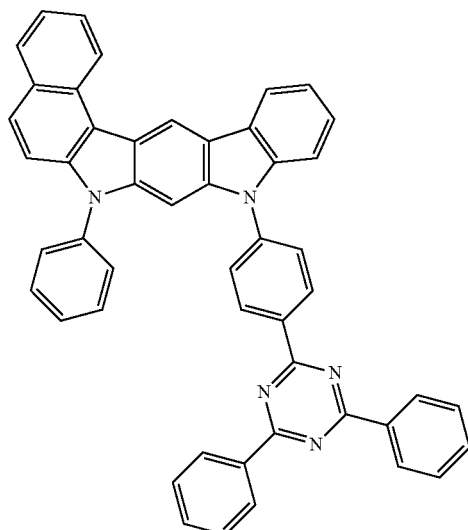
H-7
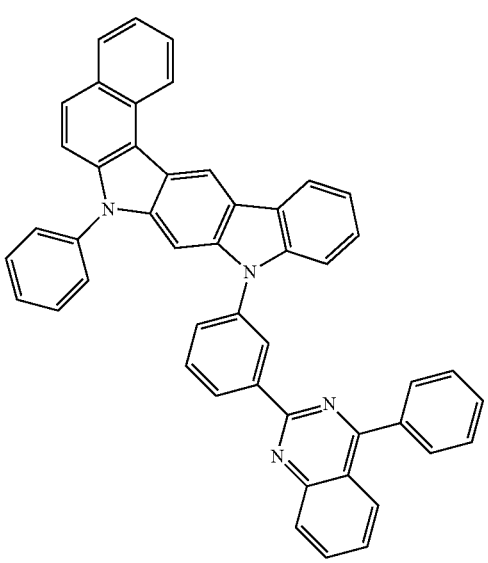
H-9

H-10
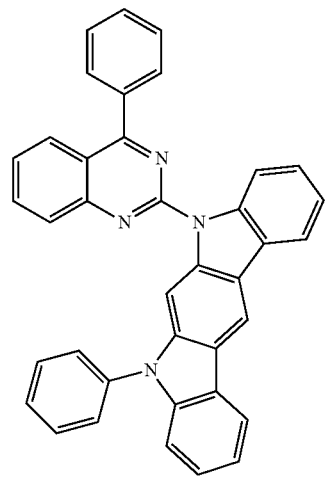
H-13
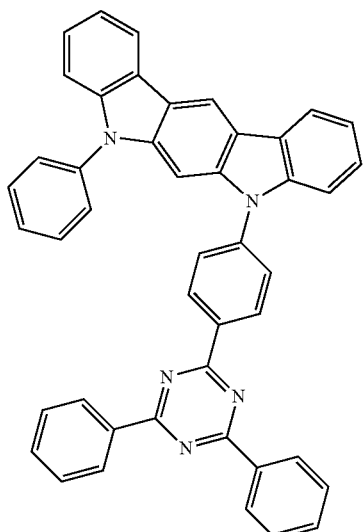
H-11
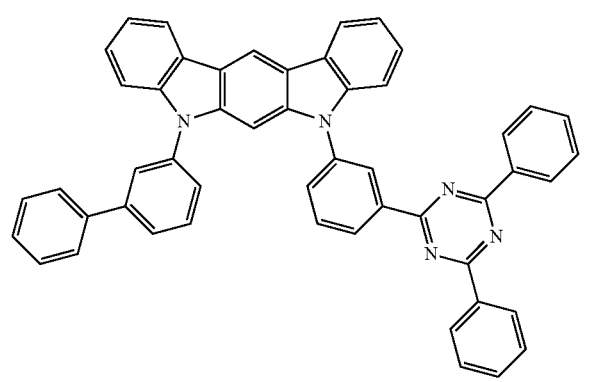
H-12
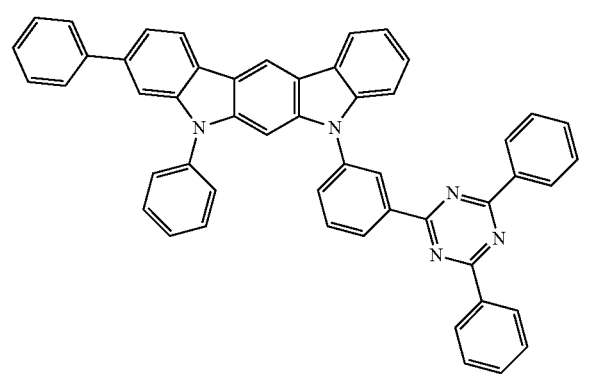
H-14
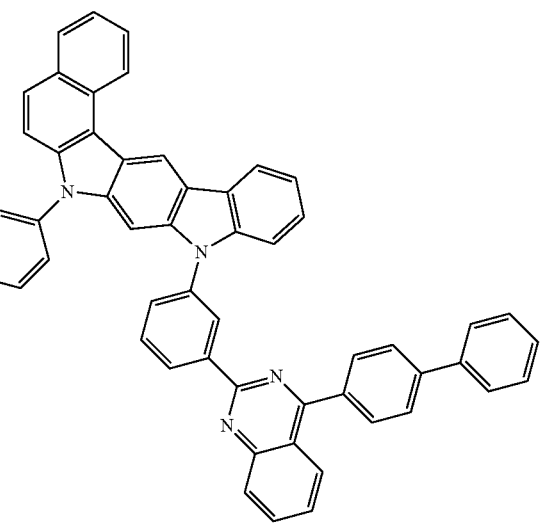

H-15
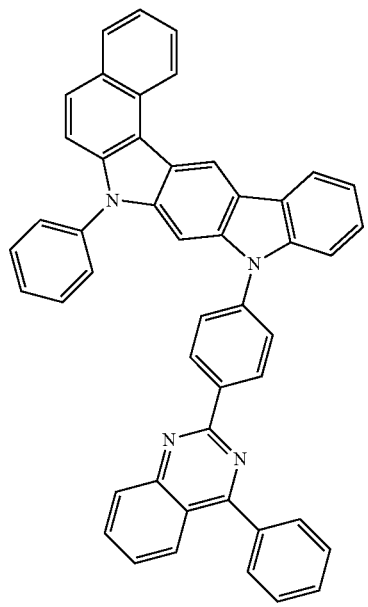
H-16
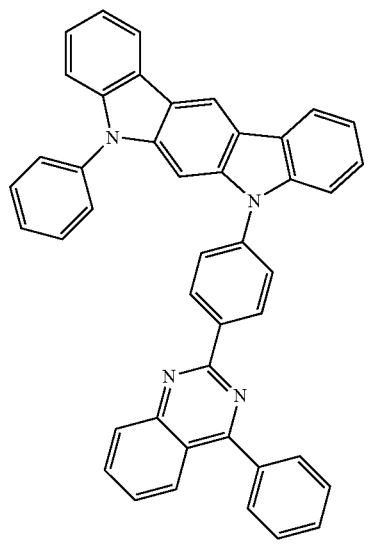
H-19
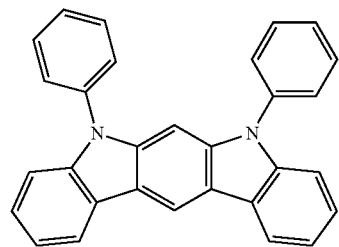
H-20
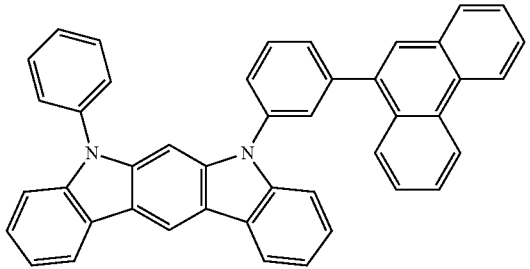
H-21
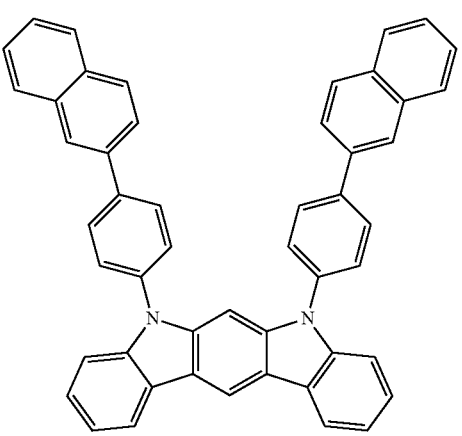
H-22
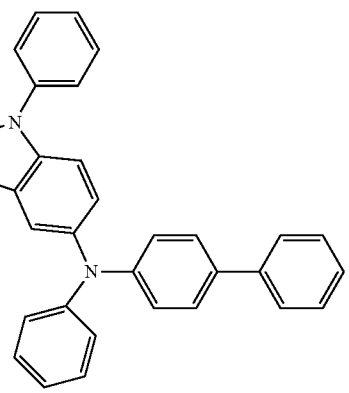
H-23
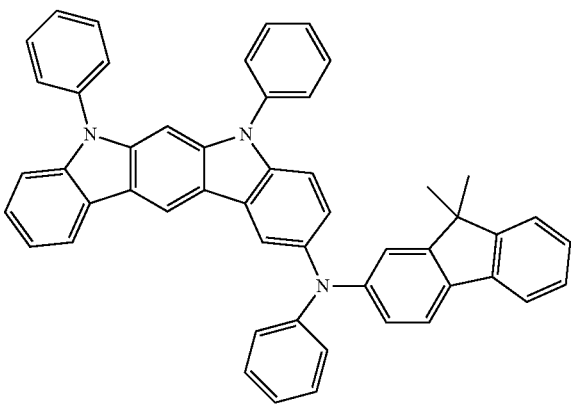

-continued
H-24
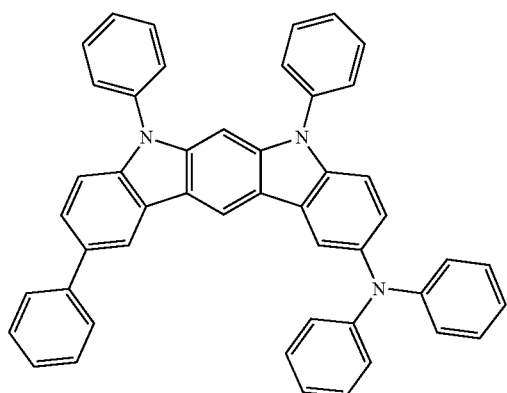
H-25
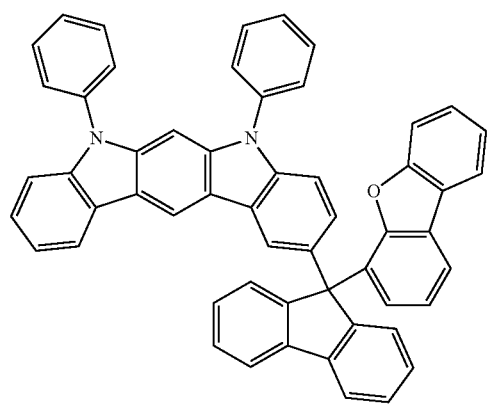
H-26
-continued
H-27
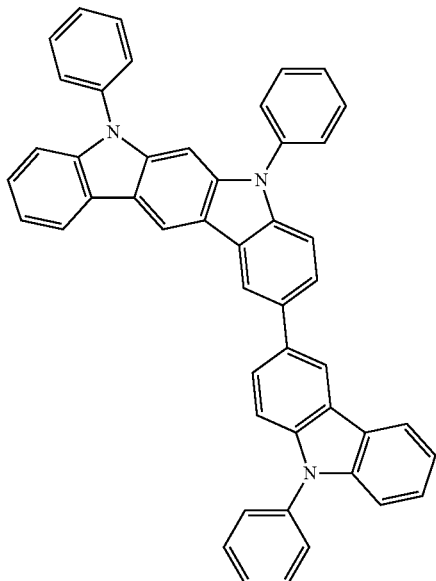
H-28
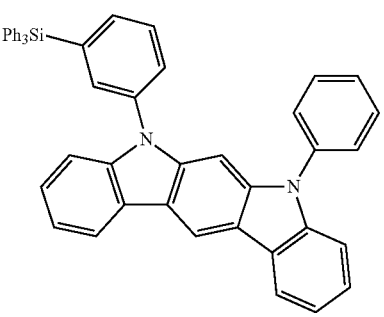
H-29
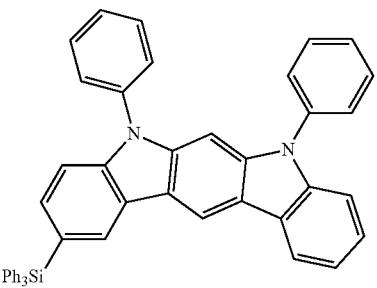
H-30
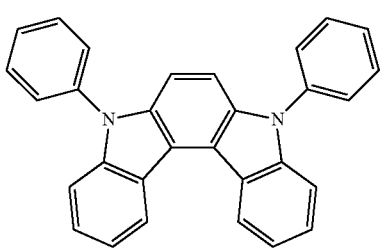

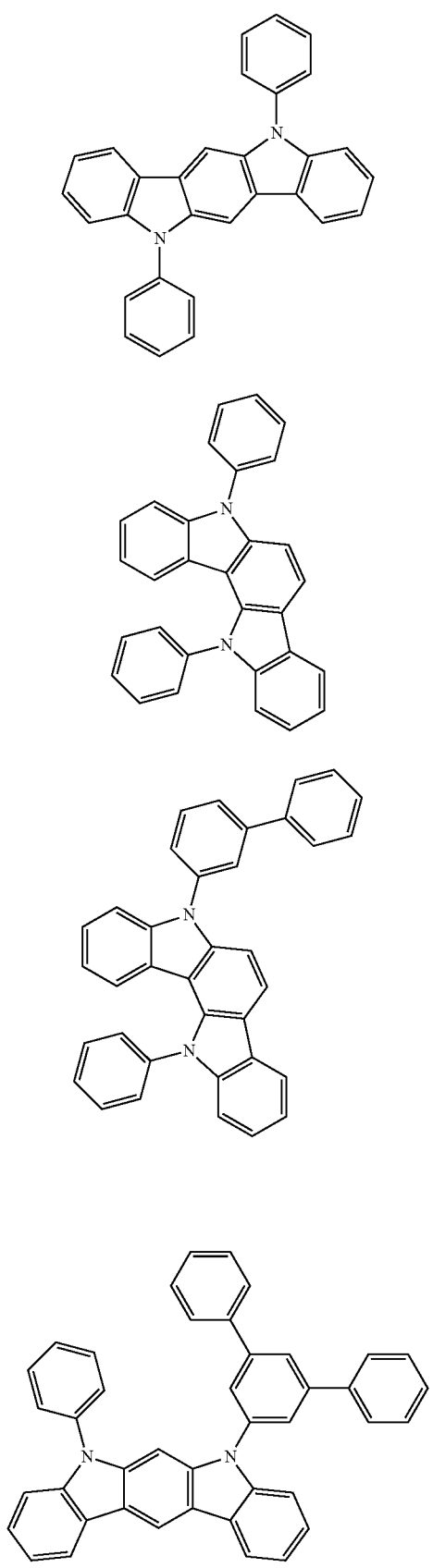
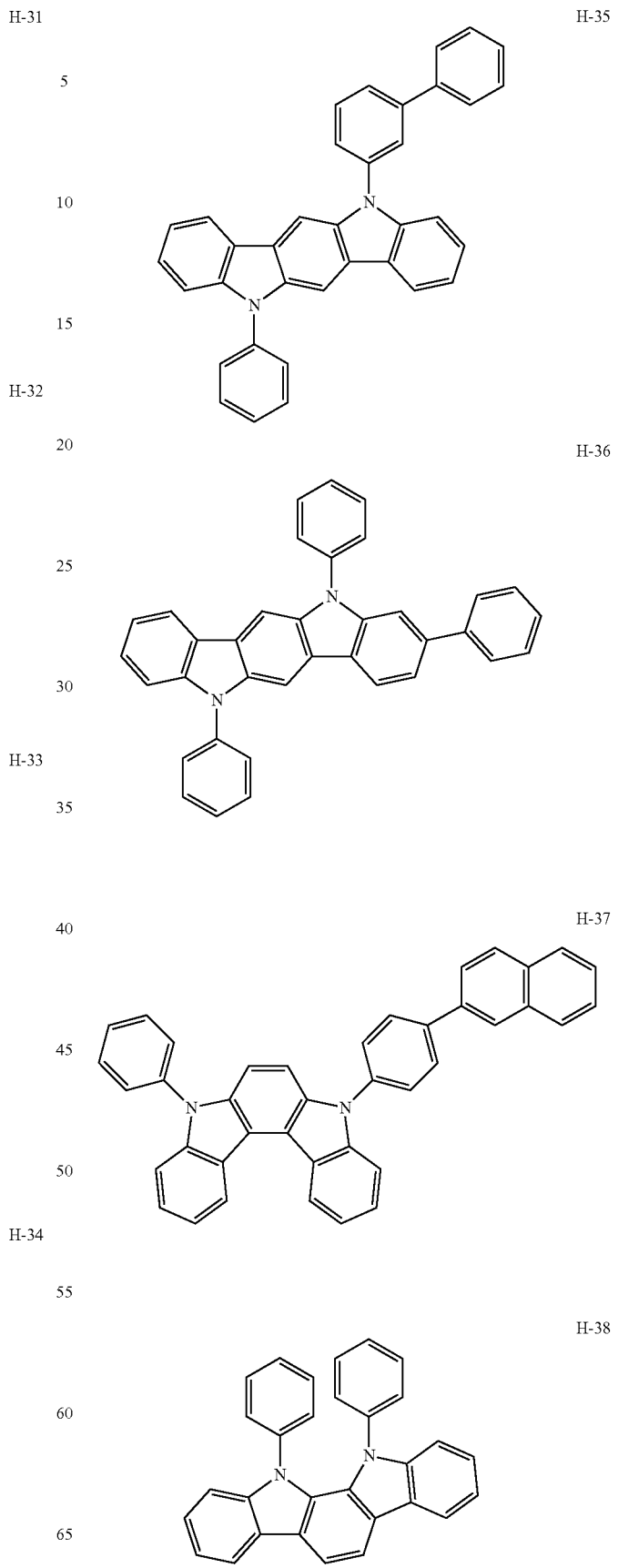

H-39
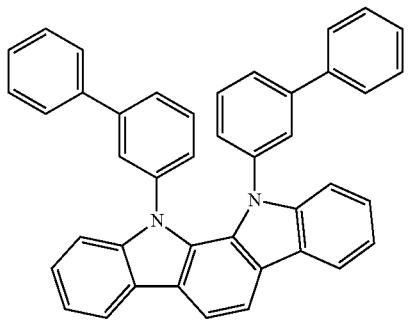
H-40
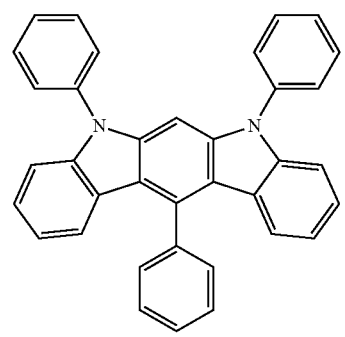
H-42
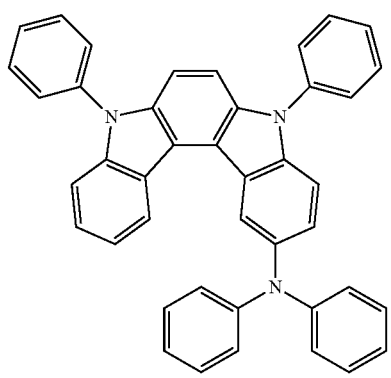
H-43
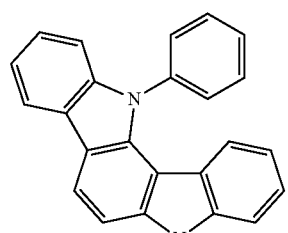
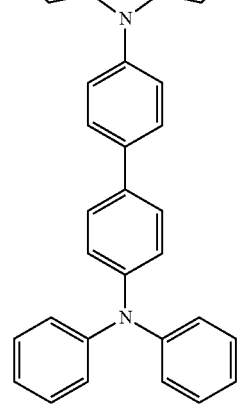
H-44
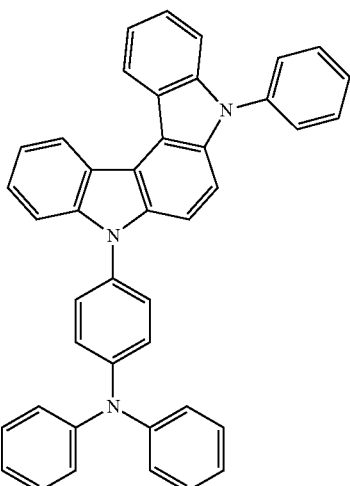
H-45
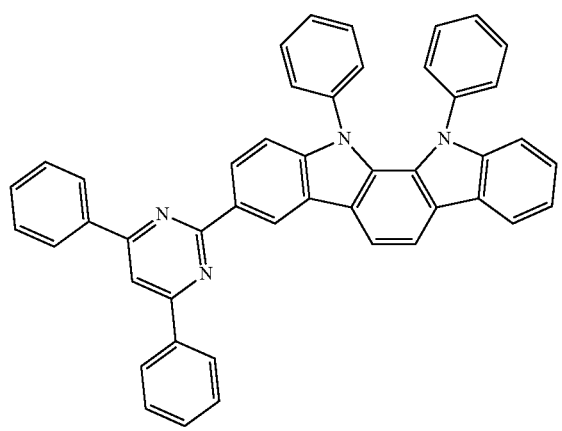
H-46
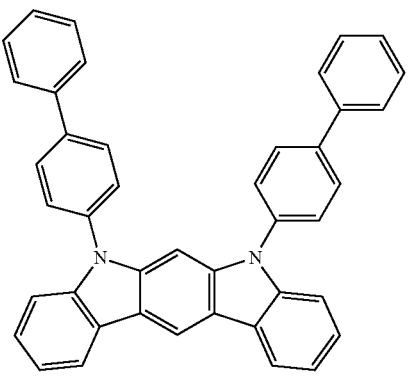

H-47
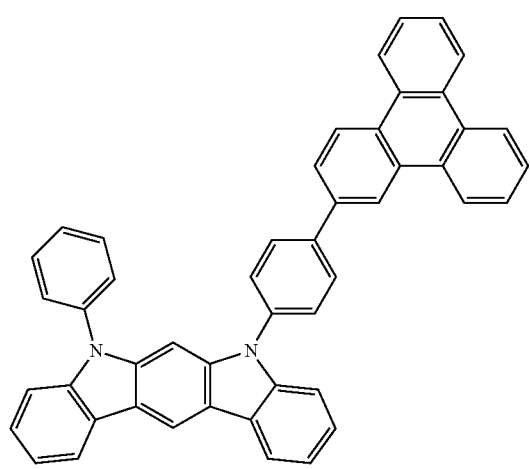
H-48
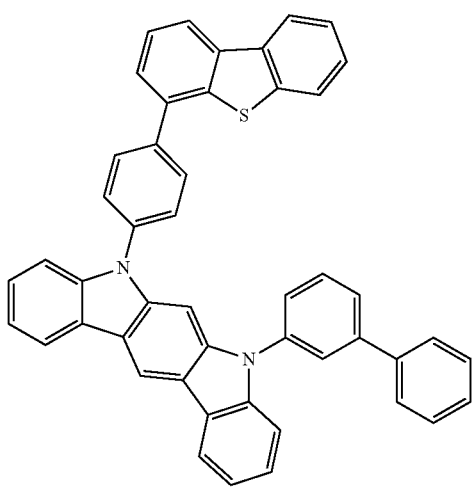
H-49
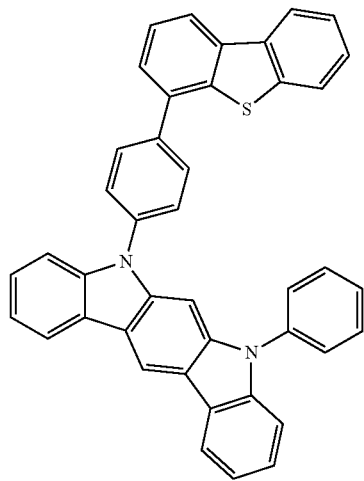
H-50
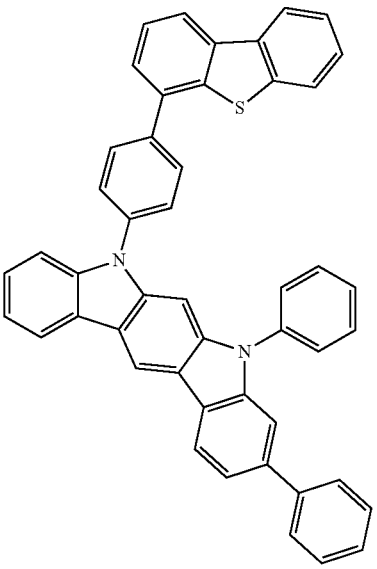
H-51
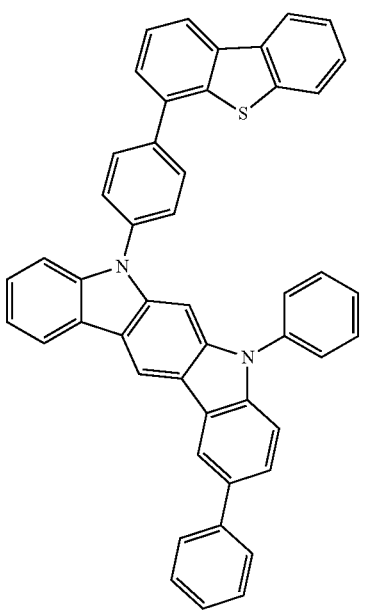
H-52
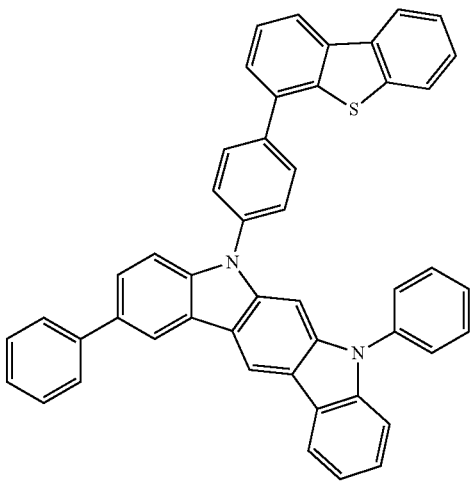

H-53
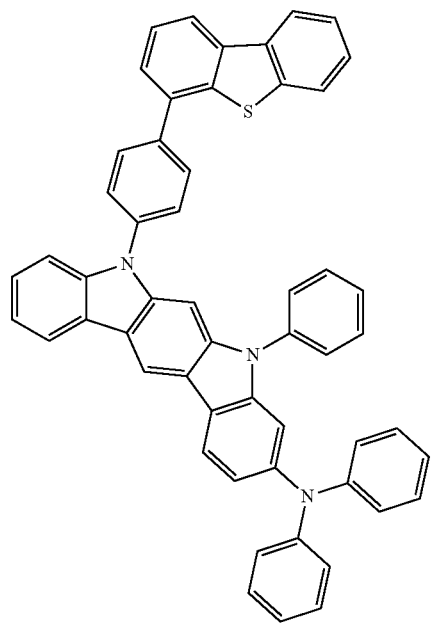
H-55
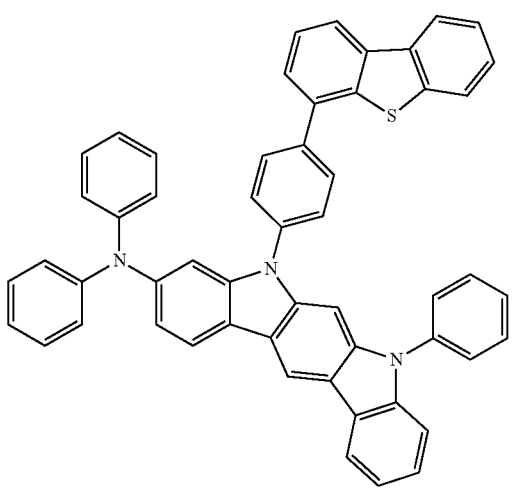
H-56
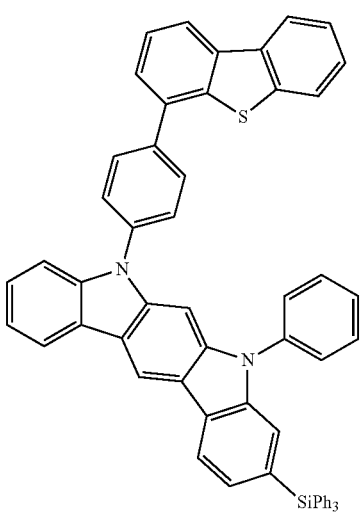
H-54
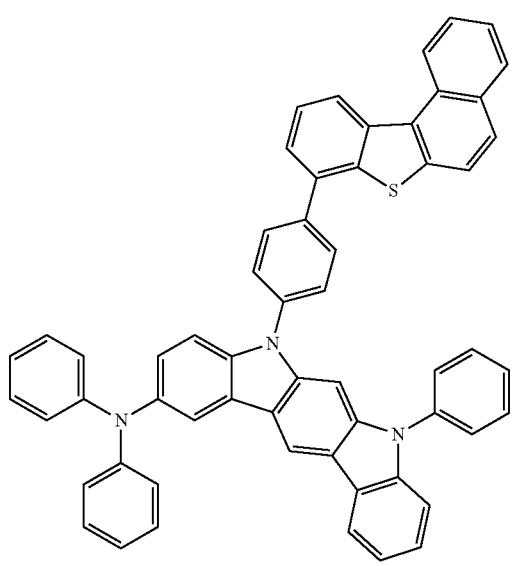
H-57
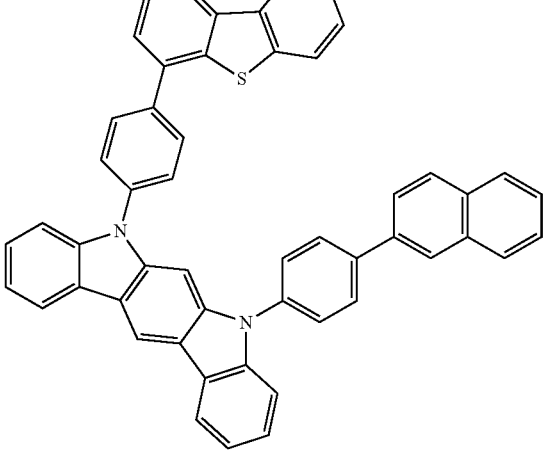

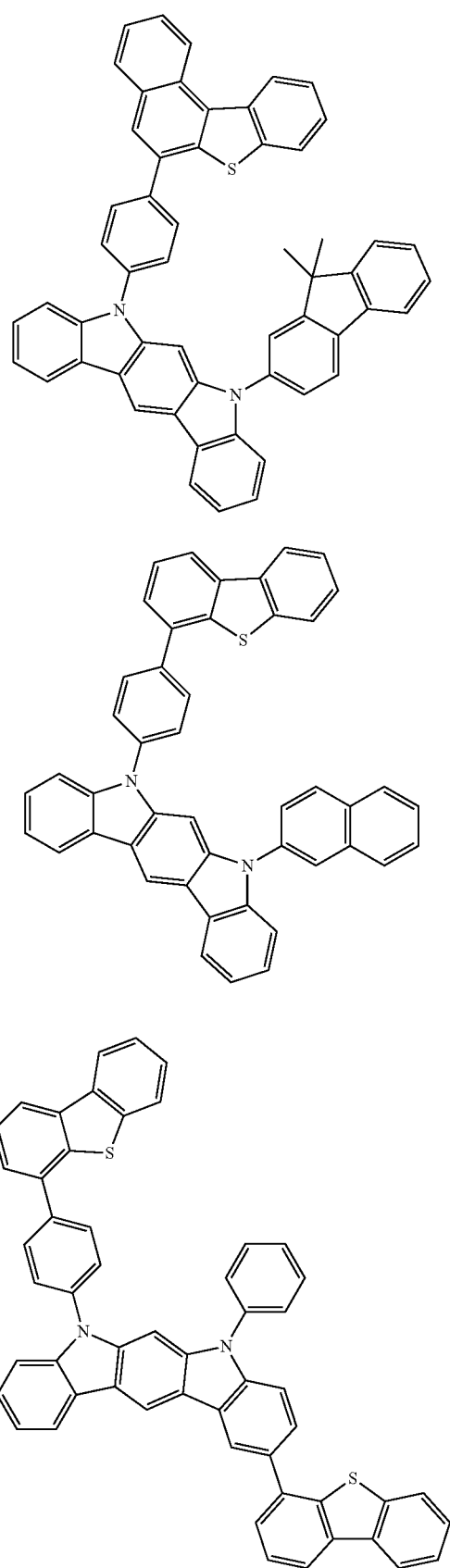
H-58
H-59
H-60
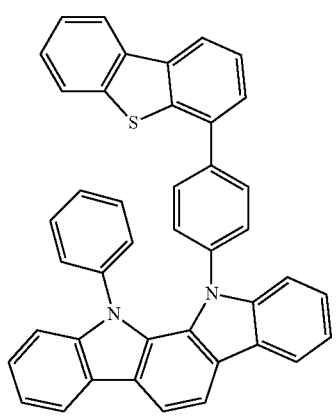
H-61
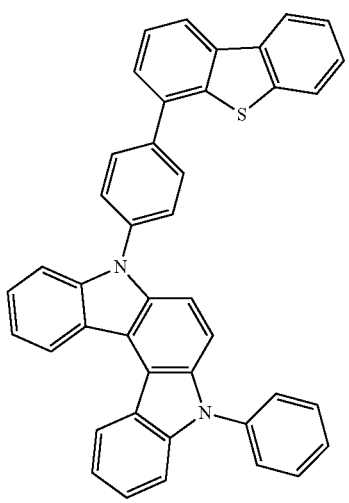
H-62
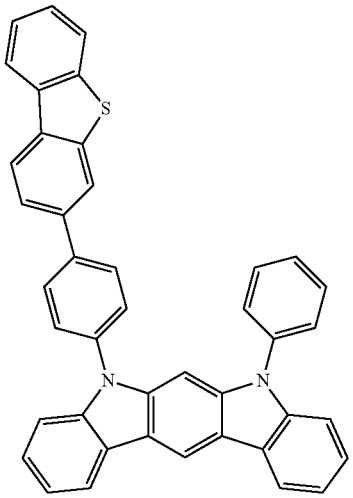
H-63

H-64
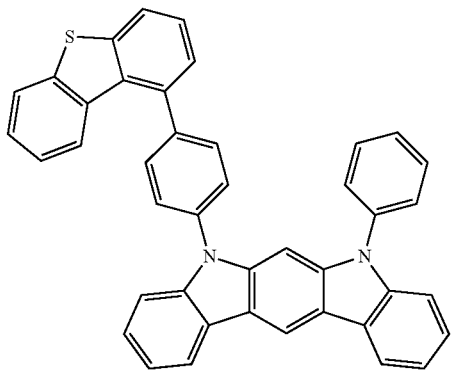
H-65
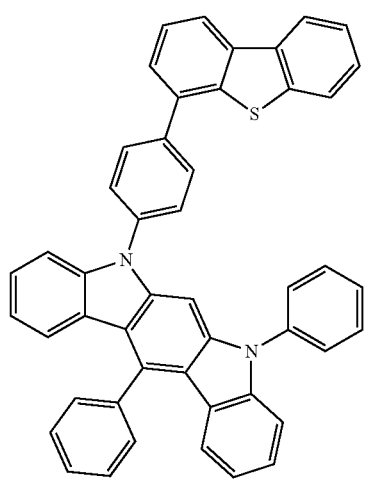
H-66
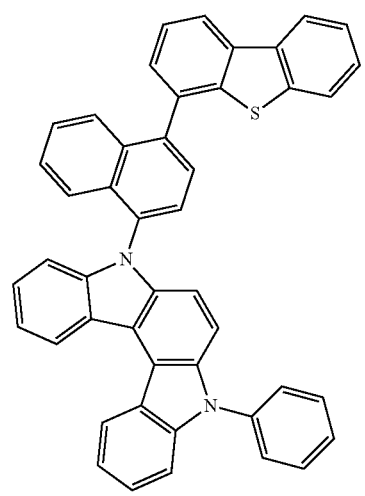
H-67
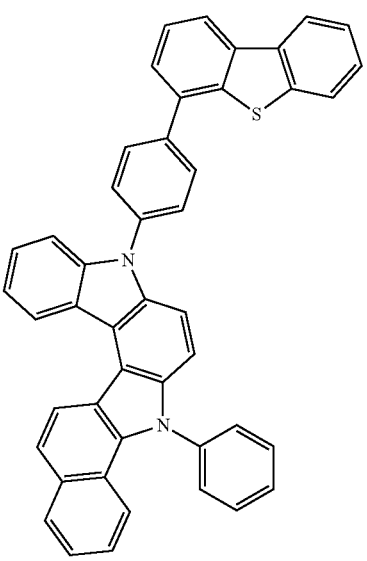
H-68
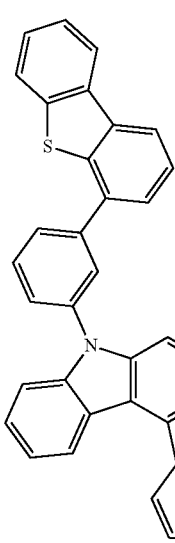
H-69
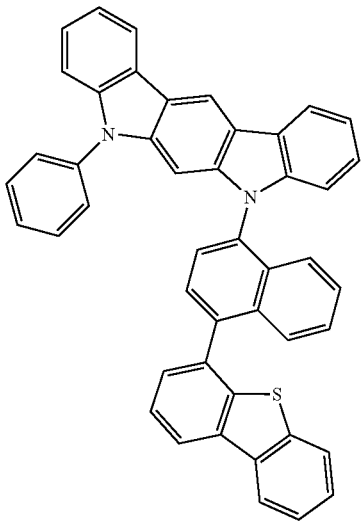

-continued
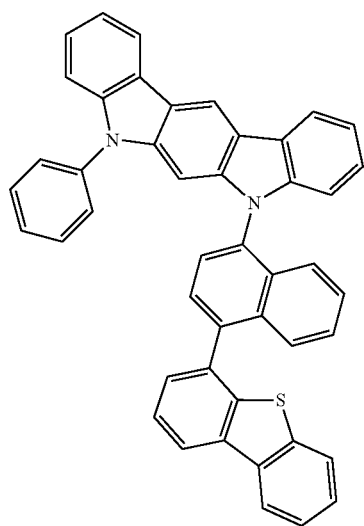
H-70
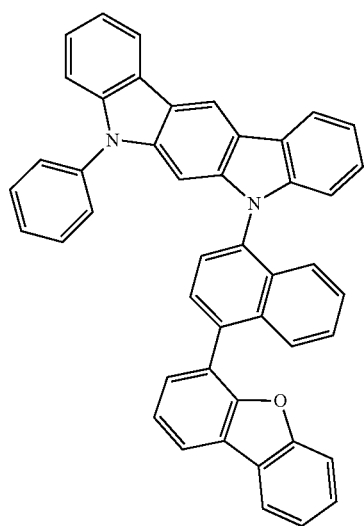
H-71
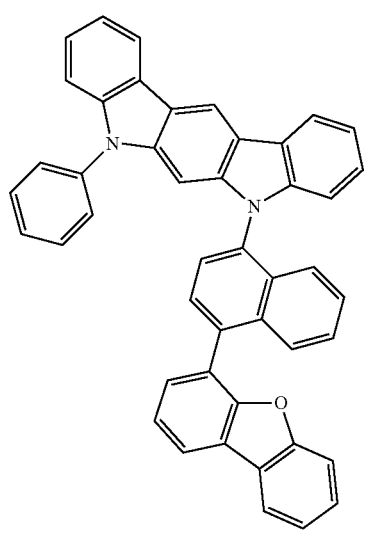
H-72
-continued
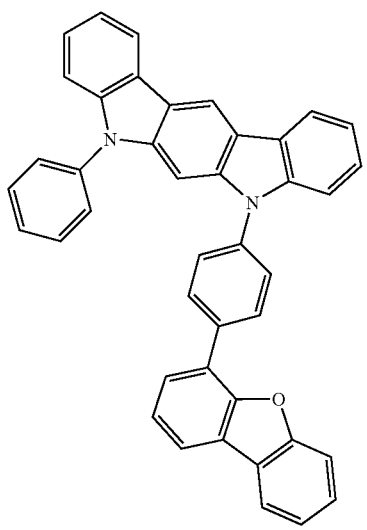
H-73
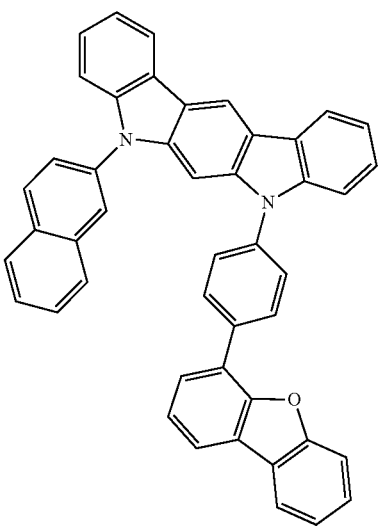
H-74
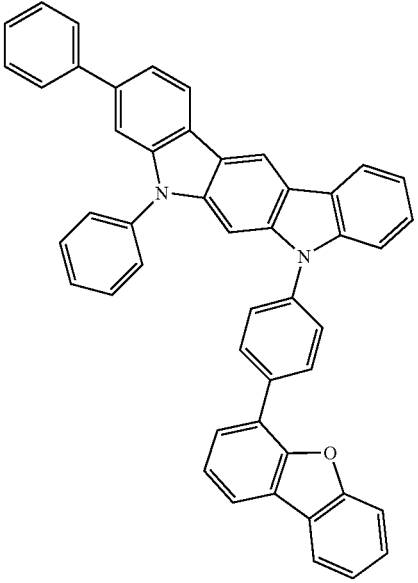
H-75

H-76
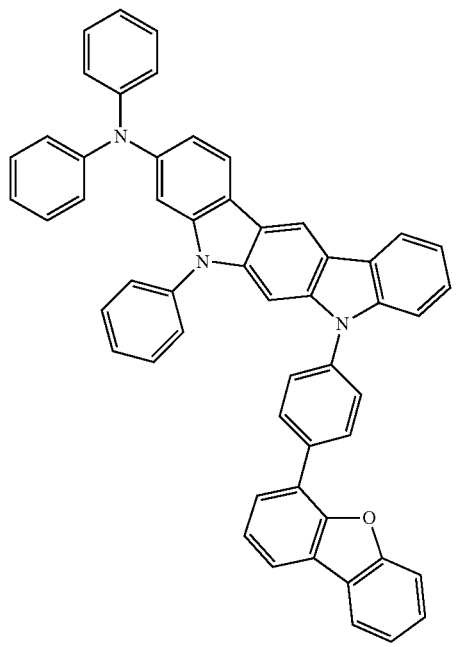
H-77
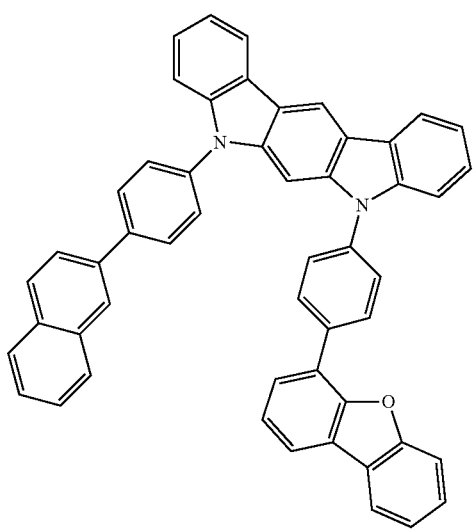
H-78
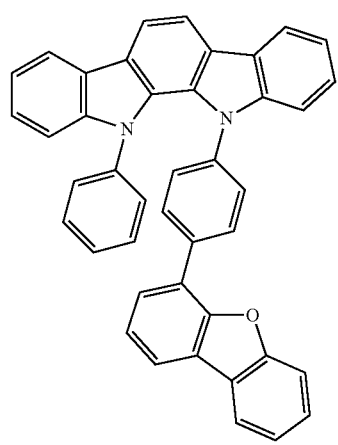
H-79
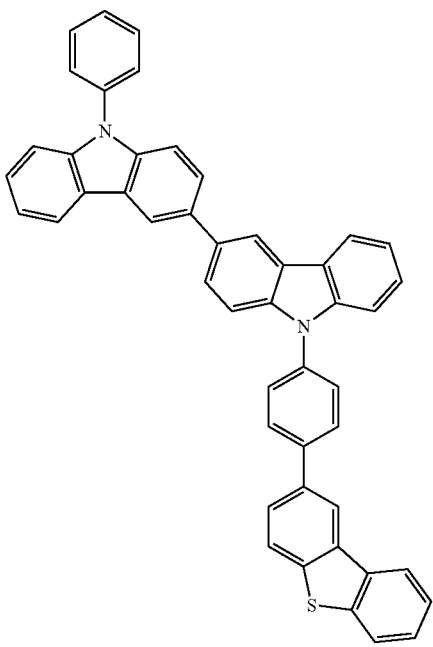
H-80
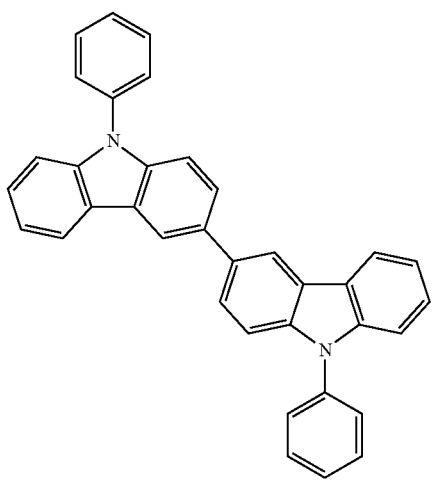

H-81
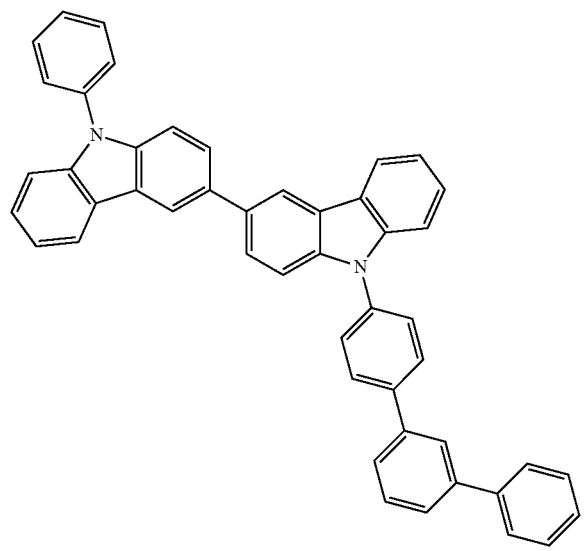
H-82
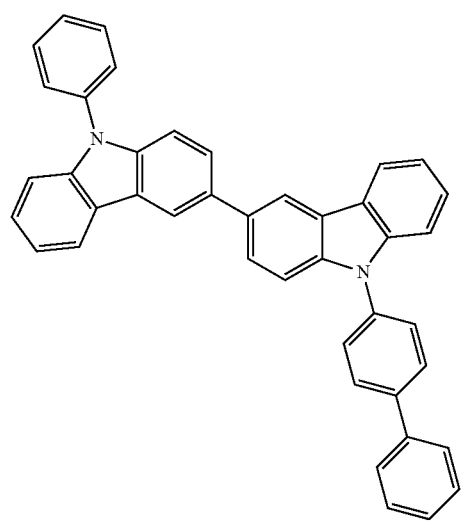
H-83
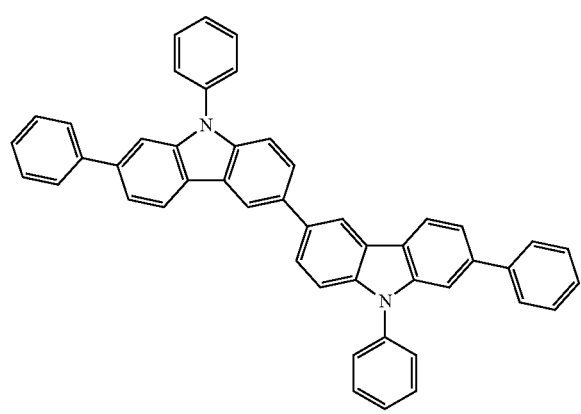
H-84
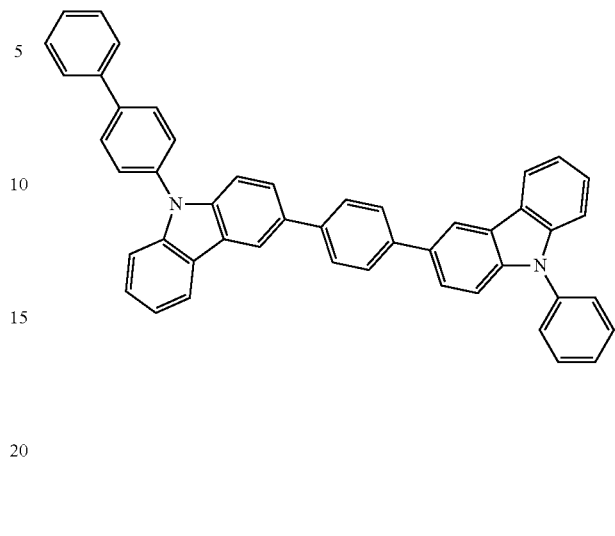
H-85
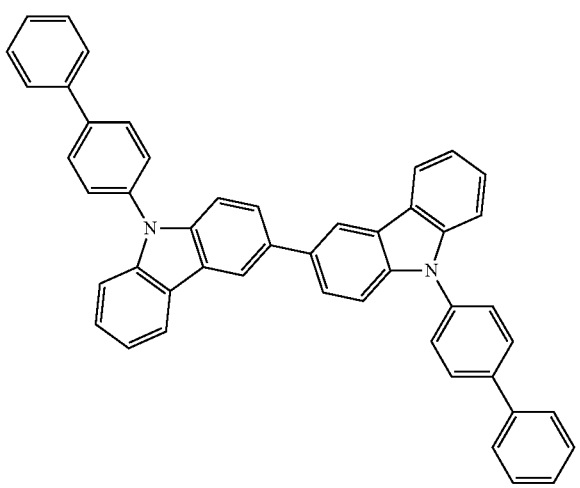
H-86
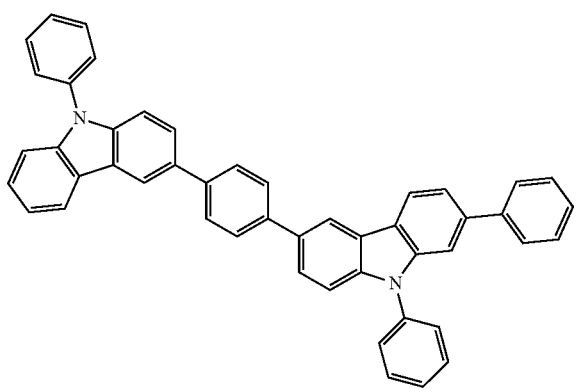

-continued
H-87
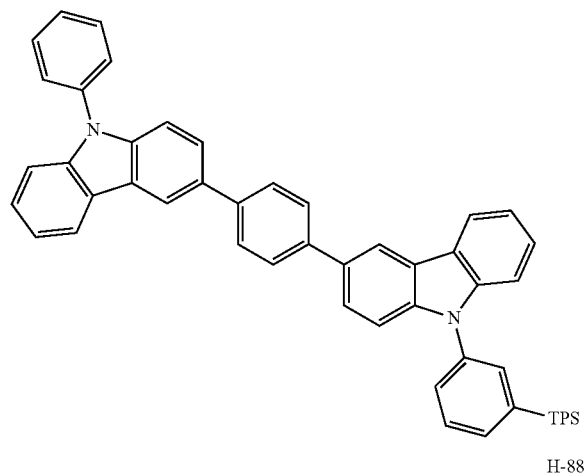
H-88
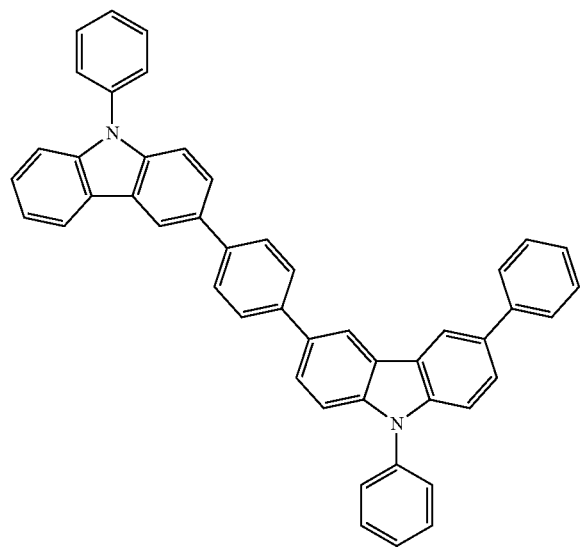
H-89
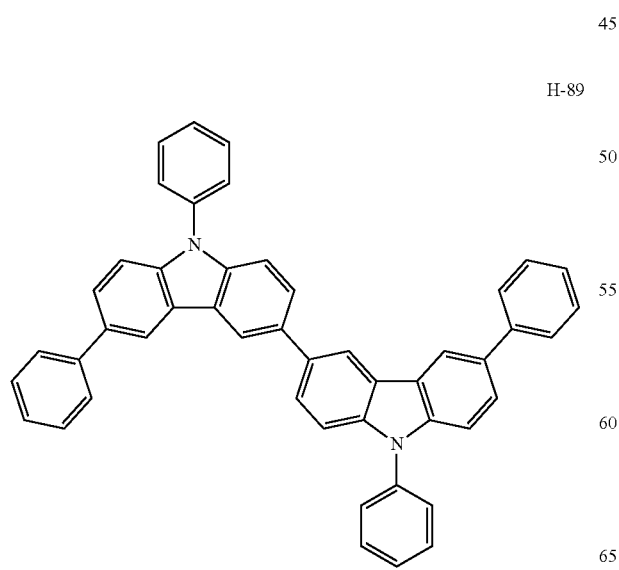
-continued
H-90
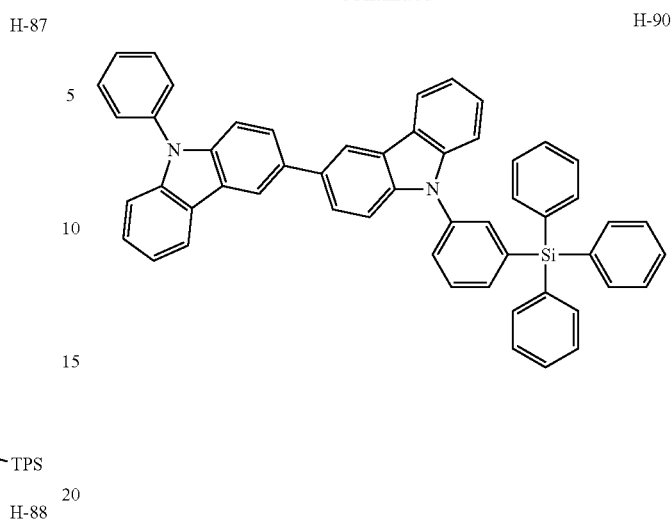
H-91
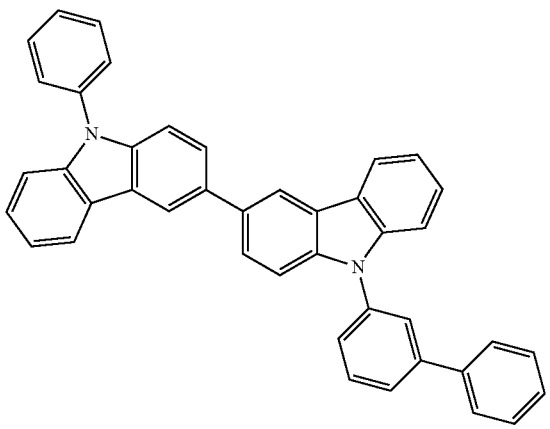
H-92
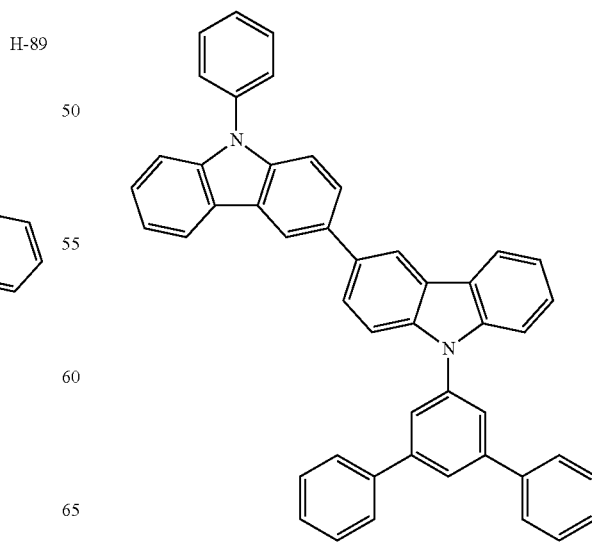

H-93
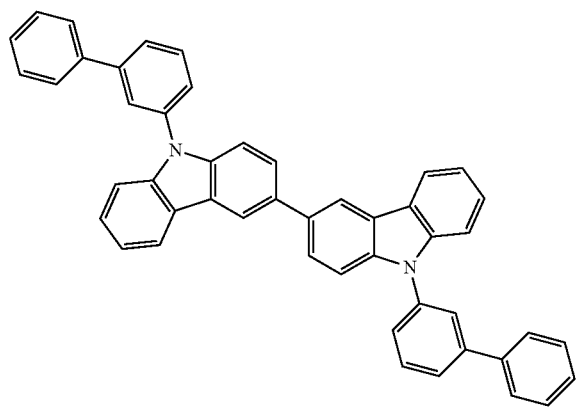
H-94
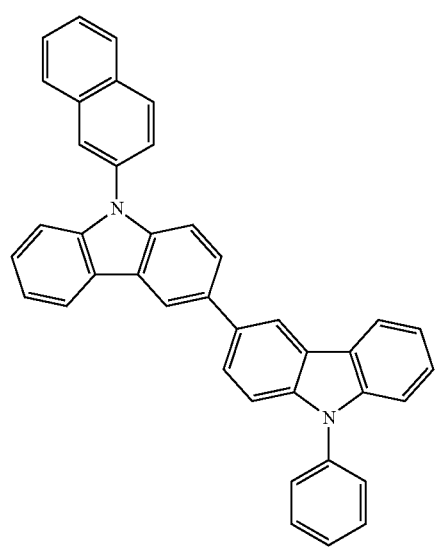
H-95
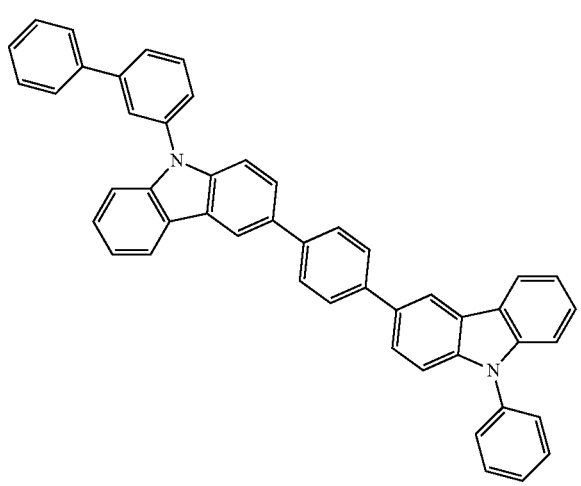
H-96
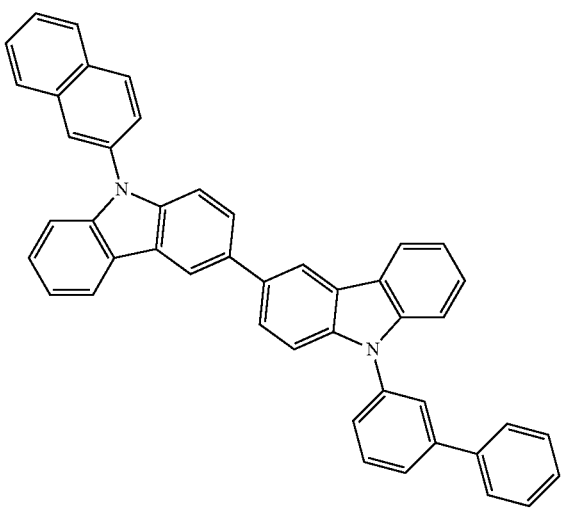
H-97
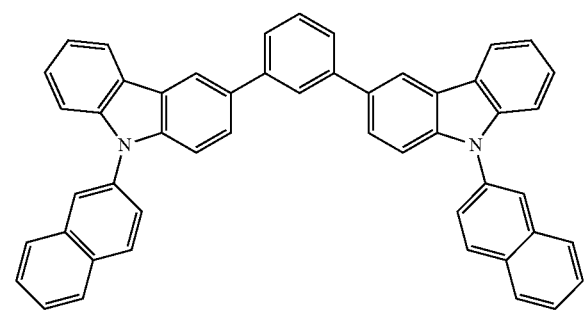
H-98
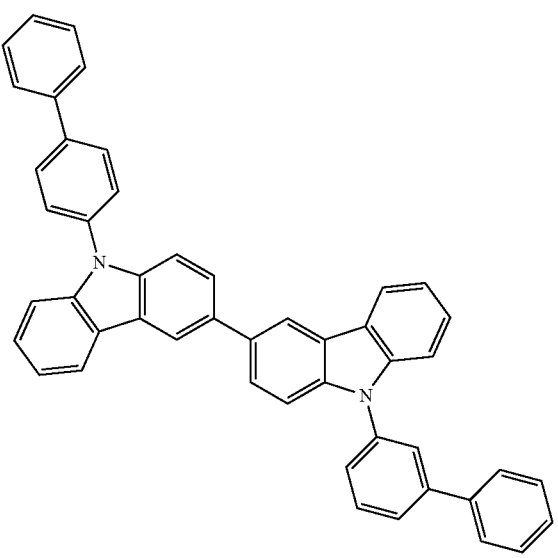

-continued
H-99
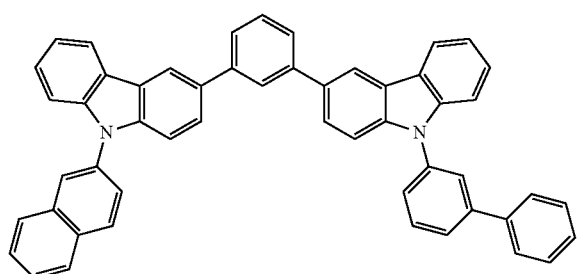
H-100
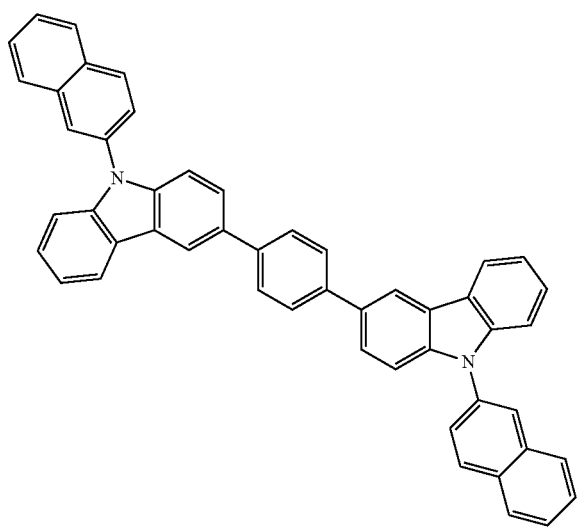
H-101
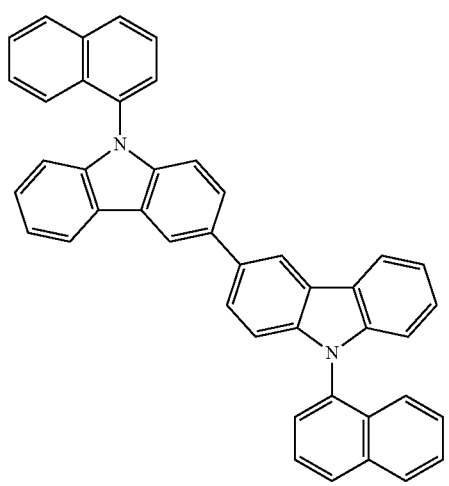
-continued
H-102
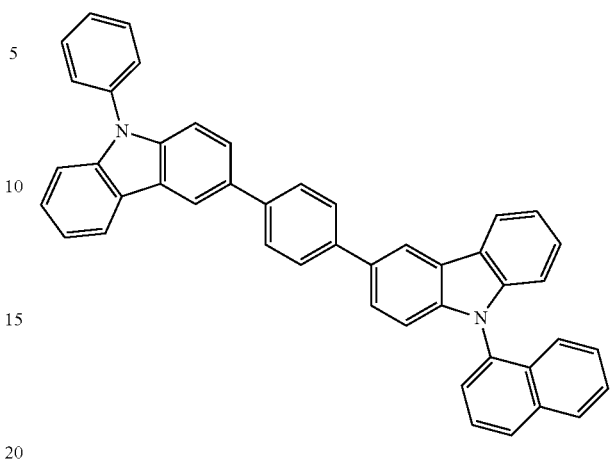
H-103
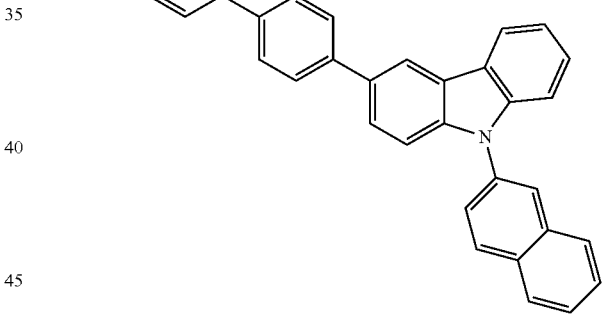
H-104
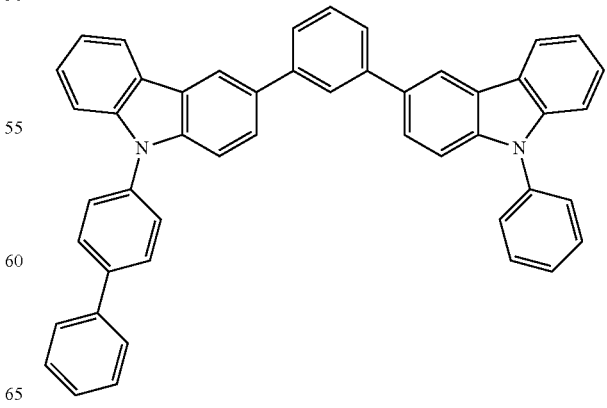

H-105
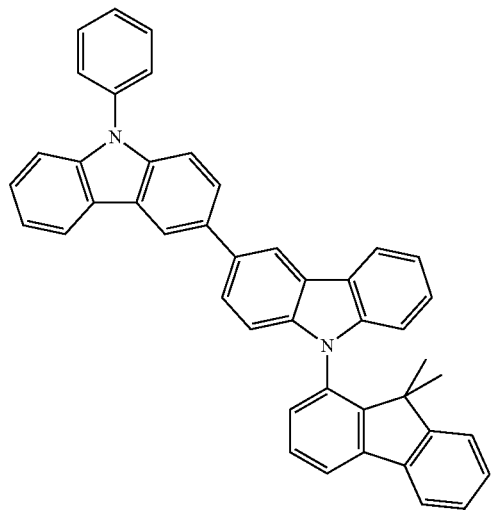
H-106
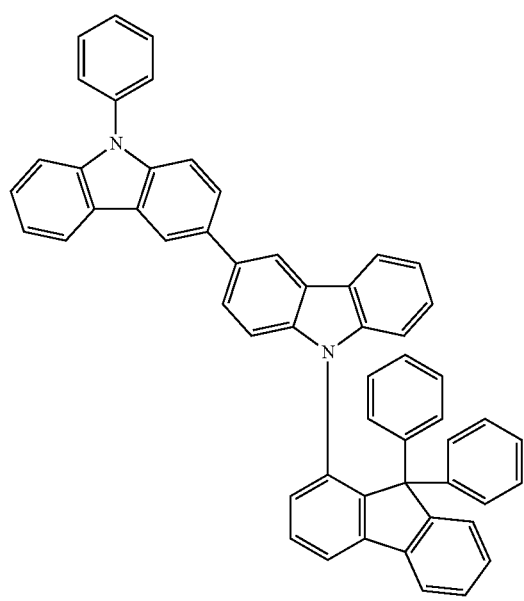
H-107
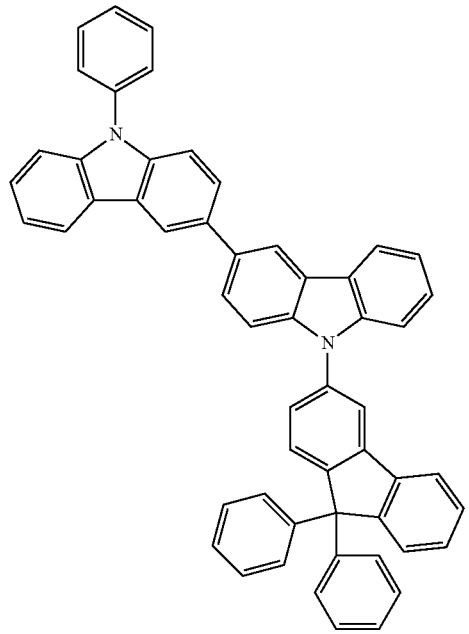
H-108
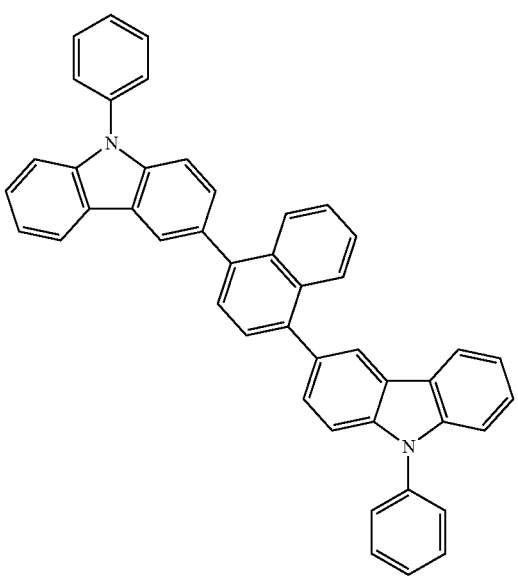

H-109
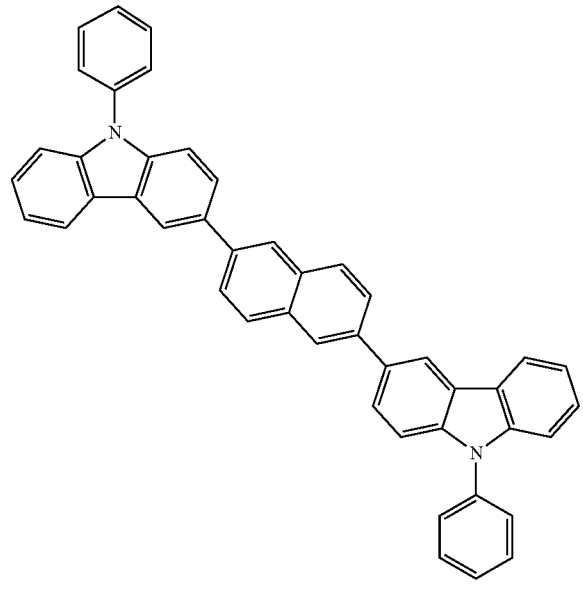
H-111
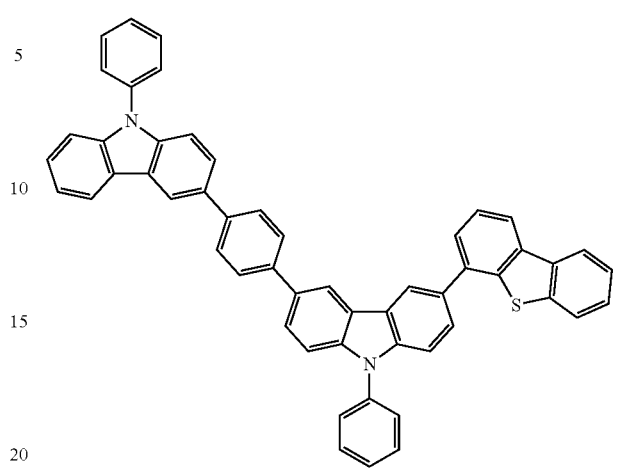
H-110
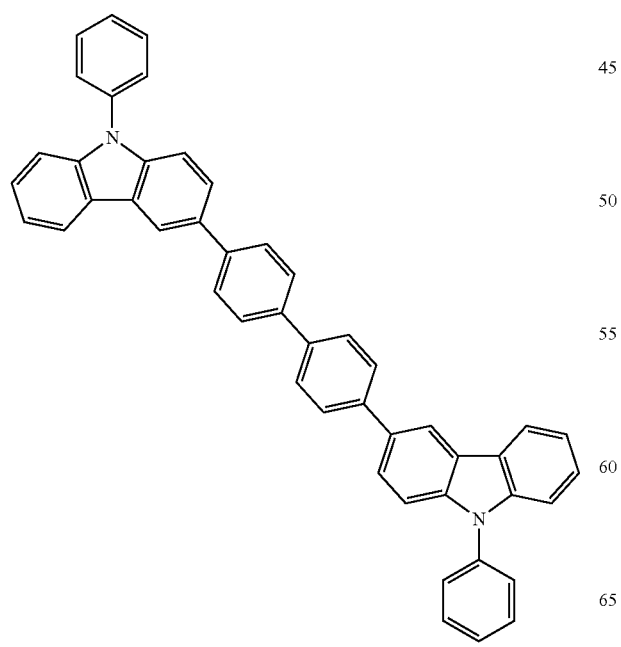
H-112
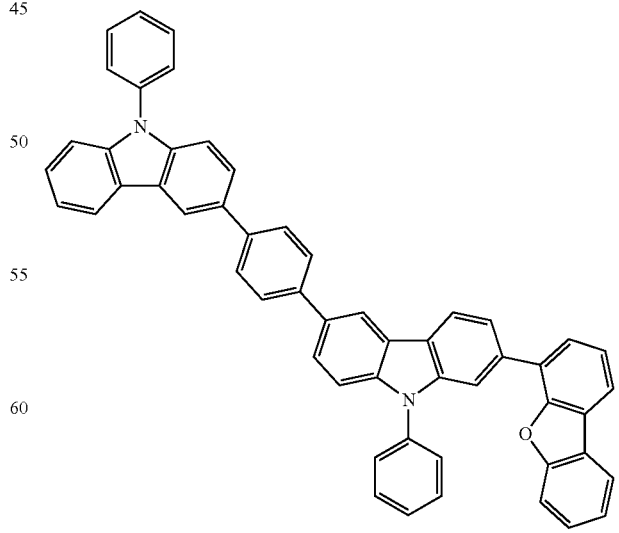

H-113
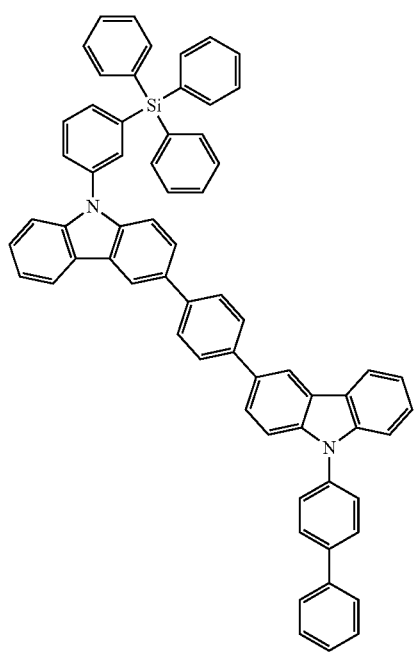
H-114
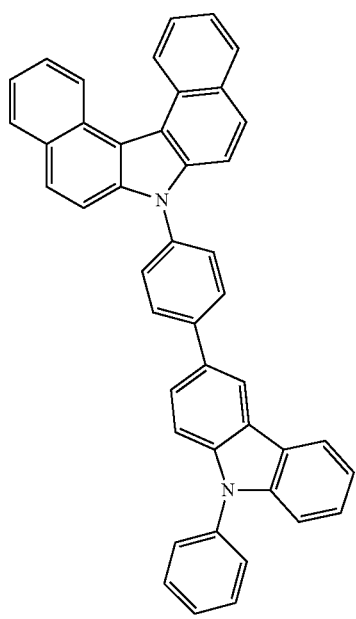
H-115
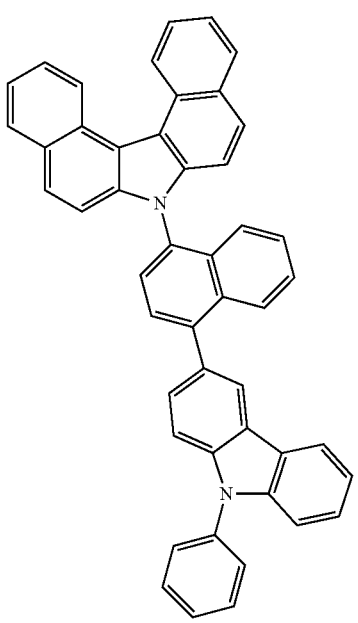
H-116
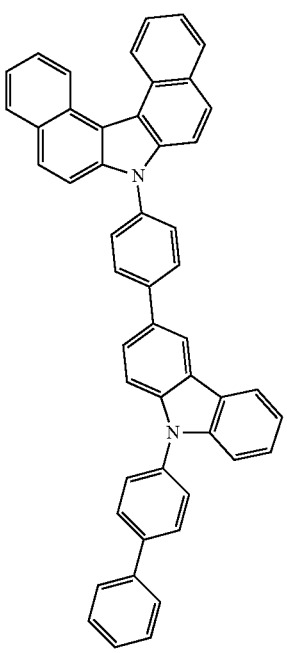

H-117
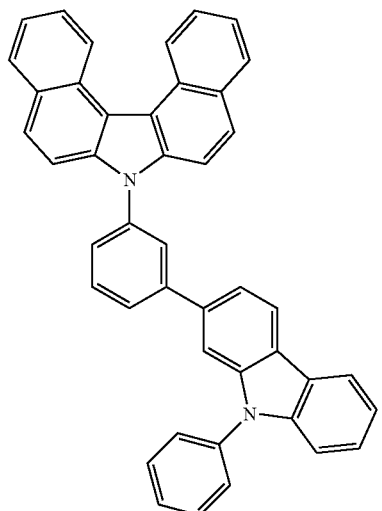
H-118
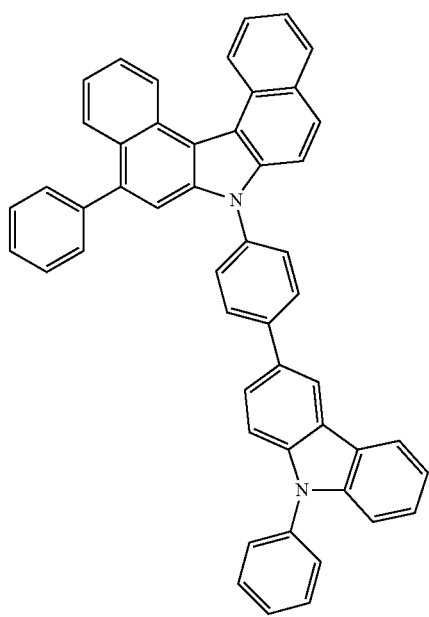
H-119
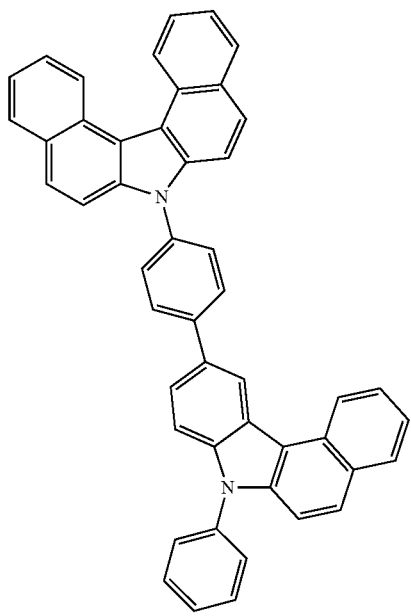
H-120
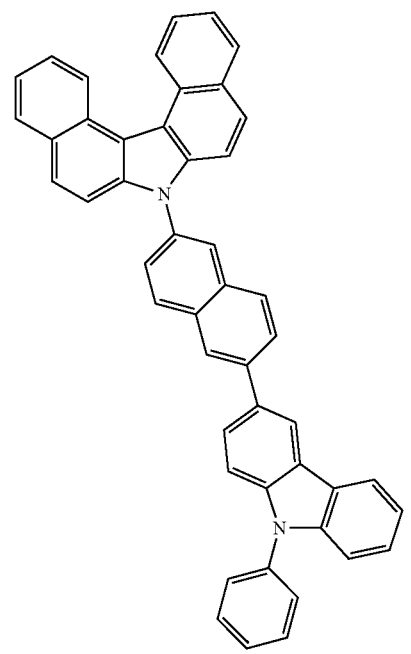

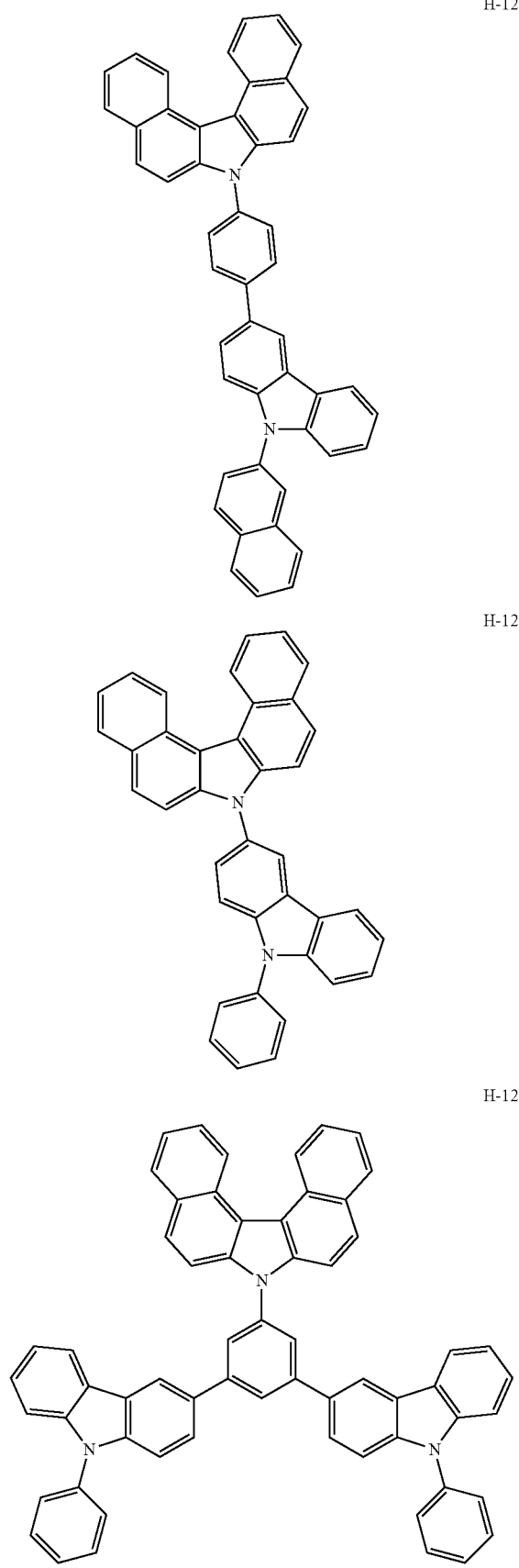
H-121
H-122
H-123
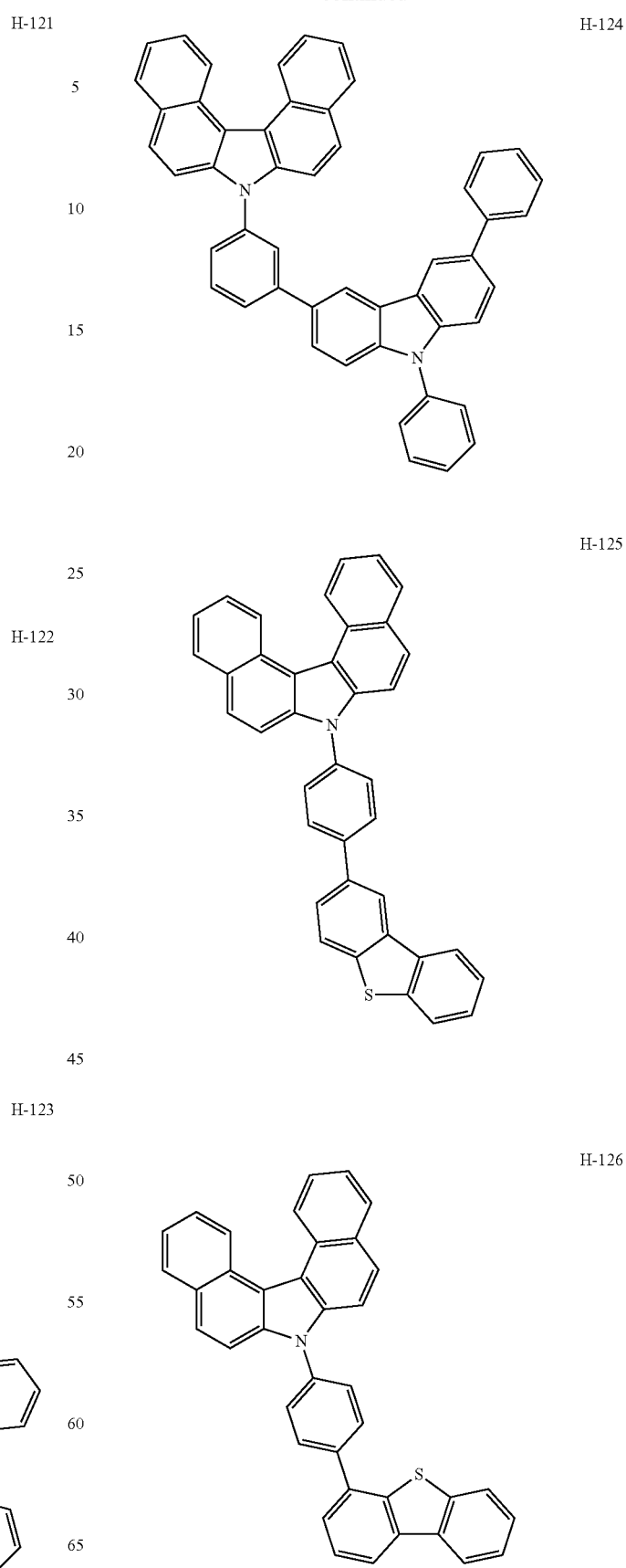
H-124
H-125
H-126

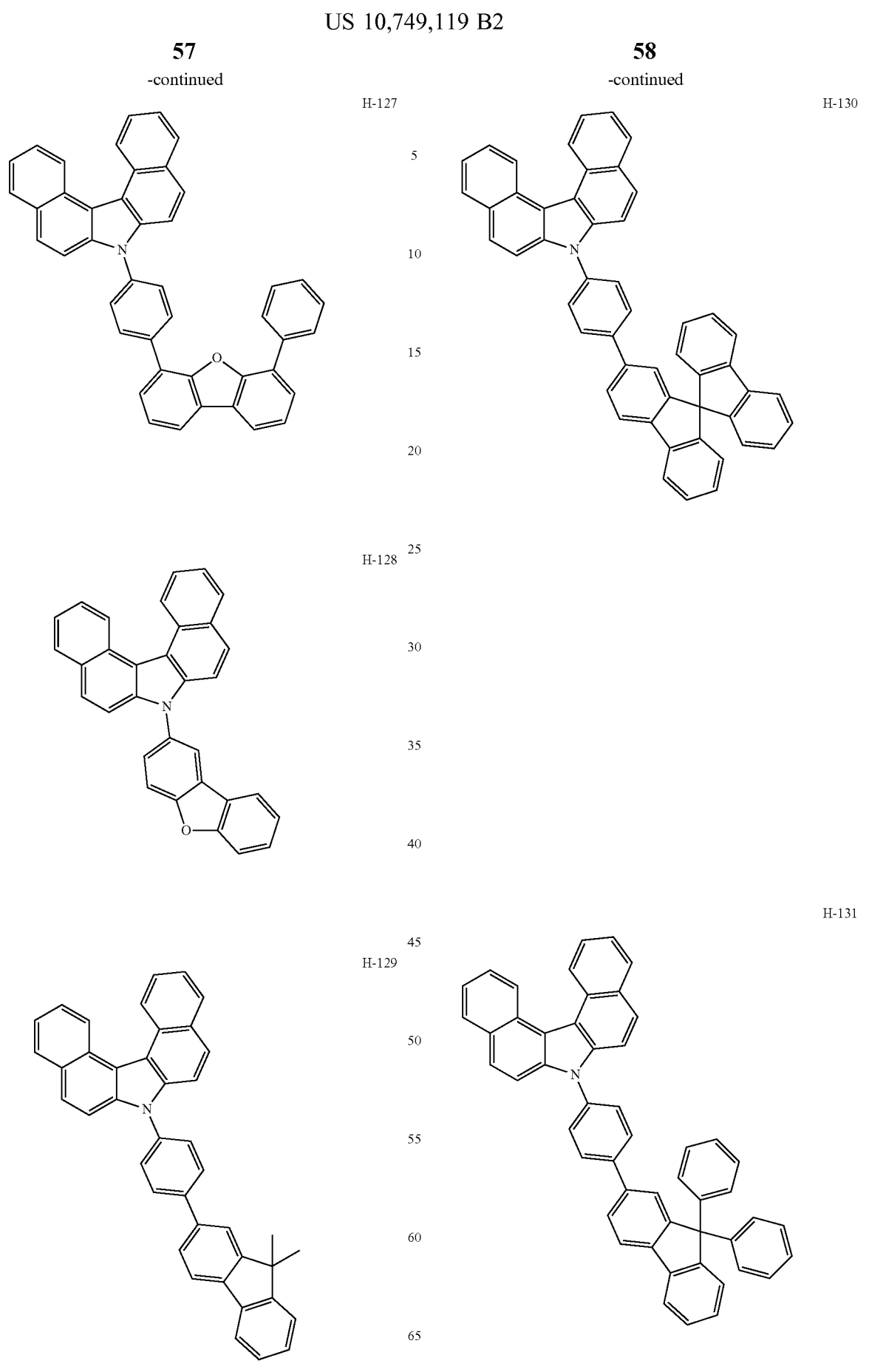

-continued

H-127

H-128

H-129

-continued

H-130

H-131

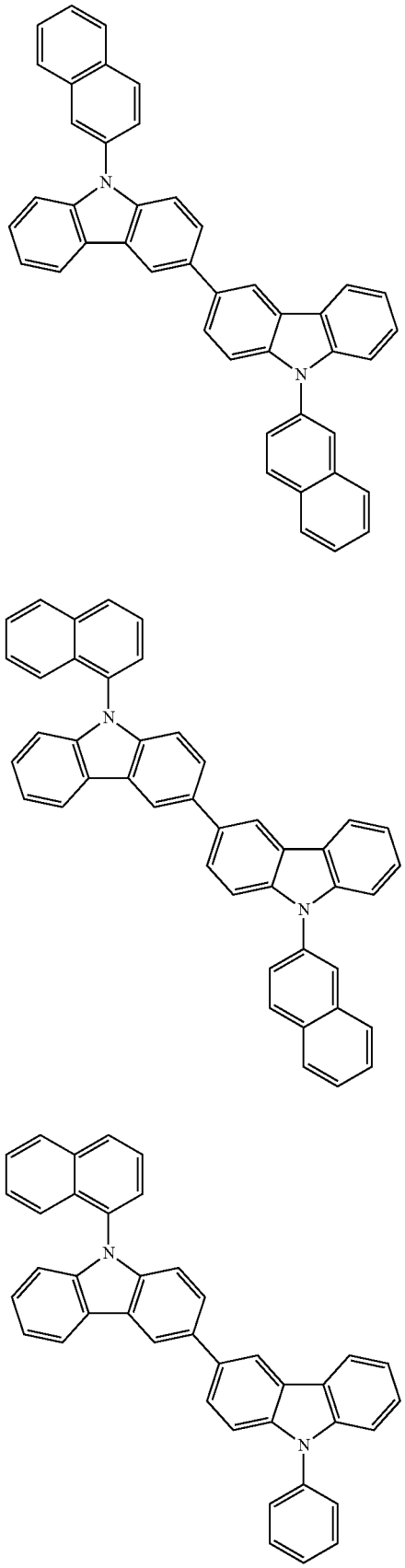
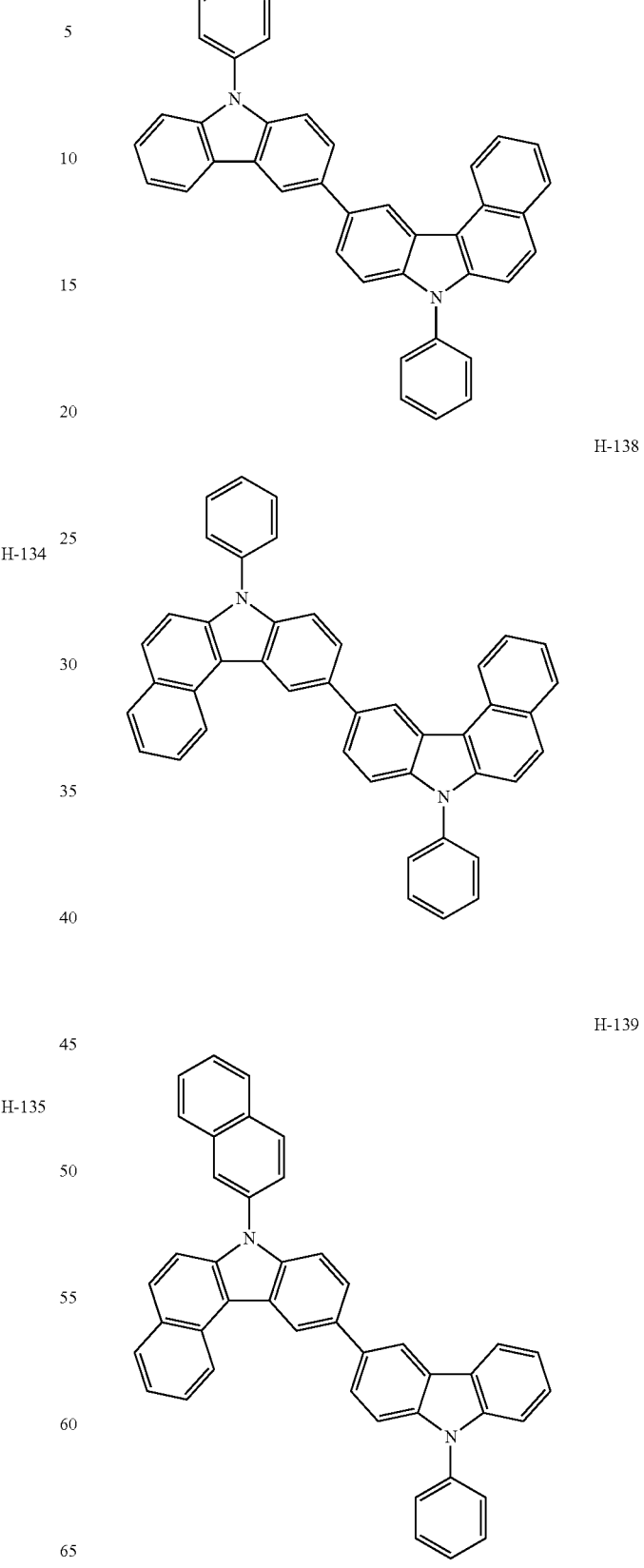

-continued
H-140
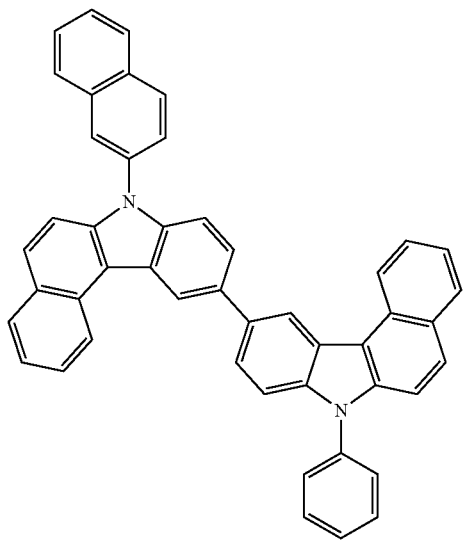
H-141
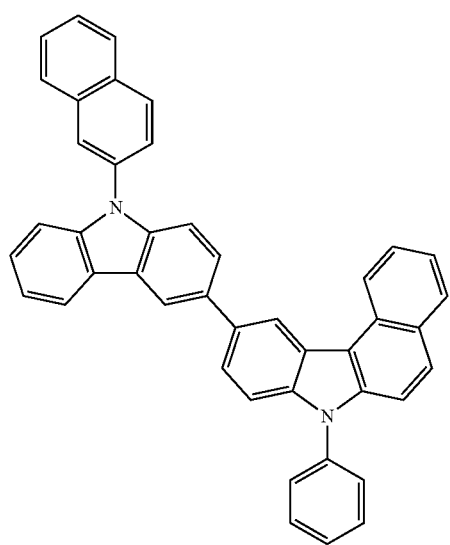
-continued
H-142
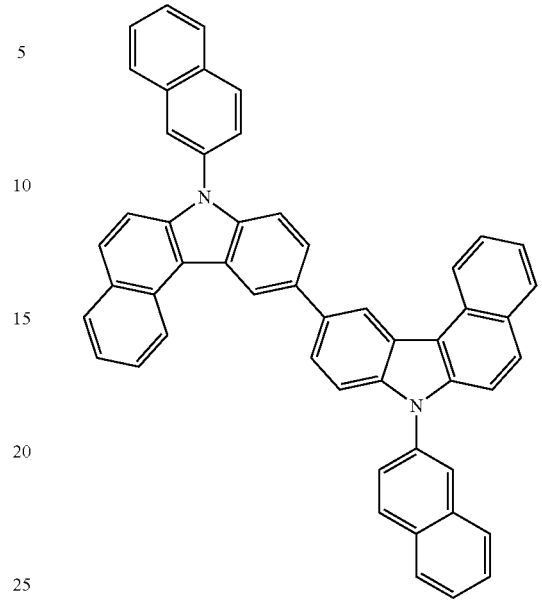
H-143
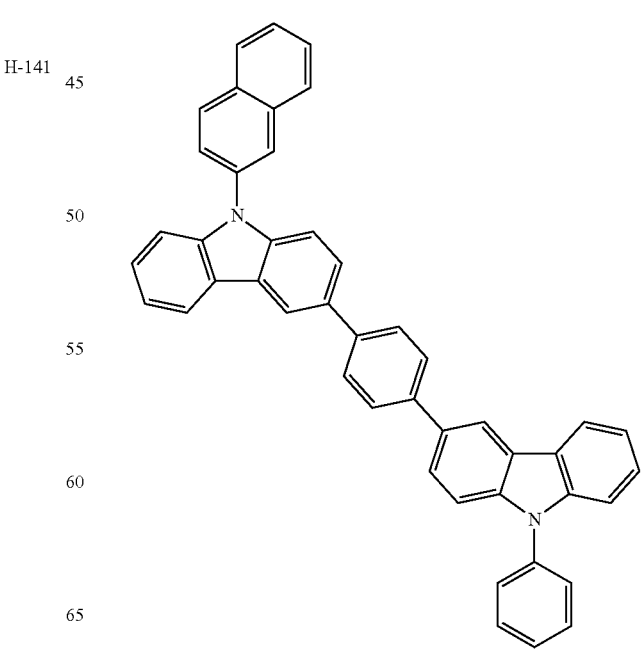

H-144
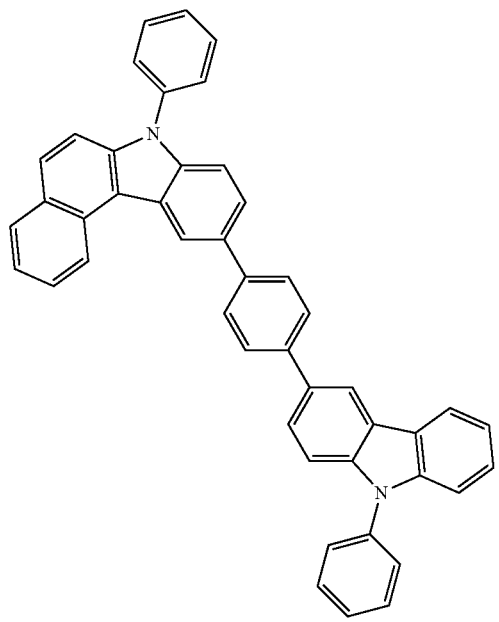
H-145
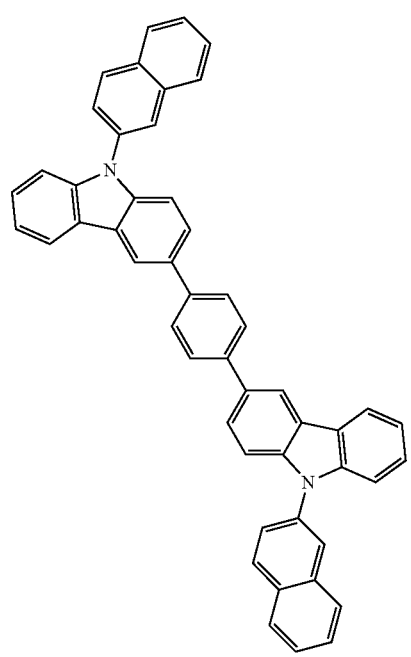
H-146
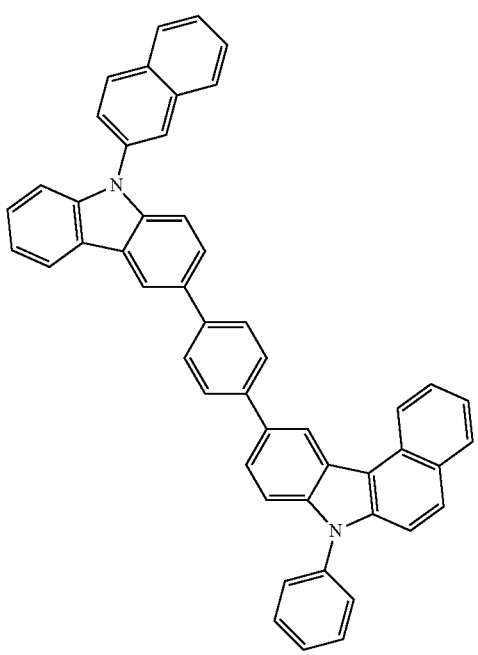
H-147
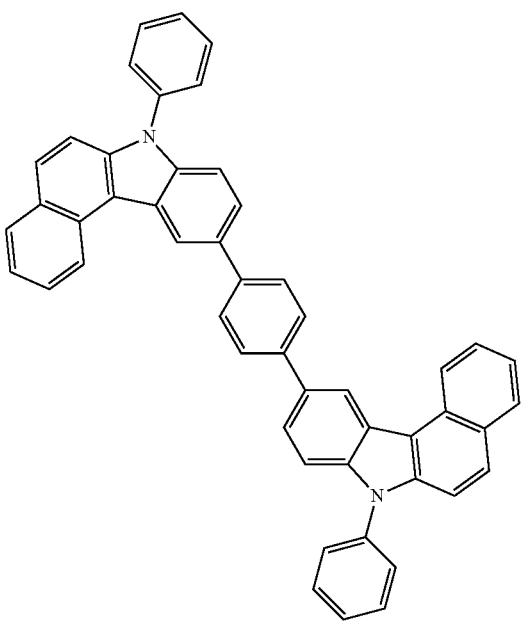

H-148
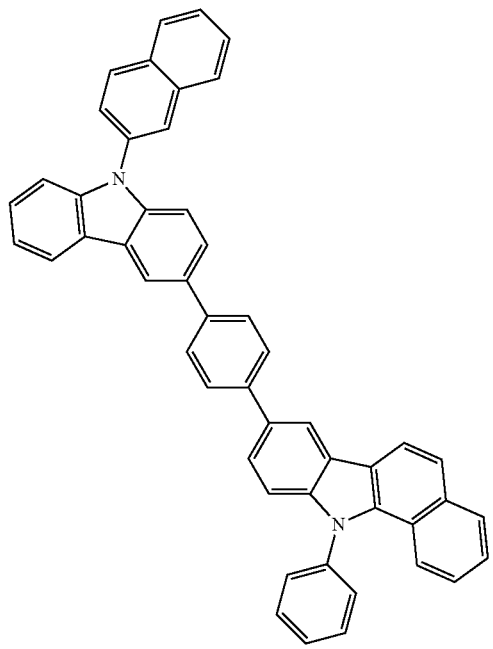
H-150
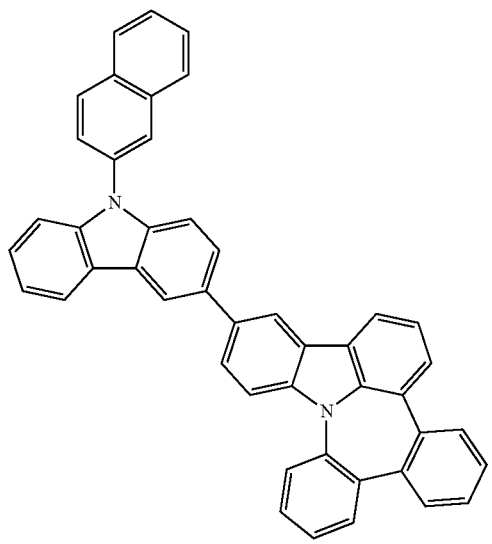
H-149
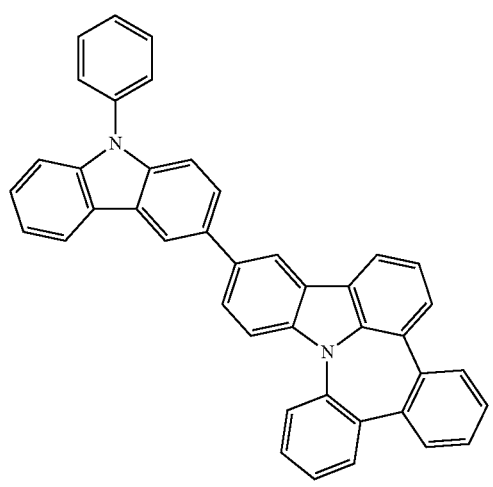
H-151
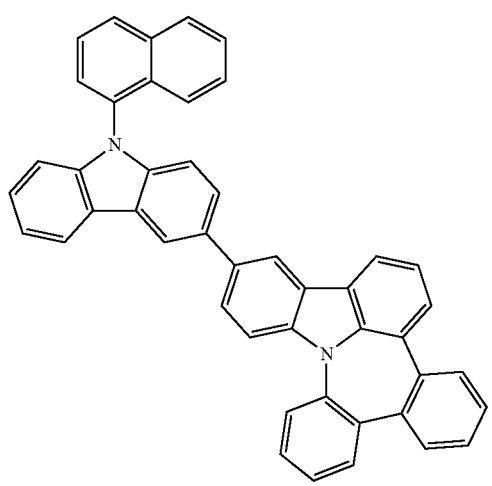

H-152
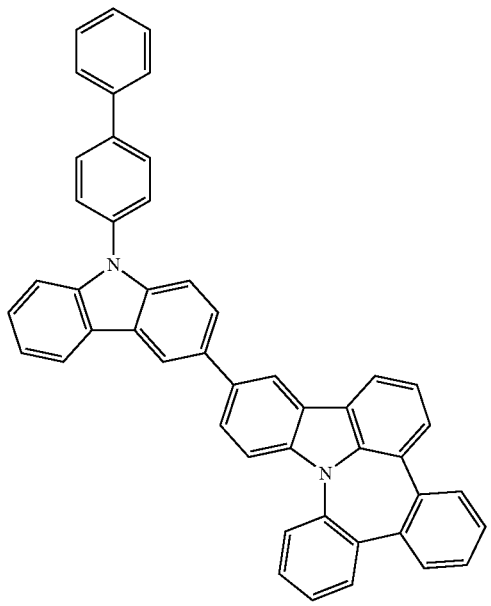
H-154
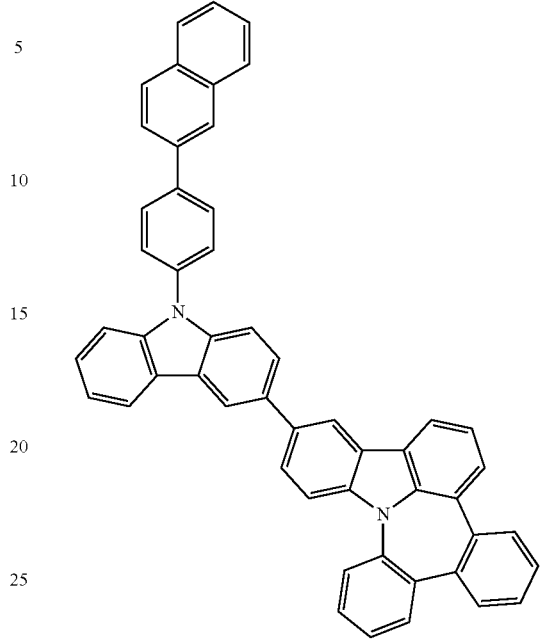
H-153
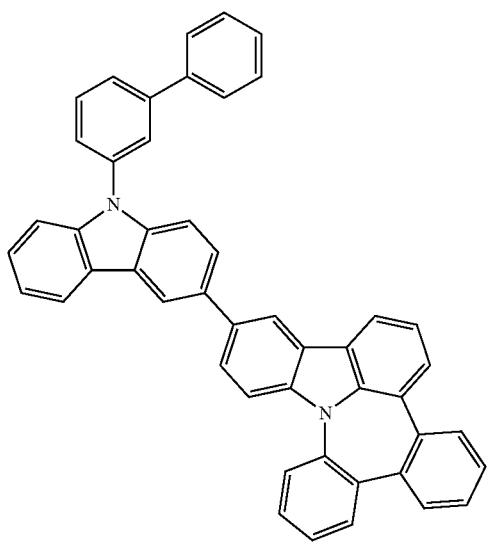
H-155
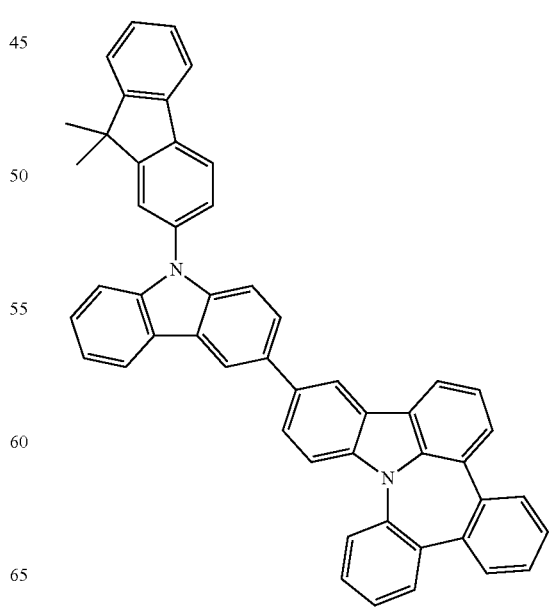

H-156
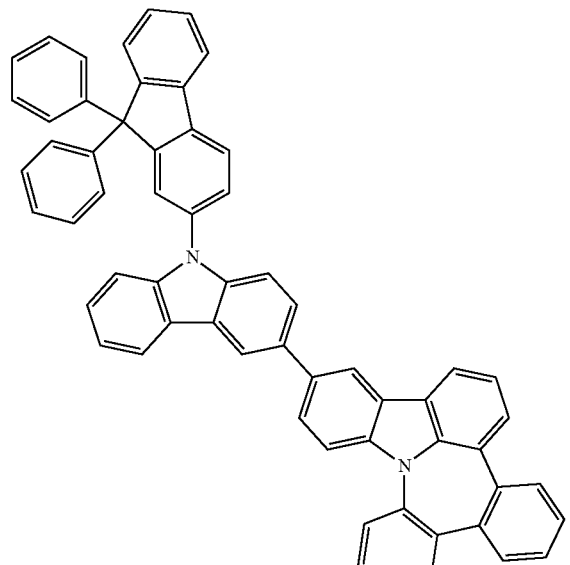
H-157
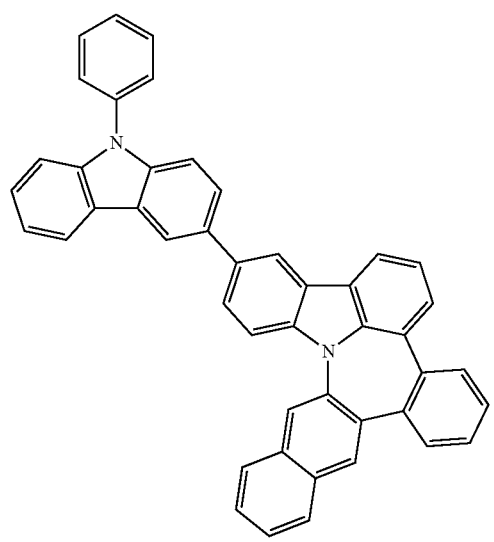
H-158
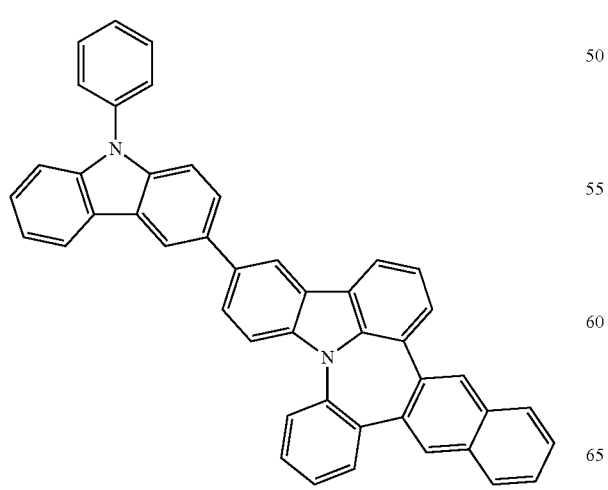
H-159
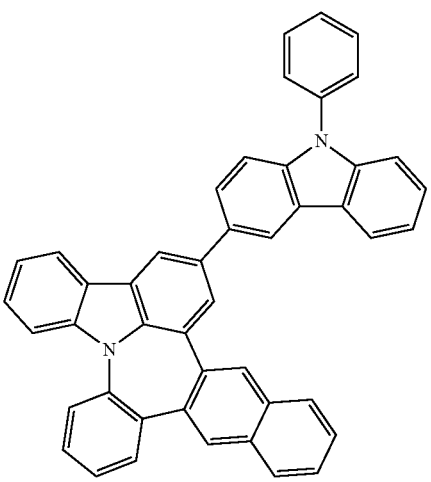
H-160
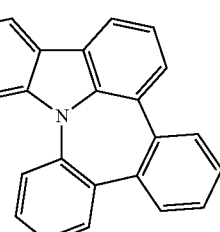

H-161
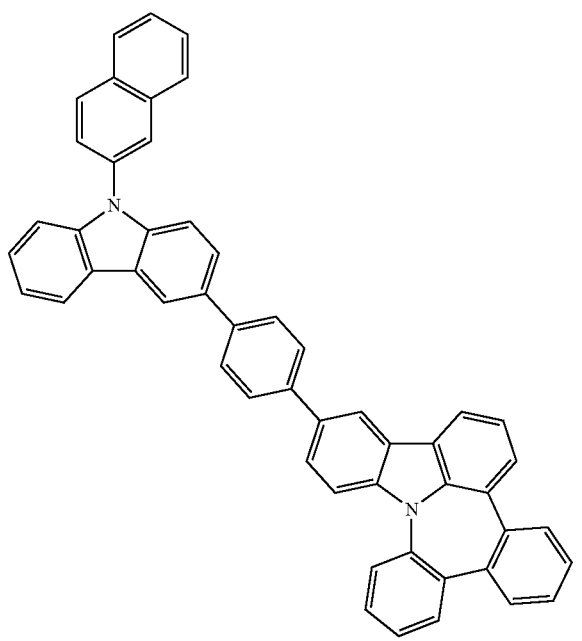
H-162
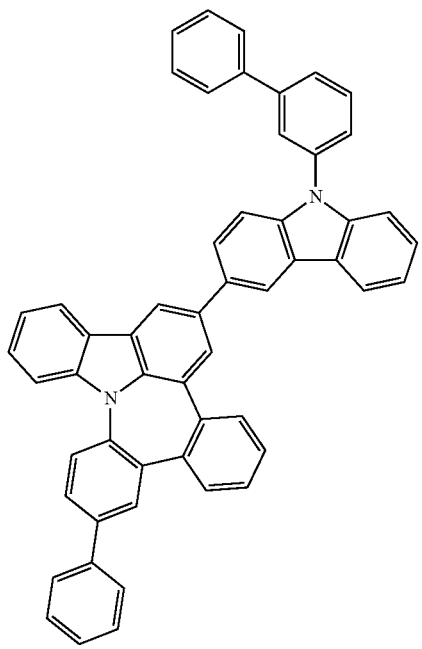
H-163
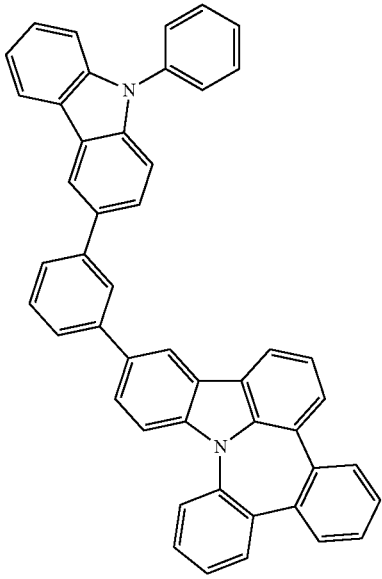
H-164
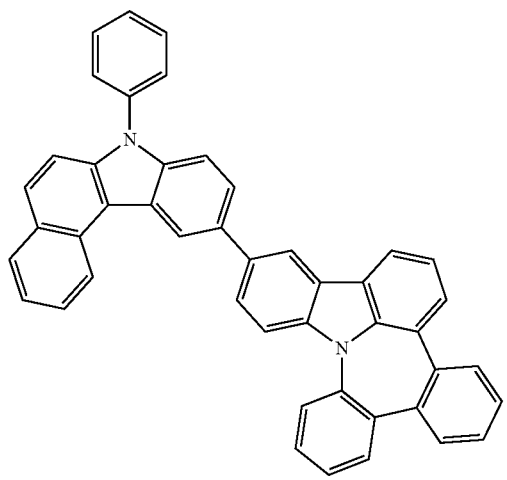

H-165
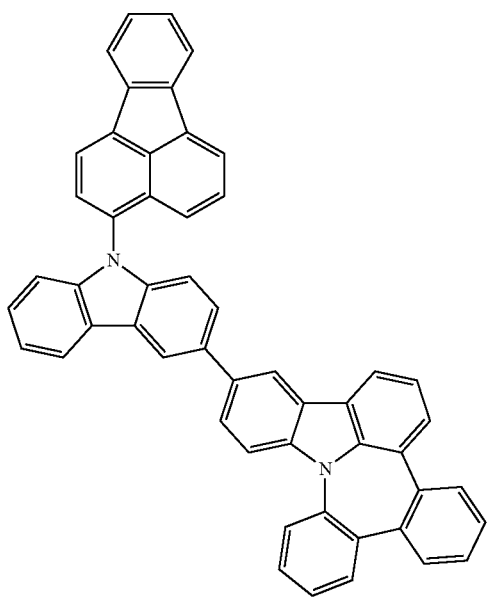
H-167
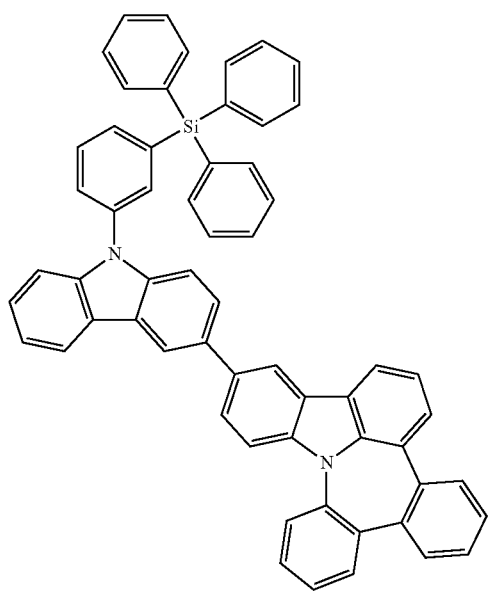
H-168
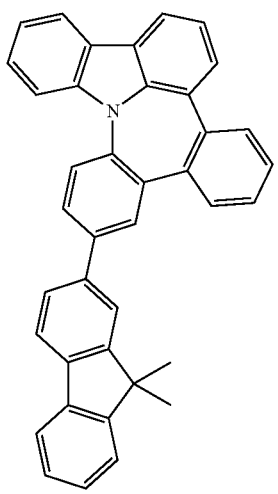
H-166
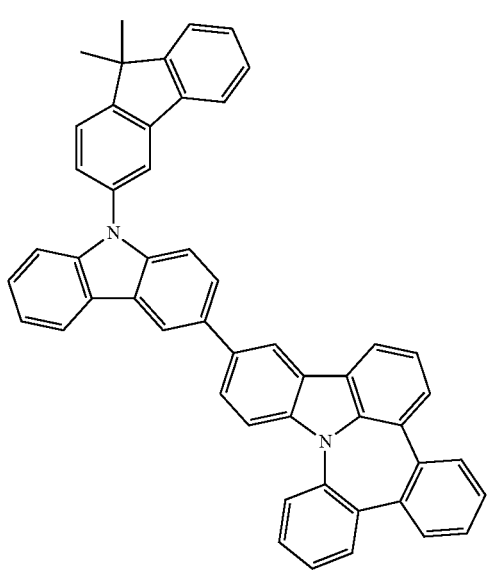
H-169
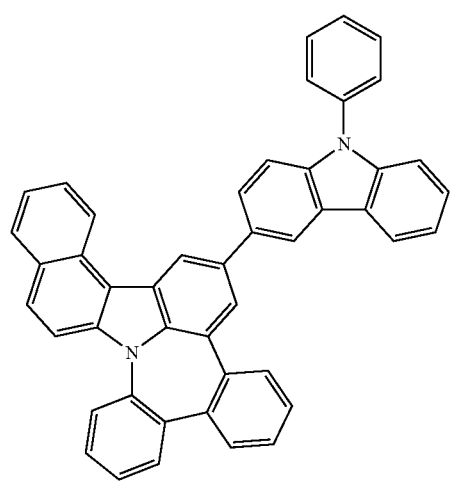

H-170
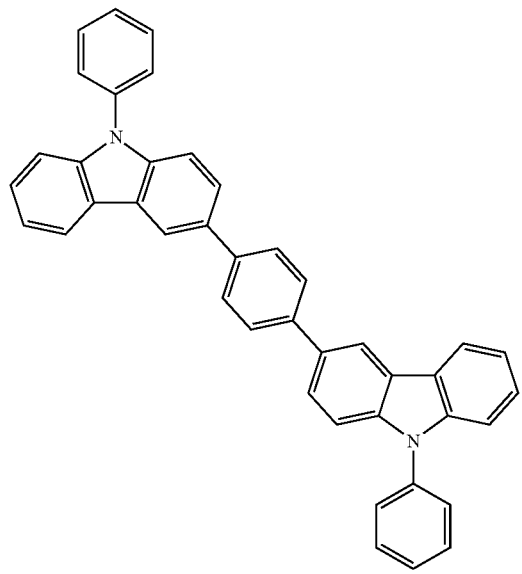
H-173
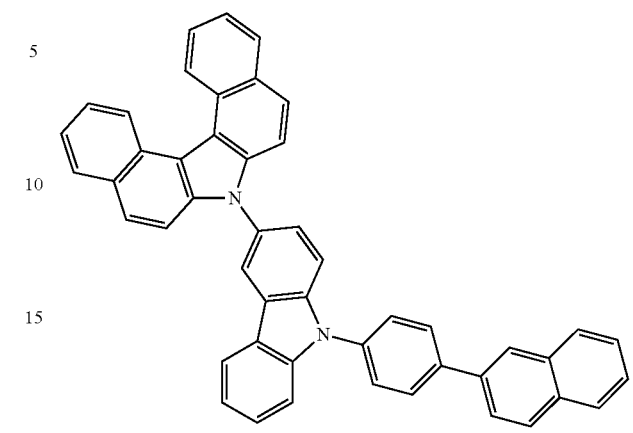
H-171
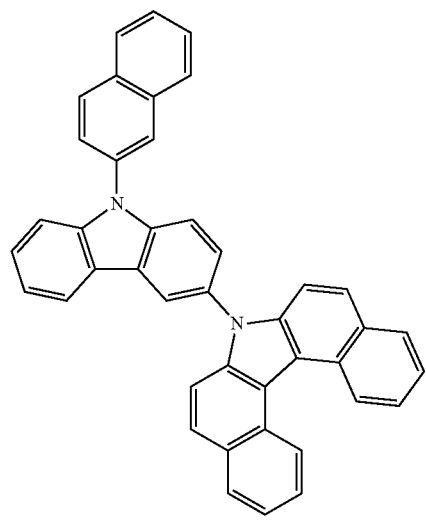
H-174
H-172
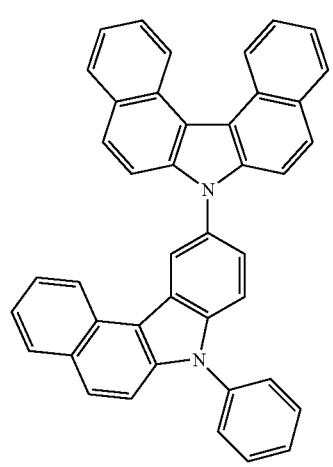
H-175
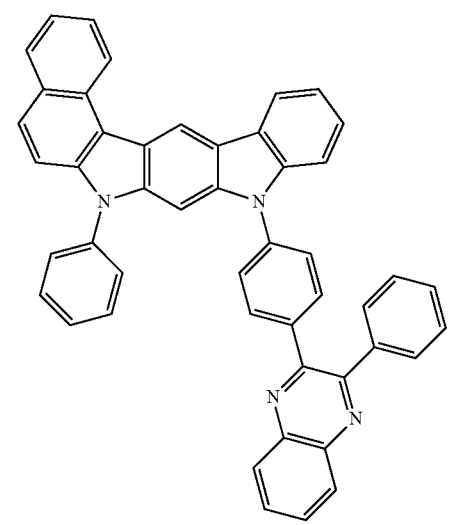

H-176
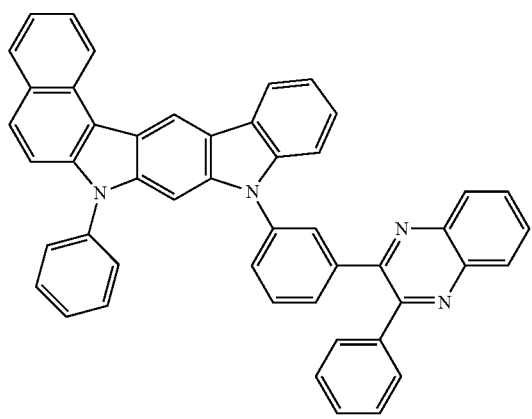
The second host compound of formula 2 may be selected from the group consisting of the following compounds, but is not limited thereto:
C-1
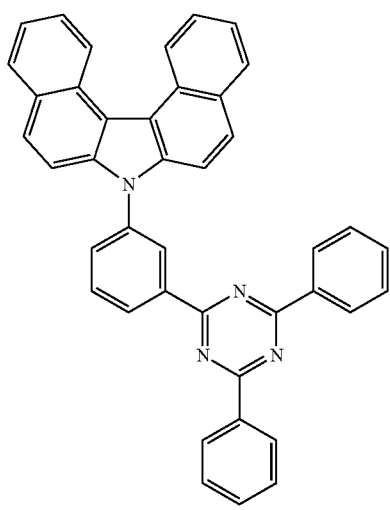
C-2
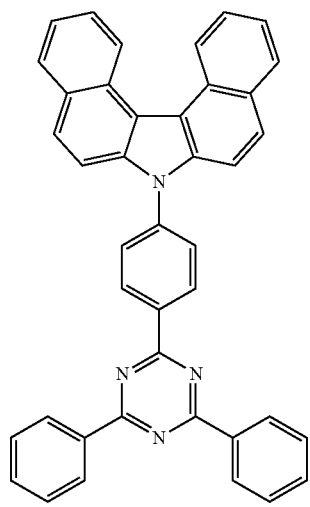
C-3
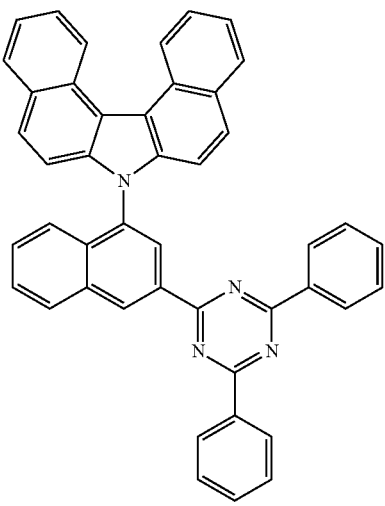
C-4
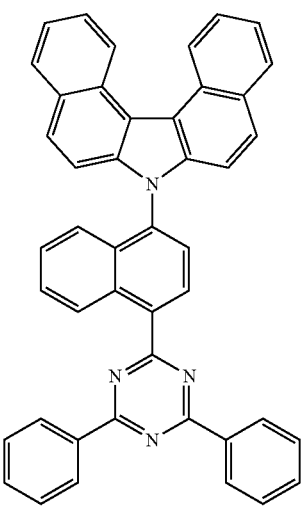
C-5
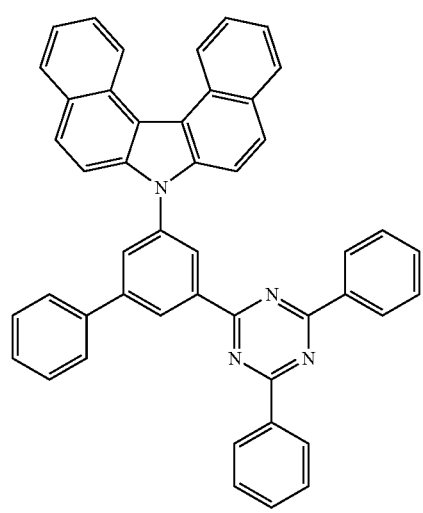

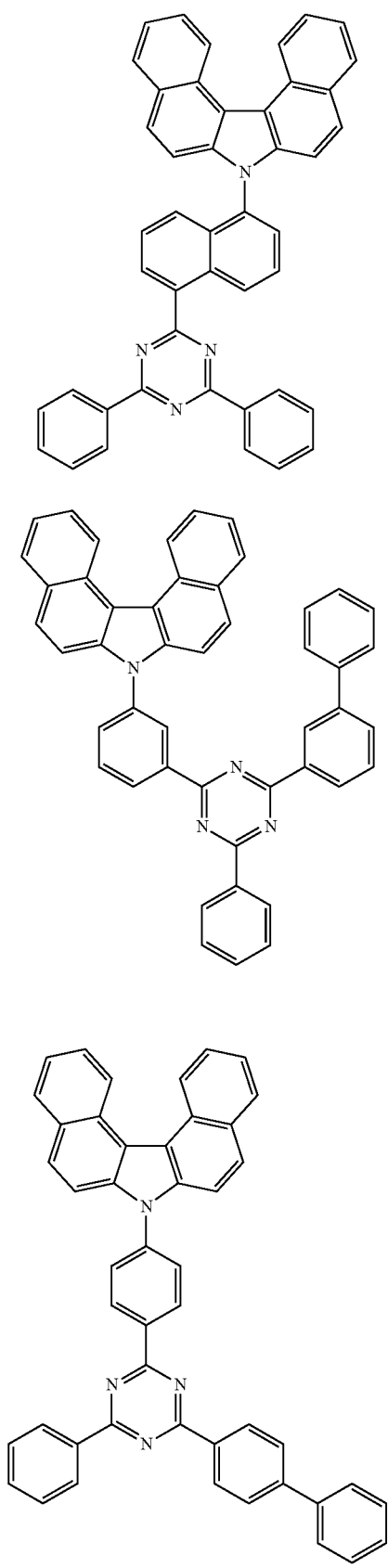
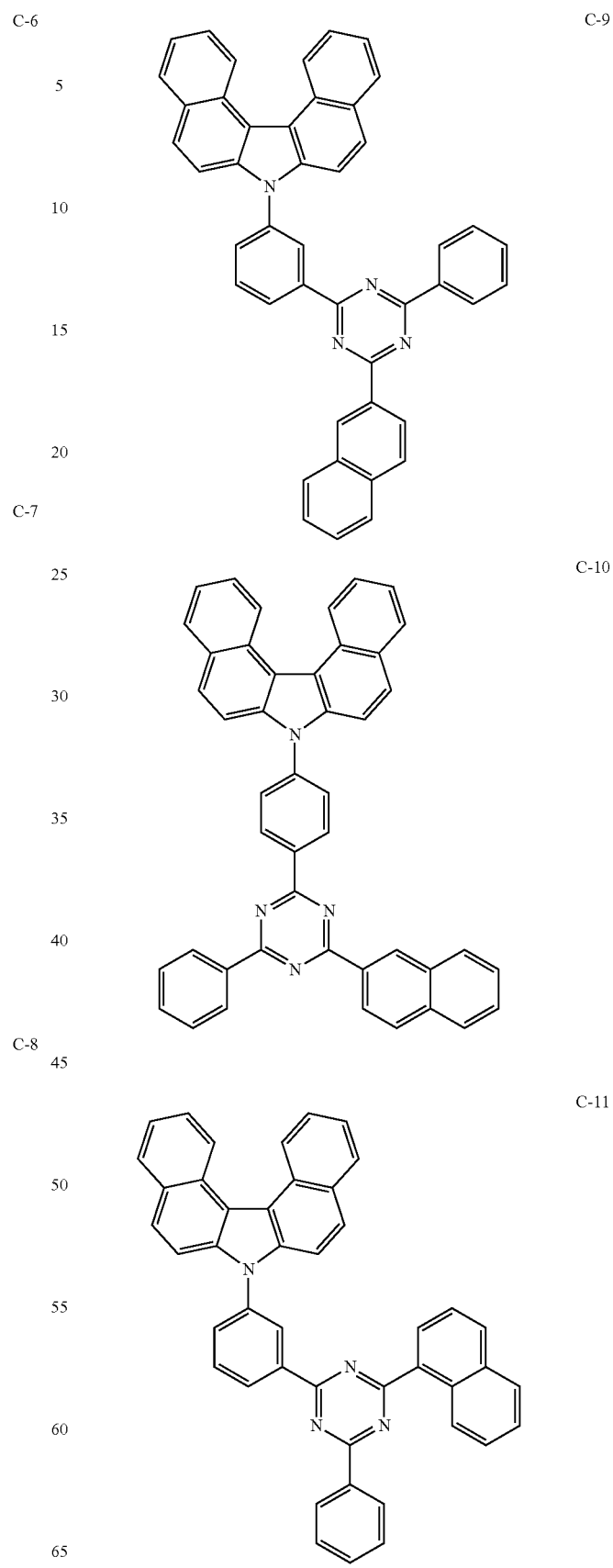

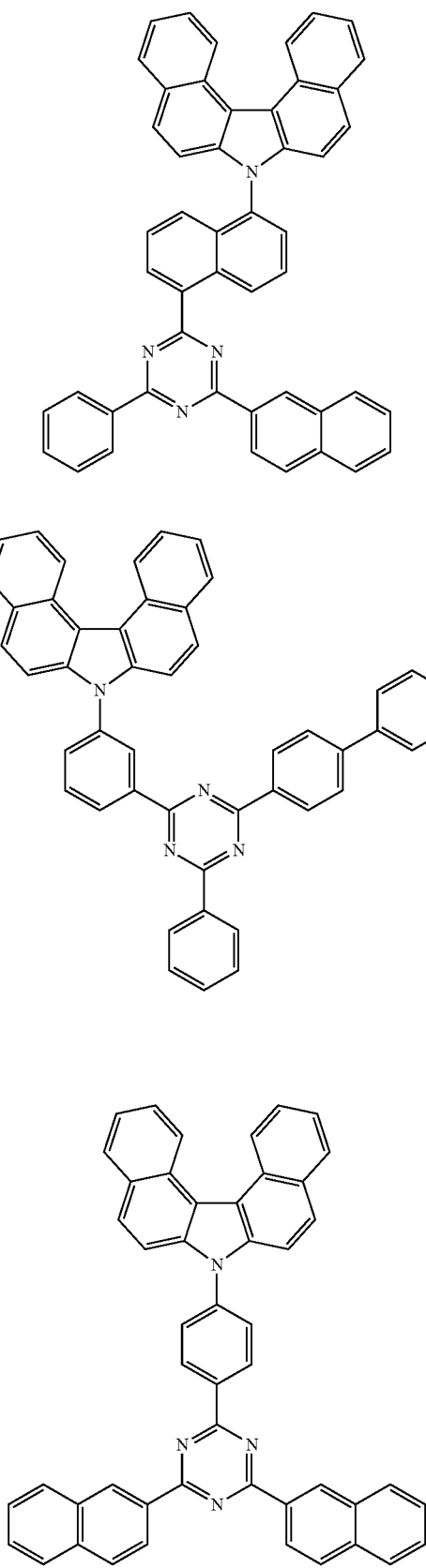
C-12
C-13
C-14
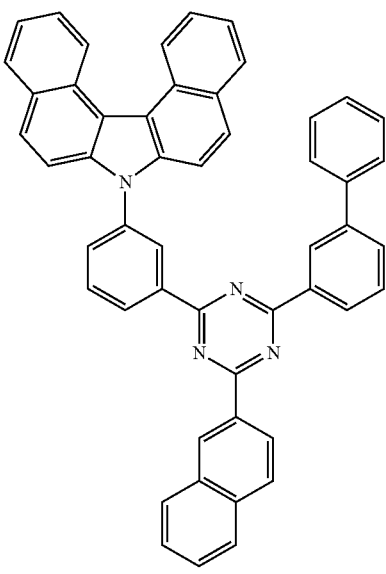
C-15
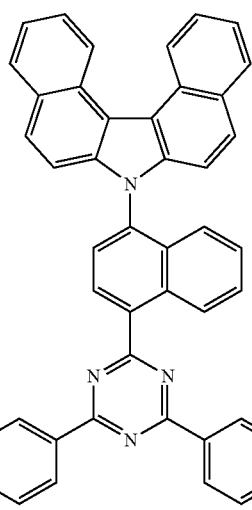
C-16
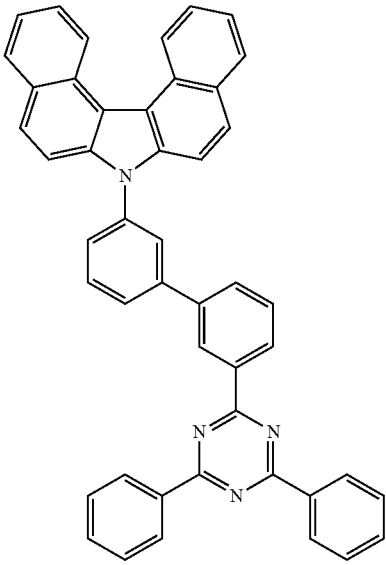
C-17

C-18
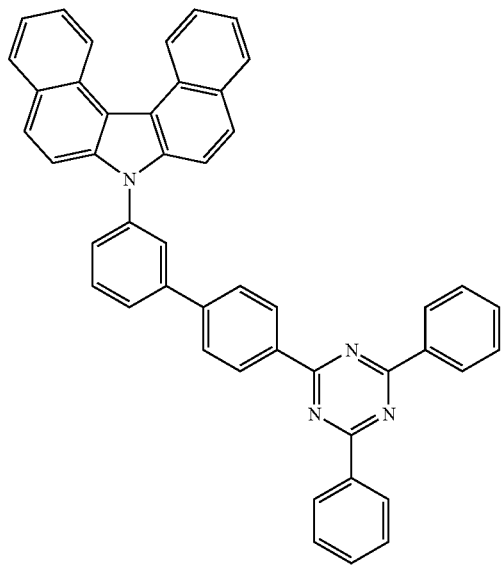
C-19
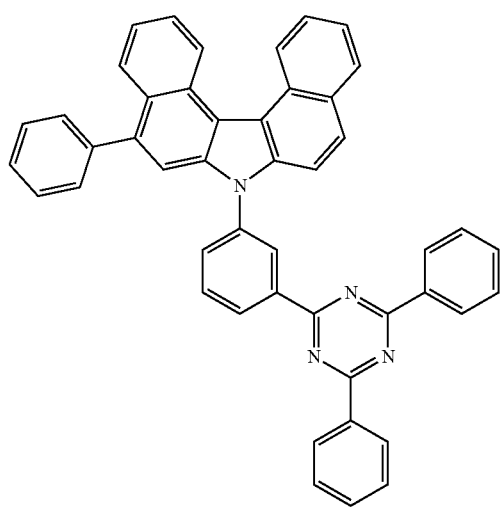
C-20
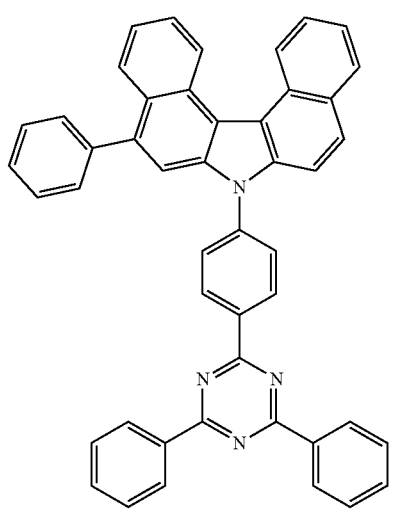
C-21
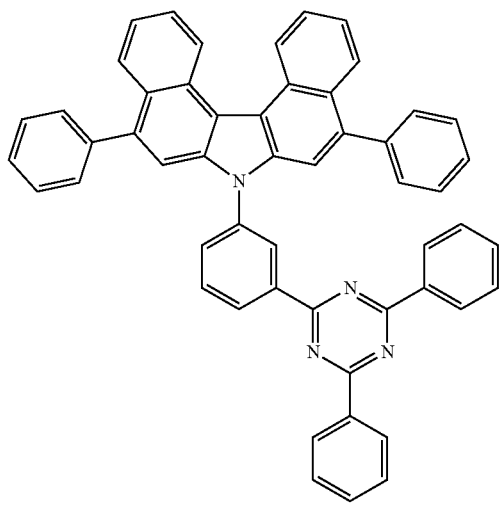
C-22
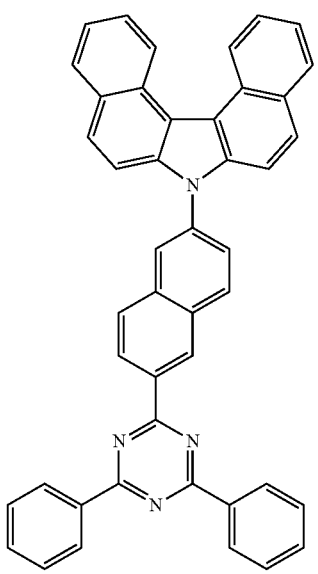
C-23
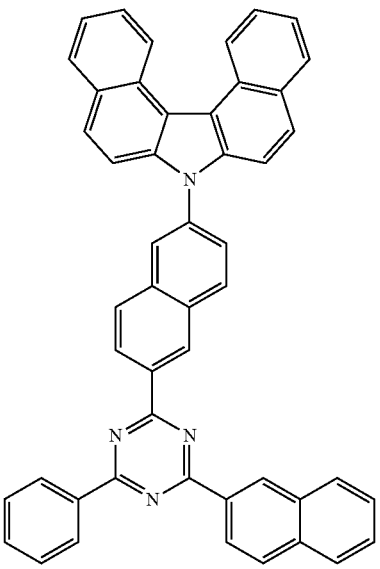

-continued
C-24
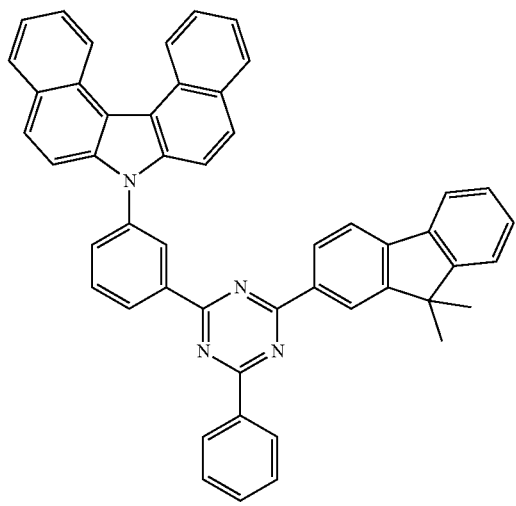
C-25
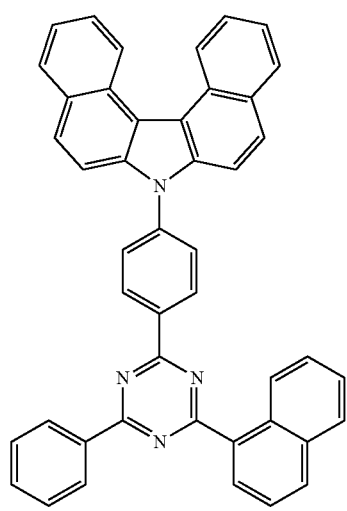
C-26
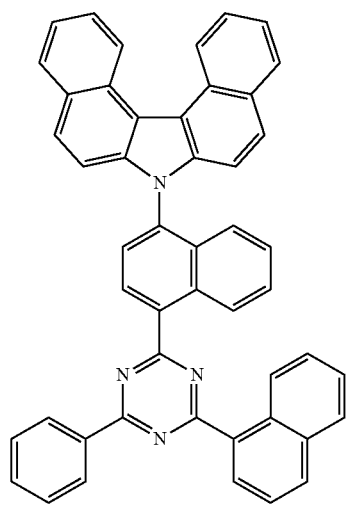
-continued
C-27
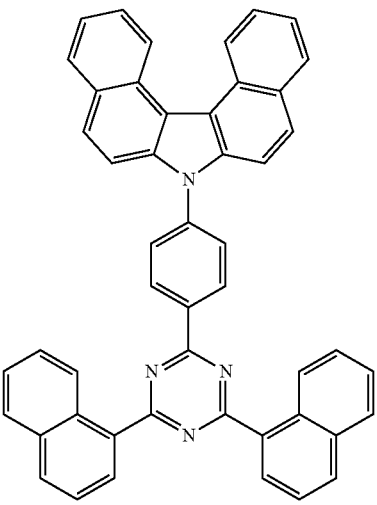
C-28
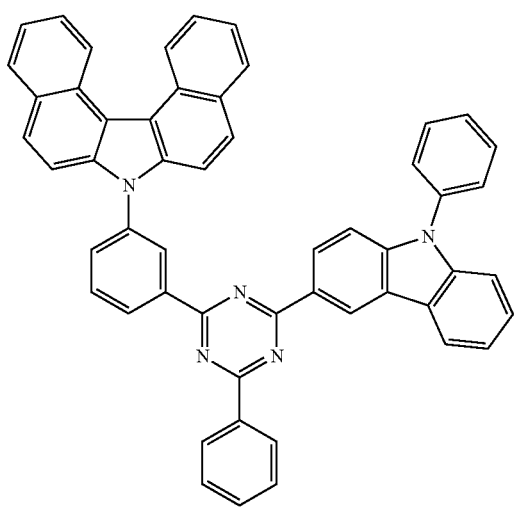
C-29
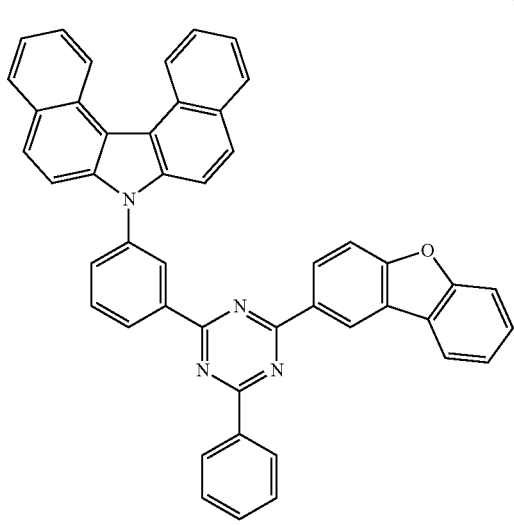

-continued
C-30
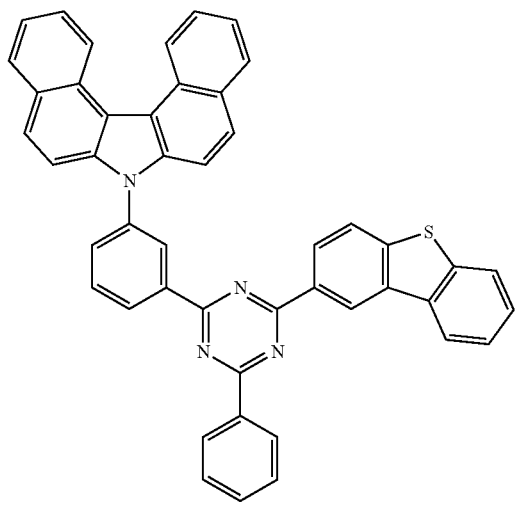
C-31
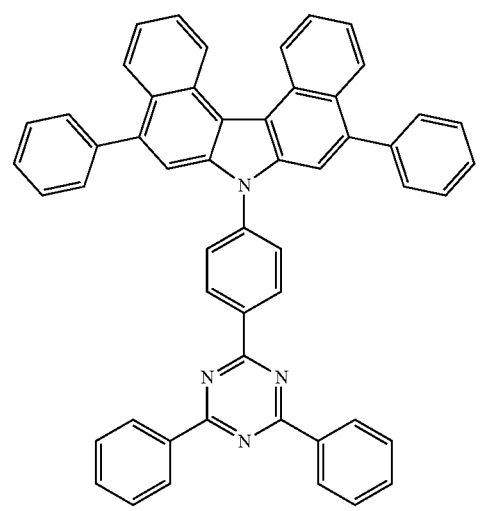
C-32
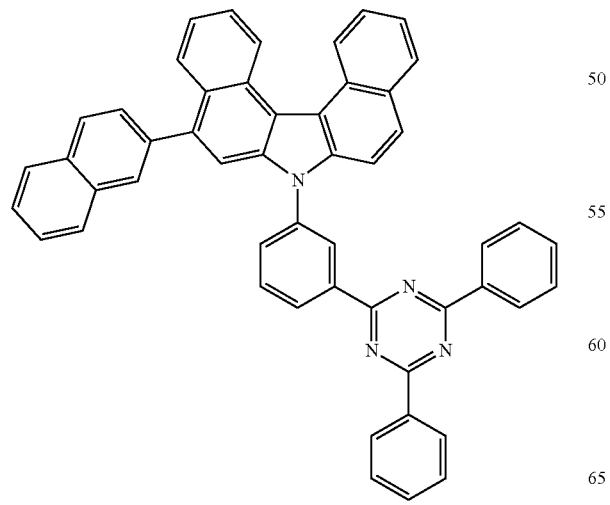
-continued
C-33
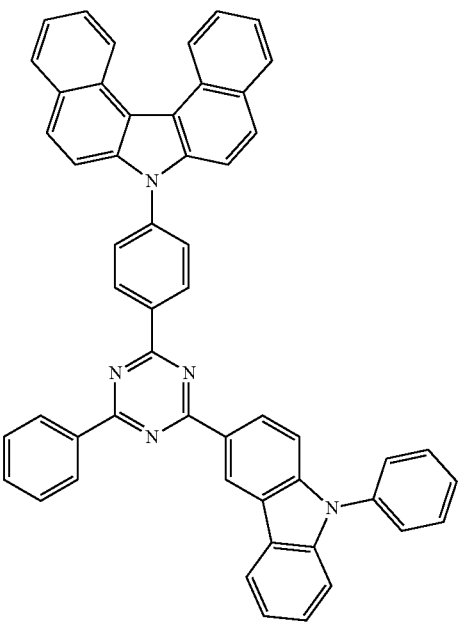
C-34
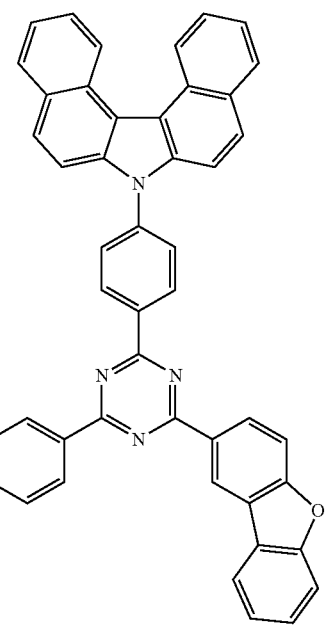

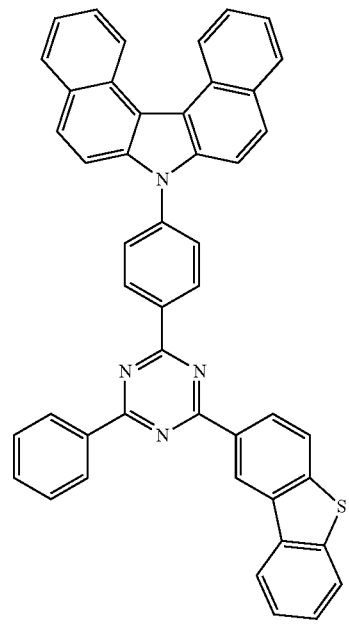
C-35
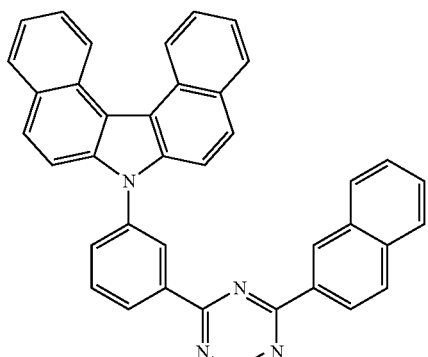
C-37
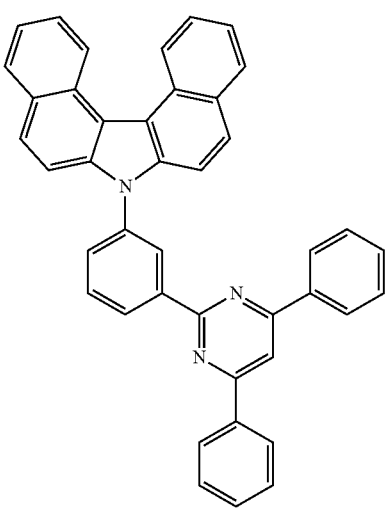
C-38
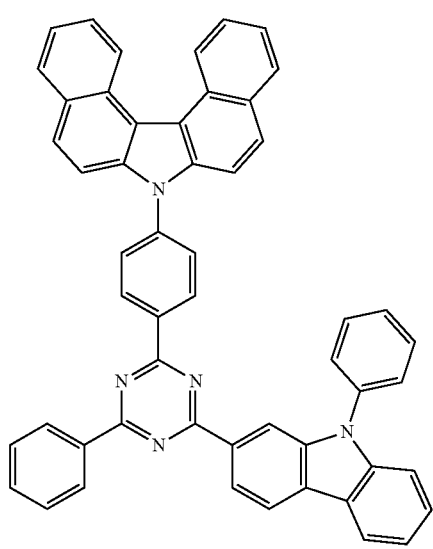
C-36
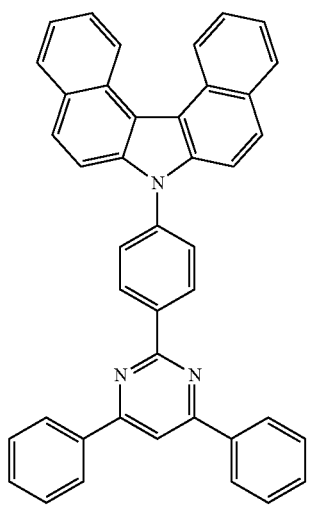
C-39

C-40
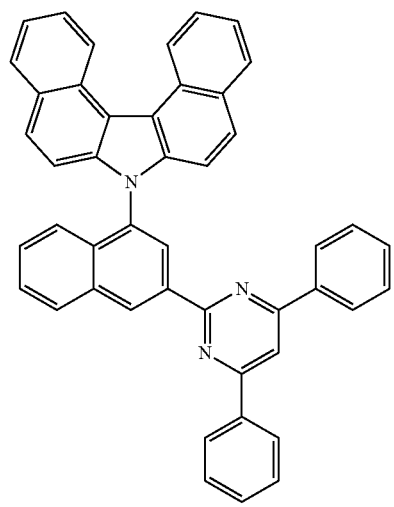
C-41
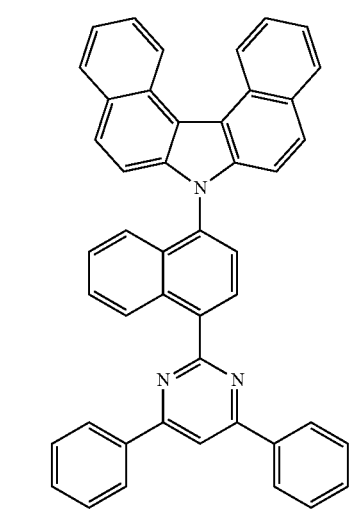
C-42
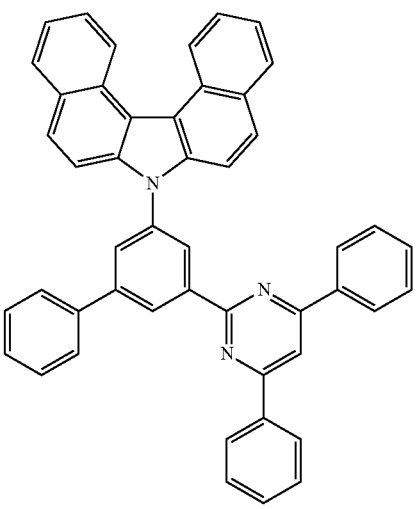
C-43
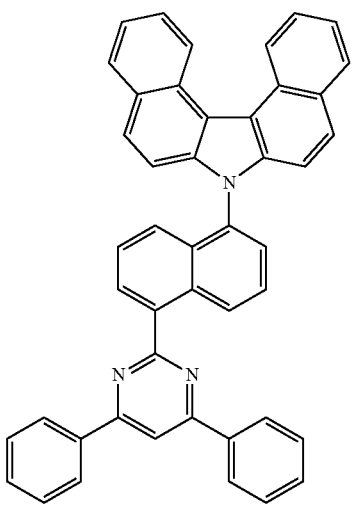
C-44
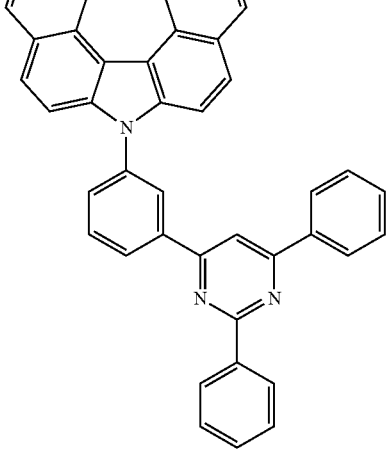
C-45
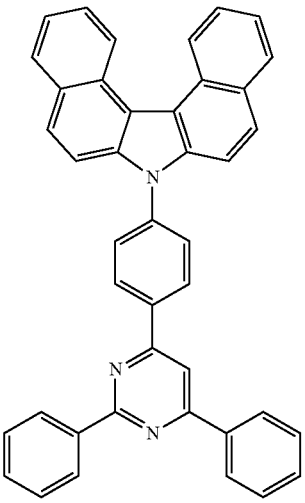

C-46
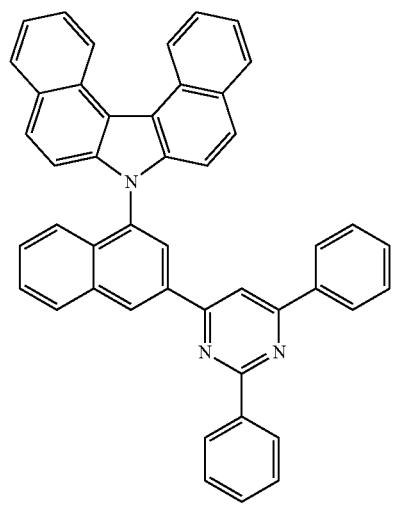
C-47
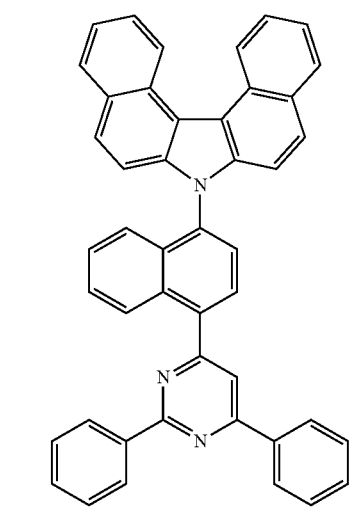
C-48
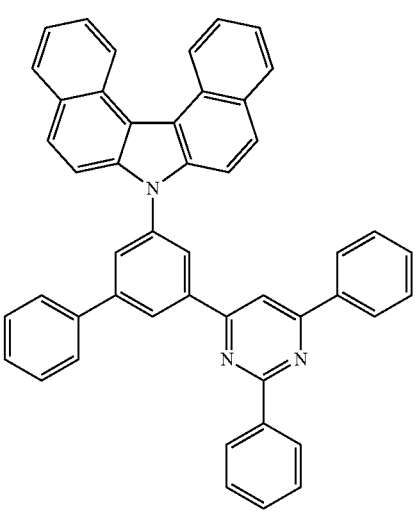
C-49
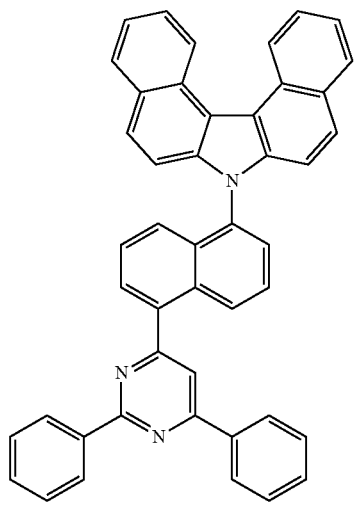
C-50
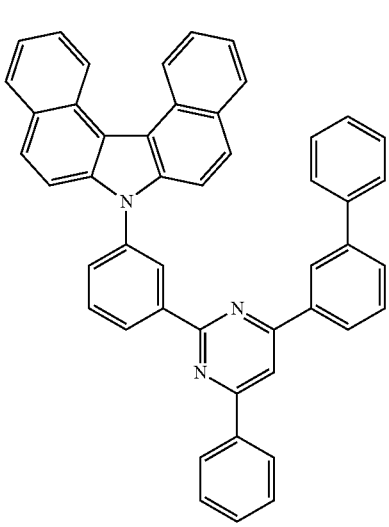
C-51
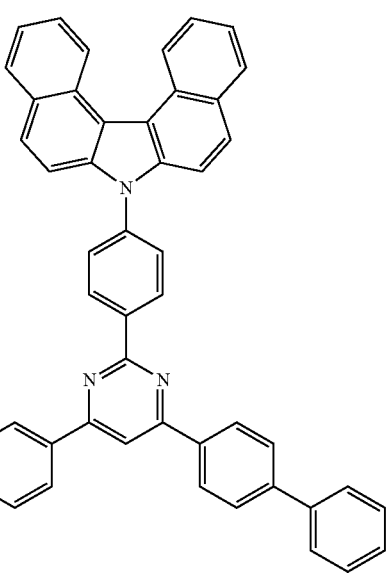

C-52
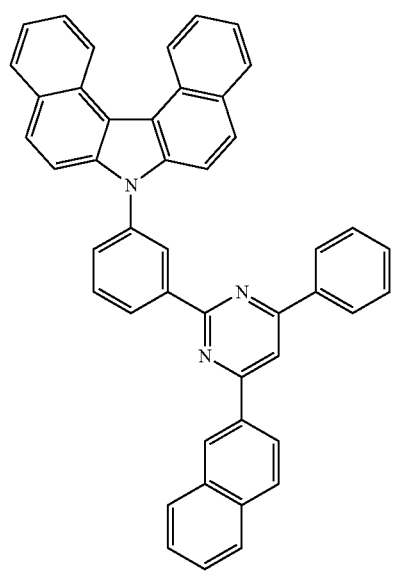
C-53
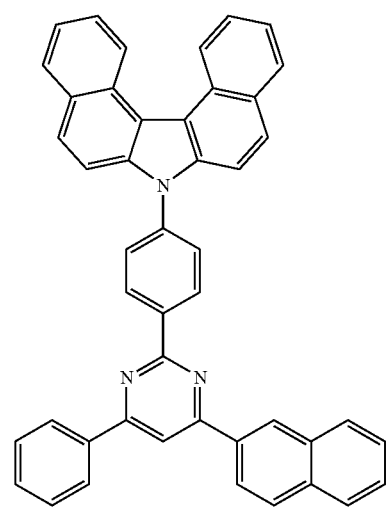
C-54
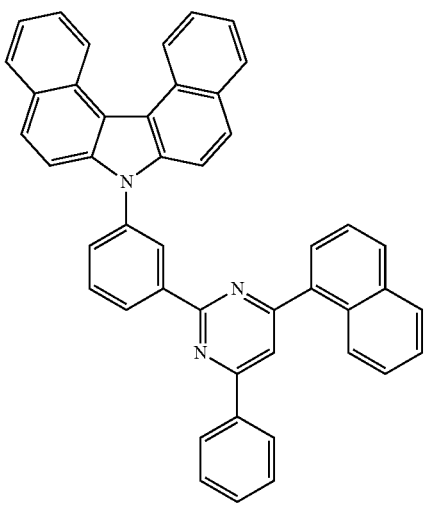
C-55
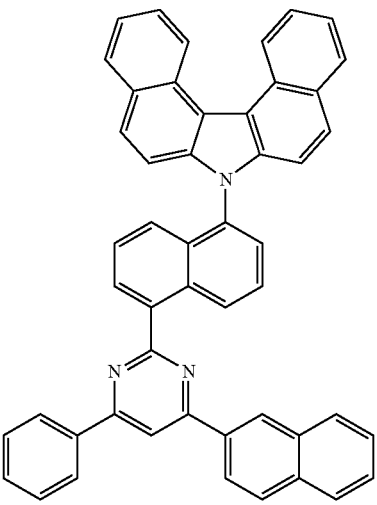
C-56
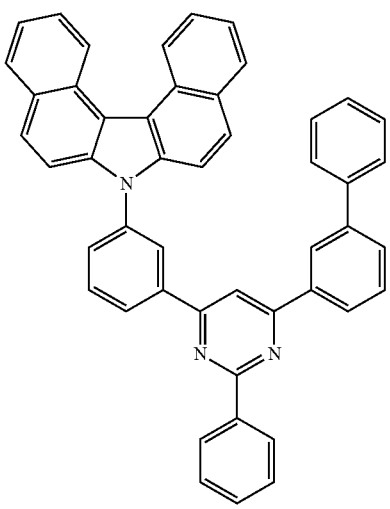
C-57
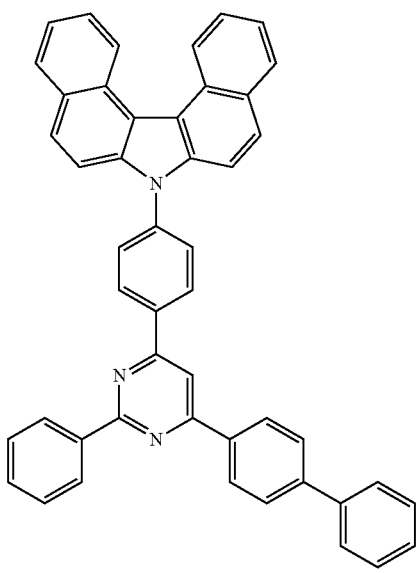

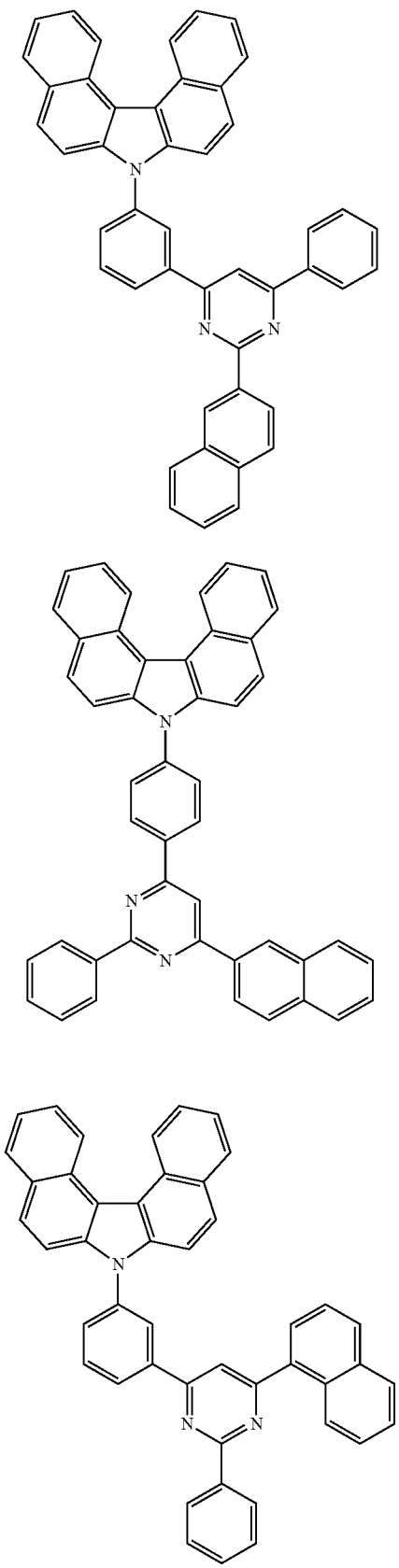
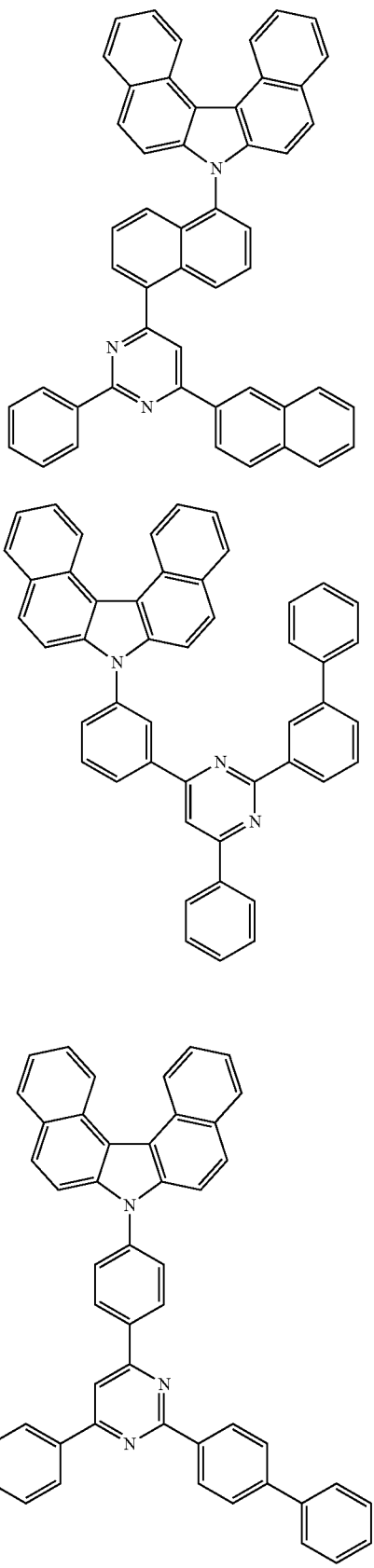

C-64
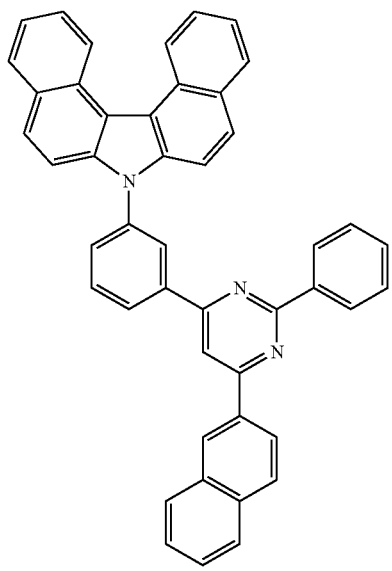
C-65
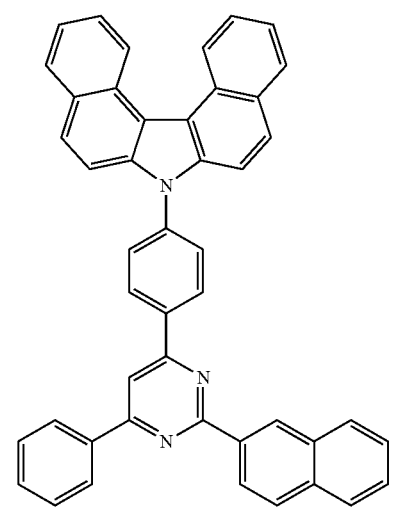
C-66
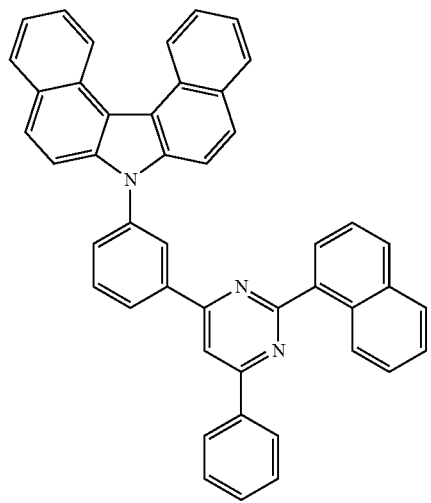
C-67
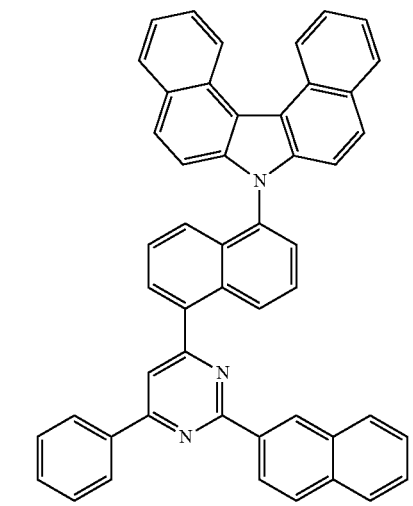
C-68
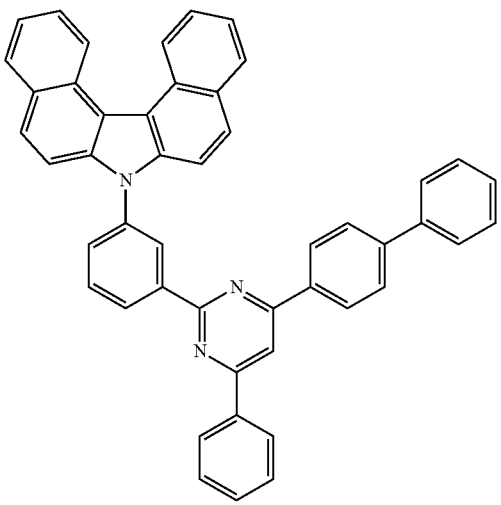
C-69
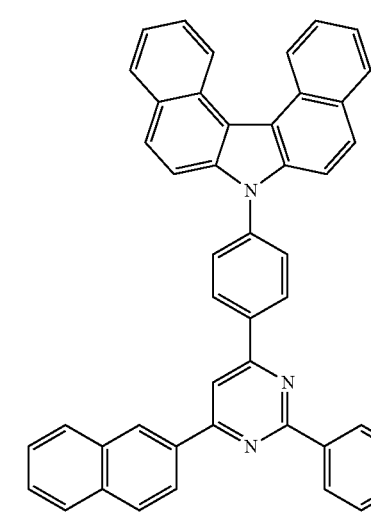

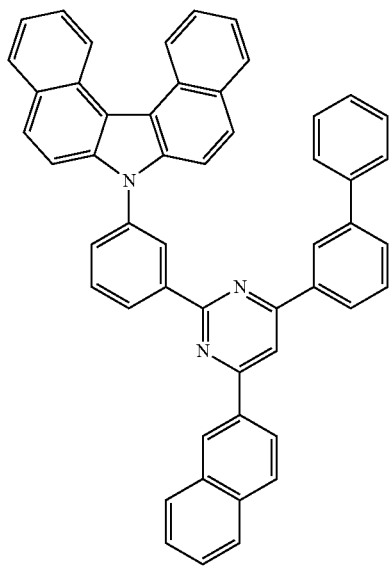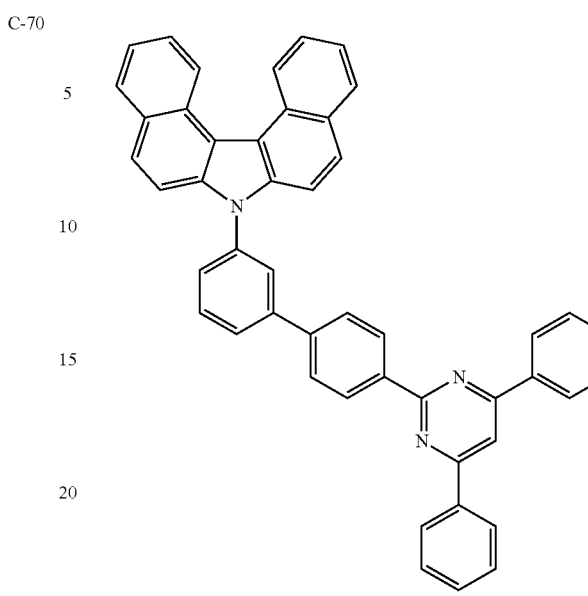

C-76 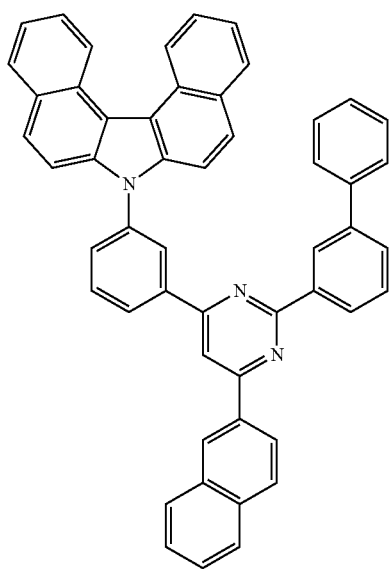
C-77 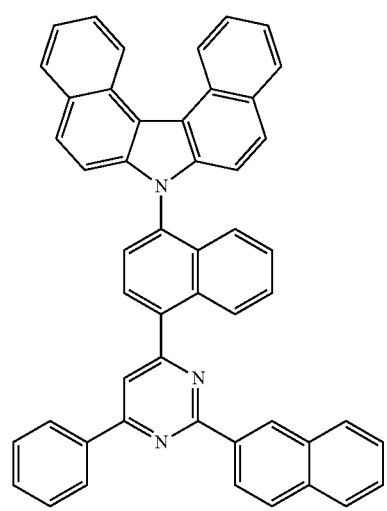
C-78 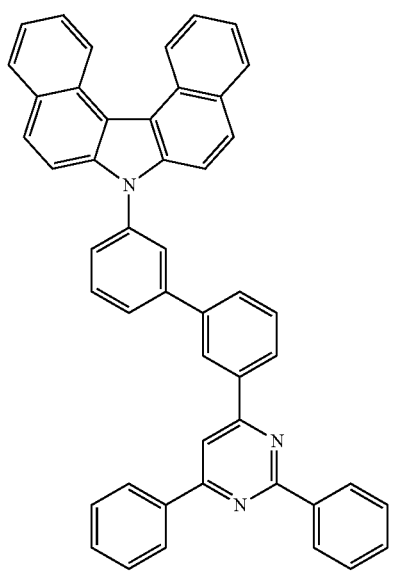
C-79 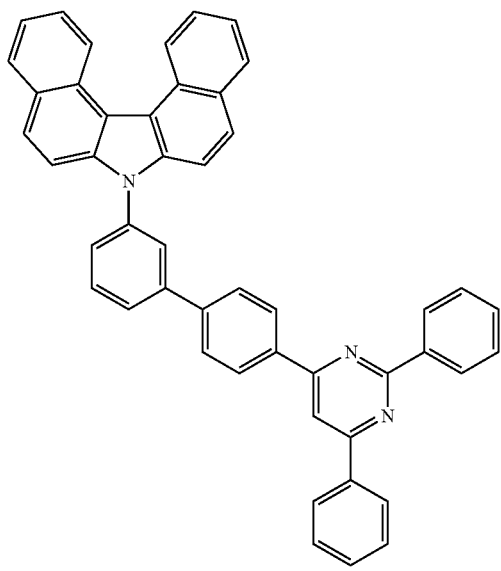
C-80 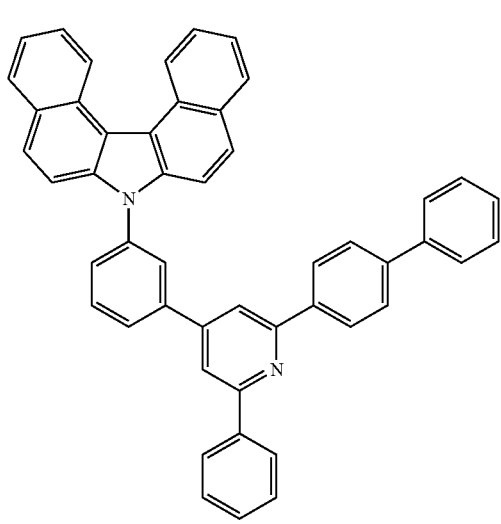
C-81 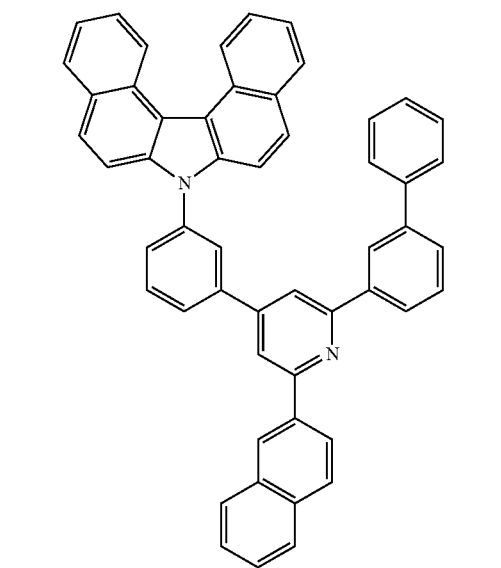

C-82
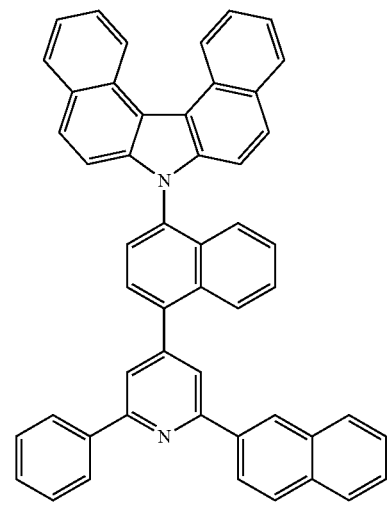
C-83
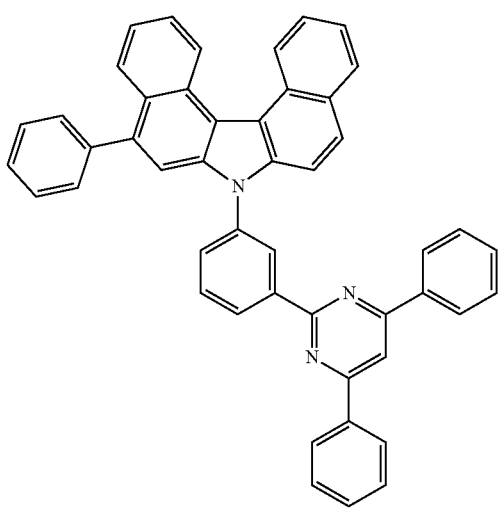
C-84
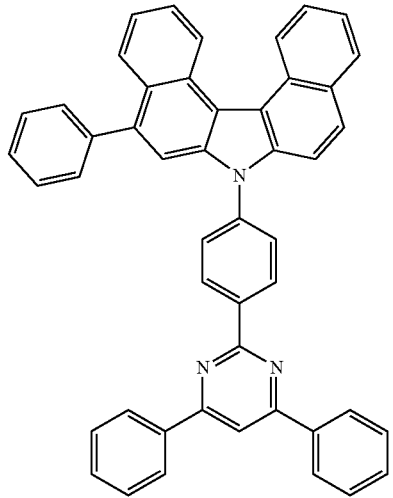
C-85
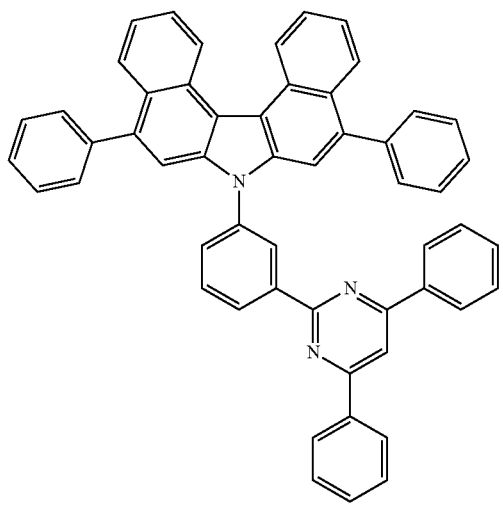
C-86
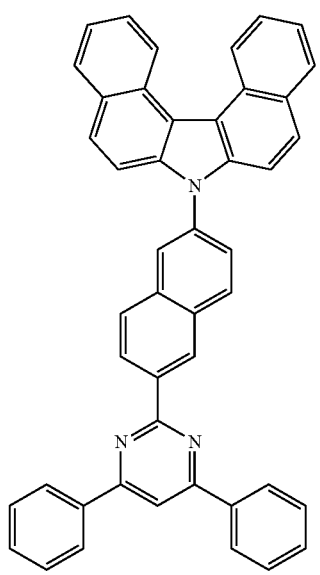
C-87
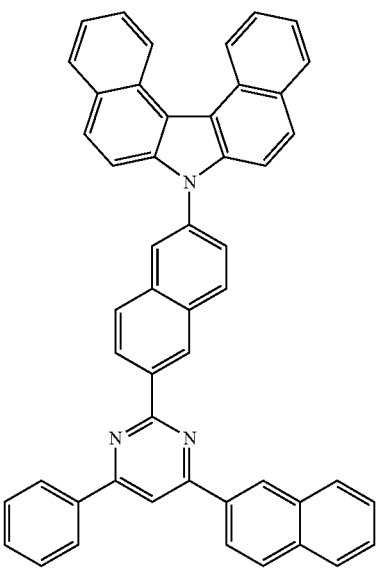

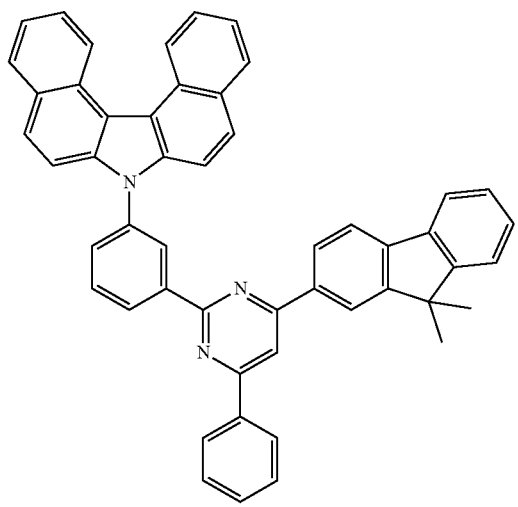
C-88
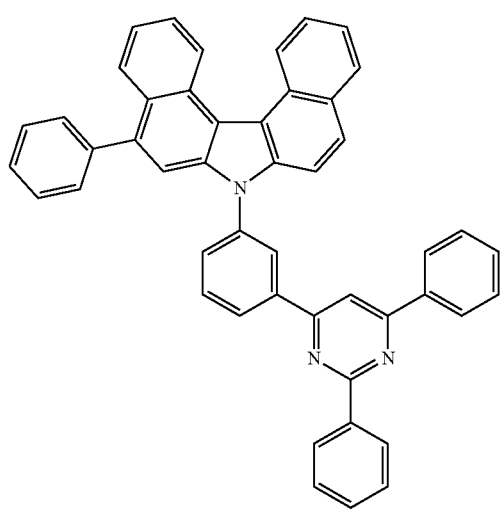
C-89
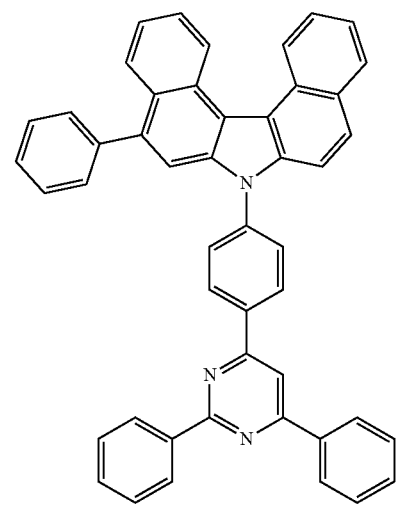
C-90
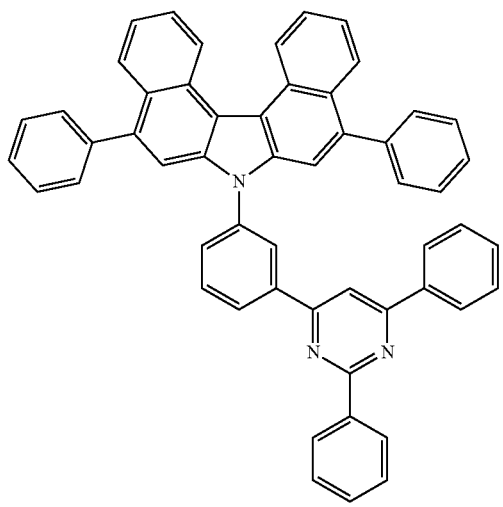
C-91
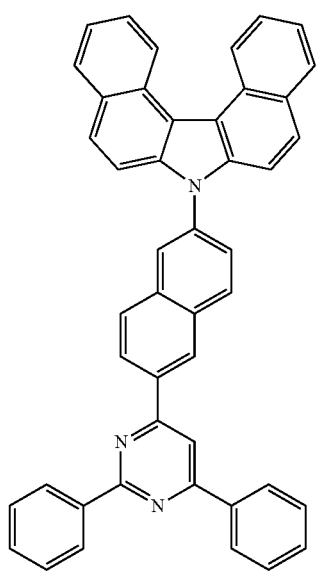
C-92
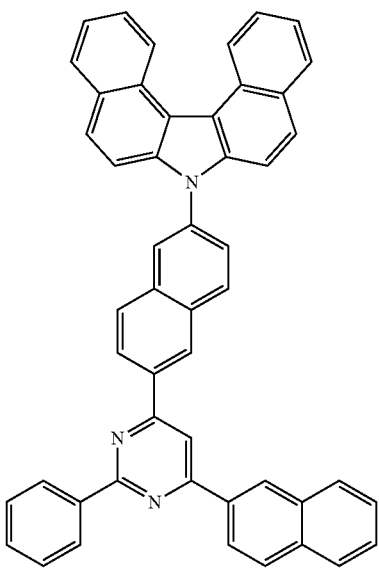
C-93

C-94
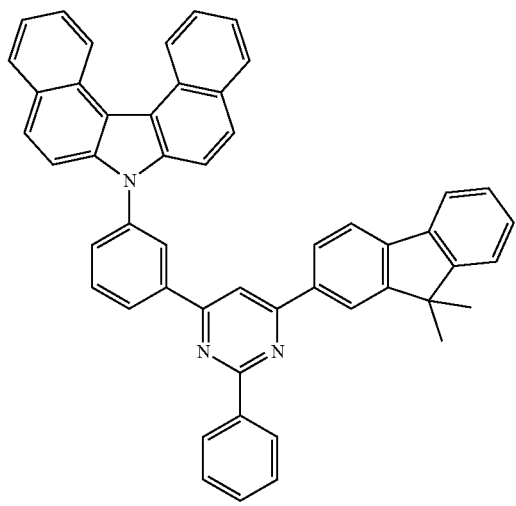
C-97
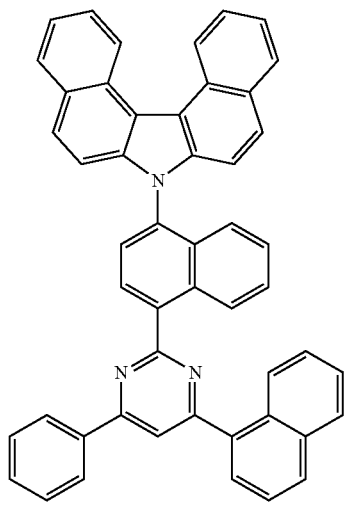
C-95
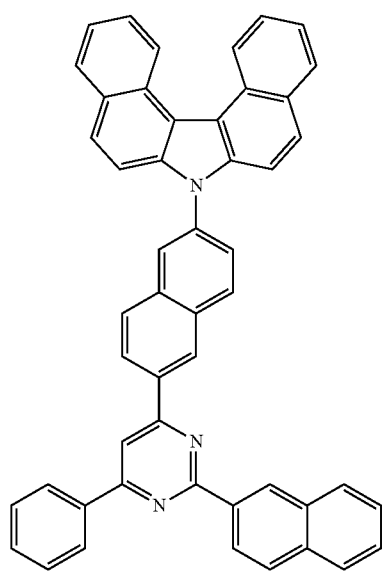
C-98
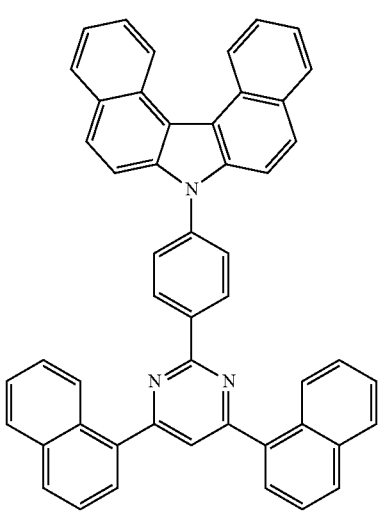
C-96
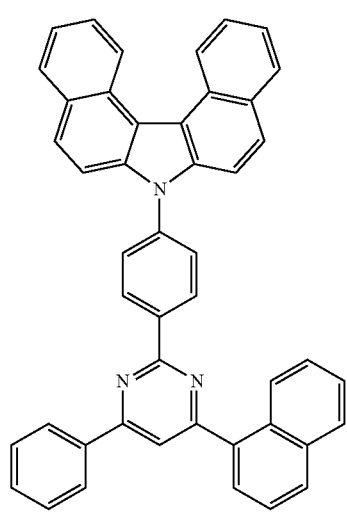
C-99
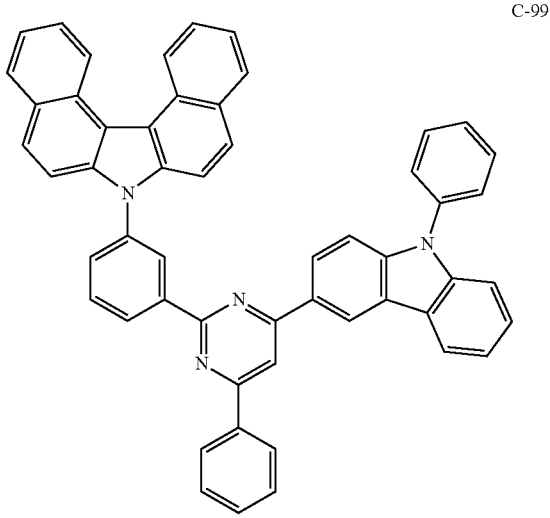

C-100
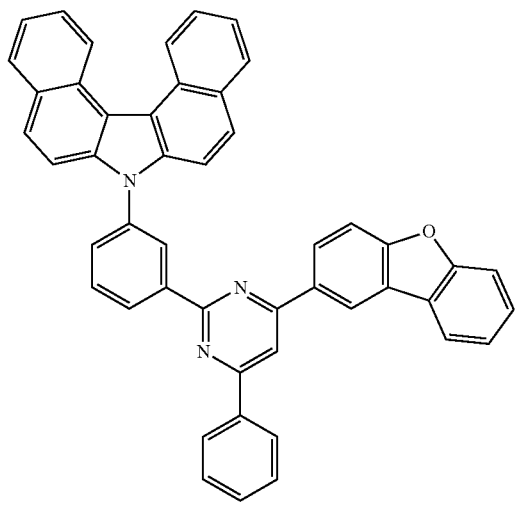
C-101
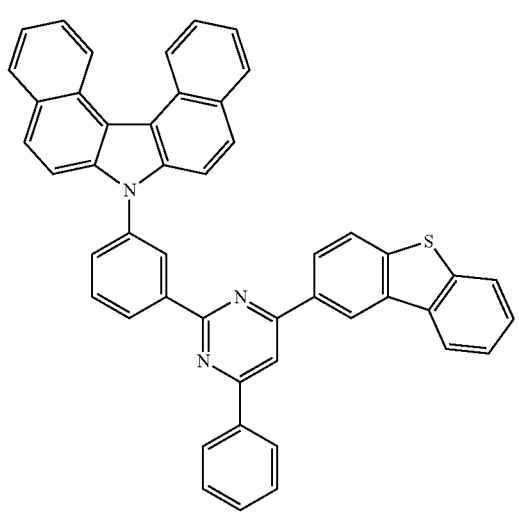
C-102
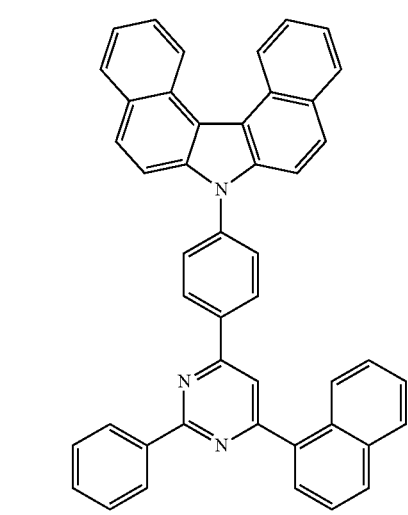
C-103
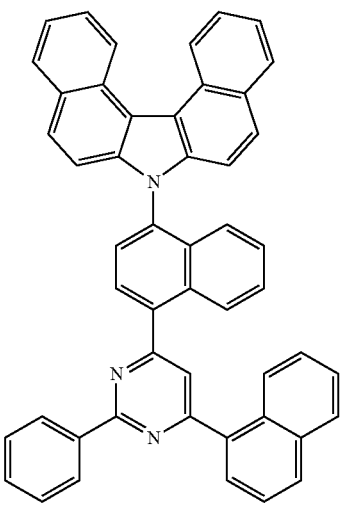
C-104
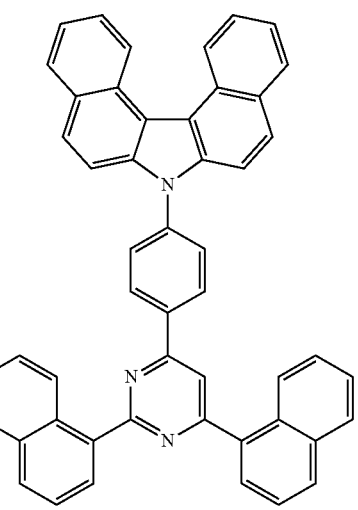
C-105
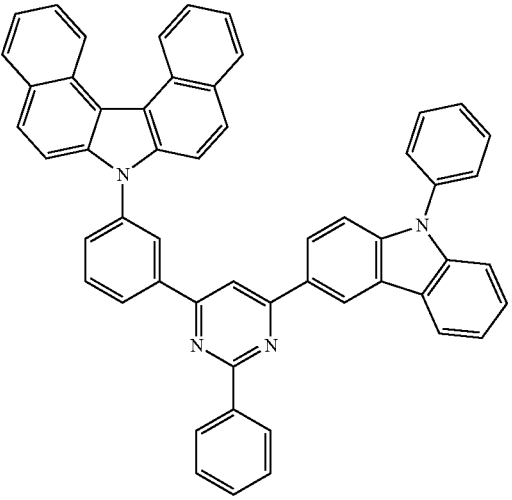

C-106
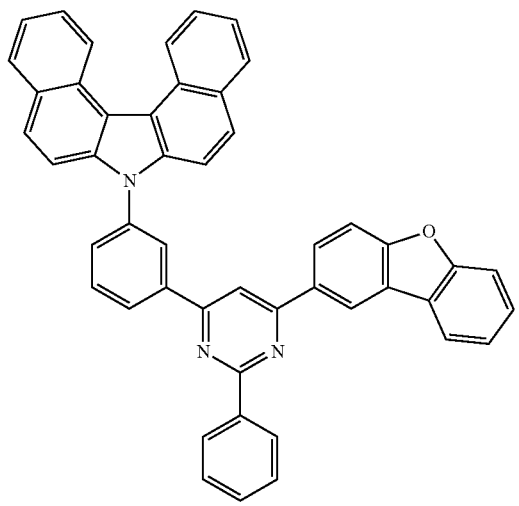
C-109
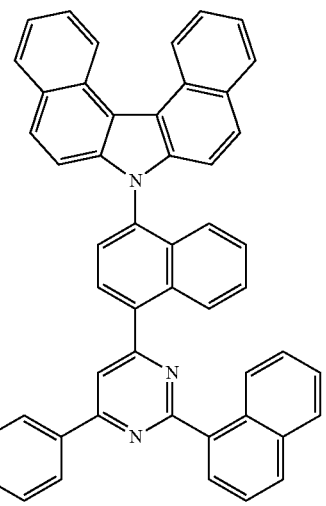
C-107
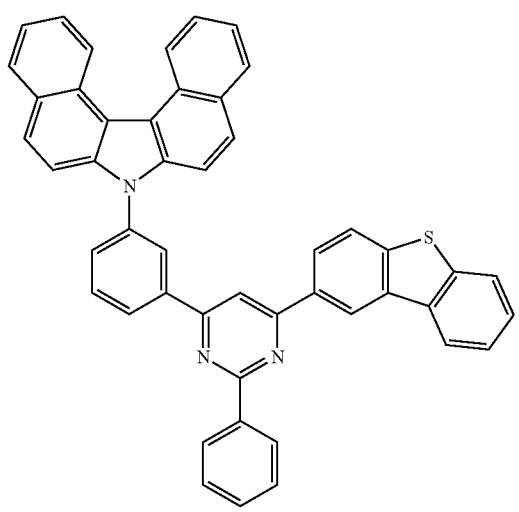
C-110
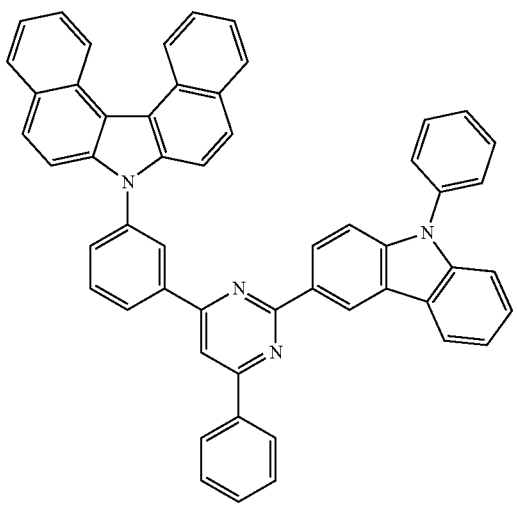
C-108
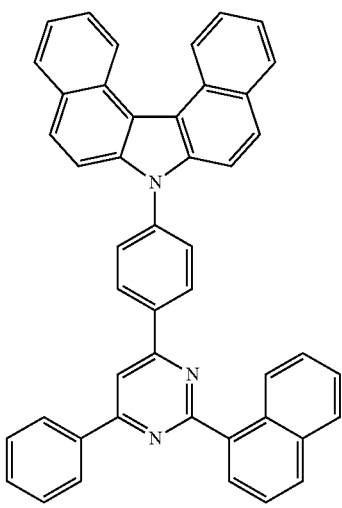
C-111
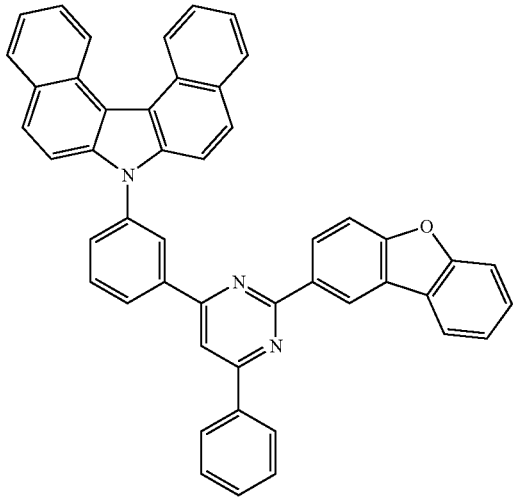

C-112
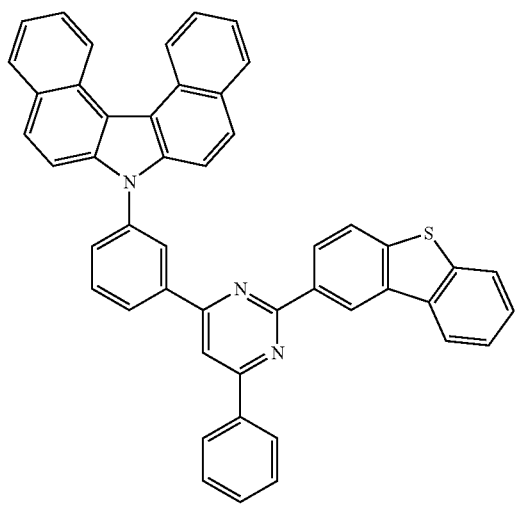
C-113
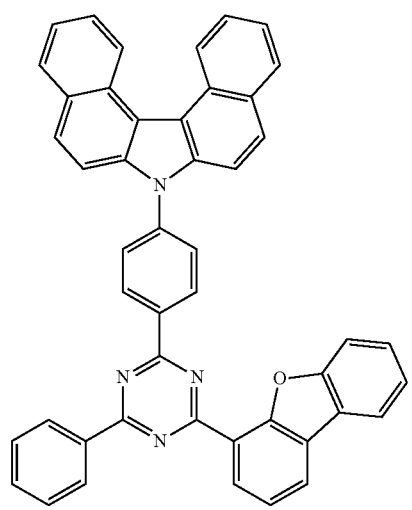
C-114
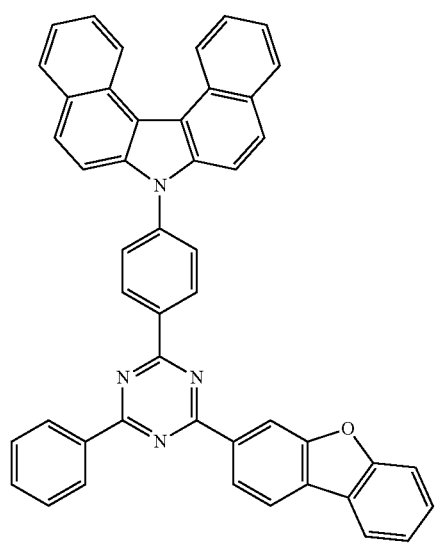
C-115
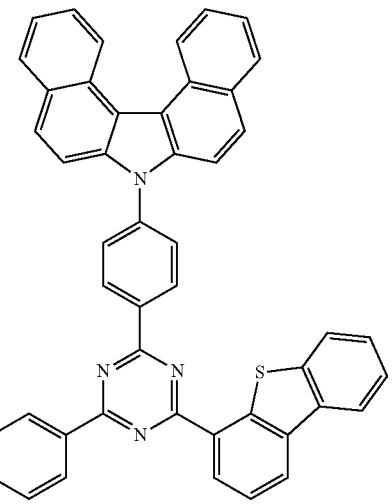
C-116
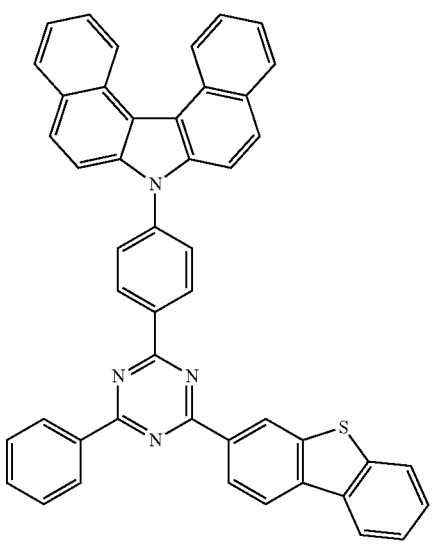
C-117
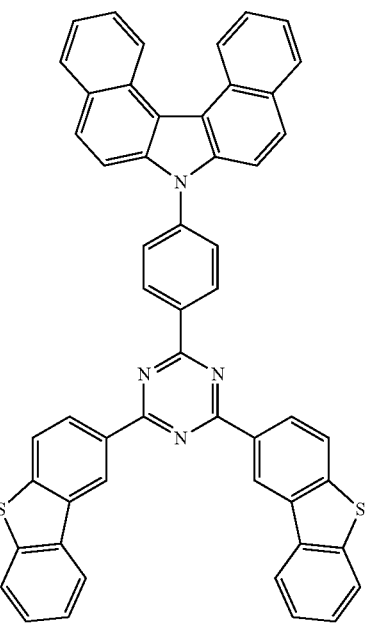

C-118
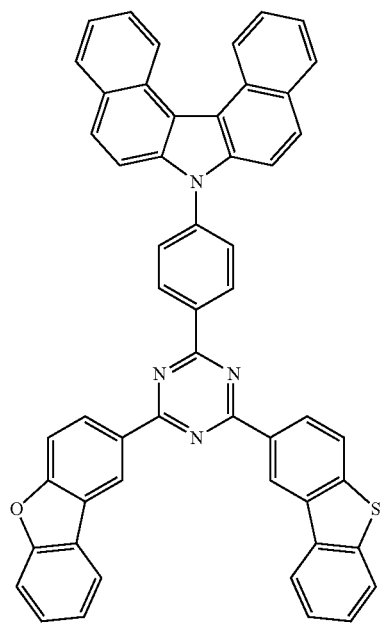
C-120
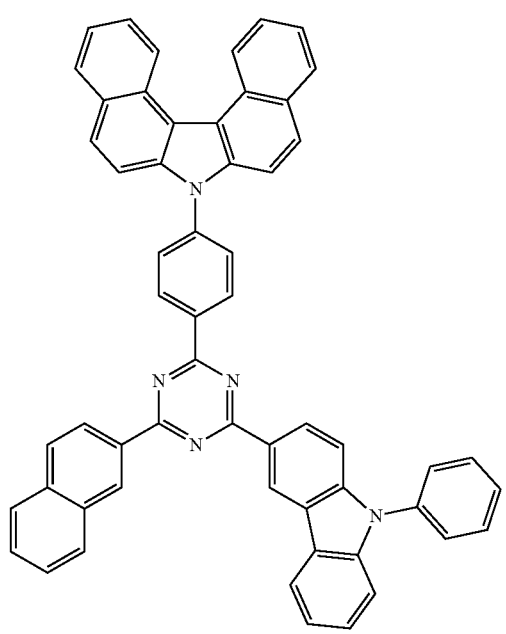
C-119
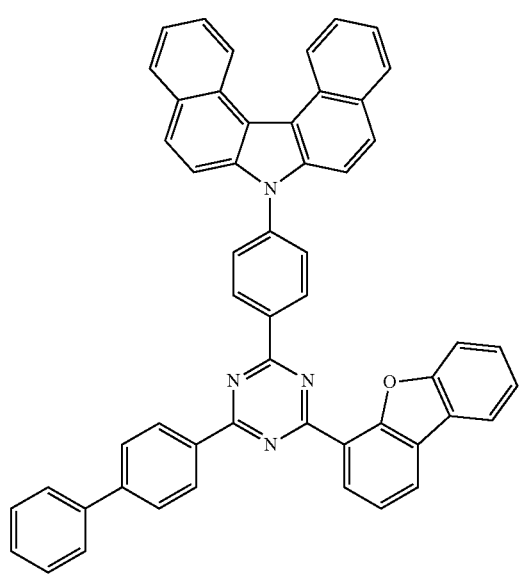
C-121
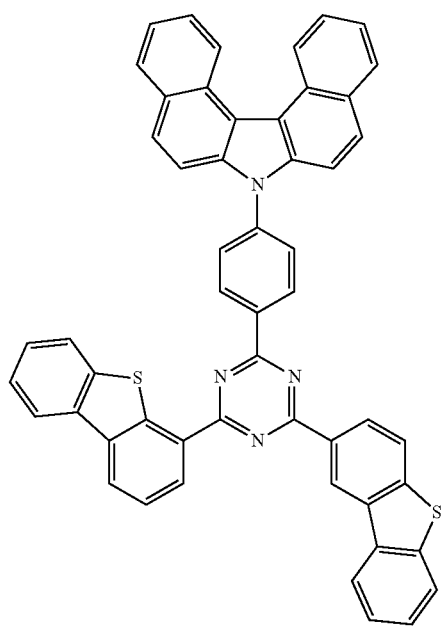

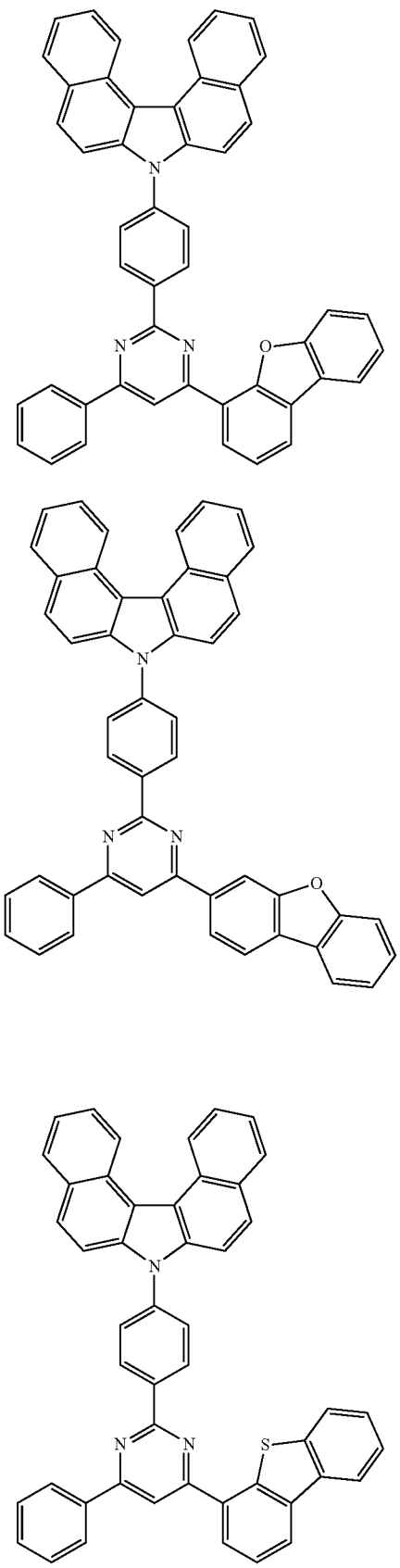

C-127
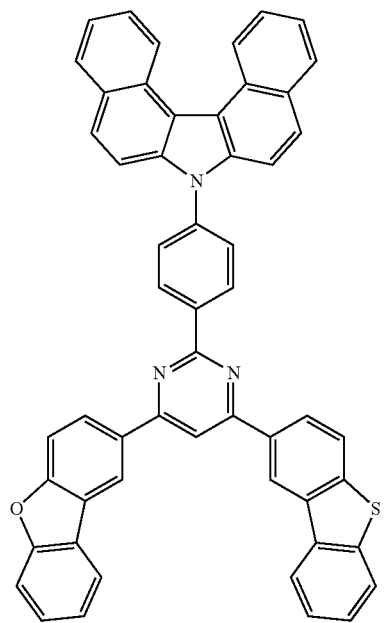
C-128
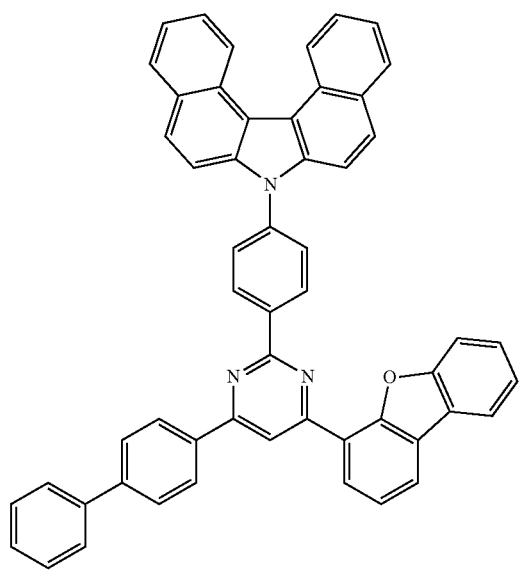
C-129
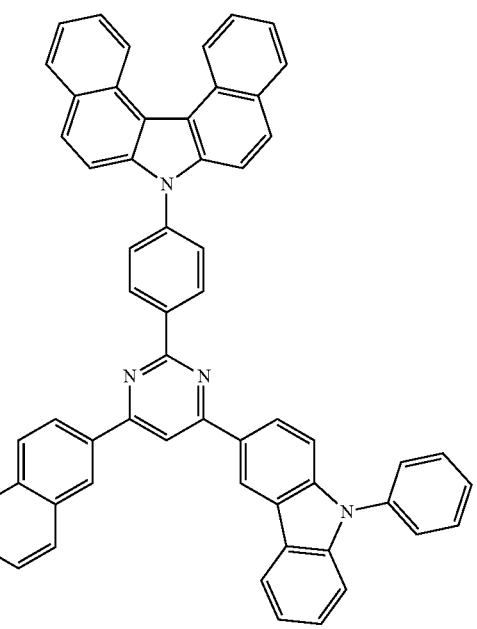
C-130
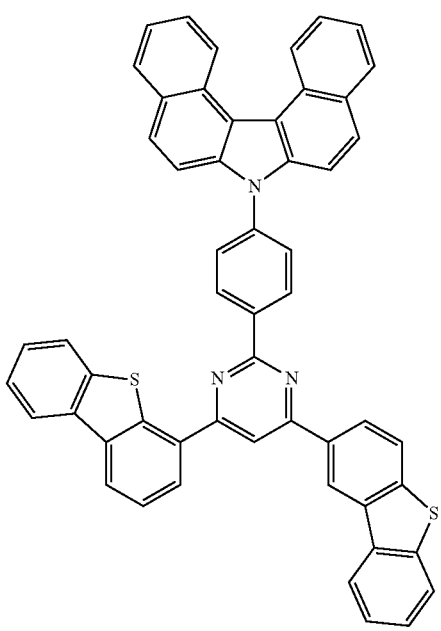

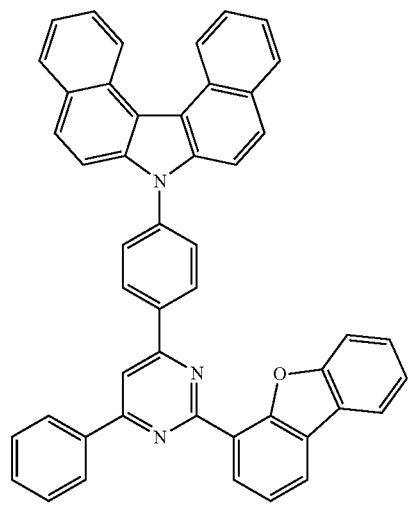
C-131
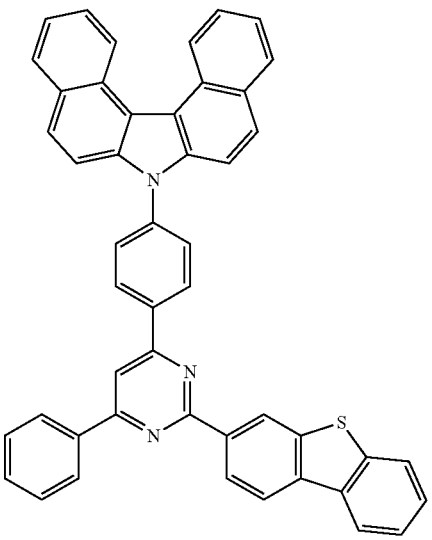
C-134
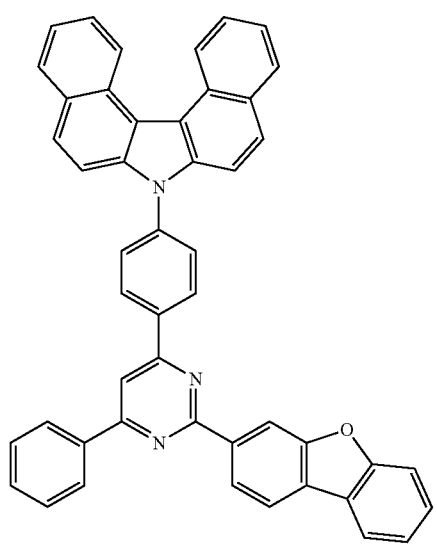
C-132
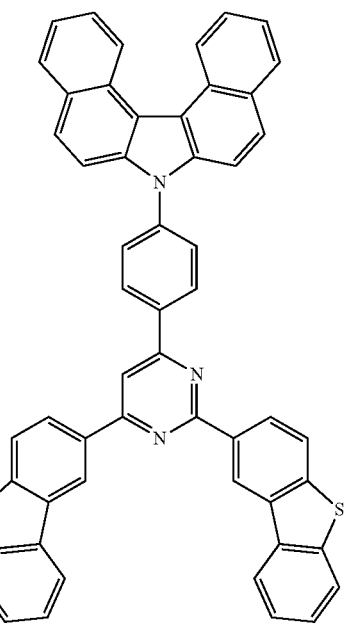
C-135
C-133

C-136
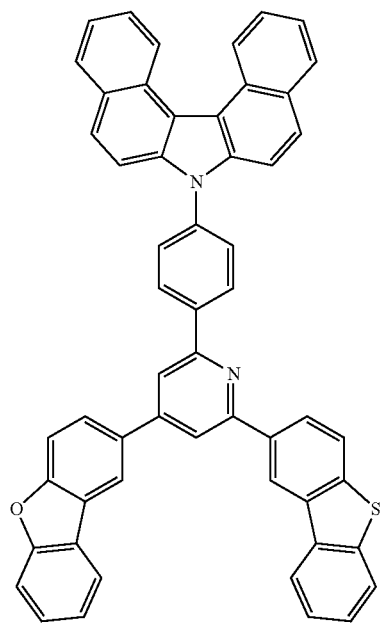
C-137
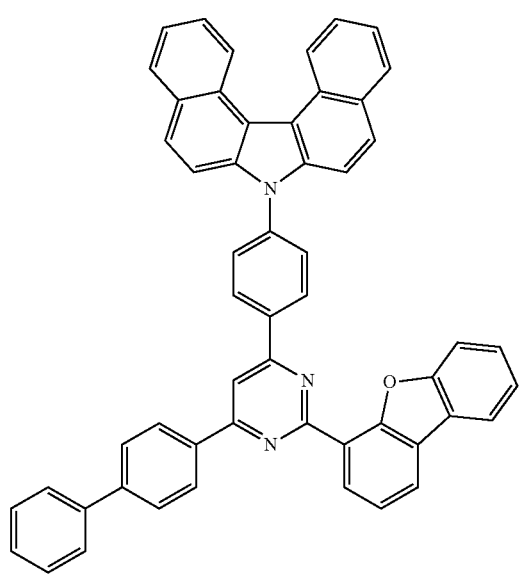
C-138
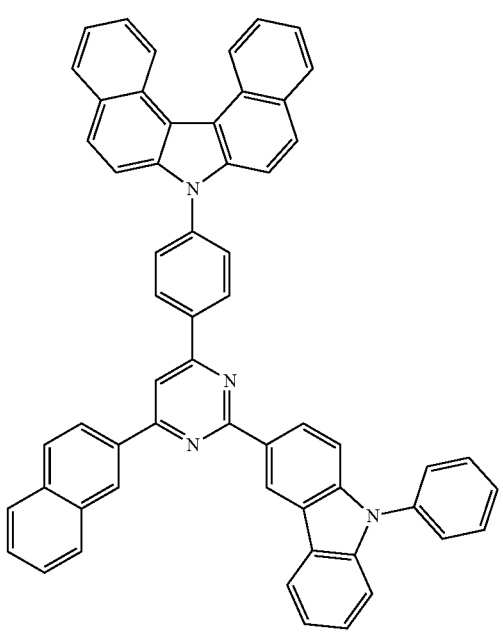
C-139
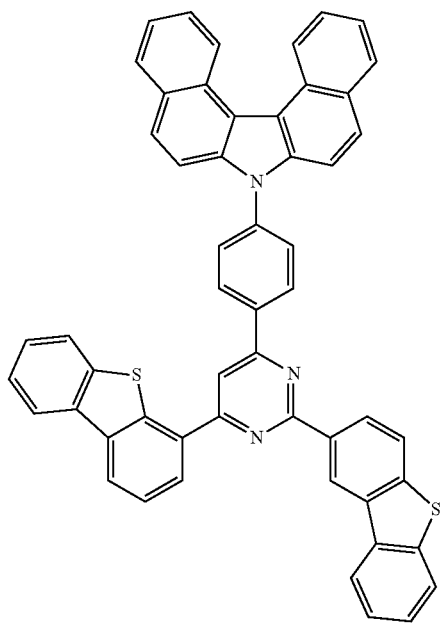

C-140 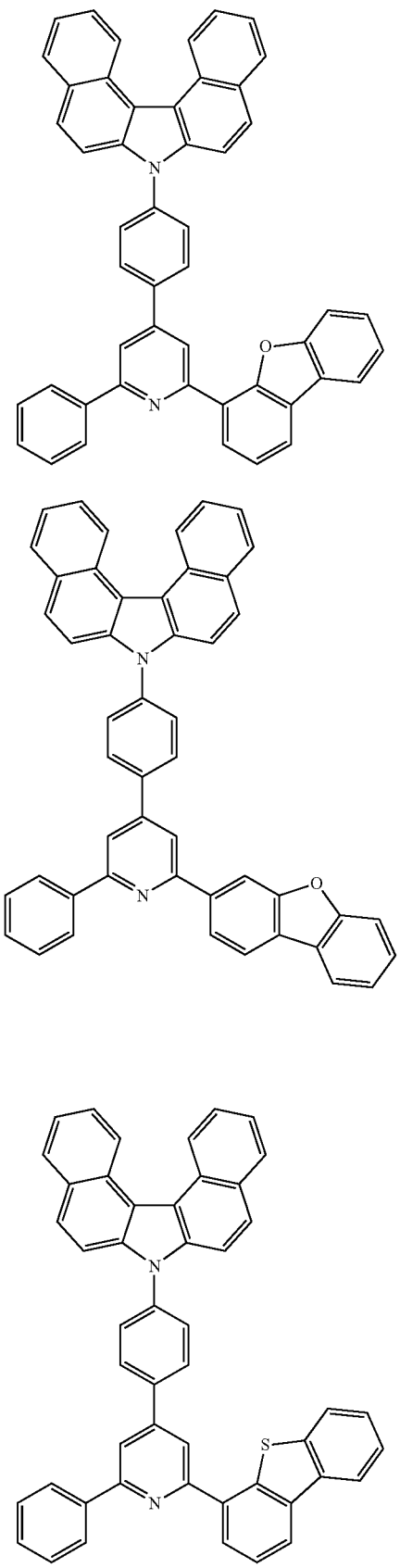
C-141
C-142
C-143 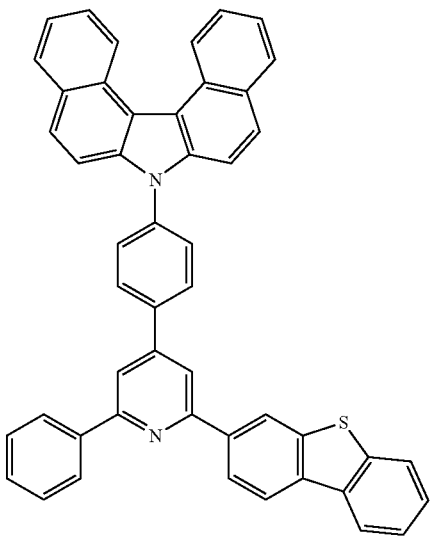
C-144 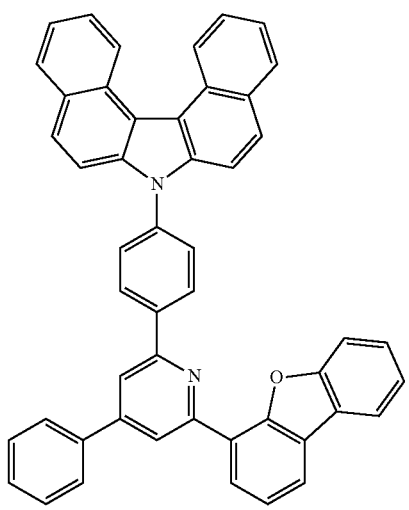
C-145 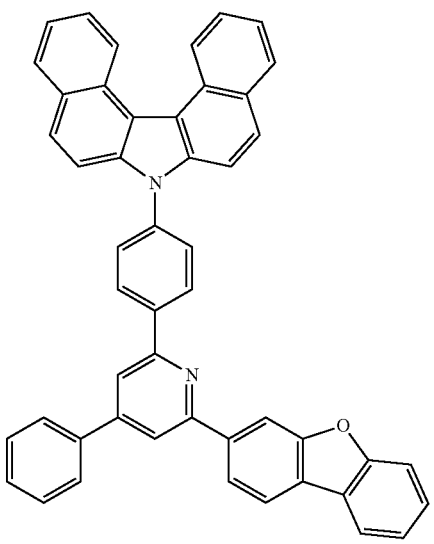

C-146
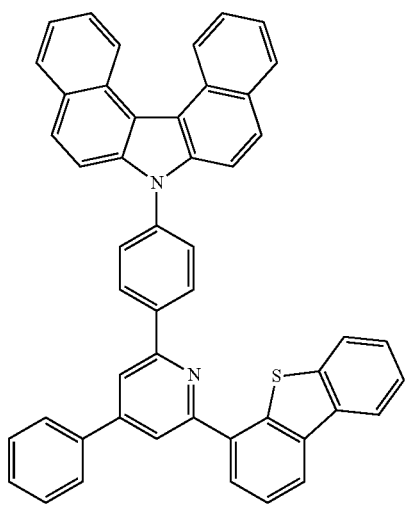
C-147
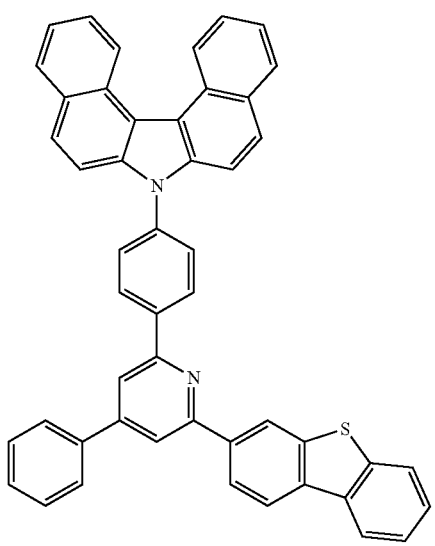
C-148
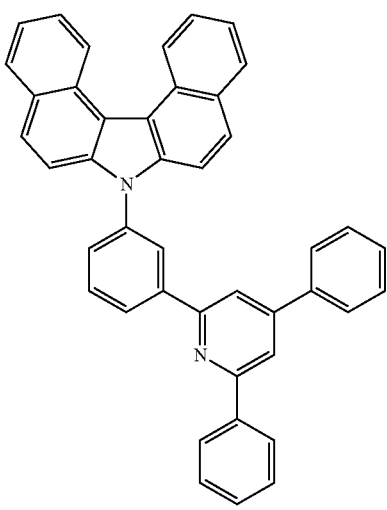
C-149
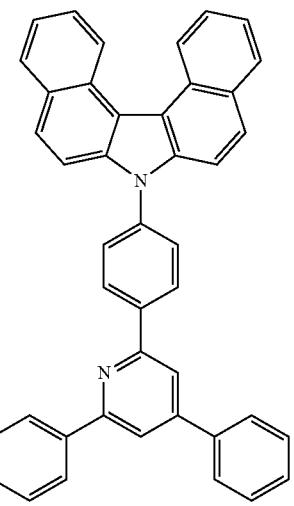
C-150
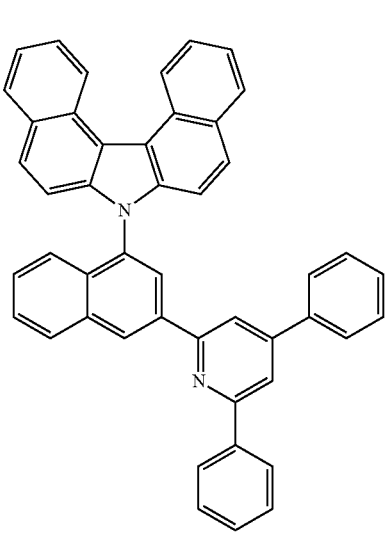
C-151
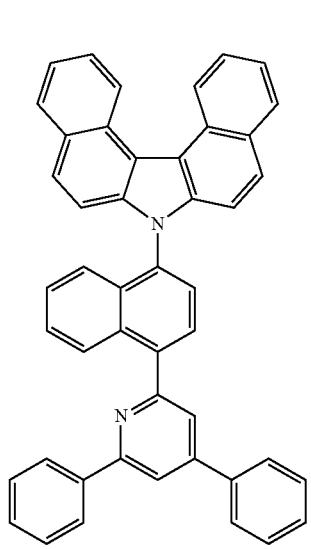

C-152 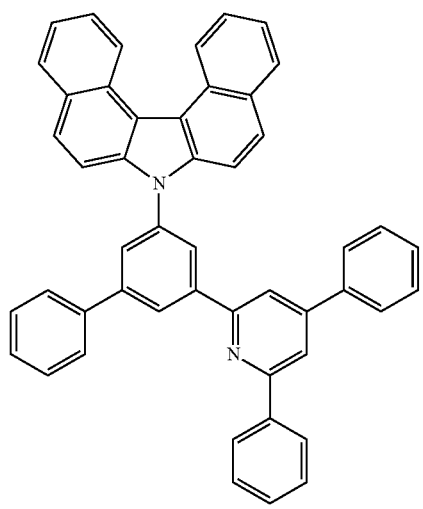
C-153 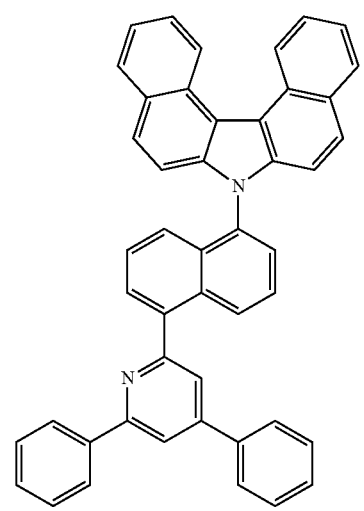
C-154 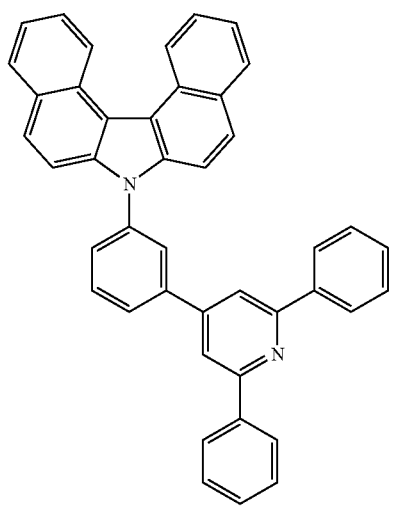
C-155 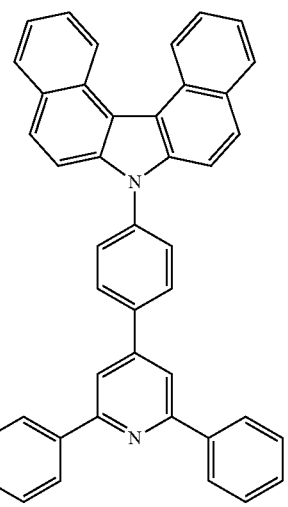
C-156 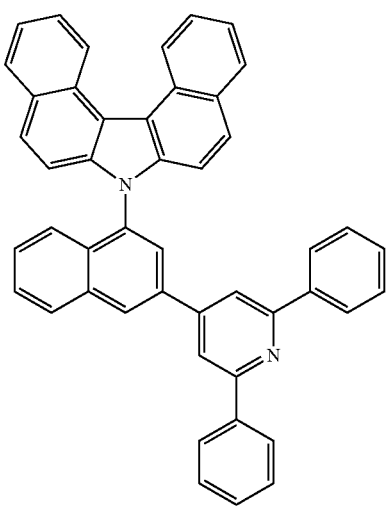
C-157 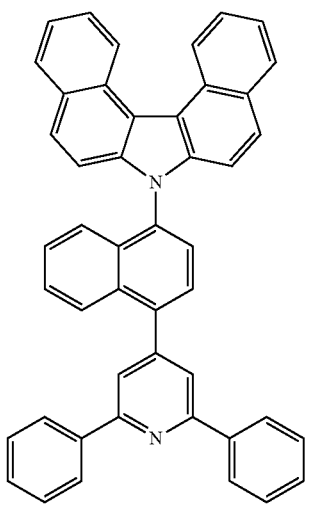

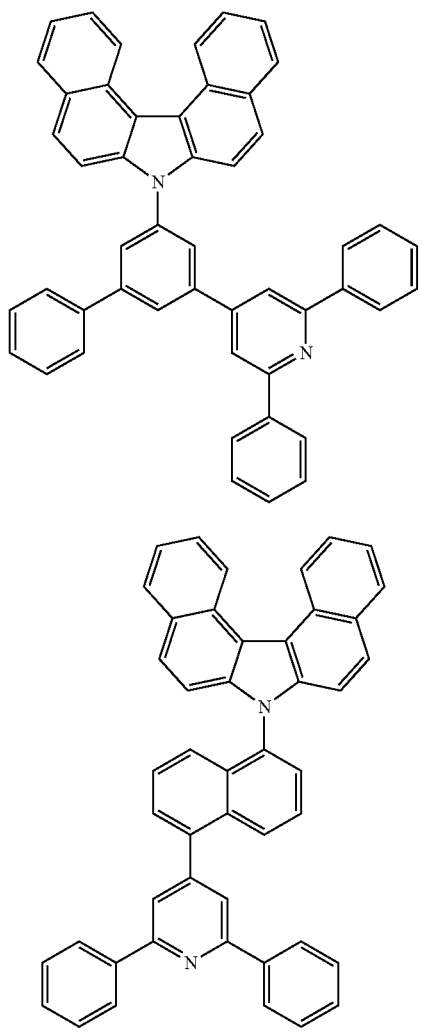
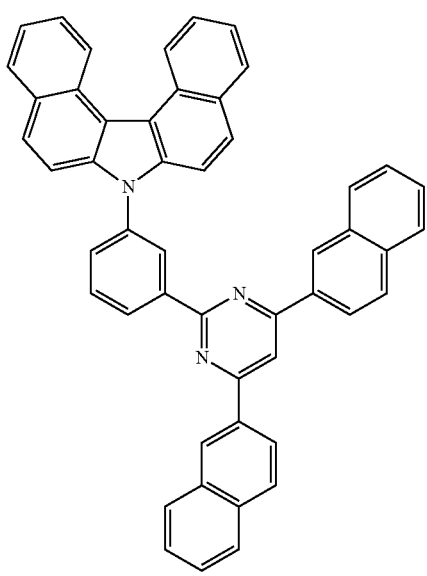
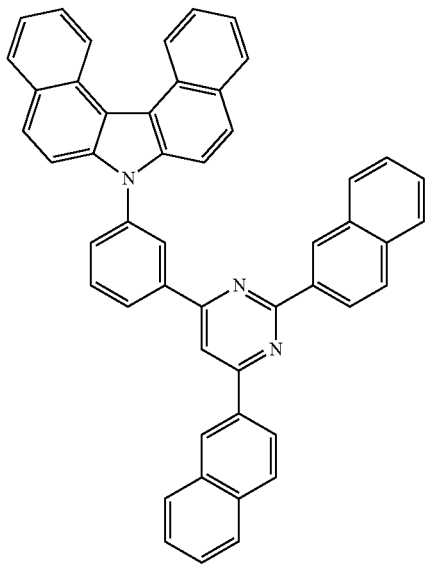

C-163

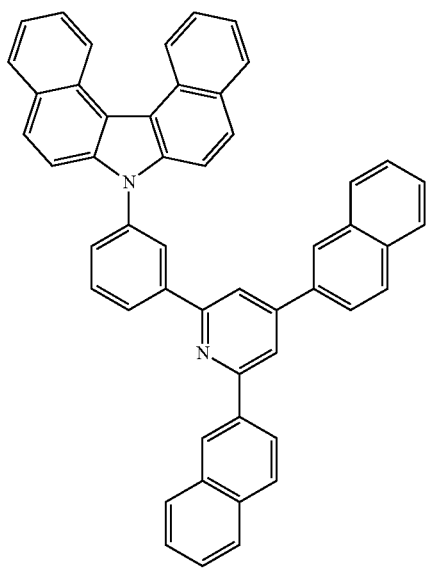

C-164

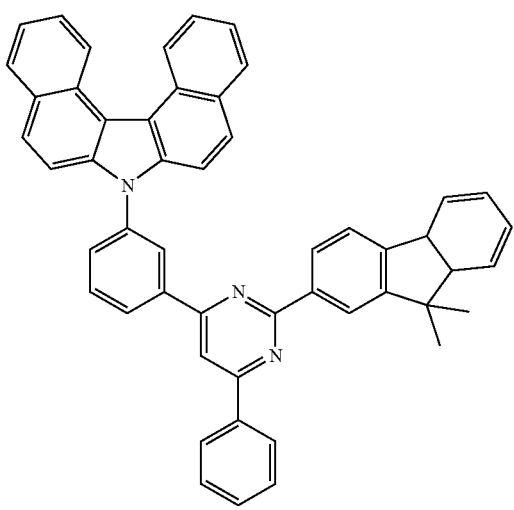

The organic electroluminescent device of the present disclosure comprises an anode; a cathode; and at least one organic layer disposed between the anode and cathode, wherein the organic layer comprises one or more light-emitting layers; the light-emitting layer comprises a host and a phosphorescent dopant; the host comprises a plurality of host compounds; and at least a first host compound of a plurality of host compounds is represented by formula 1, and a second host compound is represented by formula 2.

The light-emitting layer indicates a layer from which light is emitted, and may be a single layer or a multiple layer deposited by two or more layers. It is preferable that a doping amount of the dopant compound is less than 20 wt % based on the total amount of the host compound and the dopant compound.

The organic layer may comprise a light-emitting layer, and may further comprise at least one layer selected from a hole injection layer, a hole transport layer, an electron transport layer, an electron injection layer, an electron buffering layer, an interlayer, a hole blocking layer, and an electron blocking layer.

In the organic electroluminescent device of the present disclosure, the weight ratio in the light-emitting layer between the first host material and the second host material may be in the range of 1:99 to 99:1.

The dopant to be comprised in the organic electroluminescent device of the present disclosure is preferably at least one phosphorescent dopant. The phosphorescent dopant material for the organic electroluminescent device of the present disclosure is not limited, but may be preferably selected from metallated complex compounds of iridium (Ir), osmium (Os), copper (Cu) and platinum (Pt), more preferably selected from ortho-metallated complex compounds of iridium (Ir), osmium (Os), copper (Cu) and platinum (Pt), and even more preferably ortho-metallated iridium complex compounds.

Preferably, the phosphorescent dopant may be selected from the group consisting of compounds represented by the following formulae 101 to 103.

(101)

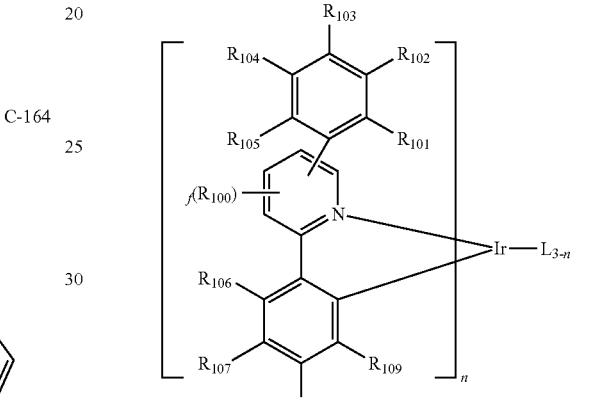

(102)

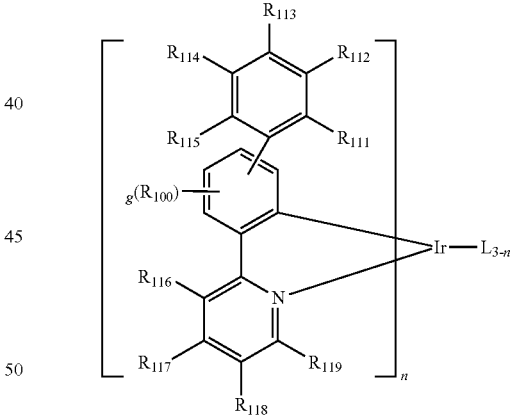

(103)

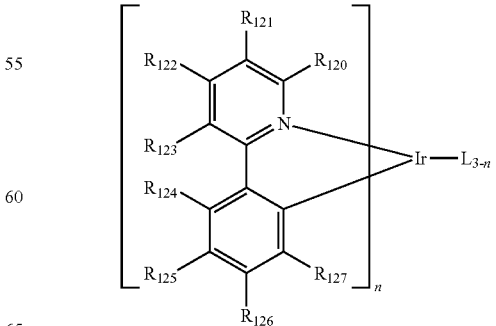

wherein L is selected from the following structures:

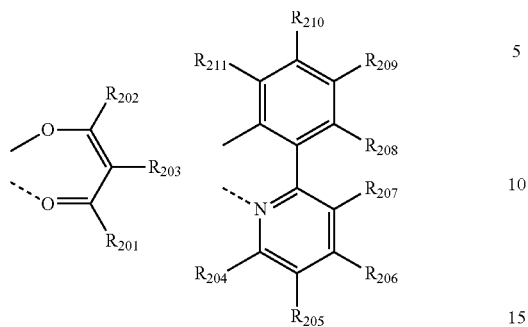

$R_{100}$ represents hydrogen, a substituted or unsubstituted (C1-C30)alkyl group, or a substituted or unsubstituted (C3-C30)cycloalkyl group;

$R_{101}$ to $R_{109}$, and $R_{111}$ to $R_{123}$, each independently, represent hydrogen, deuterium, a halogen, a (C1-C30)alkyl group unsubstituted or substituted with a halogen, a substituted or unsubstituted (C3-C30)cycloalkyl group, a substituted or unsubstituted (C6-C30)aryl group, a cyano group, or a substituted or unsubstituted (C1-C30)alkoxy group; $R_{106}$ to $R_{109}$ may be linked to an adjacent substituent(s) to form a substituted or unsubstituted fused ring, for example, a fluorene unsubstituted or substituted with an alkyl, a dibenzothiophene unsubstituted or substituted with an alkyl, or a dibenzofuran unsubstituted or substituted with an alkyl group; $R_{120}$ to $R_{123}$ may be linked to an adjacent substituent(s) to form a substituted or unsubstituted fused ring, for example, a quinoline unsubstituted or substituted with an alkyl or aryl;

$R_{124}$ to $R_{127}$, each independently, represent hydrogen, deuterium, a halogen, a substituted or unsubstituted (C1-C30)alkyl group, or a substituted or unsubstituted (C6-C30)aryl group; and $R_{124}$ to $R_{127}$ may be linked to an adjacent substituent(s) to form a substituted or unsubstituted fused ring, for example, a fluorene unsubstituted or substituted with an alkyl group, a dibenzothiophene unsubstituted or substituted with an alkyl group, or a dibenzofuran unsubstituted or substituted with an alkyl group;

$R_{201}$ to $R_{211}$, each independently, represent hydrogen, deuterium, a halogen, a (C1-C30)alkyl group unsubstituted or substituted with a halogen, a substituted or unsubstituted (C3-C30)cycloalkyl group, or a substituted or unsubstituted (C6-C30)aryl group; and $R_{208}$ to $R_{211}$ may be linked to an adjacent substituent(s) to form a substituted or unsubstituted fused ring, for example, a fluorene unsubstituted or substituted with an alkyl, a dibenzothiophene unsubstituted or substituted with an alkyl group, or a dibenzofuran unsubstituted or substituted with an alkyl group;

f and g, each independently, represent an integer of 1 to 3; where f or g is an integer of 2 or more, each of $R_{100}$ may be the same or different; and n represents an integer of 1 to 3.

Specifically, the phosphorescent dopant material includes the following:

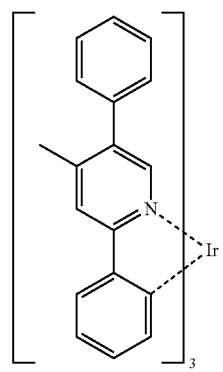

D-1

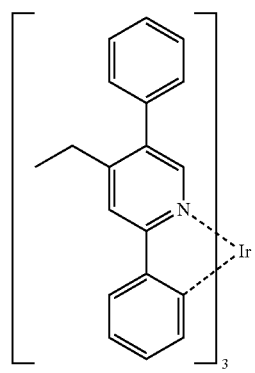

D-2

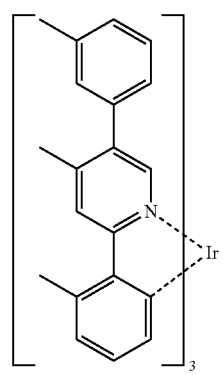

D-3

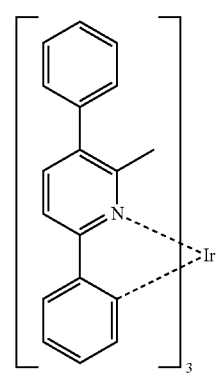

D-4

D-5
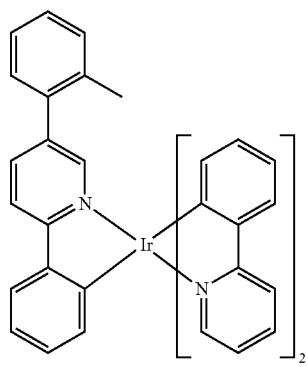
D-6
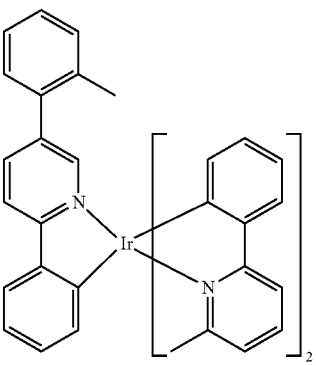
D-7
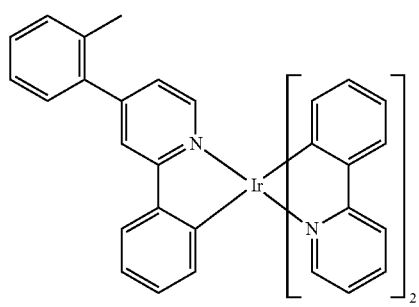
D-8
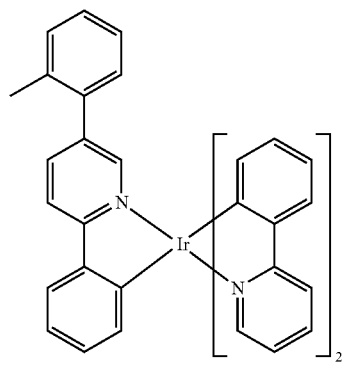
D-9
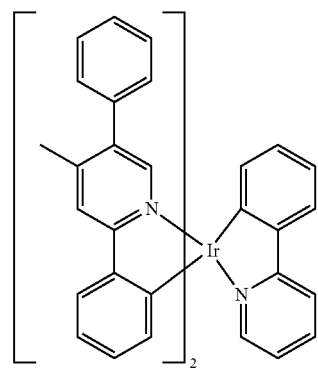
D-10
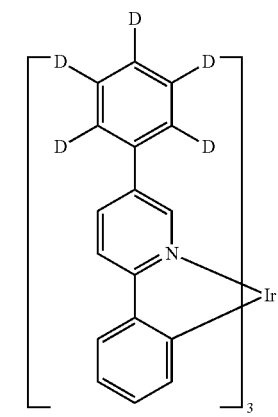
D-11
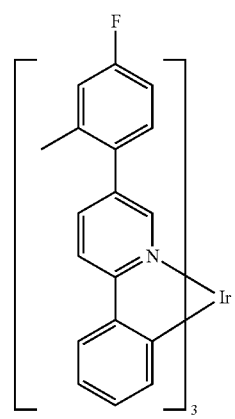
D-12
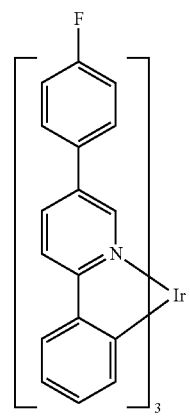

D-13 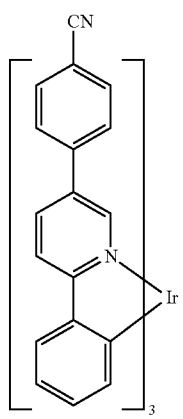
D-14
D-15
D-16
D-17 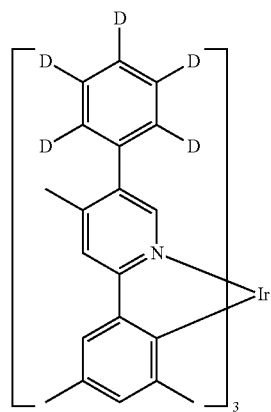
D-18 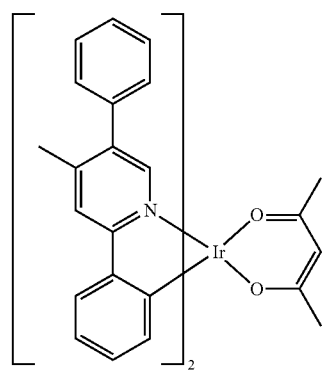
D-19 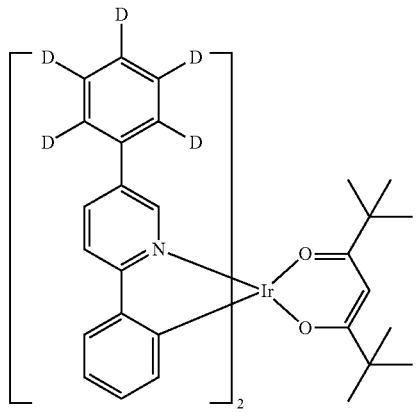
D-20 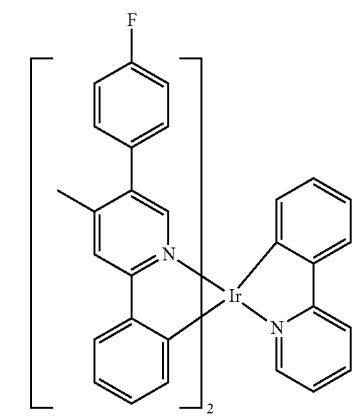

D-21
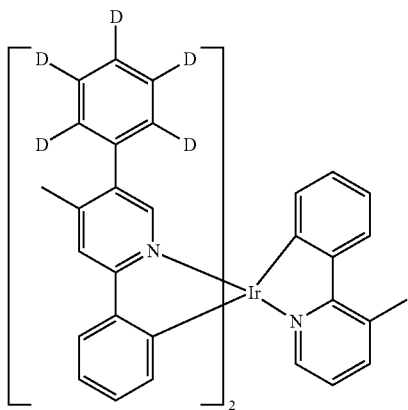
D-22
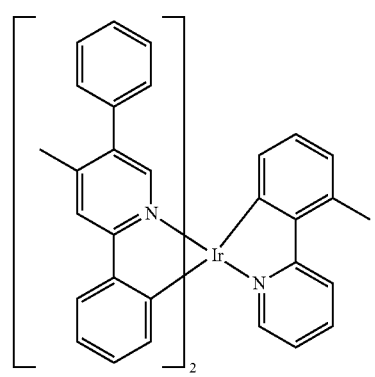
D-23
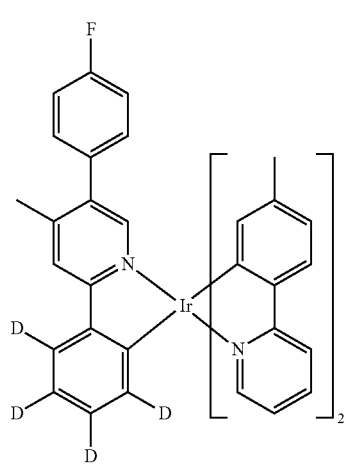
D-24
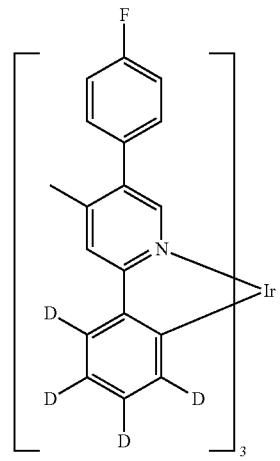
D-25
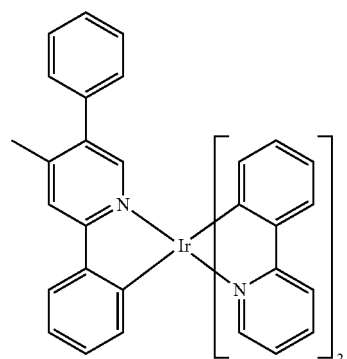
D-26
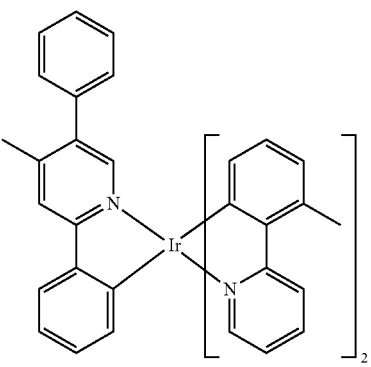
D-27
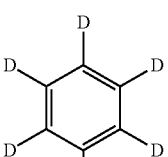
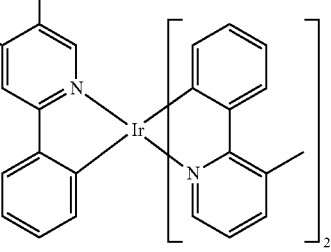

-continued
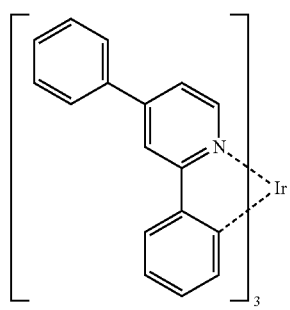
D-28
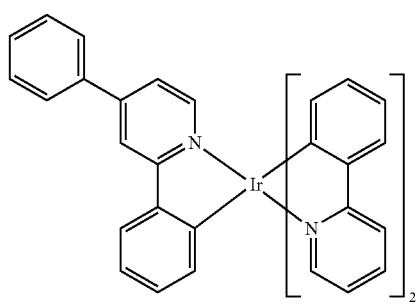
D-29
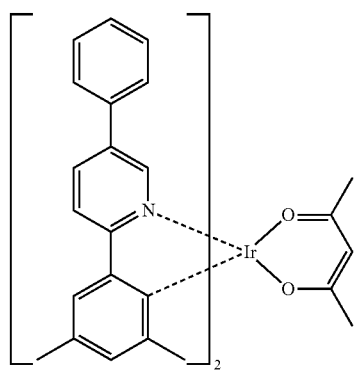
D-30
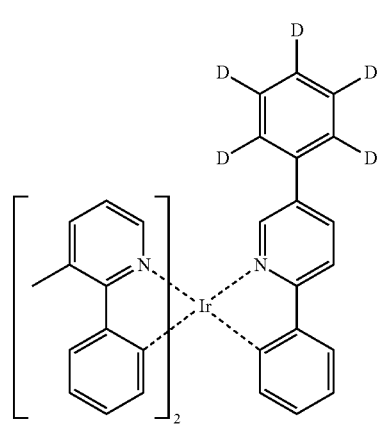
D-31
-continued
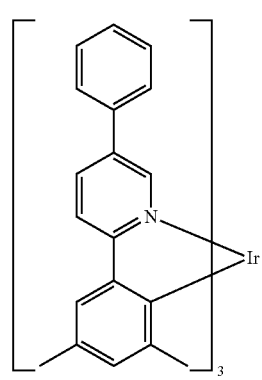
D-32
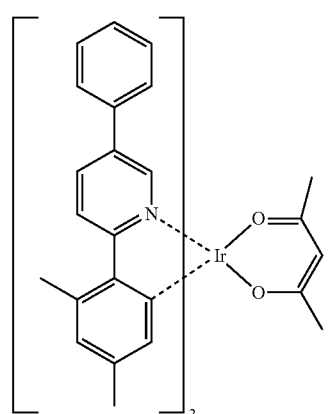
D-33
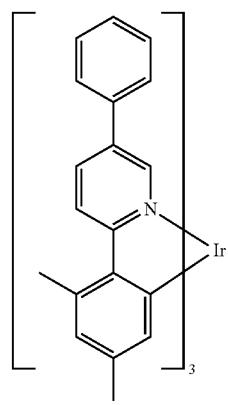
D-34
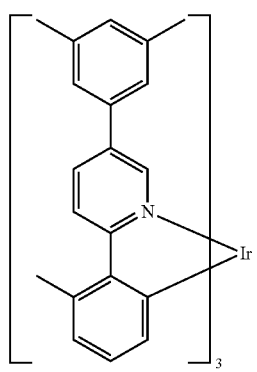
D-35

D-36 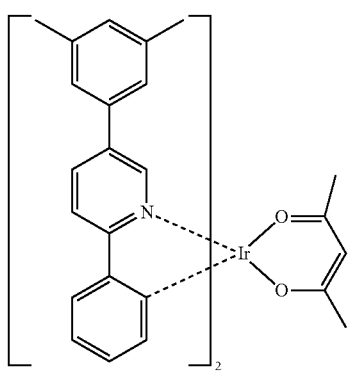
D-37 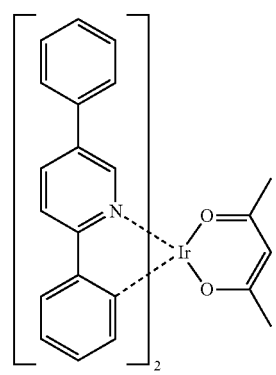
D-38 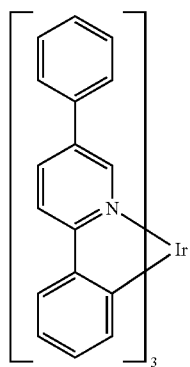
D-39 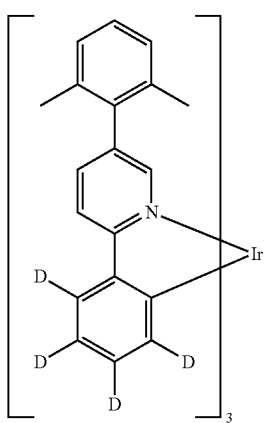
D-40 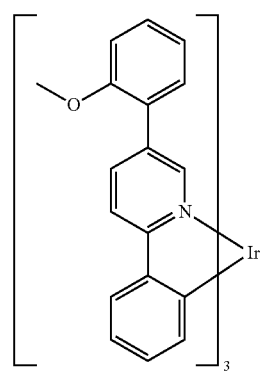
D-41 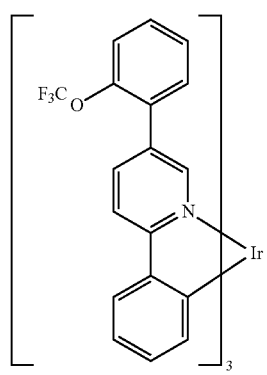
D-42 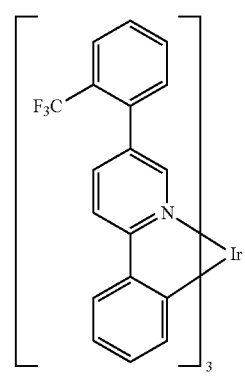
D-43 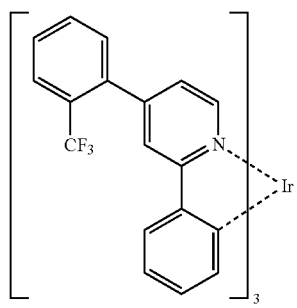

D-44 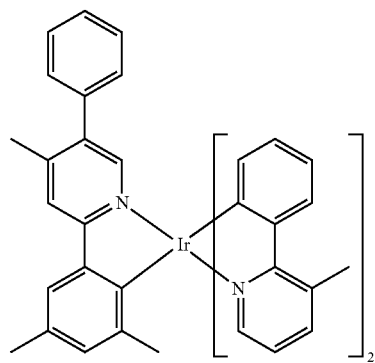
D-45 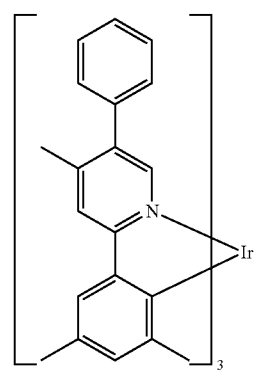
D-46 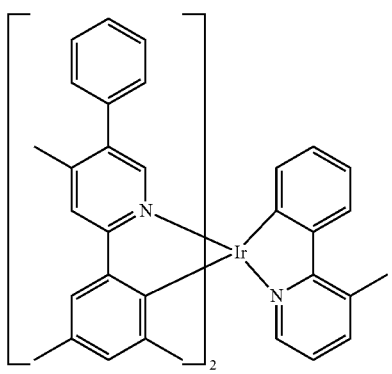
D-47 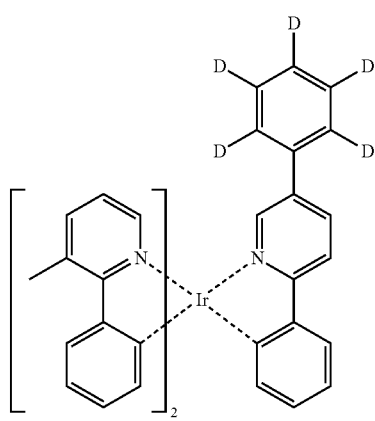
D-48 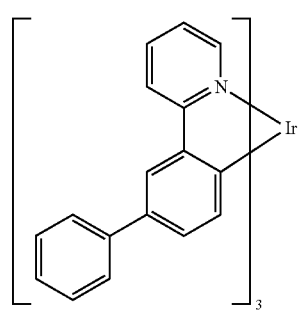
D-49 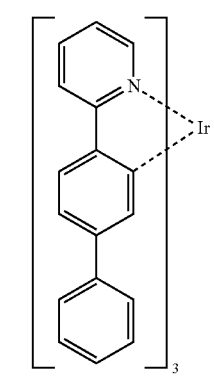
D-50 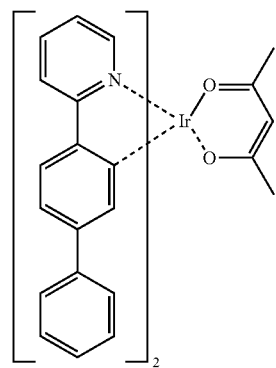
D-51 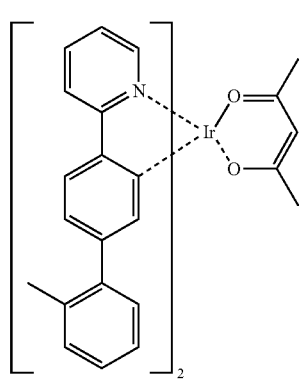

-continued
D-52
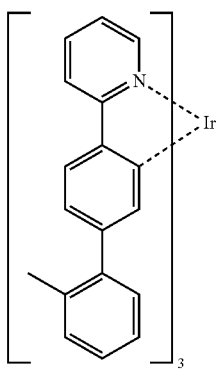
D-53
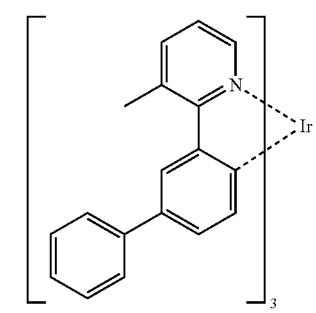
D-54
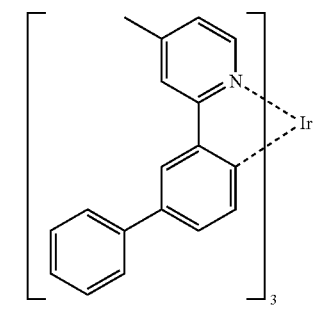
D-55
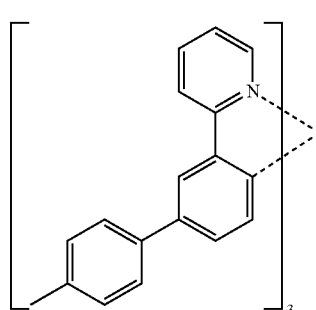
D-56
-continued
D-57
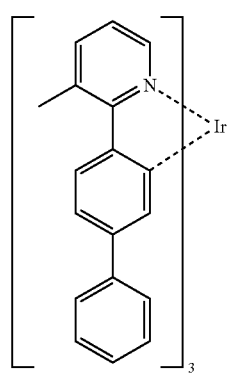
D-58
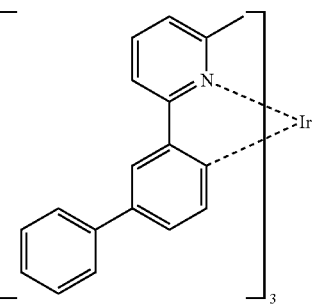
D-59
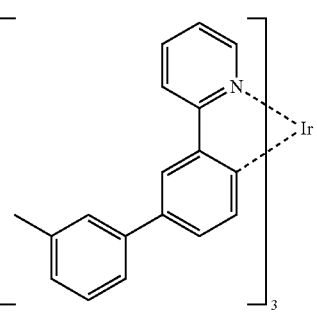
D-60

D-61
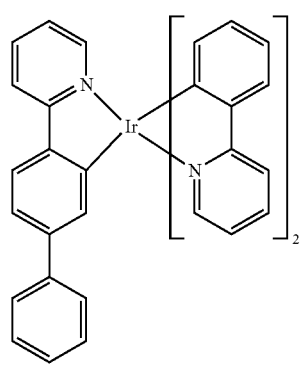
D-62
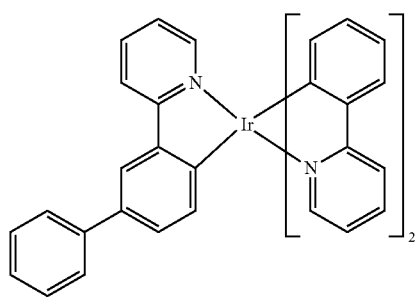
D-63
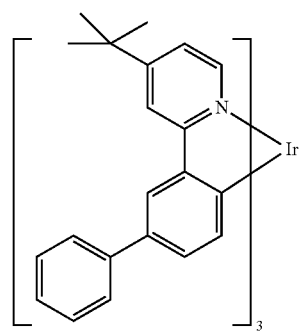
D-64
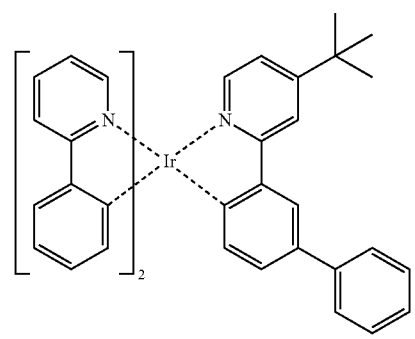
D-65
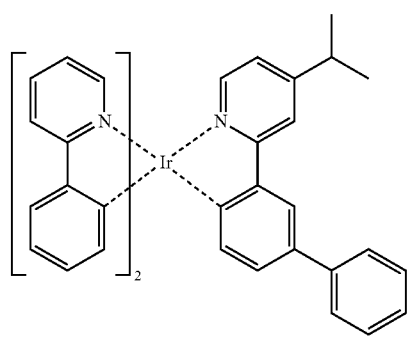
D-66
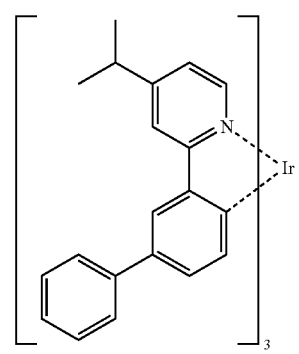
D-67
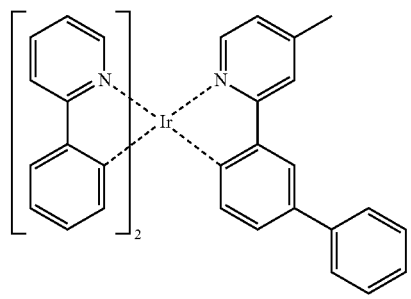
D-68
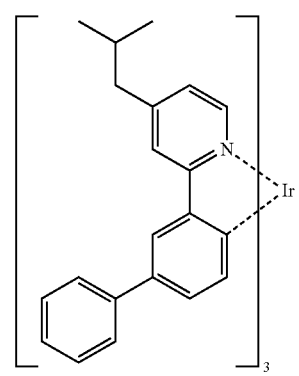

D-69
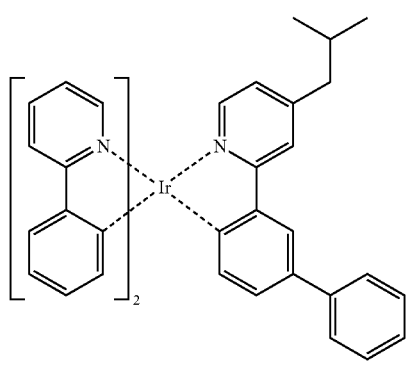
D-70
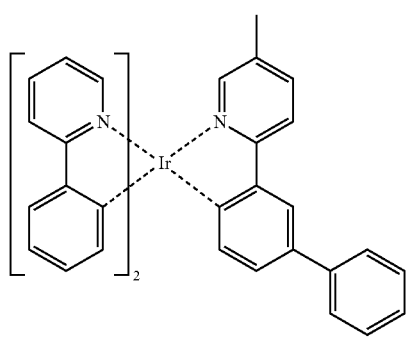
D-71
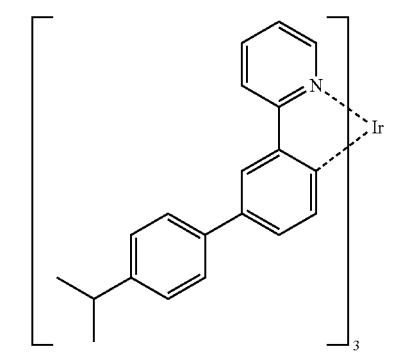
D-72
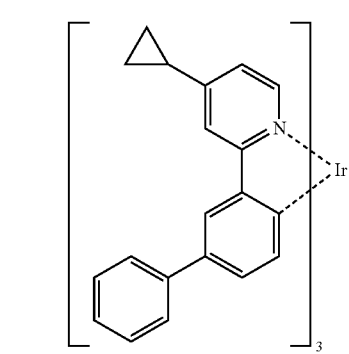
D-73
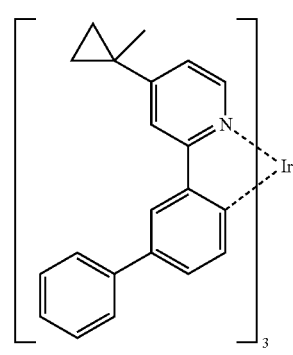
D-74
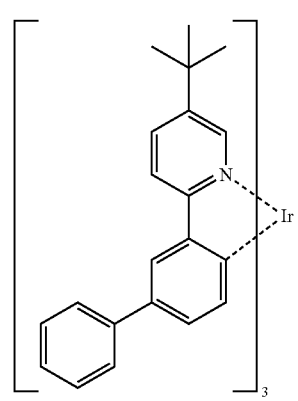
D-75
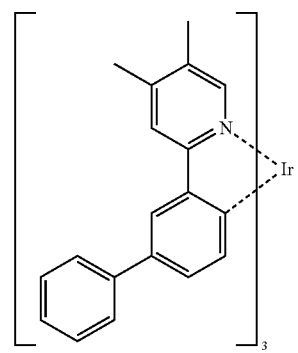
D-76
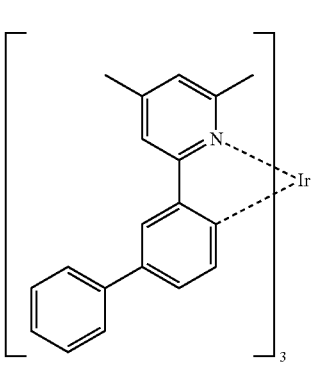

D-77 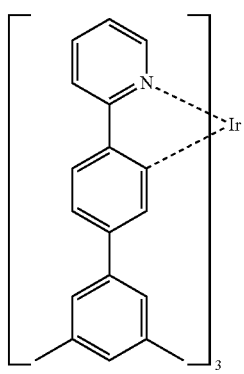
D-78 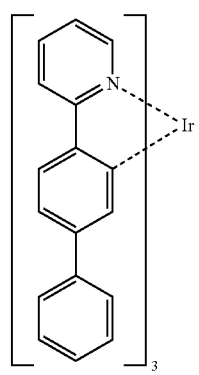
D-79 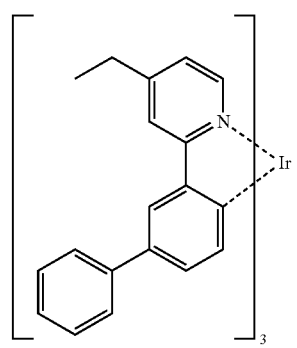
D-80 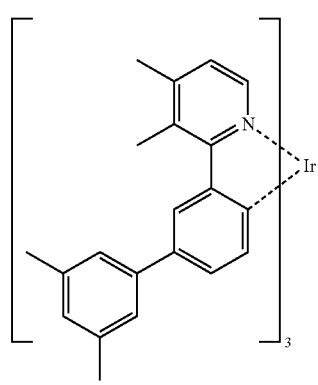
D-81 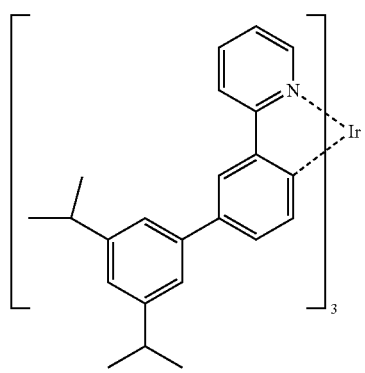
D-82 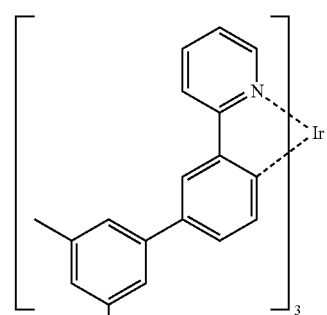
D-83 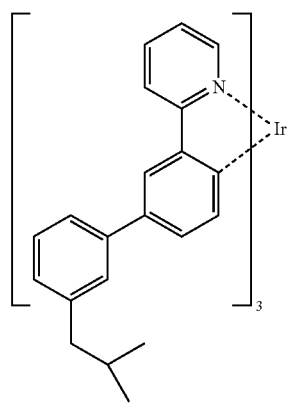
D-84 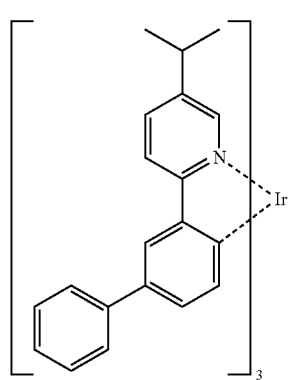

D-85
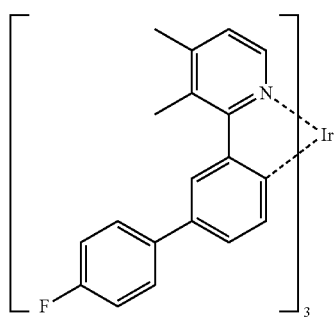
D-86
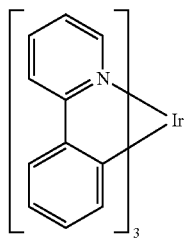
D-87
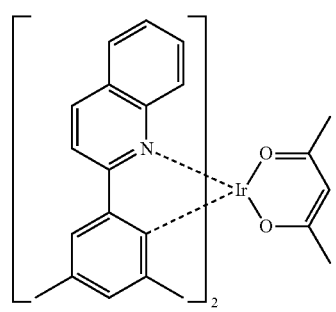
D-88
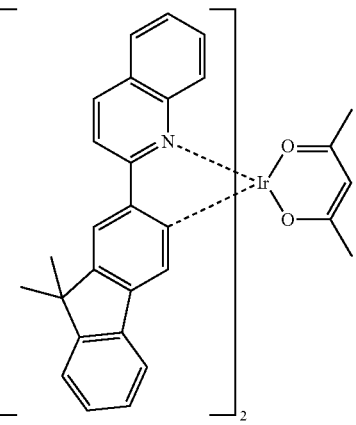
D-89
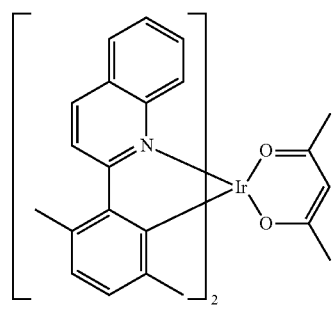
D-90
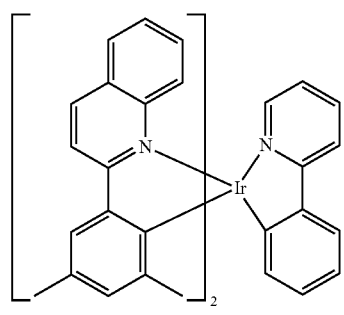
D-91
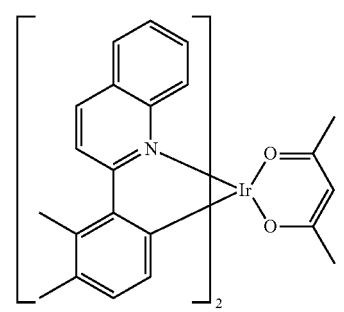
D-92
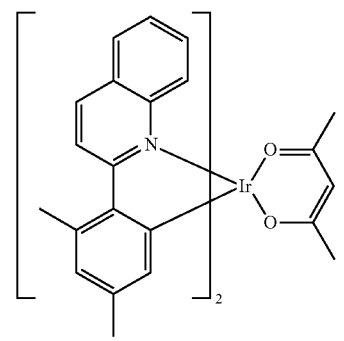
D-93
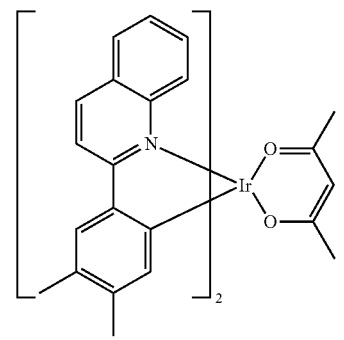

-continued
D-94
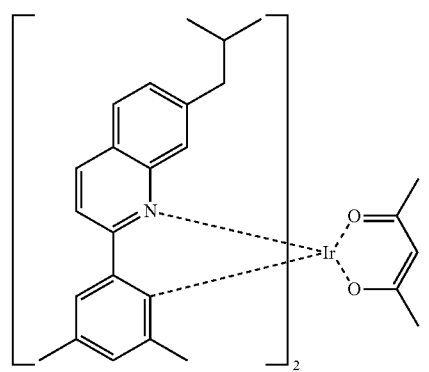
D-95
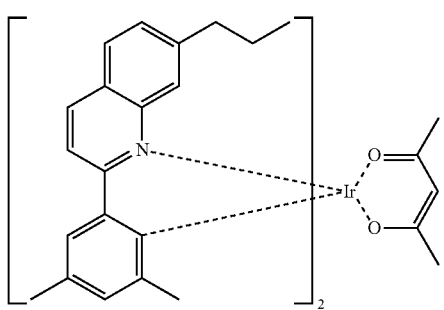
D-96
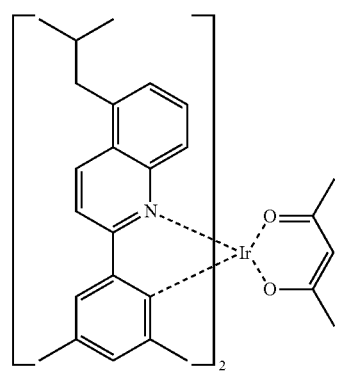
D-97
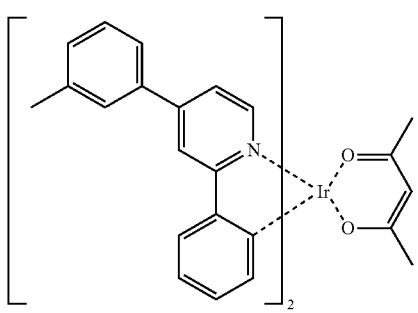
-continued
D-98
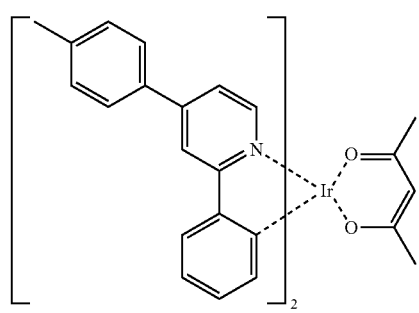
D-99
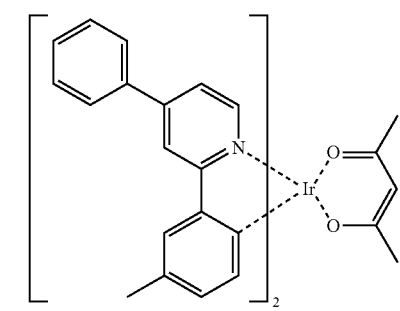
D-100
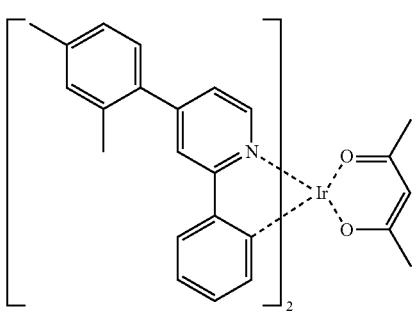
D-101
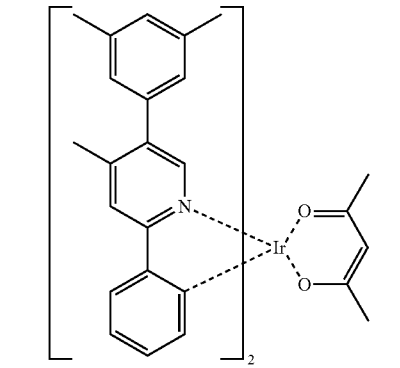
D-102
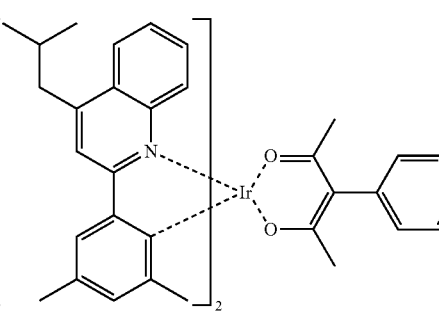

D-103
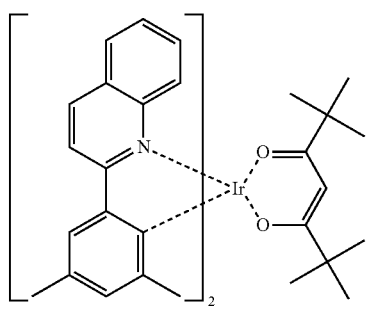
D-104
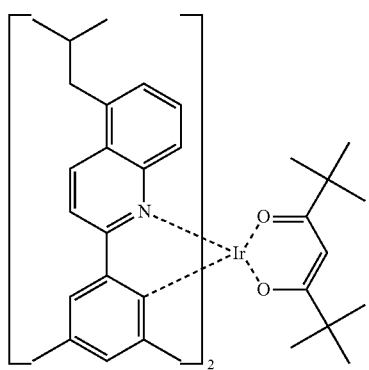
D-105
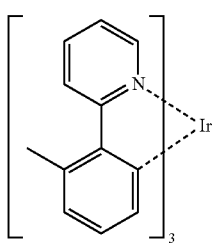
D-106
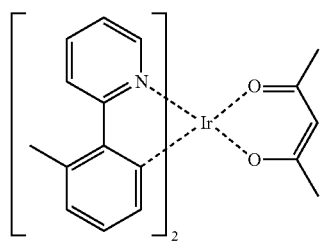
D-107
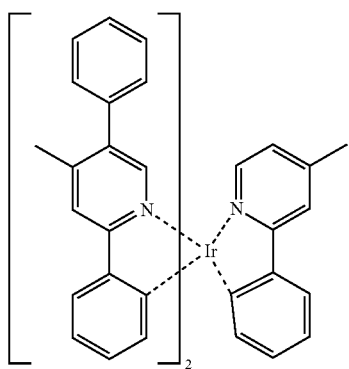
D-108
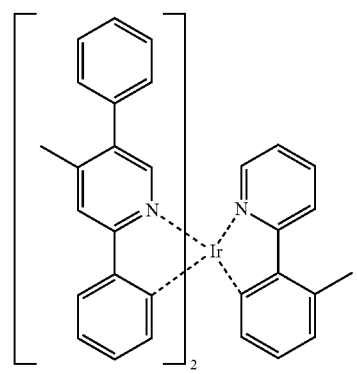
D-109
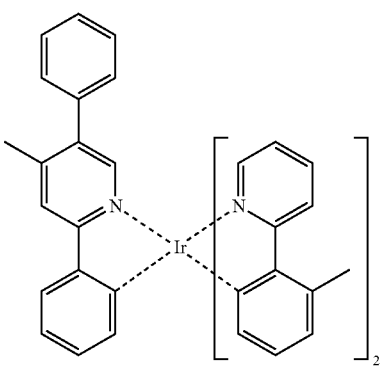
D-110
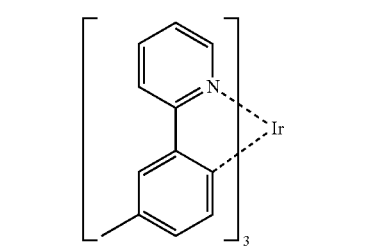
D-111
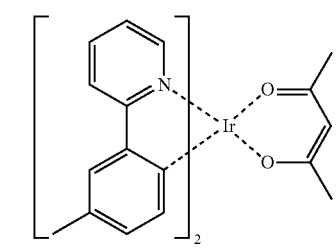
D-112
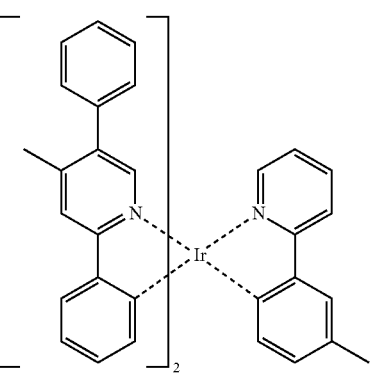

D-113 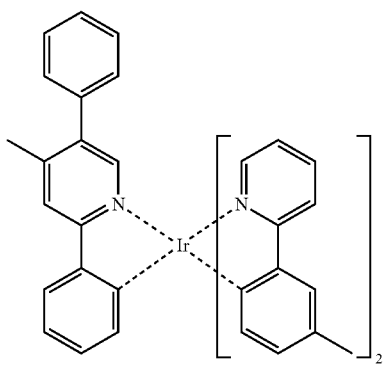
D-114 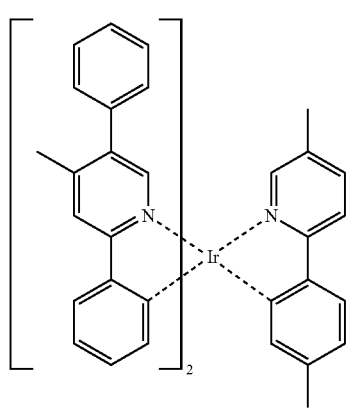
D-115 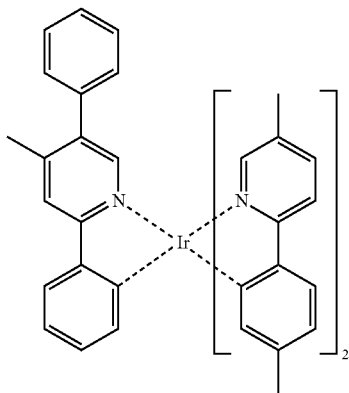
D-116 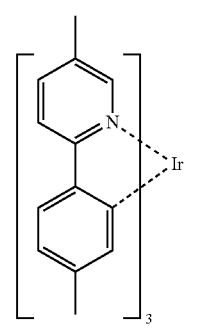
D-117 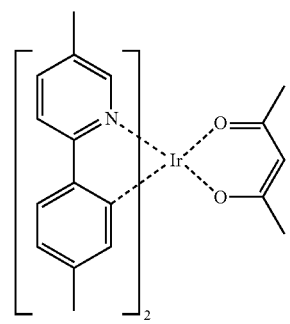
D-118 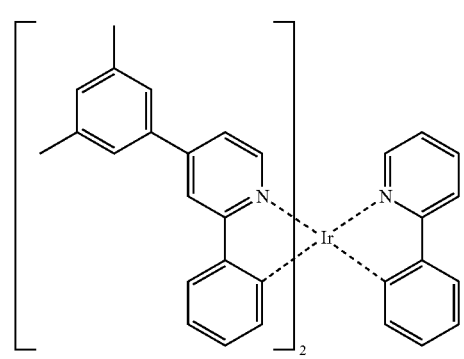
D-119 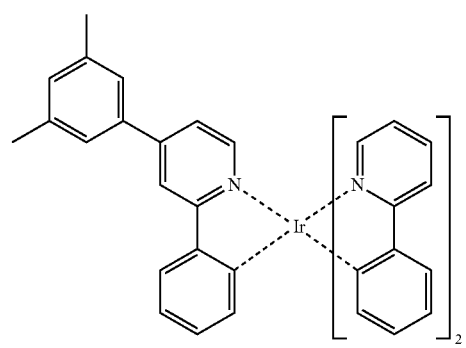
D-120 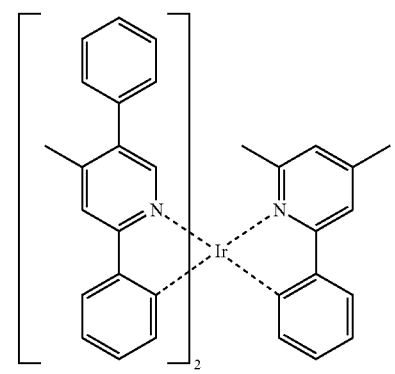

D-121
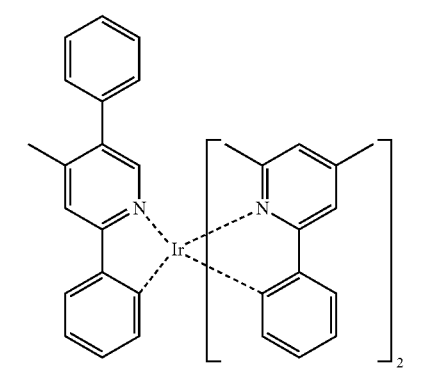
D-122
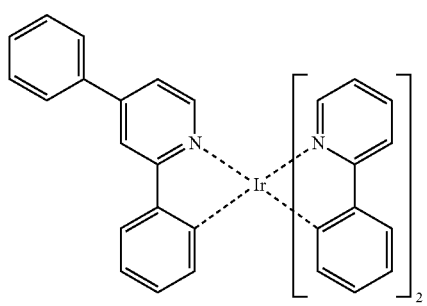
D-123
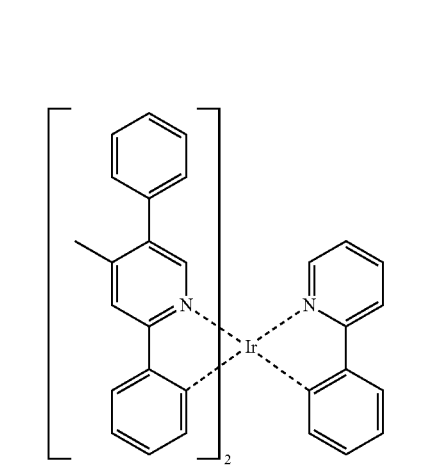
D-124
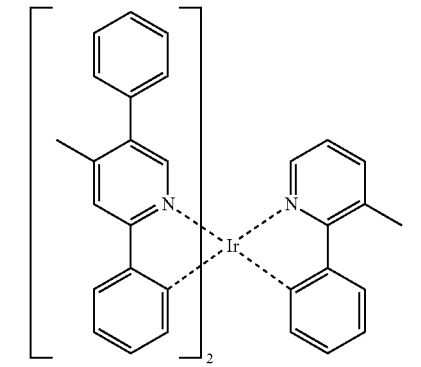
D-125
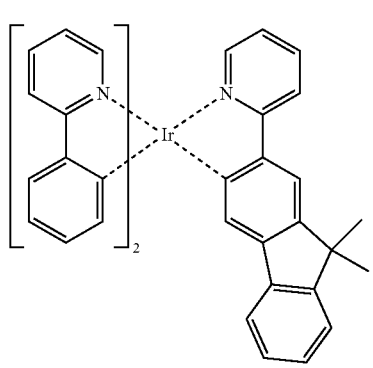
D-126
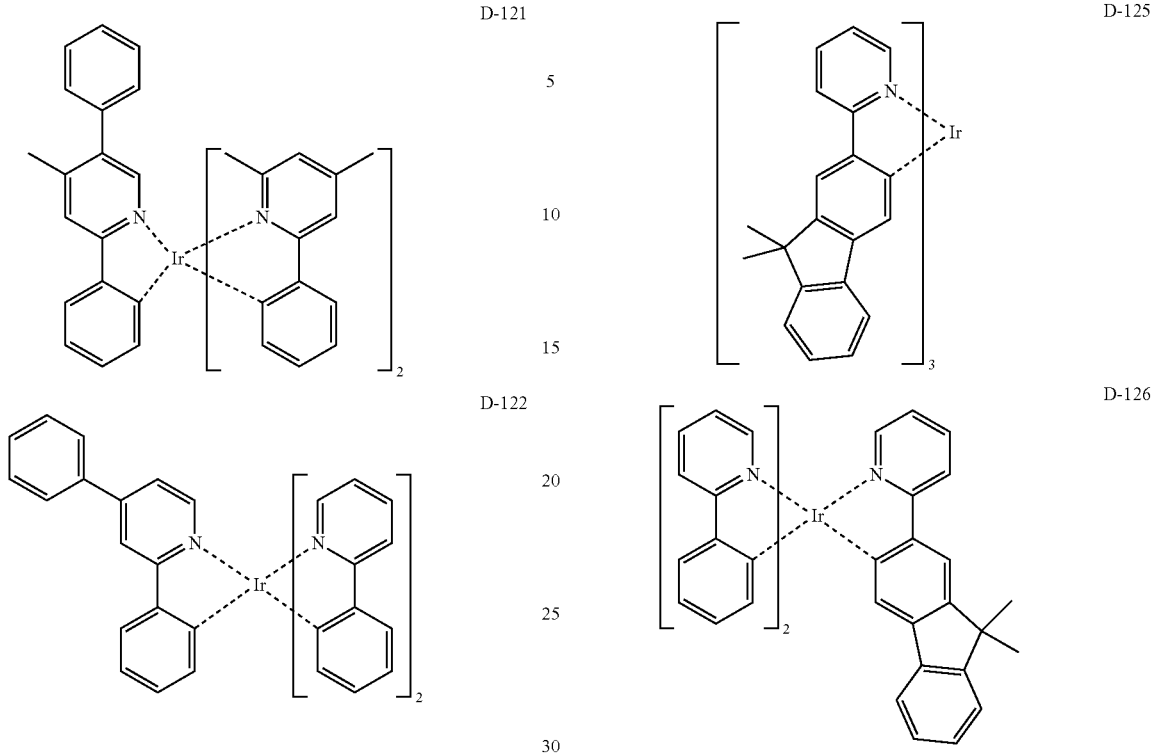
D-127
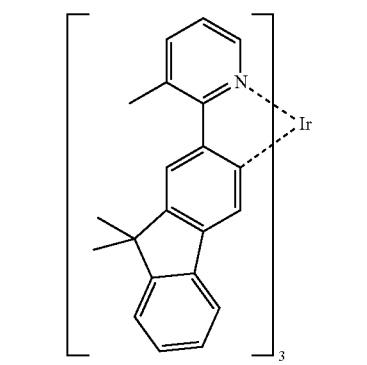
D-128
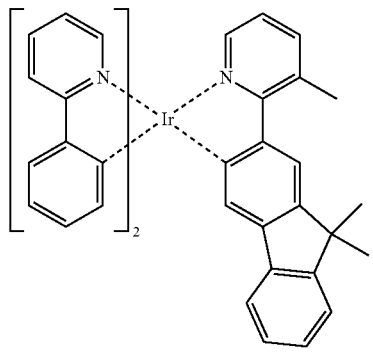

D-129 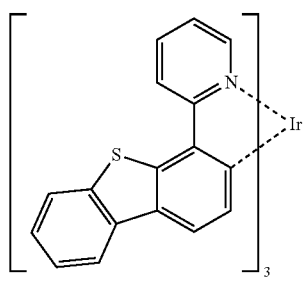
D-130 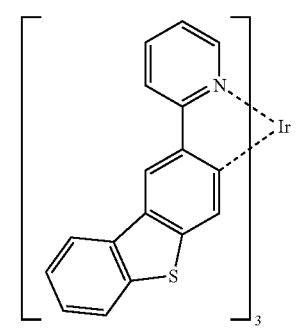
D-131 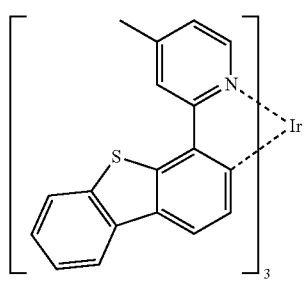
D-132 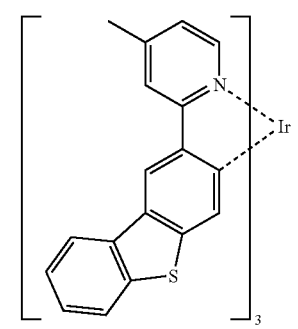
D-133 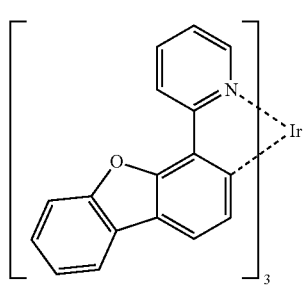
D-134 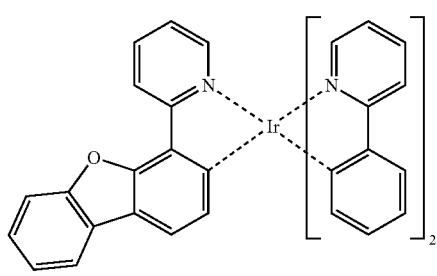
D-135 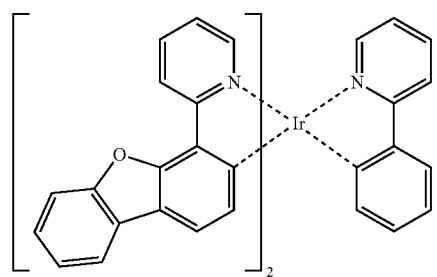
D-136 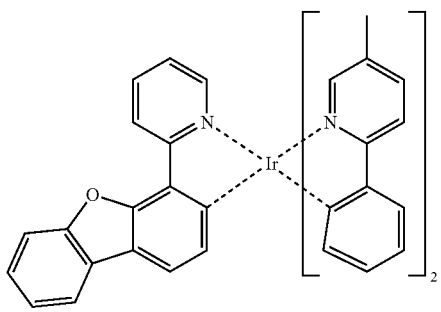
D-137 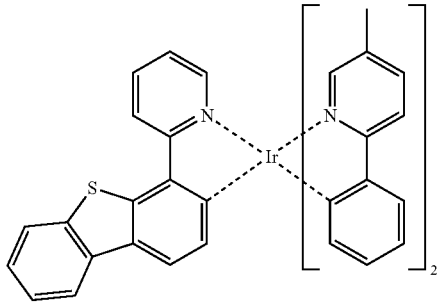
D-138 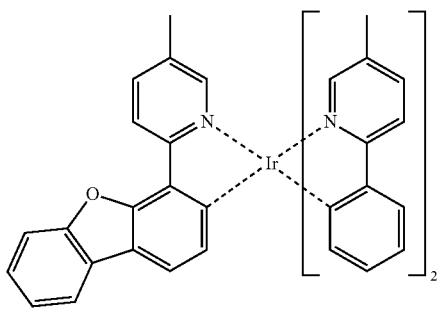

D-139
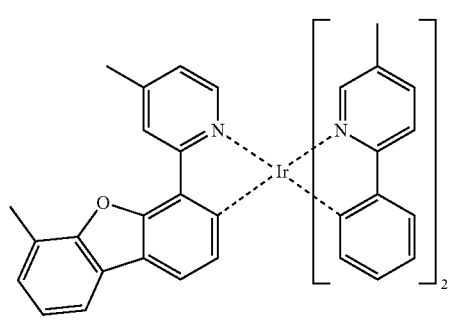
D-140
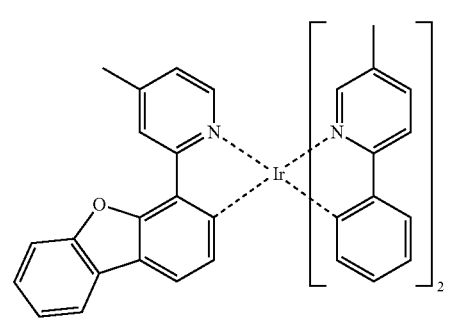
D-141
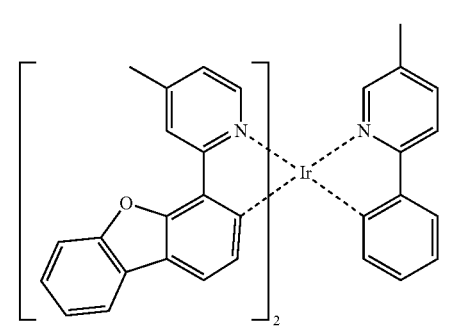
D-142
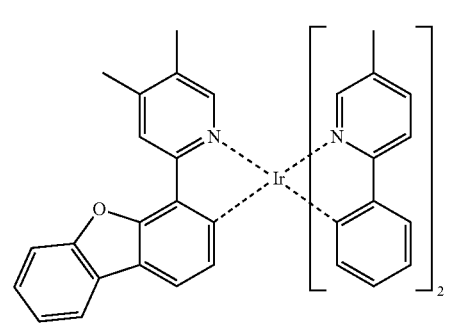
D-143
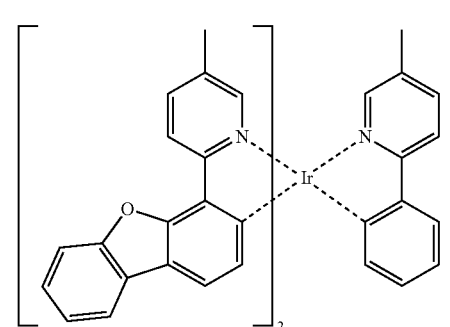
D-144
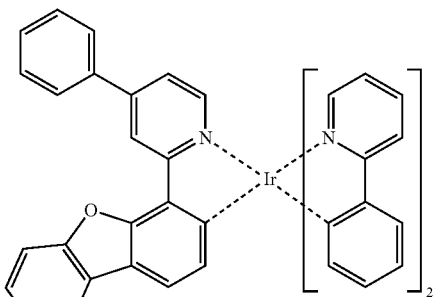
D-145
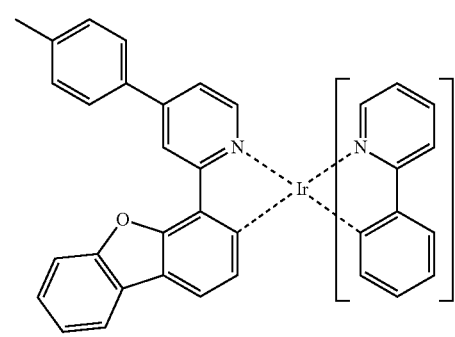
D-146
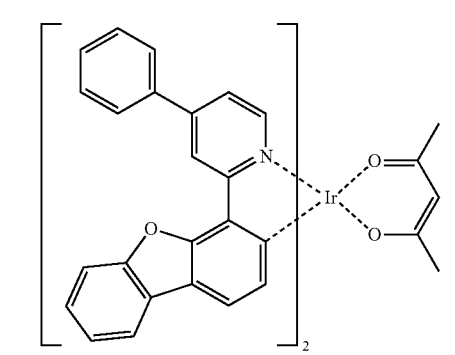
D-147
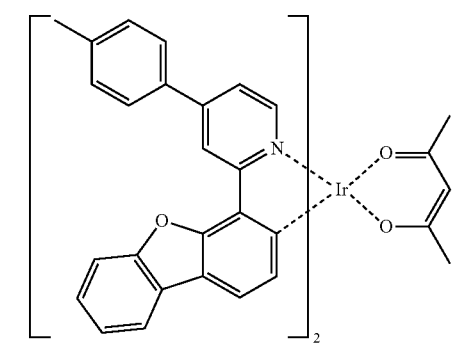

D-148
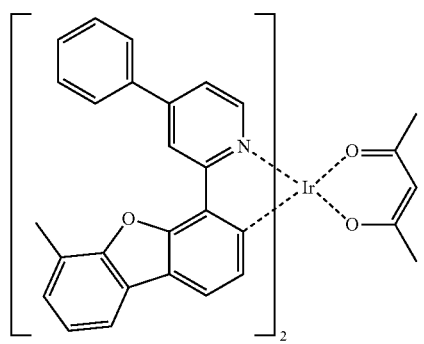
D-149
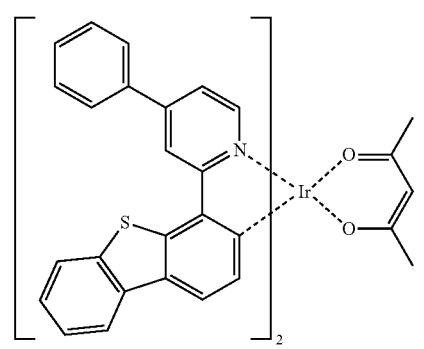
D-150
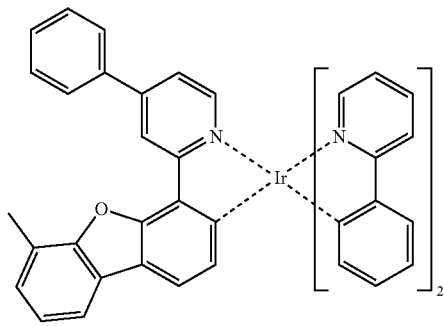
D-151
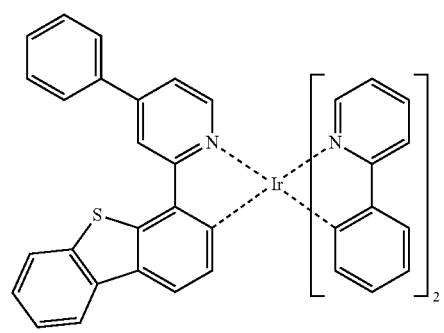
D-152
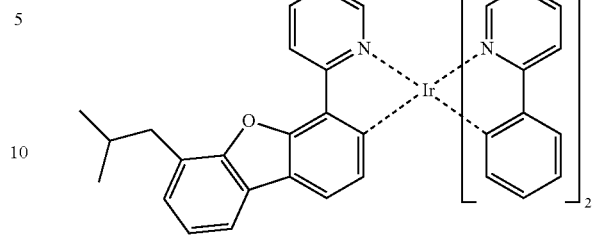
D-153
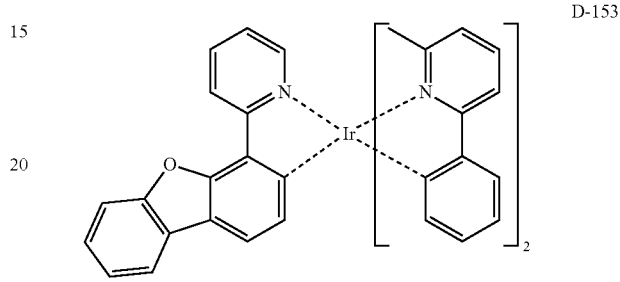
D-154
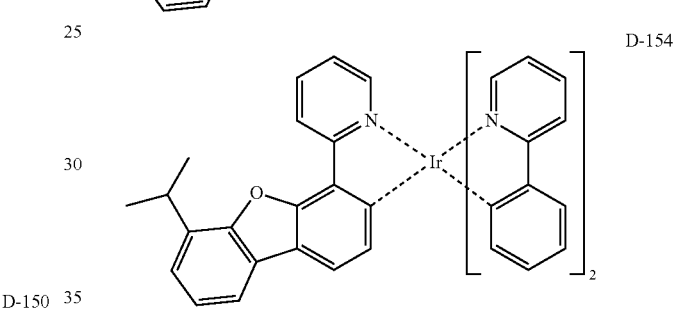
D-155
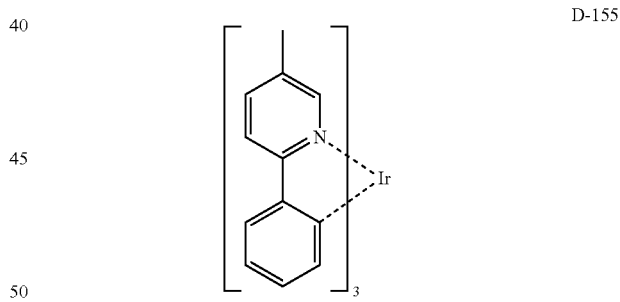
D-156
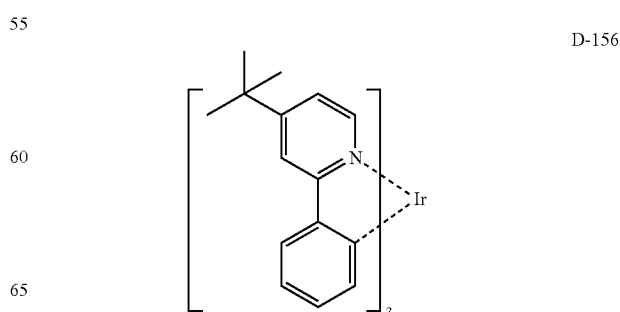

D-157
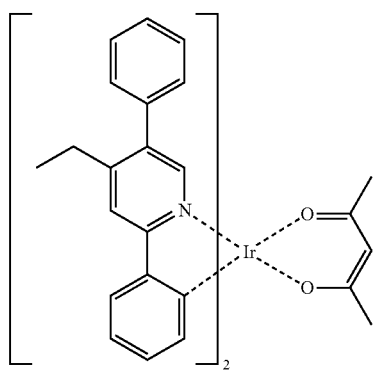
D-158
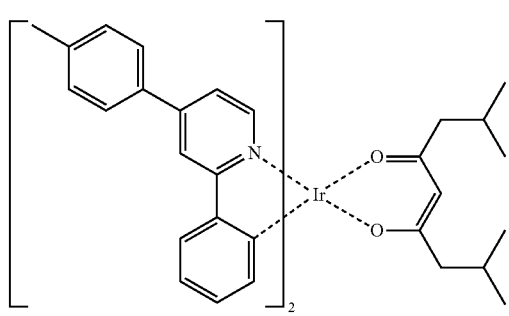
D-159
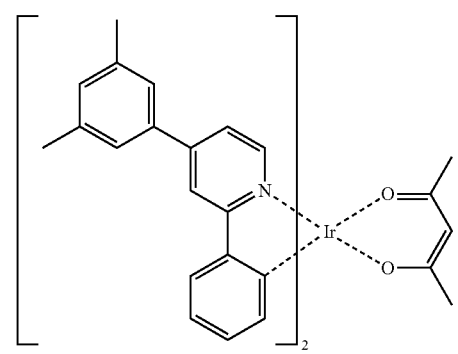
D-160
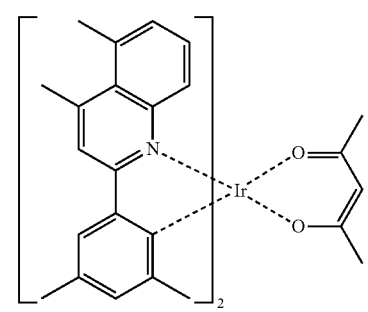
D-161
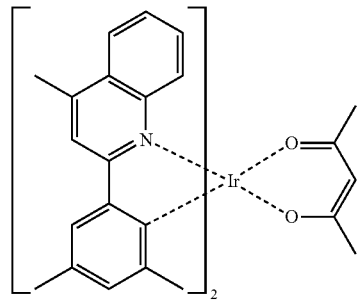
D-162
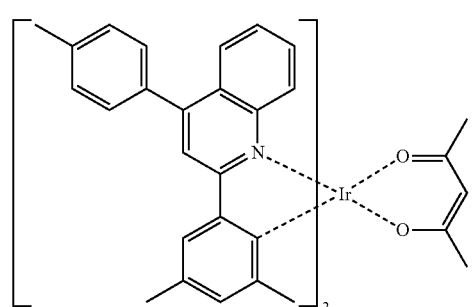
D-163
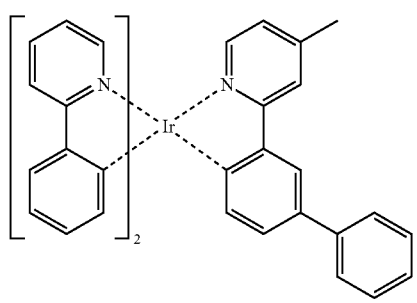
D-164
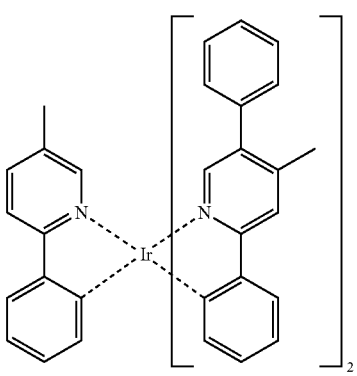
D-165
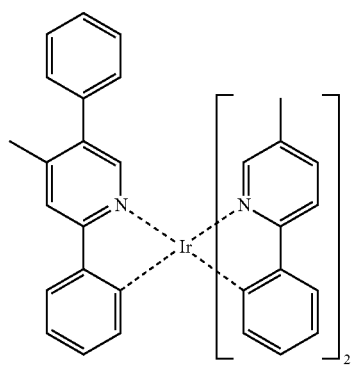

D-166
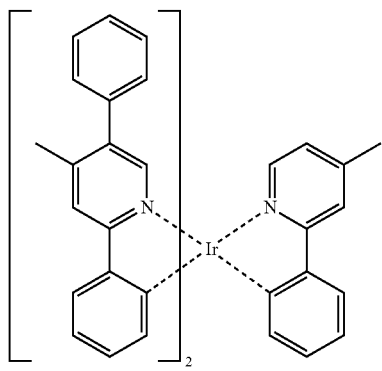
D-167
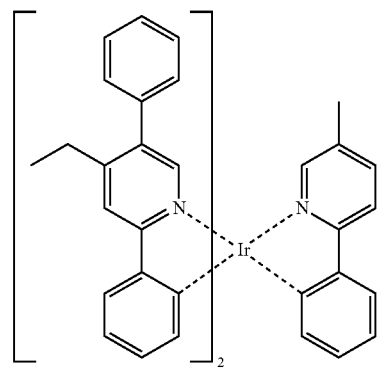
D-168
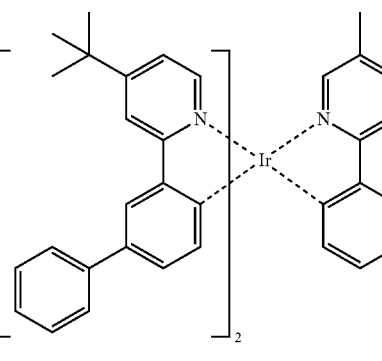
D-169
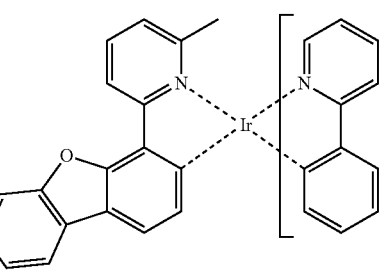
D-170
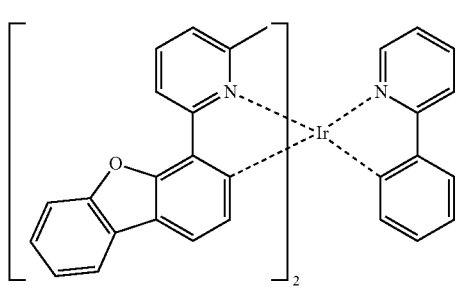
D-171
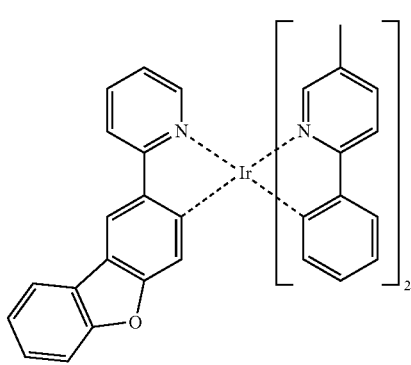
D-172
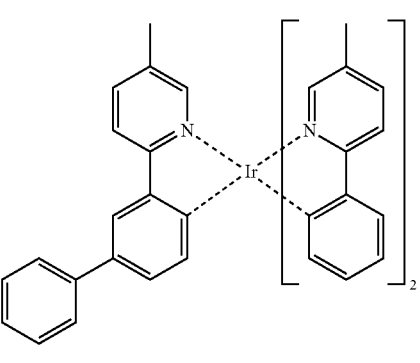
D-173
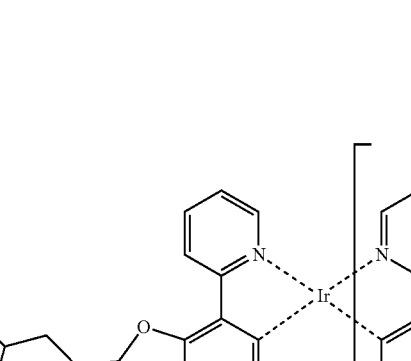
D-174
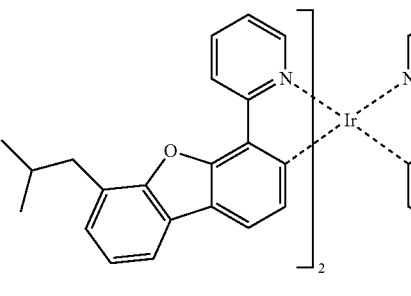

-continued
D-175
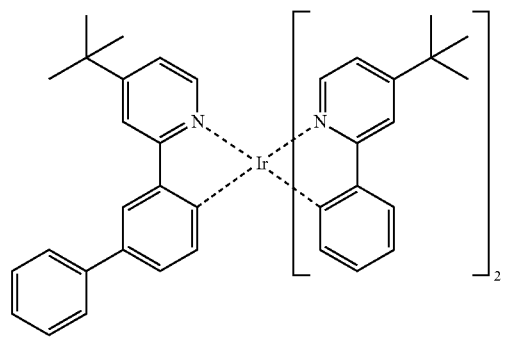
D-176
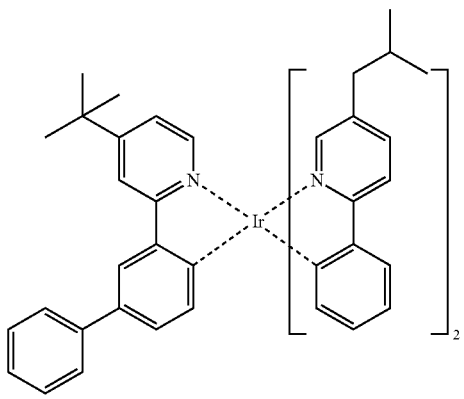
D-177
D-178
-continued
D-179
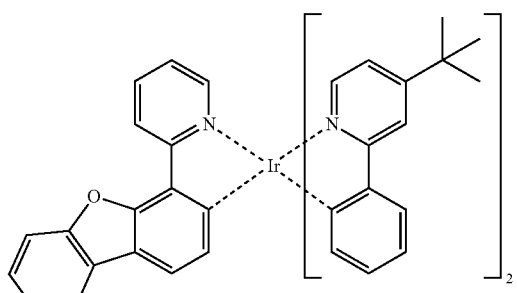
D-180
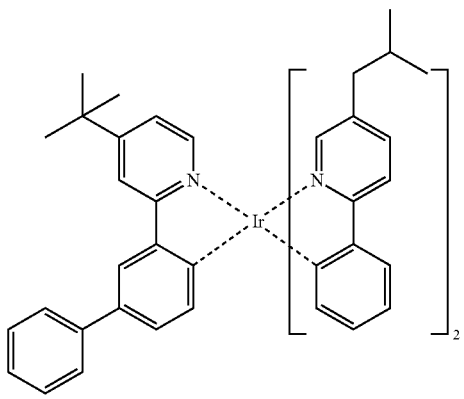
D-181
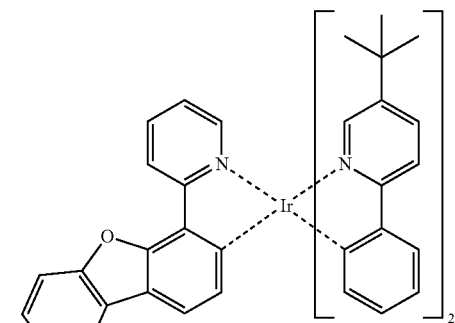
D-182
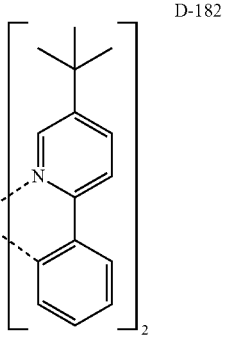

D-183 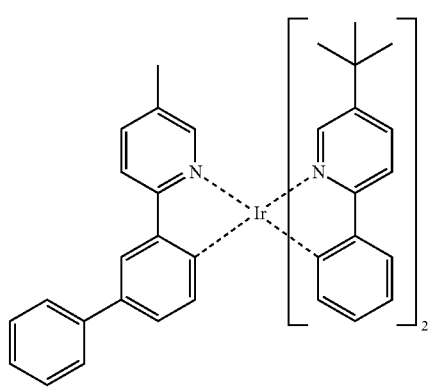
D-184 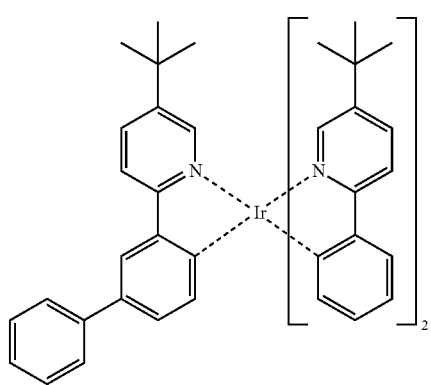
D-185 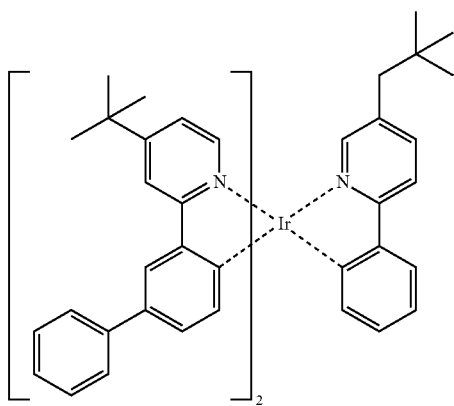
D-186 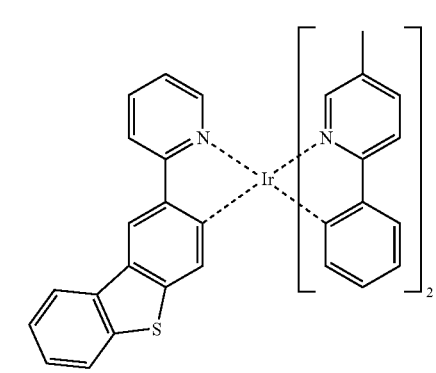
D-187 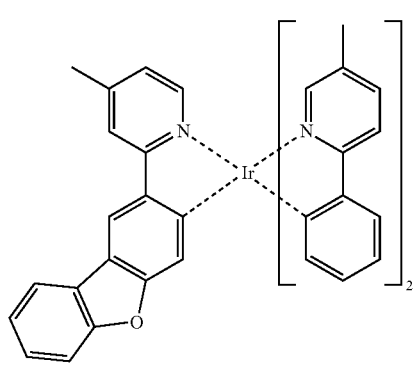
D-188 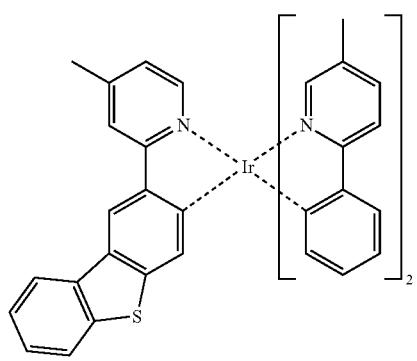
D-189 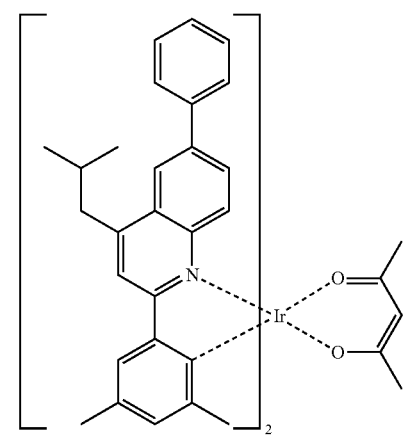
D-190 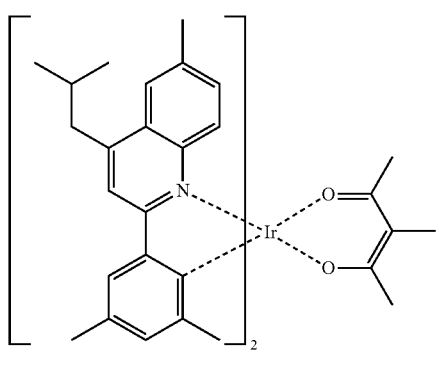

D-191
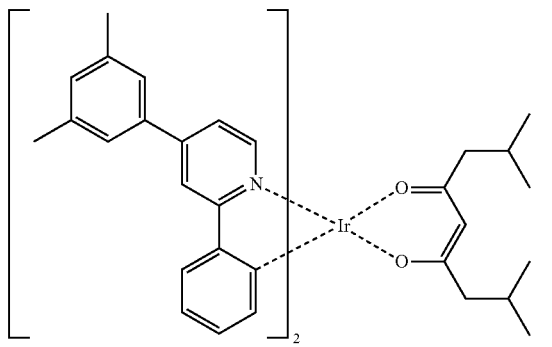
D-192
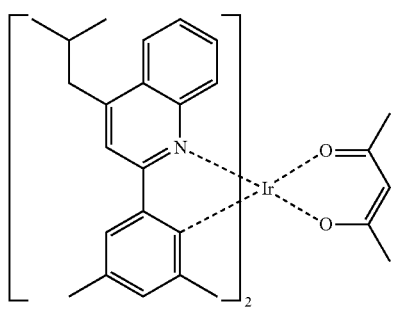
D-193
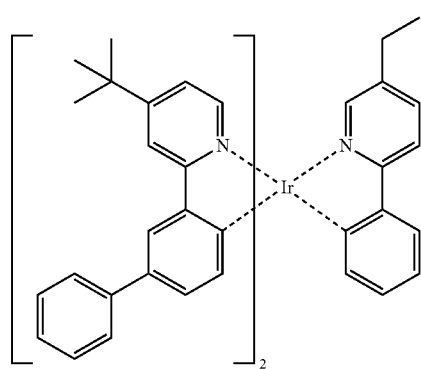
D-194
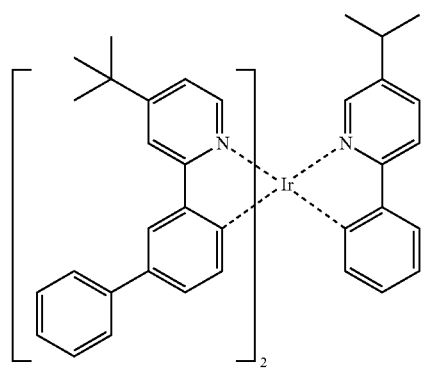
D-195
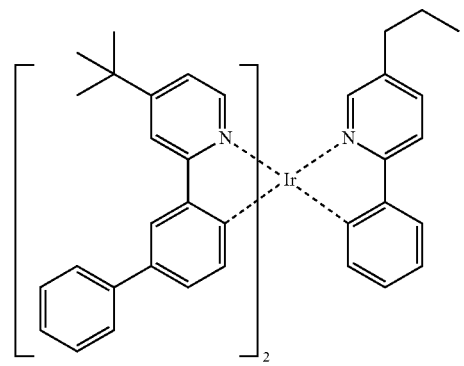
D-196
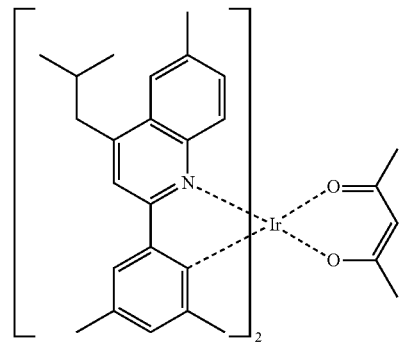
D-197
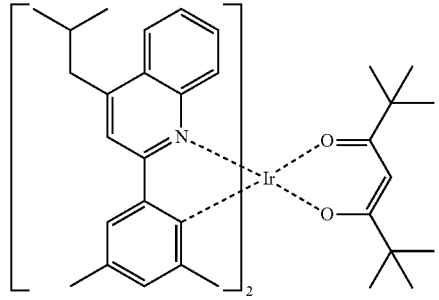
D-198

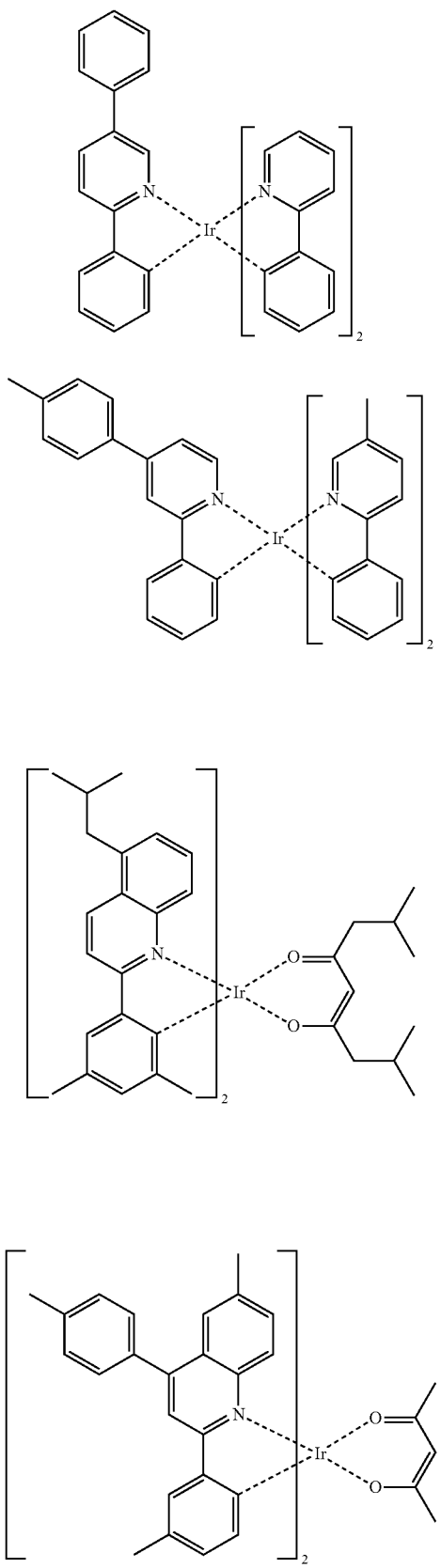
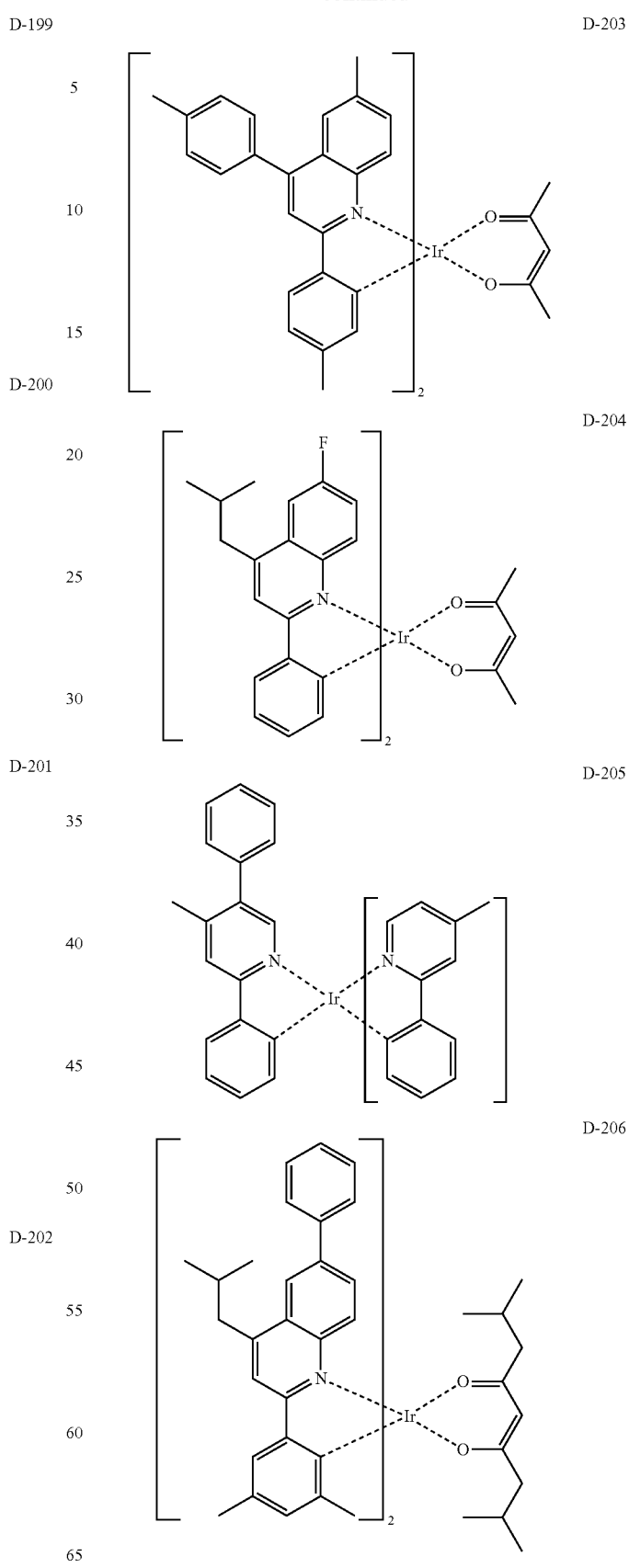

D-207

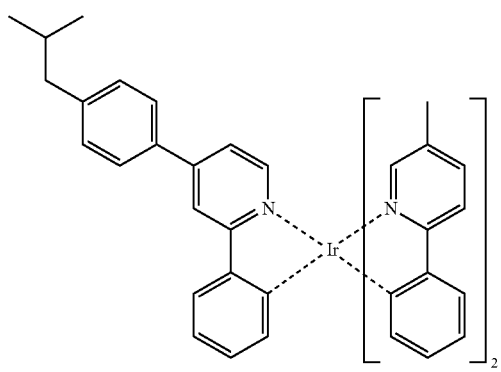

D-208

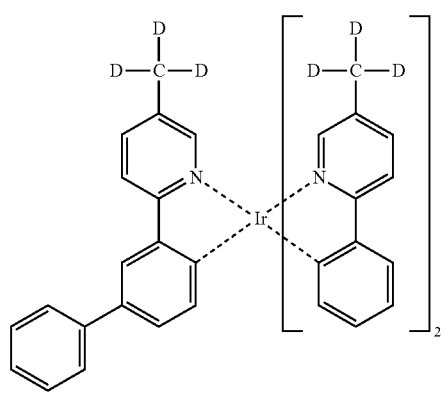

D-209

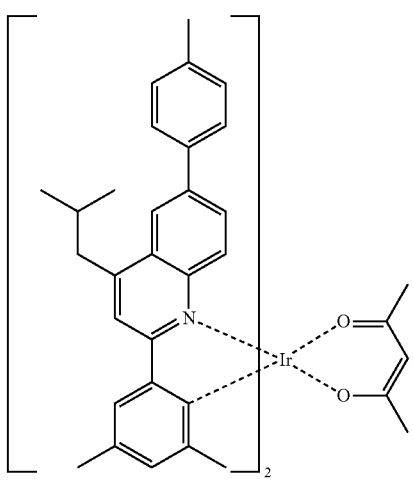

D-210

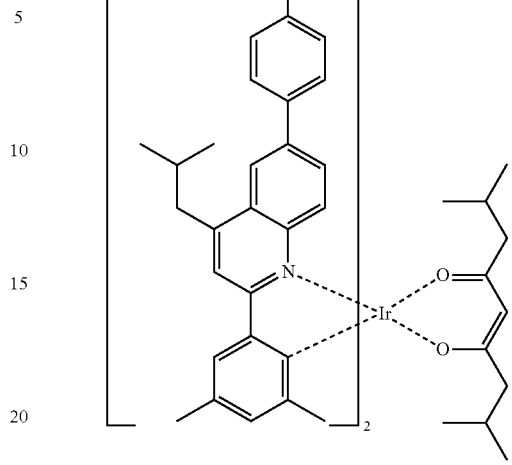

The organic electroluminescent device of the present disclosure may further comprise at least one compound selected from the group consisting of arylamine-based compounds and styrylarylamine-based compounds at the organic layer.

Also, in the organic electroluminescent device of the present disclosure, the organic layer may further comprise at least one metal selected from the group consisting of metals of Group 1, metals of Group 2, transition metals of the $4^{th}$ period, transition metals of the $5^{th}$ period, lanthanides and organic metals of the d-transition elements of the Periodic Table, or at least one complex compound comprising the metal.

Preferably, in the organic electroluminescent device of the present disclosure, at least one layer (hereinafter, "a surface layer") may be placed on an inner surface(s) of one or both electrode(s), selected from a chalcogenide layer, a metal halide layer and a metal oxide layer. Specifically, a chalcogenide (includes oxides) layer of silicon or aluminum is preferably placed on an anode surface of an electroluminescent medium layer, and a metal halide layer or a metal oxide layer is preferably placed on a cathode surface of an electroluminescent medium layer. Such a surface layer provides operation stability for the organic electroluminescent device. Preferably, the chalcogenide includes $SiO_X$ (1≤X≤2), $AlO_X$ (1≤X≤1.5), SiON, SiAlON, etc.; the metal halide includes LiF, $MgF_2$, $CaF_2$, a rare earth metal fluoride, etc.; and the metal oxide includes $Cs_2O$, $Li_2O$, MgO, SrO, BaO, CaO, etc.

A hole injection layer, a hole transport layer, an electron blocking layer, or a combination thereof may be disposed between the anode and the light-emitting layer. The hole injection layer may be composed of two or more layers in order to lower an energy barrier for injecting holes from the anode to a hole transport layer or an electron blocking layer (or a voltage for injecting a hole). Each of the layers may comprise two or more compounds. The hole transport layer or electron blocking layer may be composed of two or more layers.

An electron buffering layer, a hole blocking layer, an electron transport layer, an electron injection layer, or a combination thereof may be disposed between the light-emitting layer and the cathode. The electron buffering layer may be composed of two or more layers in order to control the electron injection and improve characteristics of interface between the light-emitting layer and the electron injection layer. Each of the layers may comprise two or more compounds. The hole blocking layer or electron transport layer may be composed of two or more layers, and each of the layers may comprise two or more compounds.

In the organic electroluminescent device of the present disclosure, a mixed region of an electron transport compound and a reductive dopant, or a mixed region of a hole transport compound and an oxidative dopant may be placed on at least one surface of a pair of electrodes. In this case, the electron transport compound is reduced to an anion, and thus it becomes easier to inject and transport electrons from the mixed region to an electroluminescent medium. Furthermore, the hole transport compound is oxidized to a cation, and thus it becomes easier to inject and transport holes from the mixed region to the electroluminescent medium. Preferably, the oxidative dopant includes various Lewis acids and acceptor compounds, and the reductive dopant includes alkali metals, alkali metal compounds, alkaline earth metals, rare-earth metals, and mixtures thereof. A reductive dopant layer may be employed as a charge generating layer to prepare an electroluminescent device having two or more light-emitting layers and emitting white light.

In order to form each layer of the organic electroluminescent device of the present disclosure, dry film-forming methods such as vacuum evaporation, sputtering, plasma, ion plating methods, etc., or wet film-forming methods such as inkjet printing, nozzle printing, slot coating, spin coating, dip coating, flow coating methods, etc., can be used. In the organic electroluminescent device of the present disclosure, the first host compound and the second host compound may be film-formed by co-evaporation or mixture-evaporation.

When using a wet film-forming method, a thin film can be formed by dissolving or diffusing materials forming each layer into any suitable solvent such as ethanol, chloroform, tetrahydrofuran, dioxane, etc. The solvent can be any solvent where the materials forming each layer can be dissolved or diffused, and where there are no problems in film-formation capability.

A co-evaporation indicates a process for two or more materials to be deposited as a mixture, by introducing each of the two or more materials into respective crucible cells, and applying electric current to the cells for each of the materials to be evaporated. Herein, a mixture-evaporation indicates a process for two or more materials to be deposited as a mixture, by mixing the two or more materials in one crucible cell before the deposition, and applying electric current to the cell for the mixture to be evaporated.

Also, the organic electroluminescent device of the present disclosure can be used for the manufacture of a display system or a lighting system.

Hereinafter, the luminescent properties of the device comprising the host compound of the present disclosure will be explained in detail with reference to the following examples.

[Device Examples 1-1 to 1-27] Production of an OLED Device by a Co-Evaporation of a First Host Compound and a Second Host Compound of the Present Disclosure as a Host An OLED device was produced comprising a plurality of host compounds of the present disclosure as follows. A transparent electrode indium tin oxide (ITO) thin film (10 Ω/sq) on a glass substrate for an organic electroluminescent device (OLED) (Geomatec) was subjected to an ultrasonic washing with acetone, ethanol, and distilled water sequentially, and was then stored in isopropanol. The ITO substrate was then mounted on a substrate holder of a vacuum vapor depositing apparatus. $N^4,N^{4'}$-diphenyl-$N^4,N^{4'}$-bis(9-phenyl-9H-carbazol-3-yl)-[1,1'-biphenyl]-4,4'-diamine was introduced into a cell of the vacuum vapor depositing apparatus, and then the pressure in the chamber of the apparatus was controlled to $10^{-6}$ torr, and evaporated by applying electric current to the cell, thereby forming a first hole injection layer having a thickness of 80 nm on the ITO substrate. Thereafter, dipyrazino[2,3-f:2',3'-h]quinoxaline-2,3,6,7,10,11-hexacarbonitrile was then introduced into another cell of the vacuum vapor depositing apparatus, and evaporated by applying electric current to the cell, thereby forming a second hole injection layer having a thickness of 5 nm on the first hole injection layer. N-([1,1'-biphenyl]-4-yl)-9,9-dimethyl-N-(4-(9-phenyl-9H-carbazol-3-yl)phenyl)-9H-fluorene-2-amine was introduced into one cell of the vacuum vapor depositing apparatus, and evaporated by applying electric current to the cell, thereby forming a first hole transport layer having a thickness of 10 nm on the second hole injection layer. N-(4-(9,9-diphenyl-9H,9'H-[2,9'-bifluorene]-9'-yl)phenyl)-(9,9-dimethyl-N-phenyl-9H-fluorene-2-amine was then introduced into another cell of the vacuum vapor depositing apparatus, and evaporated by applying electric current to the cell, thereby forming a second hole transport layer having a thickness of 60 nm on the first hole transport layer. After forming the hole injection layers and the hole transport layers, a light-emitting layer was then deposited as follows. As a host material, a first host compound and a second host compound shown in Table 1 below were introduced into two cells of the vacuum vapor depositing apparatus, respectively. A compound D-96 was introduced into another cell as a dopant. The two host compounds were evaporated at the same rate of 1:1, while the dopant was evaporated at a different rate from the host compounds, so that the dopant was deposited in a doping amount of 3 wt % based on the total amount of the host and dopant to form a light-emitting layer having a thickness of 40 nm on the hole transport layer. Next, 2,4-bis(9,9-dimethyl-9H-fluorene-2-yl)-6-(naphthalene-2-yl)-1,3,5-triazine and lithium quinolate were evaporated at the rate of 1:1 on another two cells of the vacuum vapor depositing apparatus to form an electron transport layer having a thickness of 30 nm on the light-emitting layer. After depositing lithium quinolate having a thickness of 2 nm as an electron injection layer on the electron transport layer, an Al cathode having a thickness of 80 nm was then deposited by another vacuum vapor deposition apparatus on the electron injection layer. Thus, an OLED device was produced.

[Comparative Examples 1-1 to 1-4] Production of an OLED Device Comprising a Second Host Compound of the Present Disclosure as a Sole Host An OLED device was produced in the same manner as in Device Examples 1-1 to 1-27, except that only a second host compound of Comparative Examples 1-1 to 1-4 shown in Table 1 was used as a sole host for a light-emitting layer.

[Comparative Examples 2-1 to 2-4] Production of an OLED Device Comprising a First Host Compound of the Present Disclosure as a Sole Host An OLED device was produced in the same manner as in Device Examples 1-1 to 1-27, except that only a first host compound of Comparative Examples 2-1 to 2-4 shown in Table 1 was used as a sole host for a light-emitting layer.

[Comparative Examples 3-1 to 3-3] Production of an OLED Device Comprising a First Host Compound of the Present Disclosure and a Second Host Compound of a Conventional Organic Electroluminescent Compound as a Host An OLED device was produced in the same manner as in Device Examples 1-2 and 1-14, except that only any one of Com-1 to Com-3 below, which are conventional organic electroluminescent compounds, was used as a second host for a light-emitting layer.

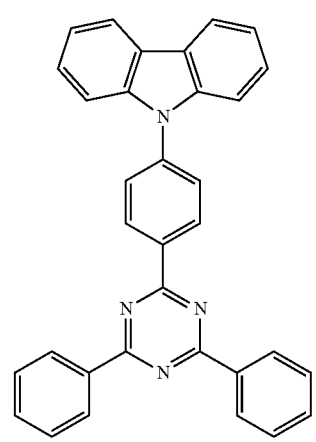

Com-1

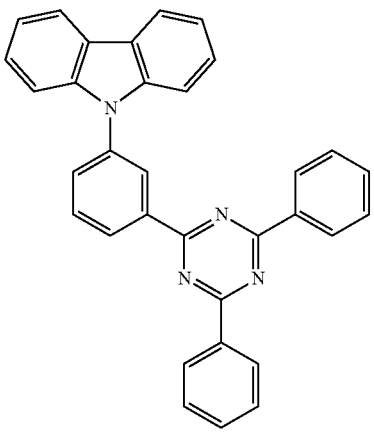

Com-2

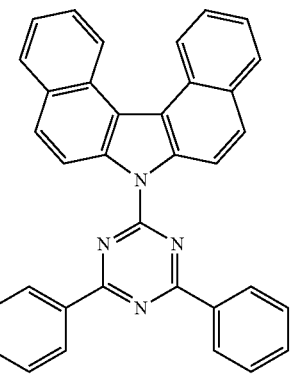

Com-3

The characteristics of the organic electroluminescent devices produced in Device Examples 1-1 to 1-27, and Comparative Examples 1-1 to 1-4, 2-1 to 2-4, and 3-1 to 3-3 are shown in Table 1 below.

TABLE 1

|  | Host | Voltage [V] | Efficiency [cd/A] | Lifespan T97 [hr] | Color visualized by light-emission |
| --- | --- | --- | --- | --- | --- |
| Device Example 1-1 | H-114:C-1 | 3.9 | 30.8 | 96 | Red |
| Device Example 1-2 | H-13:C-1 | 3.3 | 29.6 | 72 | Red |
| Device Example 1-3 | H-49:C-1 | 3.6 | 30.2 | 114 | Red |
| Device Example 1-4 | H-143:C-1 | 4.0 | 30.5 | 84 | Red |
| Device Example 1-5 | H-133:C-1 | 3.8 | 30.8 | 124 | Red |
| Device Example 1-6 | H-170:C-1 | 4.1 | 30.9 | 71 | Red |
| Device Example 1-7 | H-171:C-1 | 3.8 | 30.7 | 95 | Red |
| Device Example 1-8 | H-172:C-1 | 3.8 | 30.1 | 123 | Red |
| Device Example 1-9 | H-143:C-2 | 3.6 | 30.3 | 78 | Red |
| Device Example 1-10 | H-150:C-2 | 3.5 | 30.1 | 67 | Red |
| Device Example 1-11 | H-173:C-2 | 3.5 | 29.9 | 53 | Red |
| Device Example 1-12 | H-143:C-9 | 3.9 | 31.3 | 88 | Red |
| Device Example 1-13 | H-174:C-9 | 3.6 | 30 | 54 | Red |
| Device Example 1-14 | H-13:C-9 | 3.2 | 29.1 | 80 | Red |
| Device Example 1-15 | H-175:C-9 | 3.2 | 30.8 | 47 | Red |
| Device Example 1-16 | H-176:C-9 | 3.2 | 29.6 | 51 | Red |
| Device Example 1-17 | H-114:C-9 | 3.7 | 31.3 | 137 | Red |
| Device Example 1-18 | H-150:C-9 | 3.7 | 30.3 | 76 | Red |
| Device Example 1-19 | H-143:C-37 | 3.8 | 31.7 | 56 | Red |
| Device Example 1-20 | H-85:C-9 | 3.5 | 30.7 | 132 | Red |
| Device Example 1-21 | H-91:C-1 | 3.9 | 31.1 | 51 | Red |
| Device Example 1-22 | H-93:C-1 | 3.8 | 31.1 | 88 | Red |
| Device Example 1-23 | H-133:C-9 | 3.7 | 31.3 | 97 | Red |
| Device Example 1-24 | H-96:C-9 | 3.7 | 31.4 | 61 | Red |
| Device Example 1-25 | H-173:C-9 | 3.7 | 30.8 | 91 | Red |
| Device Example 1-26 | H-85:C-1 | 3.6 | 29.2 | 94 | Red |
| Device Example 1-27 | H-1:C-1 | 3.2 | 29.0 | 61 | Red |
| Comparative Example 1-1 | C-1 | 3.7 | 31.0 | 31 | Red |
| Comparative Example 1-2 | C-2 | 3.2 | 28.7 | 15 | Red |

TABLE 1-continued

|  | Host | Voltage [V] | Efficiency [cd/A] | Lifespan T97 [hr] | Color visualized by light-emission |
|---|---|---|---|---|---|
| Comparative Example 1-3 | C-9 | 3.7 | 31 | 23 | Red |
| Comparative Example 1-4 | C-37 | 3.7 | 29.6 | 17 | Red |
| Comparative Example 2-1 | H-143 | 9.0 | 3.5 | X | Red |
| Comparative Example 2-2 | H-49 | 7.8 | 3.1 | X | Red |
| Comparative Example 2-3 | H-114 | 8.1 | 13.6 | X | Red |
| Comparative Example 2-4 | H-150 | 7.6 | 4.3 | X | Red |
| Comparative Example 3-1 | H-13:Com1 | 3.2 | 29.5 | 12 | Red |
| Comparative Example 3-2 | H-13:Com2 | 3.3 | 31.8 | 5 | Red |
| Comparative Example 3-3 | H-13:Com3 | 3.3 | 29.3 | 23 | Red |

* X indicates that lifespan of the device cannot be measured since the time is too short.

The driving voltage, the luminous efficiency and the color visualized by light-emission in Table 1 are based on a luminance of 1,000 nits of the organic electroluminescent devices, and the lifespan is the time taken to be 97% of the luminance when the early luminance at 5000 nits and a constant current is taken as 100% of the luminance.

From Table 1 above, it can be seen that an organic electroluminescent device comprising a plurality of host materials of the present disclosure has long lifespan while maintaining high luminous efficiency compared to conventional devices using only a sole host or a conventional organic electroluminescent compound.

The invention claimed is:

1. An organic electroluminescent device comprising at least one light-emitting layer disposed between an anode and a cathode, wherein the light-emitting layer comprises a host and a phosphorescent dopant, wherein the host comprises a plurality of host compounds, wherein at least a first host compound of a plurality of host compounds is represented by the following formula 1:

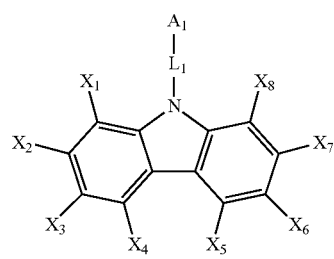

(1)

wherein $A_1$ represents a substituted or unsubstituted (C6-C30)aryl group, or a substituted or unsubstituted (5- to 30-membered)heteroaryl group, and $A_1$ may be linked to $X_1$ or $X_8$, provided that, when formula 1 is represented by the following formula 5,

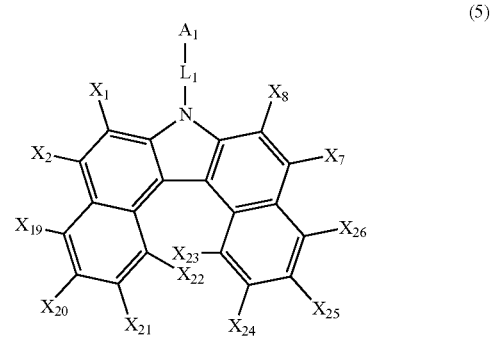

(5)

the (5- to 30-membered)heteroaryl of $A_1$ is selected from the group consisting of furyl, thiophenyl, pyrrolyl, imidazolyl, pyrazolyl, thiazolyl, thiadiazolyl, isothiazolyl, isoxazolyl, oxazolyl, oxadiazolyl, tetrazinyl, triazolyl, tetrazolyl, furazanyl, pyrazinyl, pyridazinyl, benzofuranyl, benzothiophenyl, isobenzofuranyl, dibenzofuranyl, dibenzothiophenyl, benzimidazolyl, benzothiazolyl, benzoisothiazolyl, benzoisoxazolyl, benzoxazolyl, isoindolyl, indolyl, benzoindolyl, indazolyl, benzothiadiazolyl, quinolyl, isoquinolyl, cinnolinyl, quinazolinyl, quinoxalinyl, carbazolyl, phenoxazinyl, phenanthridinyl and benzodioxolyl;

$L_1$ represents a single bond, or a substituted or unsubstituted (C6-C30)arylene group;

$X_1$ to $X_8$, and $X_{19}$ to $X_{26}$, each independently, represent hydrogen, deuterium, a halogen, a cyano group, a carboxyl group, a nitro group, a hydroxyl group, a substituted or unsubstituted (C1-C30)alkyl group, a substituted or unsubstituted (C3-C30)cycloalkyl group, a substituted or unsubstituted (C3-C30)cycloalkenyl group, a substituted or unsubstituted (3- to 7-membered)heterocycloalkyl group, a substituted or unsubstituted (C6-C30)aryl group, a substituted or unsubstituted (3- to 30-membered)heteroaryl group, —$NR_5R_6$, or $SiR_7R_8R_9$; or may be linked to an adjacent substituent(s) to form a substituted or unsubstituted mono- or polycyclic (C3-C30), alicyclic or aromatic ring, whose carbon atom(s) may be replaced with at least one hetero atom selected from nitrogen, oxygen, and sulfur;

$R_5$ to $R_9$, each independently, represent hydrogen, deuterium, a halogen, a cyano group, a carboxyl group, a nitro group, a hydroxyl group, a substituted or unsubstituted (C1-C30)alkyl group, a substituted or unsubstituted (C3-C30)cycloalkyl group, a substituted or unsubstituted (C3-C30)cycloalkenyl group, a substituted or unsubstituted (3- to 7-membered)heterocycloalkyl group, a substituted or unsubstituted (C6-C30)

aryl group, or a substituted or unsubstituted (3- to 30-membered)heteroaryl group; or may be linked to an adjacent substituent(s) to form a substituted or unsubstituted mono- or polycyclic (C3-C30), alicyclic or aromatic ring, whose carbon atom(s) may be replaced with at least one hetero atom selected from nitrogen, oxygen, and sulfur;

and a second host compound is represented by the following formula 2:

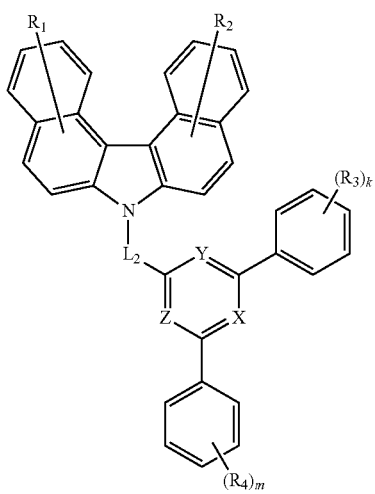

(2)

wherein

X, Y and Z, each independently, represent N or $CR_{10}$; provided that at least one of X, Y and Z represent N;

$L_2$ represents a substituted or unsubstituted (C6-C30) arylene group;

$R_1$ to $R_4$, each independently, represent hydrogen, deuterium, a halogen, a cyano group, a carboxyl group, a nitro group, a hydroxyl group, a substituted or unsubstituted (C1-C30)alkyl group, a substituted or unsubstituted (C3-C30)cycloalkyl group, a substituted or unsubstituted (C3-C30)cycloalkenyl group, a substituted or unsubstituted (3- to 7-membered)heterocycloalkyl group, a substituted or unsubstituted (C6-C30) aryl group, a substituted or unsubstituted (3- to 30-membered)heteroaryl group, $-NR_{11}R_{12}$, or $SiR_{13}R_{14}R_{15}$;

$R_{10}$ to $R_{15}$, each independently, represent hydrogen, deuterium, a halogen, a cyano group, a carboxyl group, a nitro group, a hydroxyl group, a substituted or unsubstituted (C1-C30)alkyl group, a substituted or unsubstituted (C3-C30)cycloalkyl group, a substituted or unsubstituted (C3-C30)cycloalkenyl group, a substituted or unsubstituted (3- to 7-membered)heterocycloalkyl group, a substituted or unsubstituted (C6-C30) aryl group, or a substituted or unsubstituted (3- to 30-membered)heteroaryl group;

k and m, each independently, represent an inter of 1 to 5; and where k or m represents an integer of 2 or more, each of $R_3$ or $R_4$ may be the same or different; and the heteroaryl and the heterocycloalkyl, each independently, contain at least one hetero atom selected from B, N, O, S, Si, and P.

2. The organic electroluminescent device according to claim 1, wherein formula 1 is represented by any one of the following formulae 3 to 5:

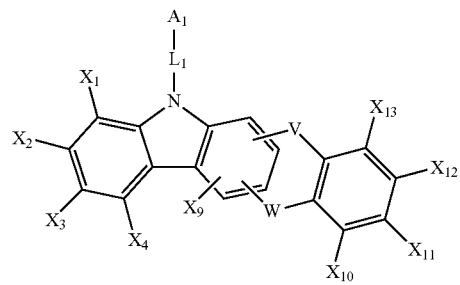

(3)

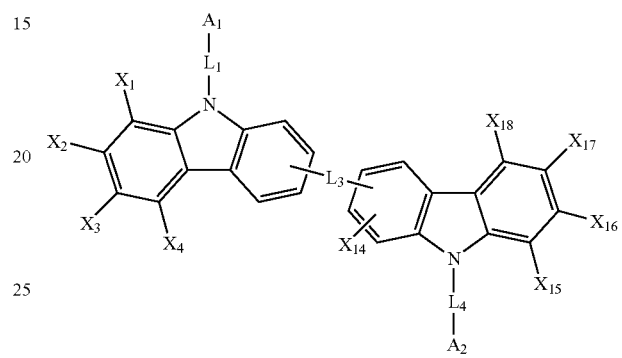

(4)

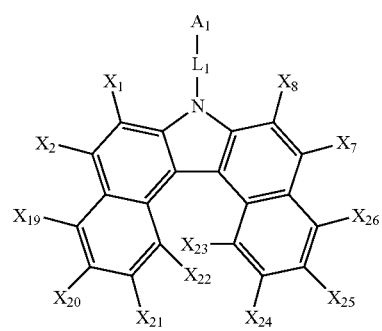

(5)

wherein

V and W represent a single bond or $NR_{16}$; provided that both V and W are not a single bond or $NR_{16}$;

$R_{16}$ represents hydrogen, deuterium, a halogen, a cyano group, a carboxyl group, a nitro group, a hydroxyl group, a substituted or unsubstituted (C1-C30)alkyl group, a substituted or unsubstituted (C3-C30)cycloalkyl group, a substituted or unsubstituted (C3-C30) cycloalkenyl group, a substituted or unsubstituted (3- to 7-membered)heterocycloalkyl group, a substituted or unsubstituted (C6-C30)aryl group, or a substituted or unsubstituted (3- to 30-membered)heteroaryl group;

$A_2$ represents a substituted or unsubstituted (C6-C30)aryl group, and $A_2$ may be linked to $X_{14}$ or $X_{15}$;

$L_3$ and $L_4$, each independently, represent a single bond, or a substituted or unsubstituted (C6-C30)arylene group;

$X_9$ to $X_{18}$ each independently, represent hydrogen, deuterium, a halogen, a cyano group, a carboxyl group, a nitro group, a hydroxyl group, a substituted or unsubstituted (C1-C30)alkyl group, a substituted or unsubstituted (C3-C30)cycloalkyl group, a substituted or unsubstituted (C3-C30)cycloalkenyl group, a substituted or unsubstituted (3- to 7-membered)heterocycloalkyl group, a substituted or unsubstituted (C6-C30) aryl group, a substituted or unsubstituted (3- to 30-membered)heteroaryl group, —NR$_5$R$_6$, or —SiR$_7$R$_8$R$_9$; or may be linked to an adjacent substituent(s) to form a substituted or unsubstituted mono- or polycyclic (C3-C30), alicyclic or aromatic ring, whose carbon atom(s) may be replaced with at least one hetero atom selected from nitrogen, oxygen, and sulfur;

A$_1$, L$_1$, X$_1$ to X$_4$, X$_7$, X$_8$, X$_{19}$ to X$_{26}$ and R$_5$ to R$_9$ are as defined in claim 1.

3. The organic electroluminescent device according to claim 1, wherein L$_2$ in formula 2 is represented by any one of the following formulae 7 to 19:

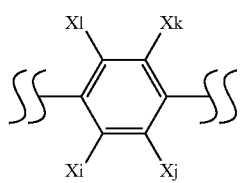
(7)

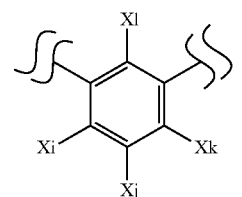
(8)

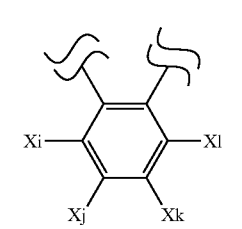
(9)

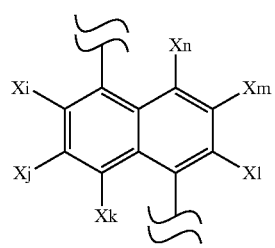
(10)

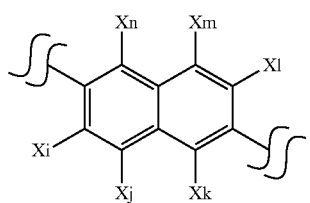
(11)

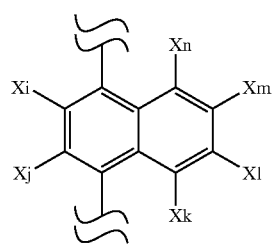
(12)

-continued

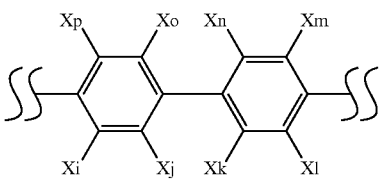
(13)

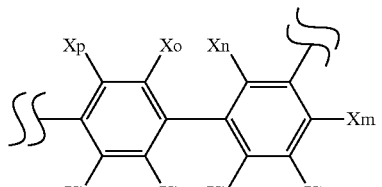
(14)

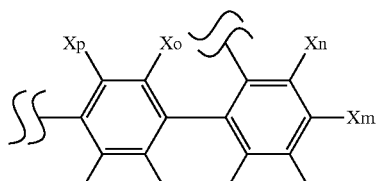
(15)

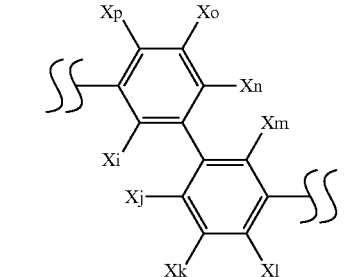
(16)

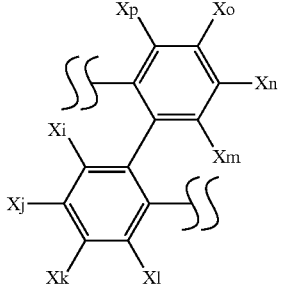
(17)

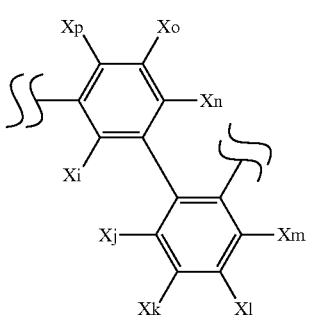
(18)

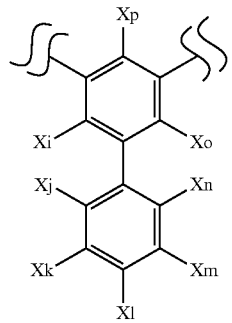

(19)

wherein

Xi to Xp, each independently, represent hydrogen, deuterium, a halogen, a cyano group, a substituted or unsubstituted (C1-C30)alkyl group, a substituted or unsubstituted (C2-C30)alkenyl group, a substituted or unsubstituted (C2-C30)alkynyl group, a substituted or unsubstituted (C3-C30)cycloalkyl group, a substituted or unsubstituted (C6-C60)aryl group, a substituted or unsubstituted (3- to 30-membered)heteroaryl group, a substituted or unsubstituted tri(C1-C30)alkylsilyl- group, a substituted or unsubstituted tri(C6-C30)aryl-silyl group, a substituted or unsubstituted di(C1-C30)alkyl(C6-C30)arylsilyl group, a substituted or unsubstituted (C1-C30)alkyldi(C6-C30)arylsilyl group, or a substituted or unsubstituted mono- or di-(C6-C30)arylamino group; or may be linked to an adjacent substituent(s) to form a substituted or unsubstituted mono- or polycyclic (C3-C30), alicyclic or aromatic ring, whose carbon atom(s) may be replaced with at least one hetero atom selected from nitrogen, oxygen, and sulfur.

4. The organic electroluminescent device according to claim 1, wherein the substituents of the substituted alkyl group, the substituted cycloalkyl group, the substituted cycloalkenyl group, the substituted heterocycloalkyl group, the substituted aryl(ene) group, the substituted heteroaryl group, and the substituted mono- or polycyclic, alicyclic or aromatic ring in $A_1$, $L_1$, $L_2$, $X_1$ to $X_8$, and $R_1$ to $R_{15}$, each independently, are at least one selected from the group consisting of deuterium; a halogen; a cyano; a carboxyl; a nitro; a hydroxyl; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (3- to 30-membered) heteroaryl unsubstituted or substituted with a (C6-C30)aryl; a (C6-C30)aryl unsubstituted or substituted with a cyano, a (3- to 30-membered)heteroaryl or tri(C6-C30)arylsilyl; a tri(C1-C30)alkylsilyl; a tri(C6-C30)arylsilyl; a di(C1-C30)alkyl(C6-C30)arylsilyl; a (C1-C30)alkyldi(C6-C30)arylsilyl; an amino; a mono- or di-(C1-C30)alkylamino; a mono- or di-(C6-C30)arylamino; a (C1-C30)alkyl(C6-C30)arylamino; a (C1-C30)alkylcarbonyl; a (C1-C30)alkoxycarbonyl; a (C6-C30)arylcarbonyl; a di(C6-C30)arylboronyl; a di(C1-C30)alkylboronyl; a (C1-C30)alkyl(C6-C30)arylboronyl; a (C6-C30)aryl(C1-C30)alkyl; and a mono- or di-(C1-C30)alkyl(C6-C30)aryl.

5. The organic electroluminescent device according to claim 1, wherein the compound represented by formula 1 is selected from the group consisting of:

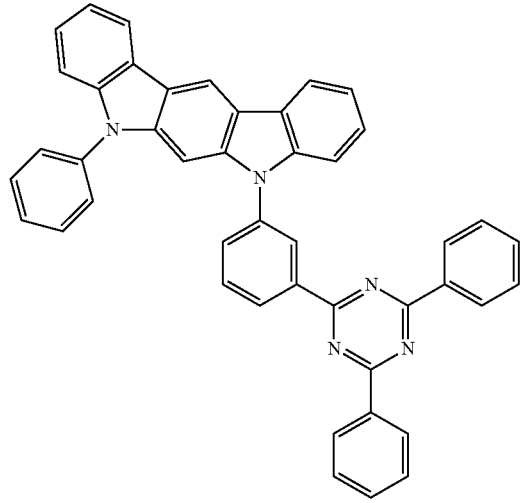

H-1

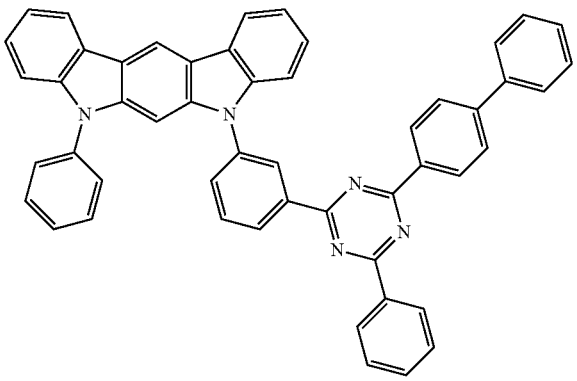

H-2

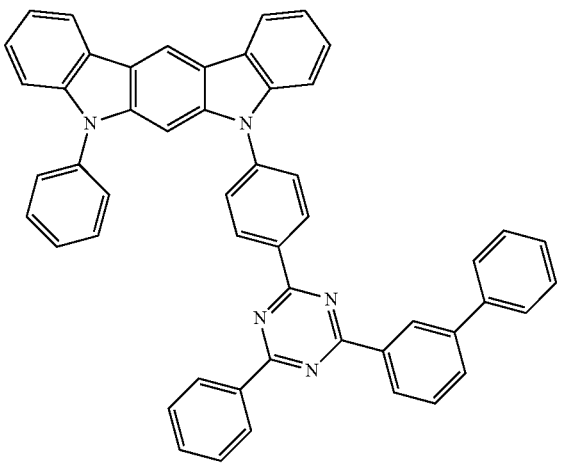

H-3

H-4
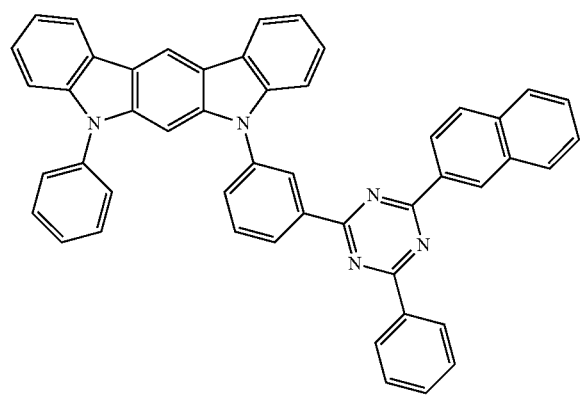
H-5
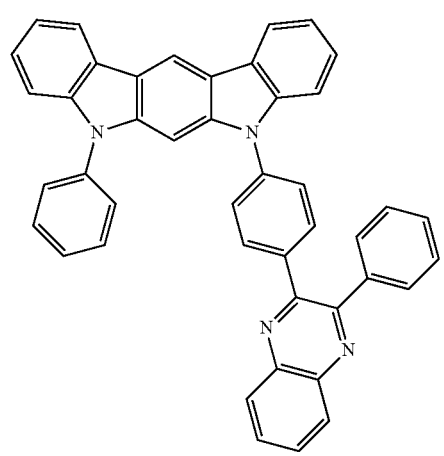
H-6
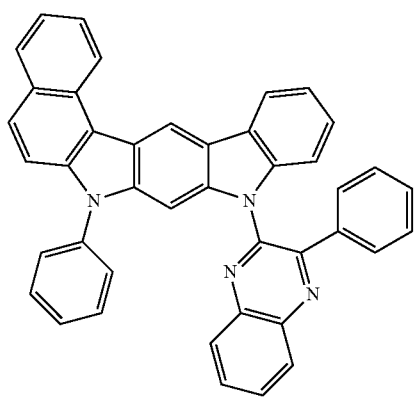
H-7
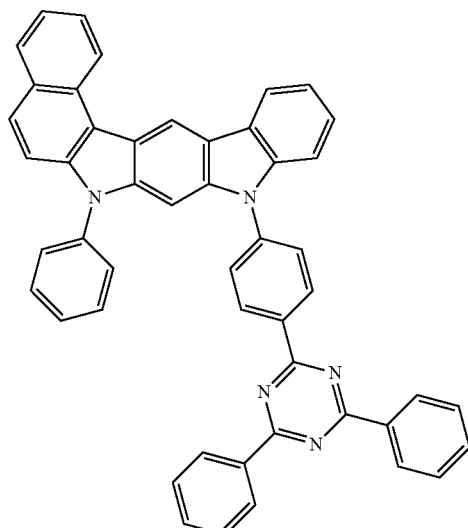
H-8
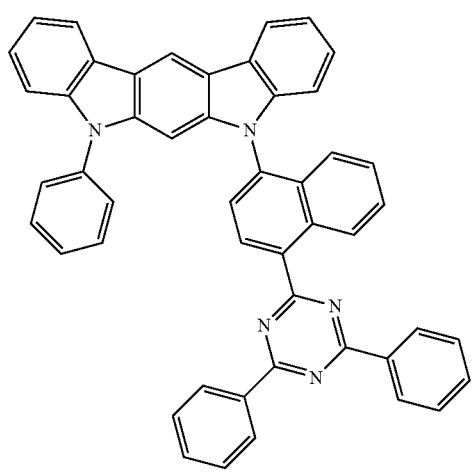
H-9
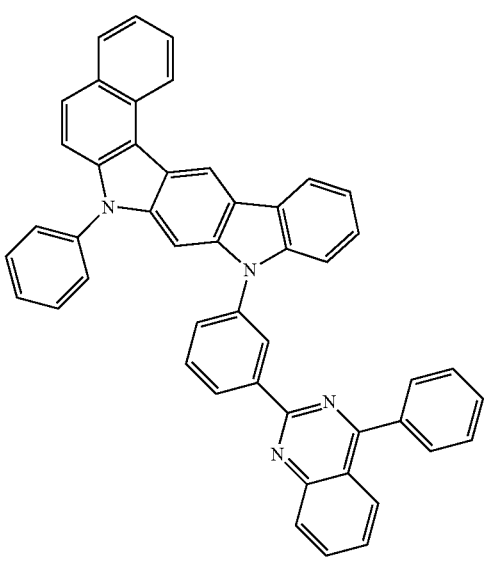

H-10
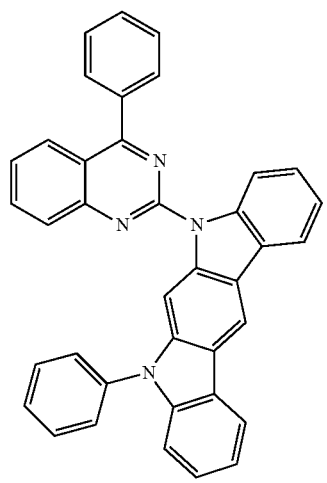
H-13
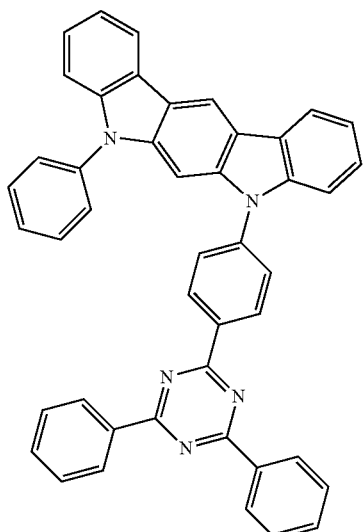
H-11
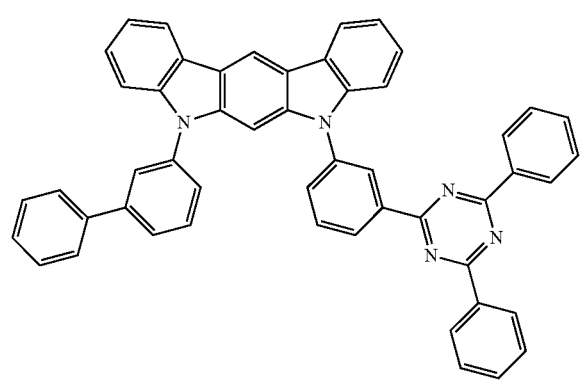
H-14
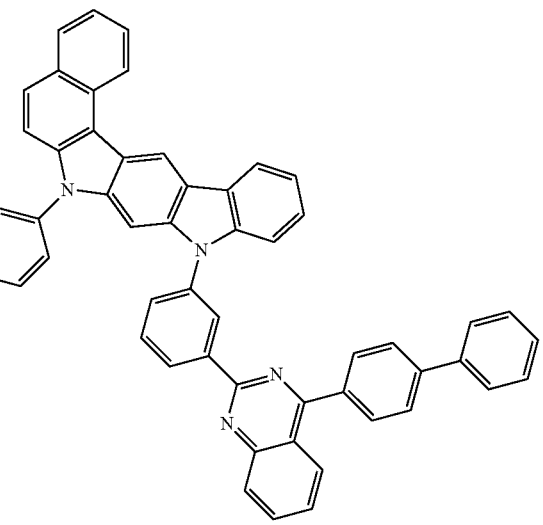
H-12
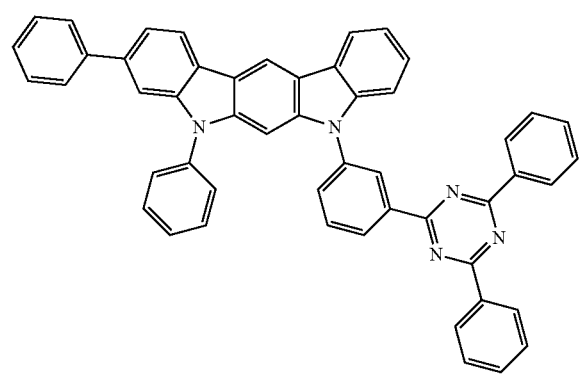

H-15
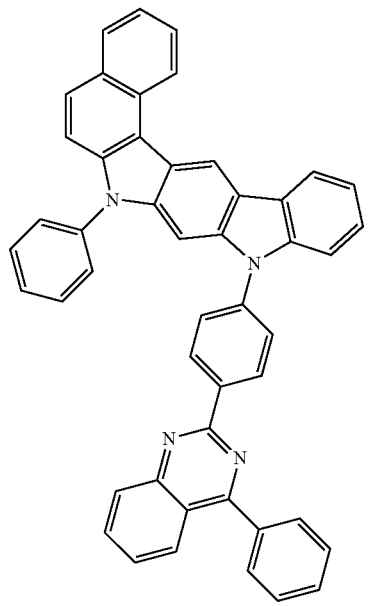
H-16
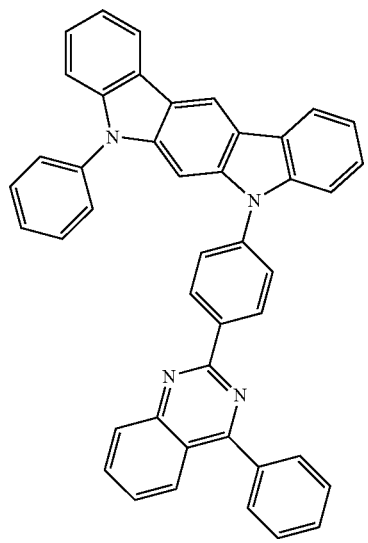
H-19
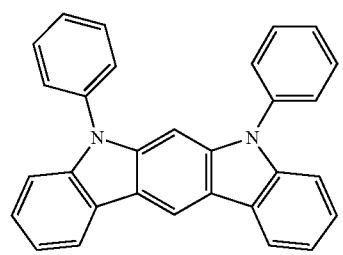
H-20
H-21
H-22
H-23
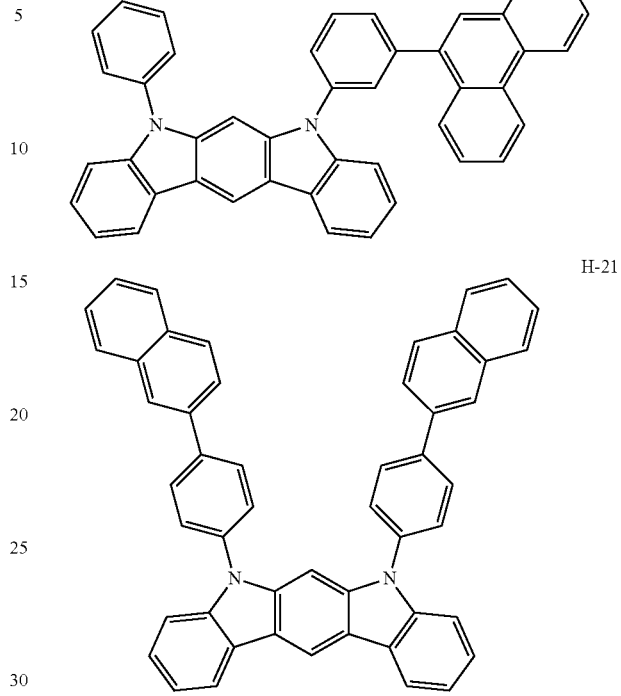

H-24
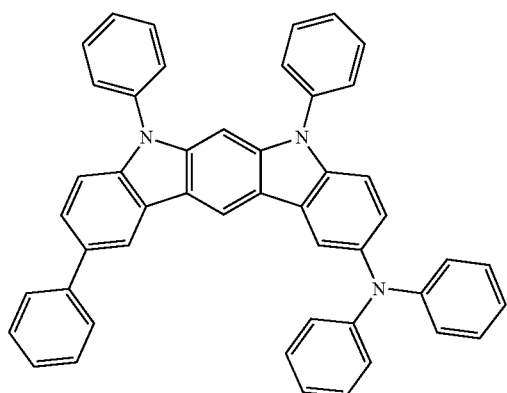
H-25
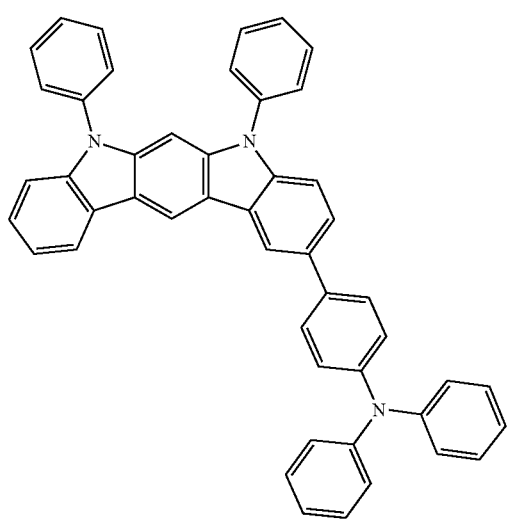
H-26
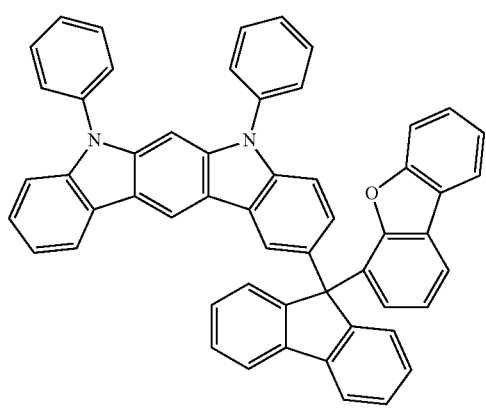
H-27
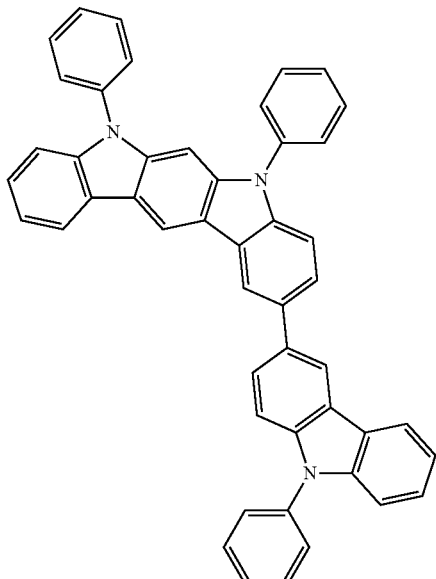
H-28
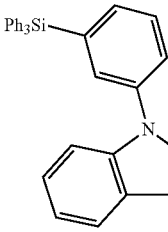
H-29
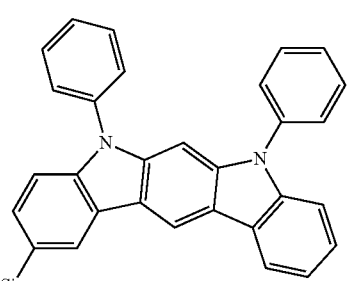
H-30
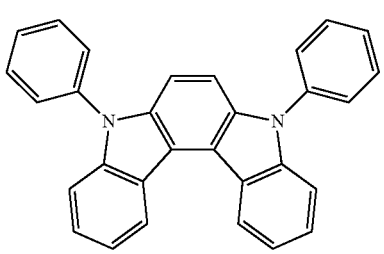

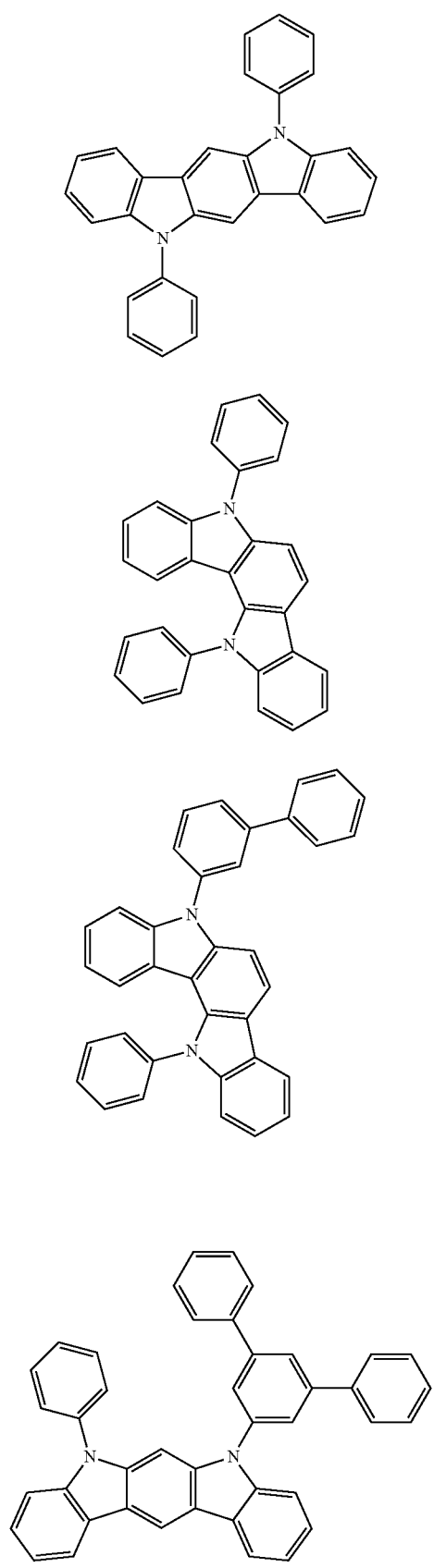
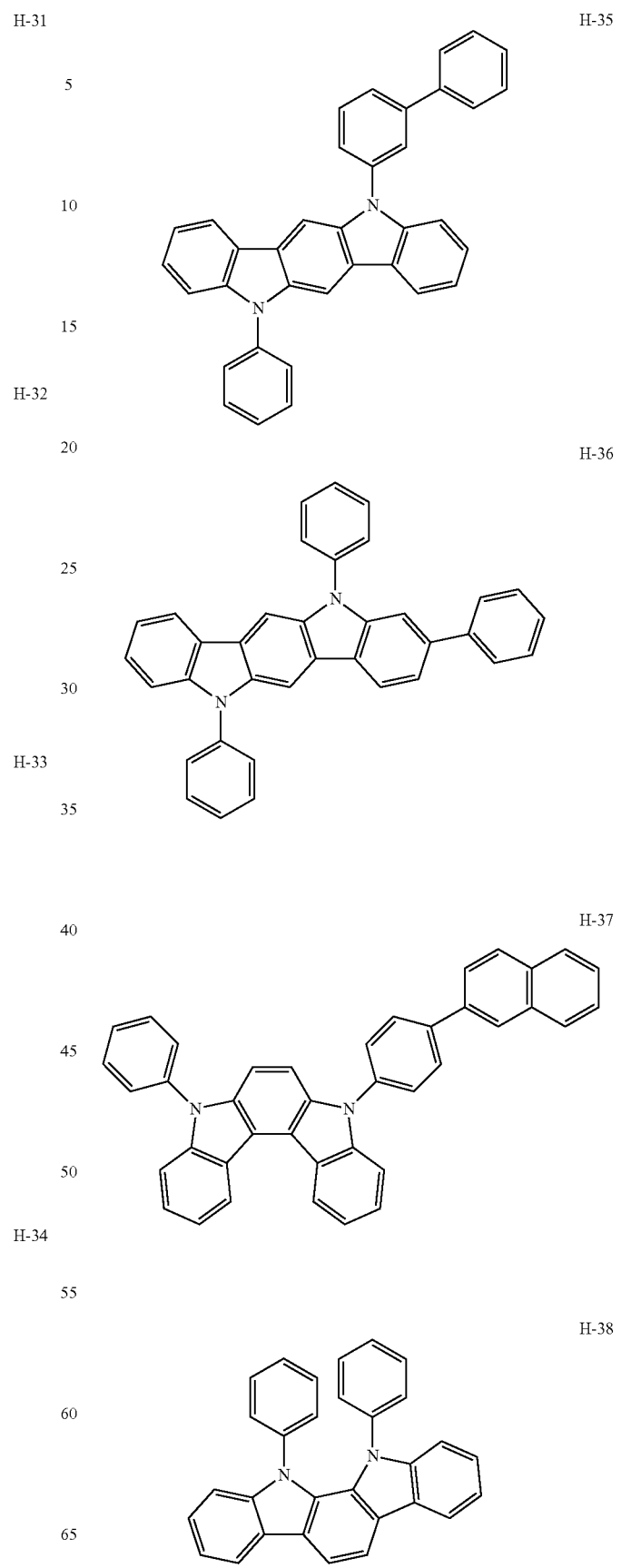

H-39
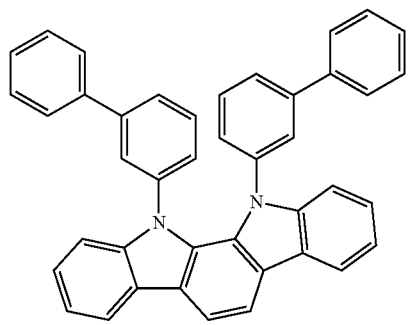
H-40
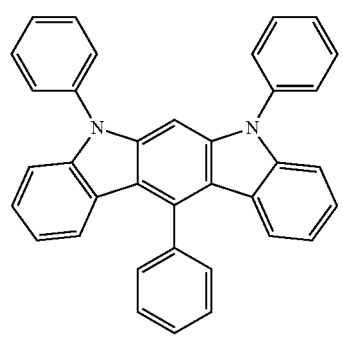
H-42
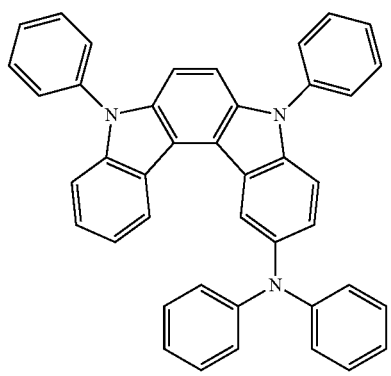
H-43
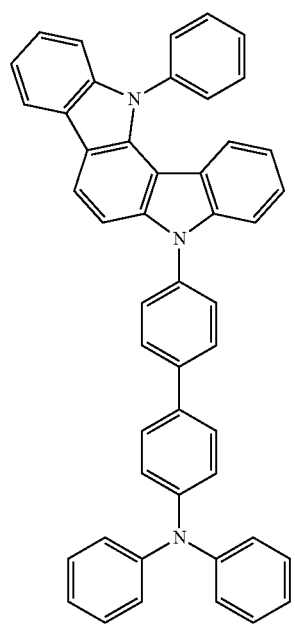
H-44
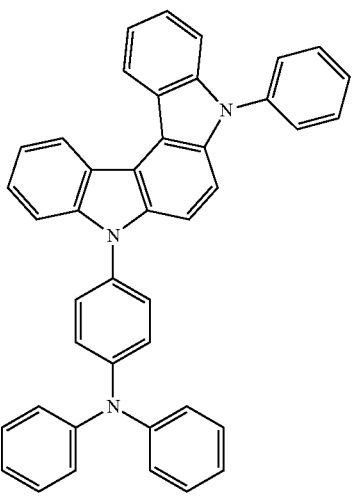
H-45
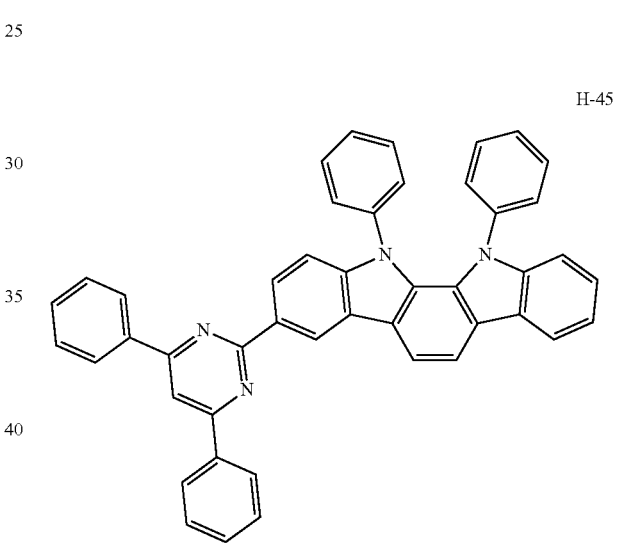
H-46
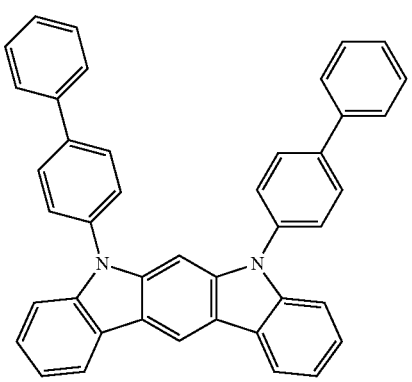

H-47
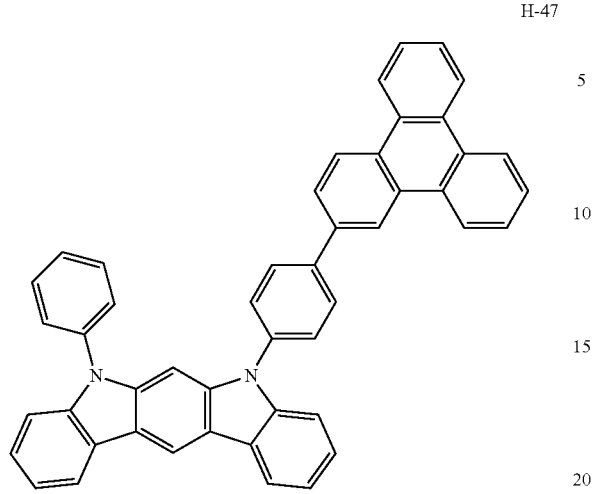
H-50
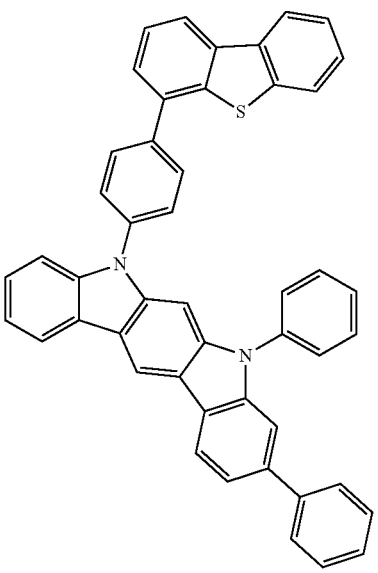
H-48
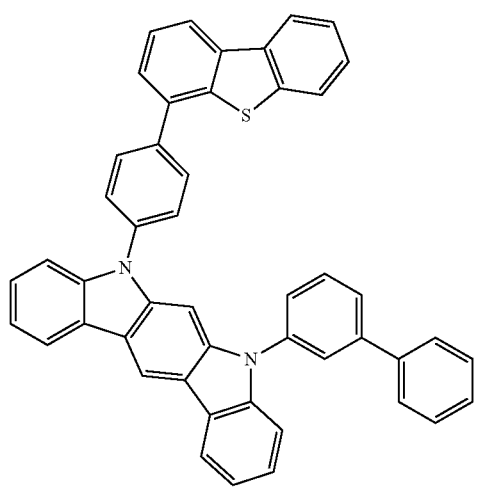
H-51
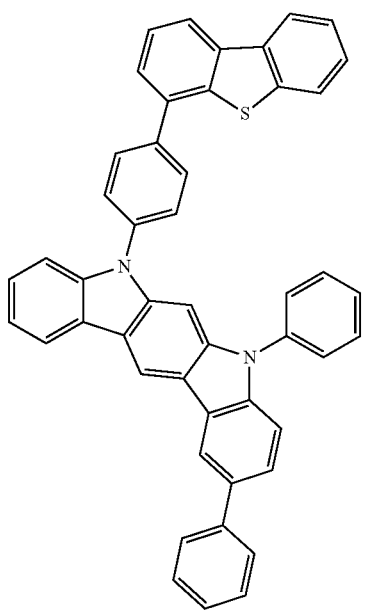
H-49
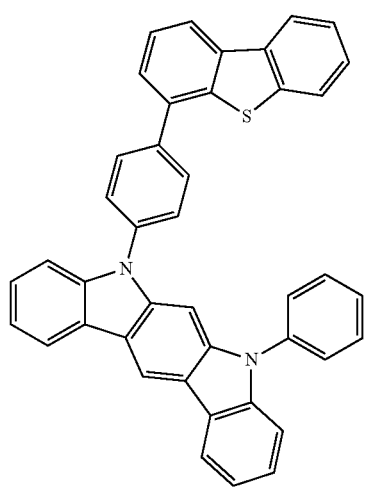
H-52

H-53
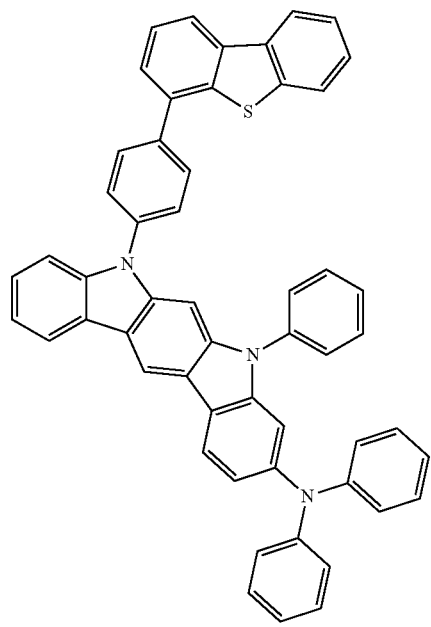
H-54
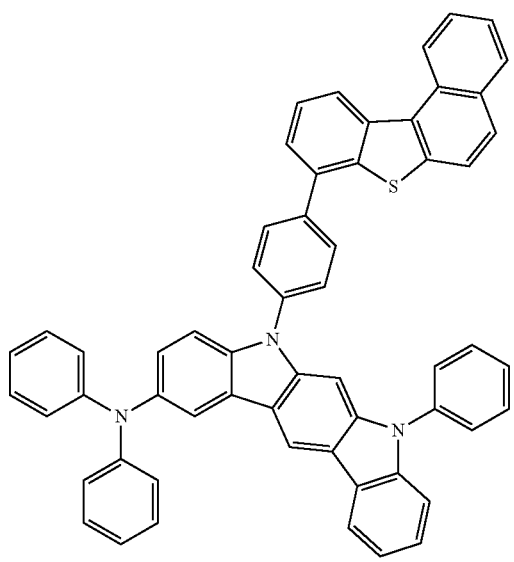
H-55
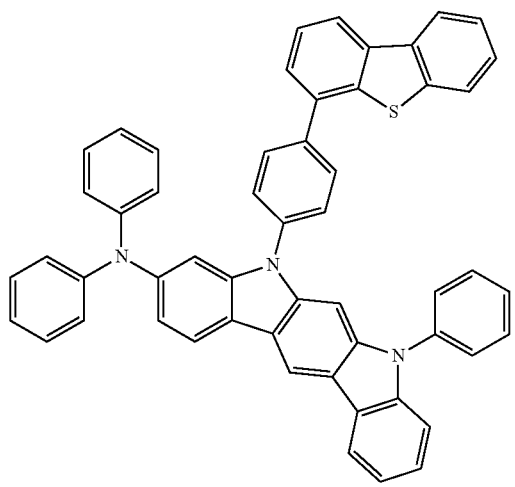
H-56
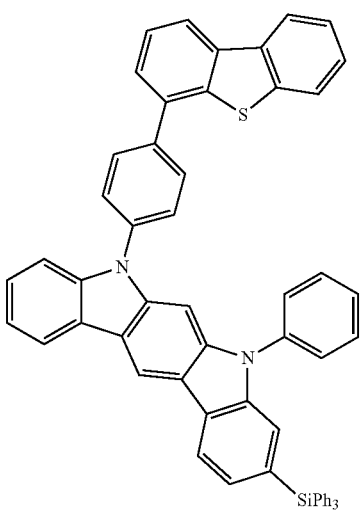
H-57
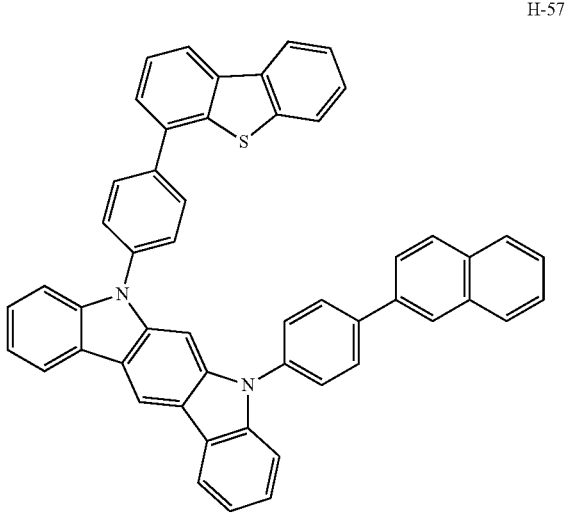

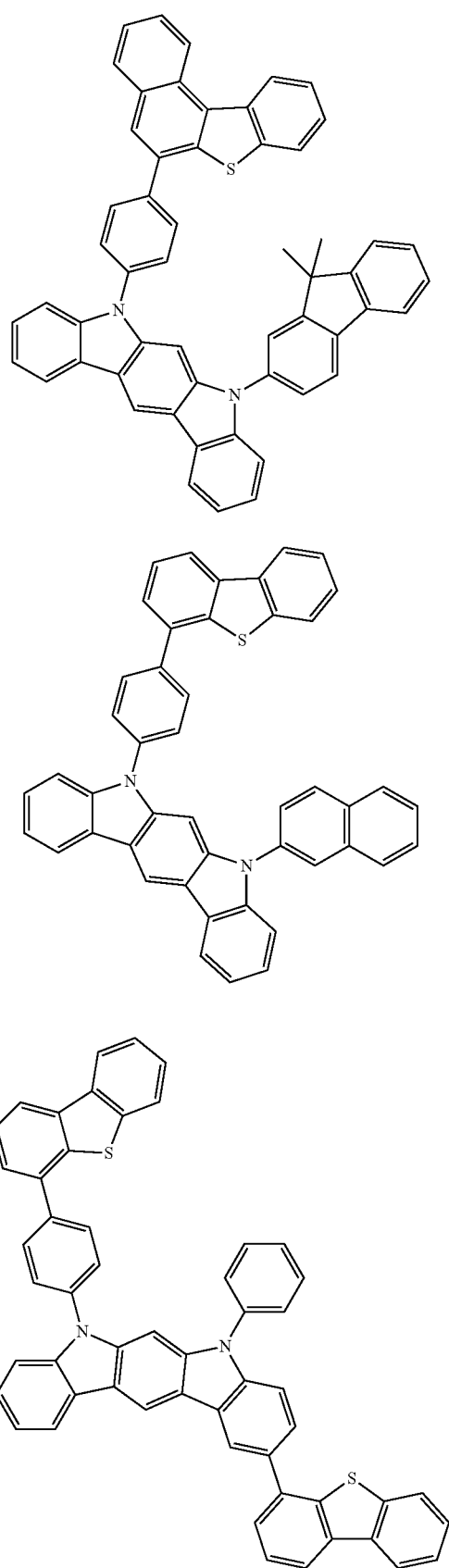
H-58
H-59
H-60
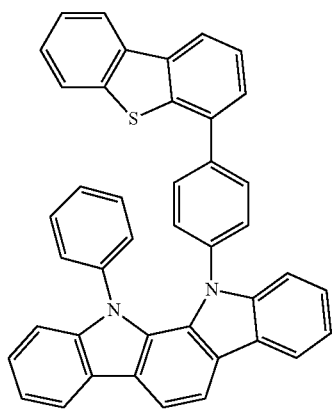
H-61
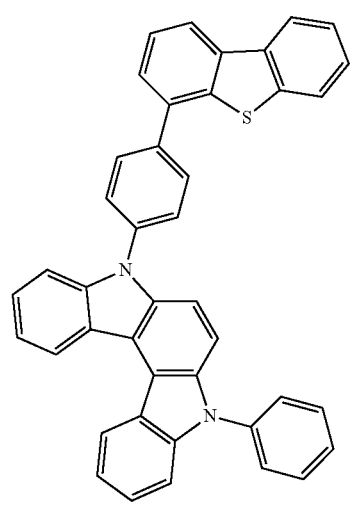
H-62
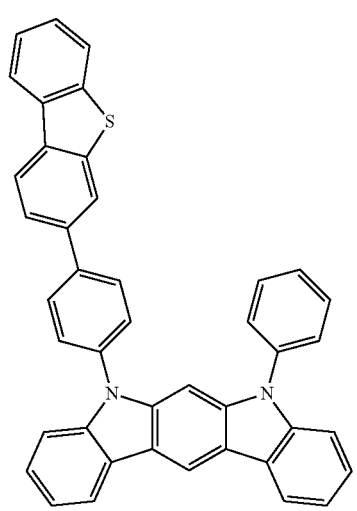
H-63

-continued
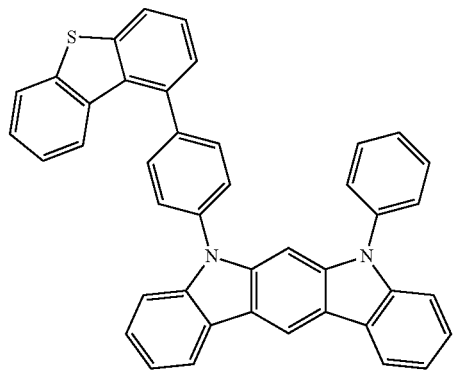
H-64
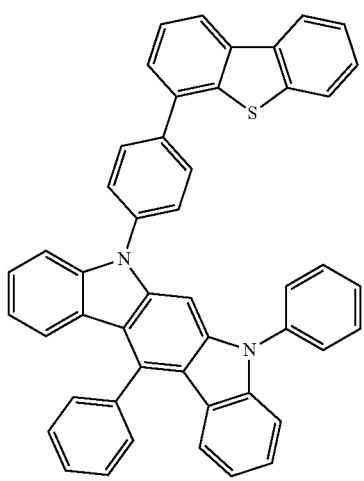
H-65
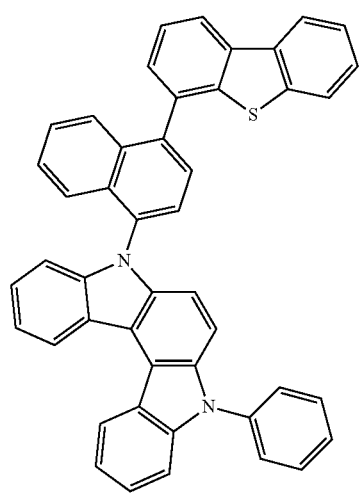
H-66
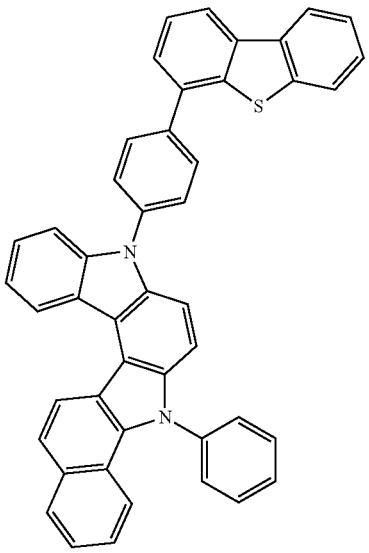
H-67
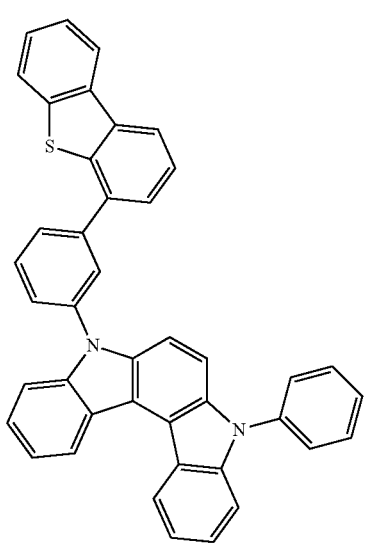
H-68
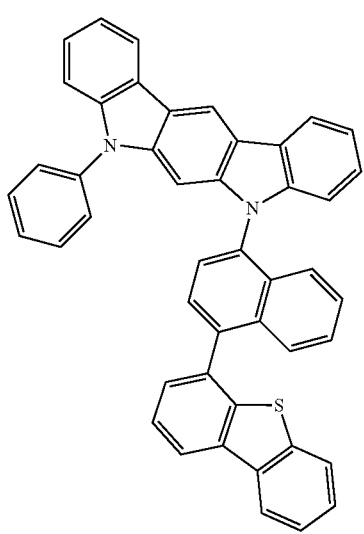
H-69

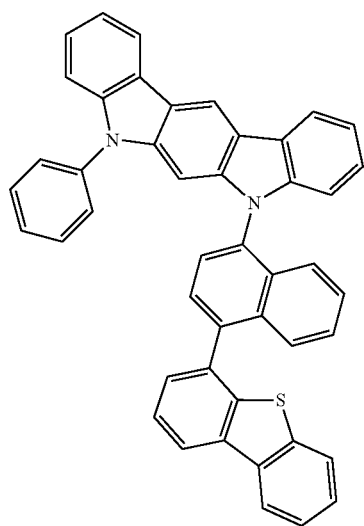
H-70
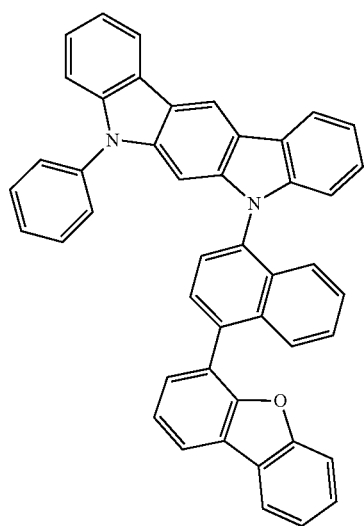
H-71
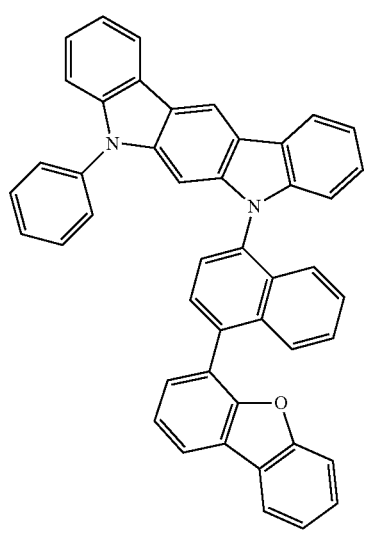
H-72
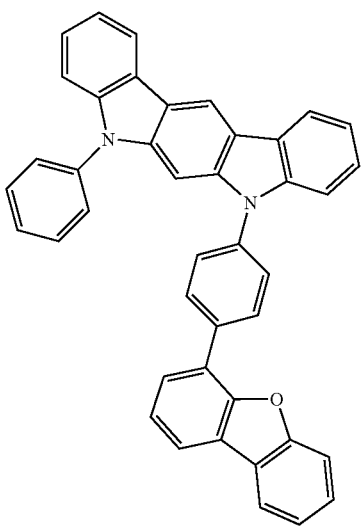
H-73
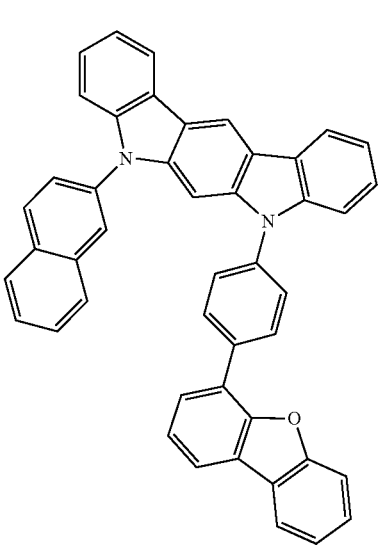
H-74
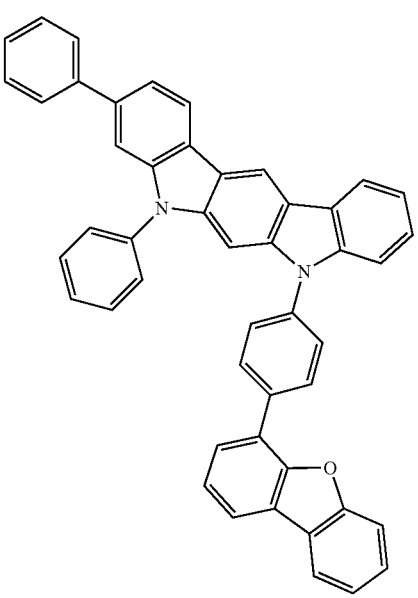
H-75

H-76
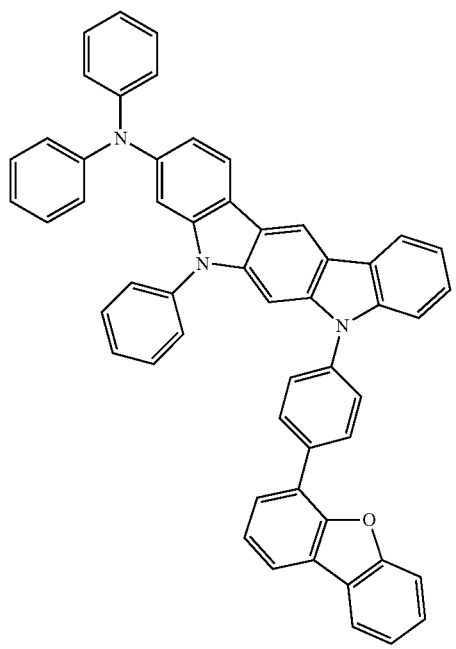
H-77
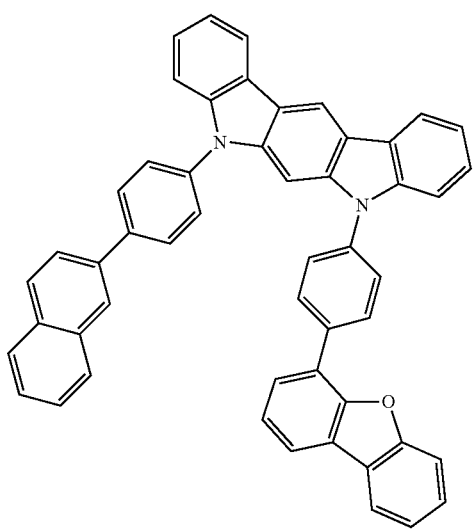
H-78
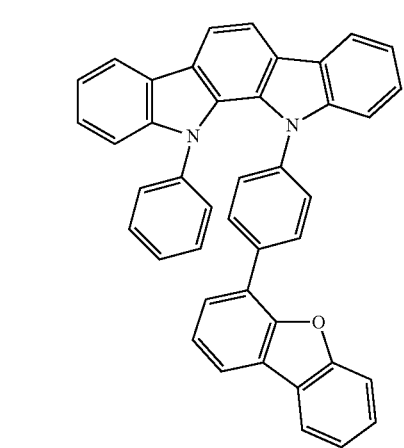
H-79
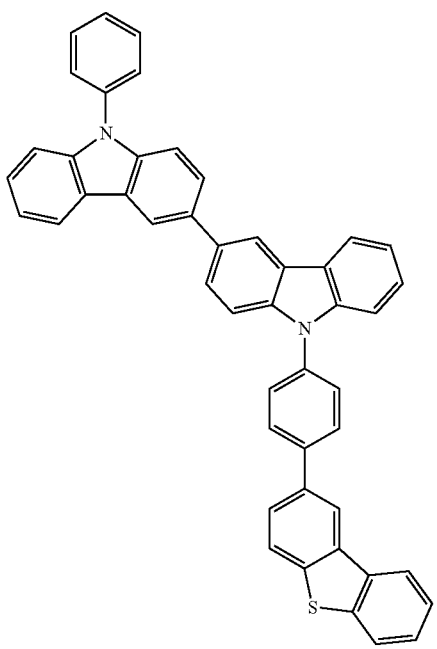
H-80
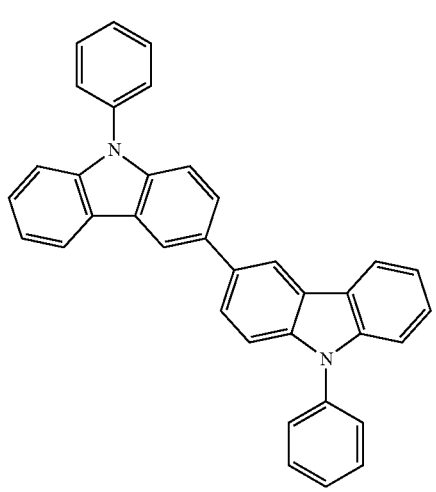

H-81
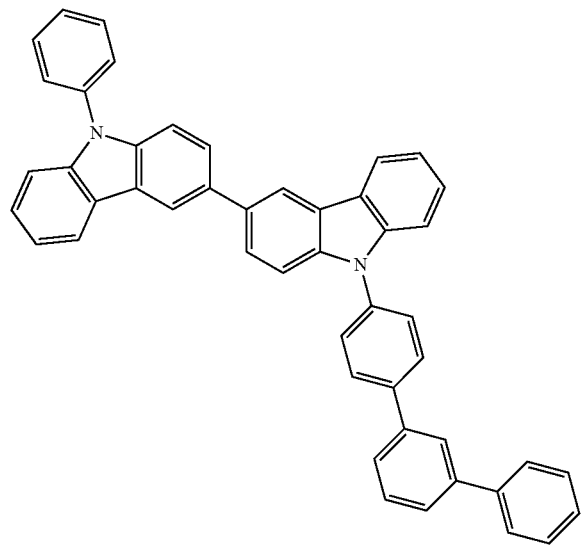
H-82
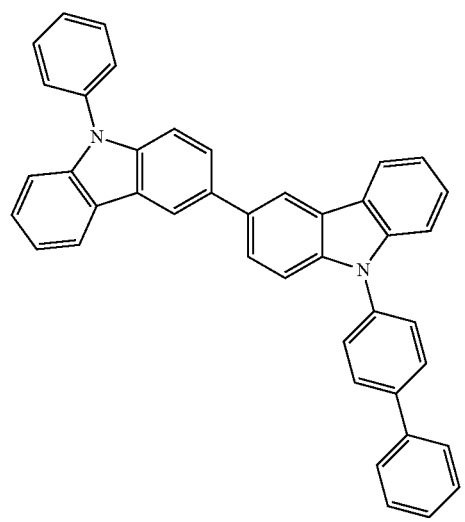
H-83
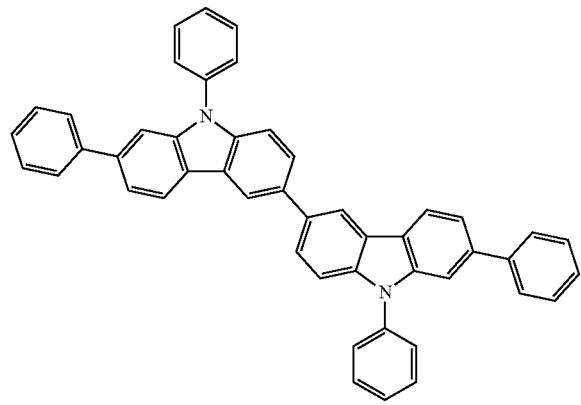
H-84
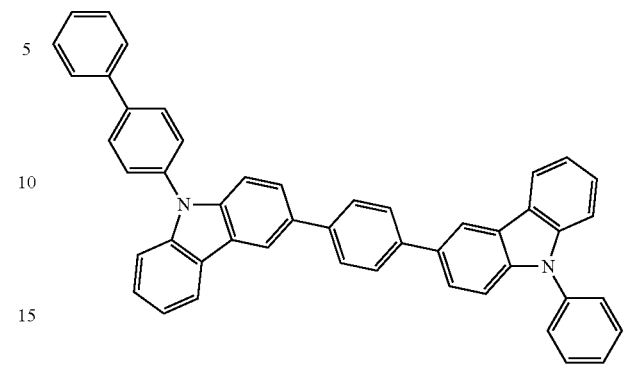
H-85
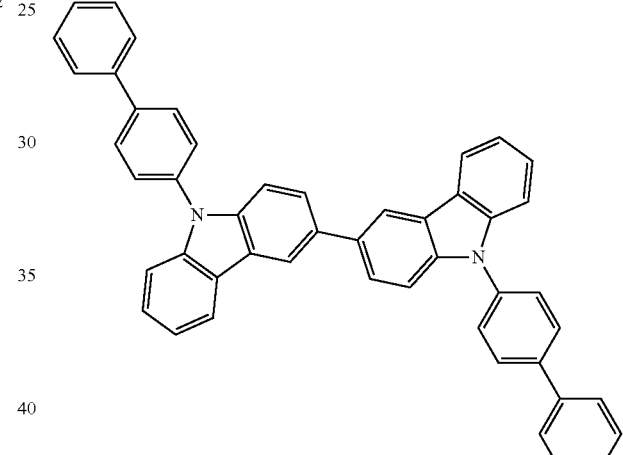
H-86
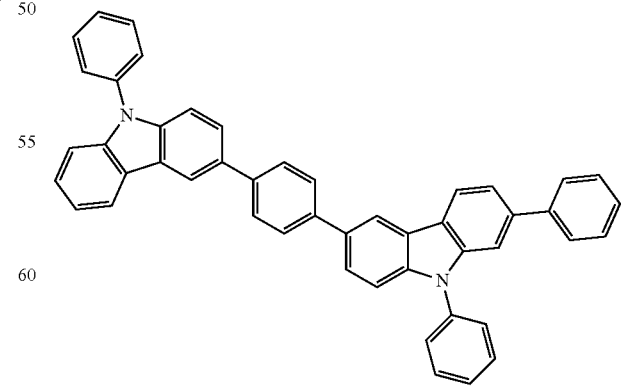

227
-continued
H-87
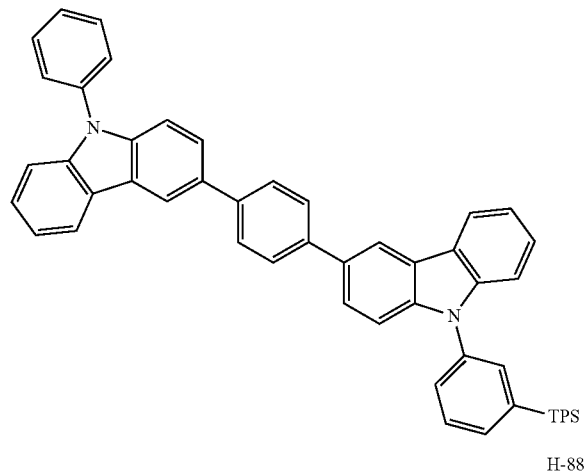
H-88
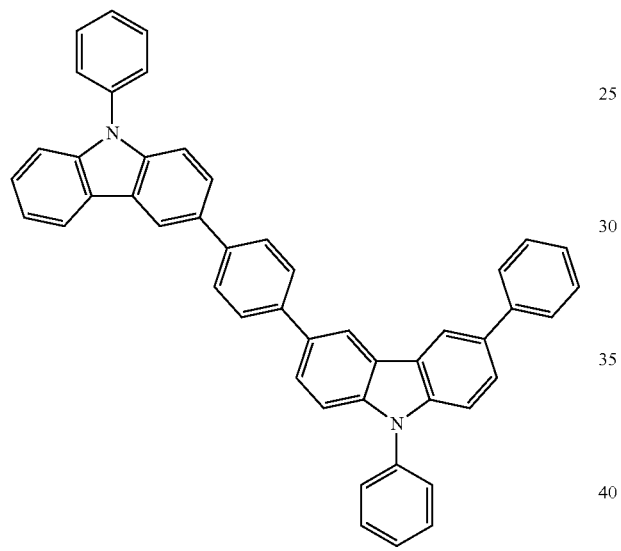
H-89
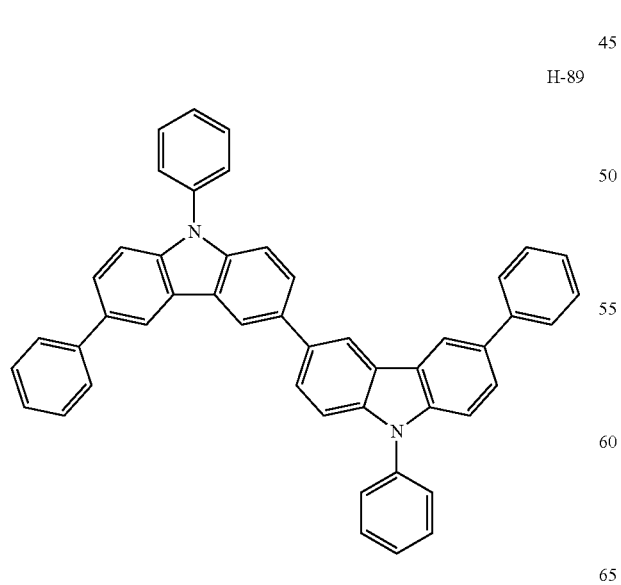
228
-continued
H-90
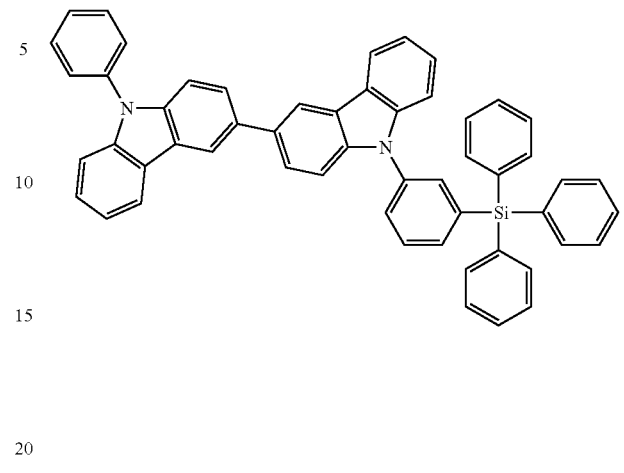
H-91
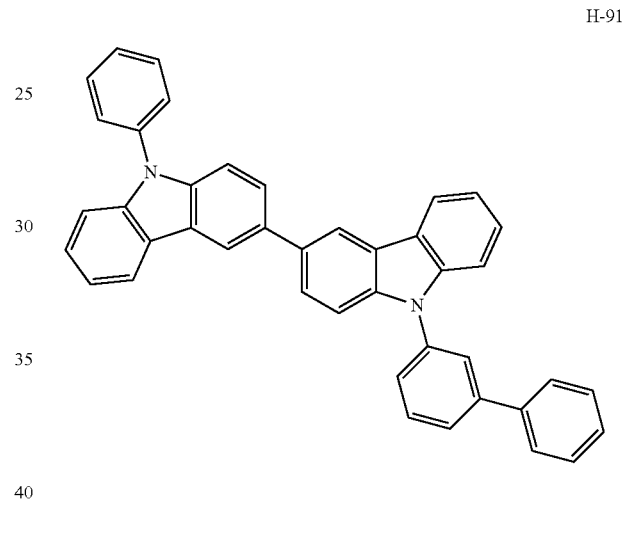
H-92
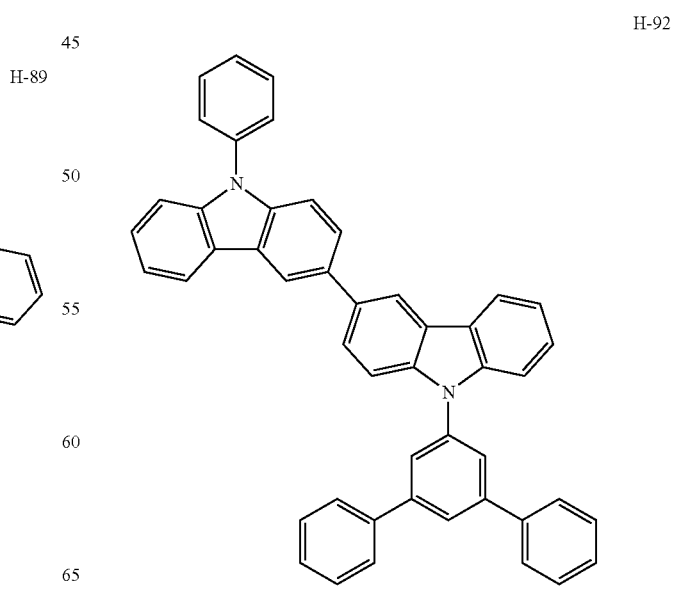

H-93
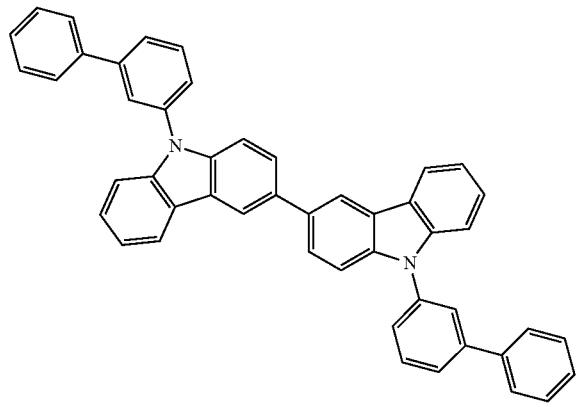
H-96
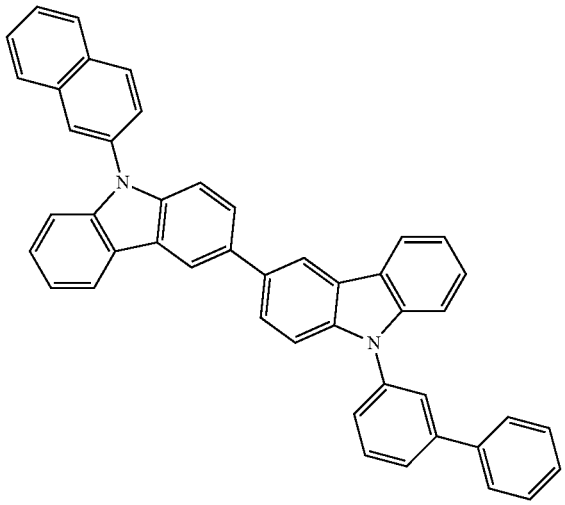
H-94
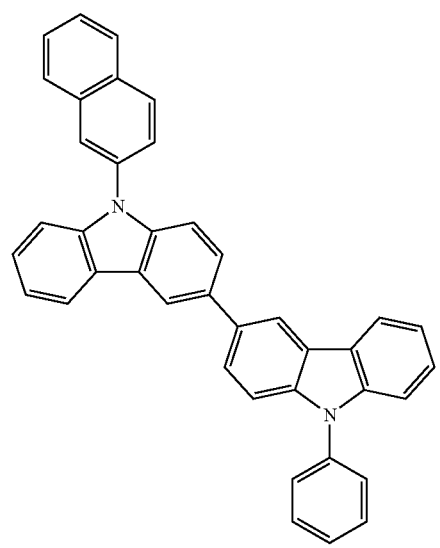
H-97
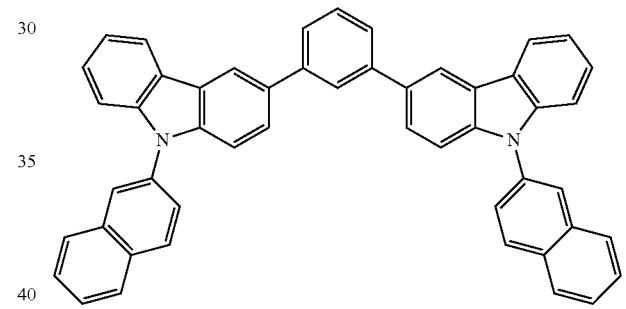
H-95
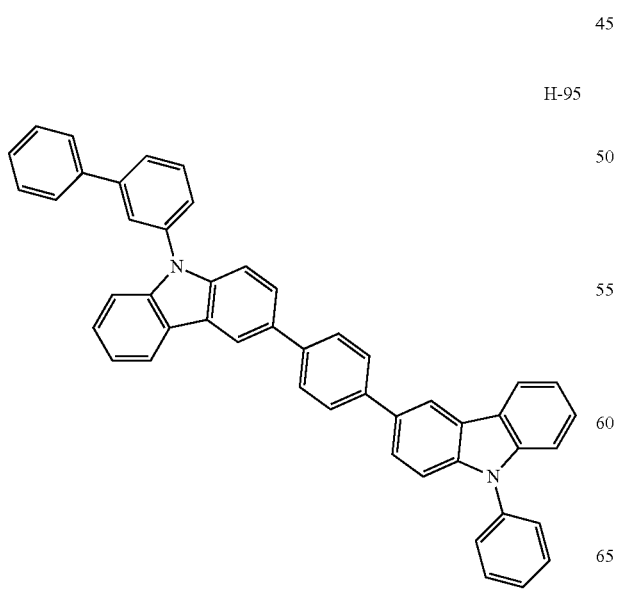
H-98
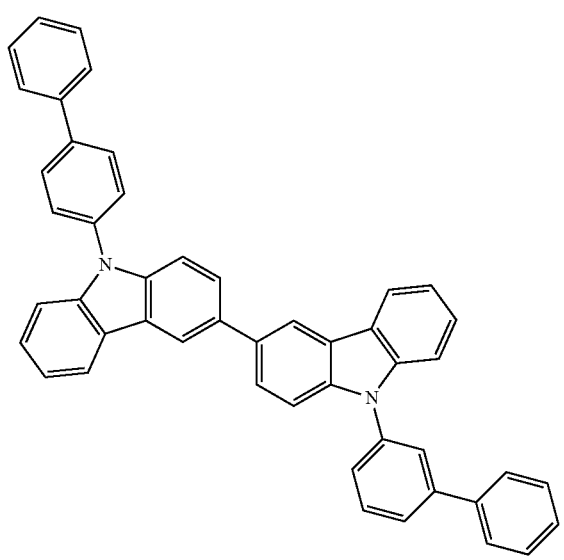

-continued
H-99
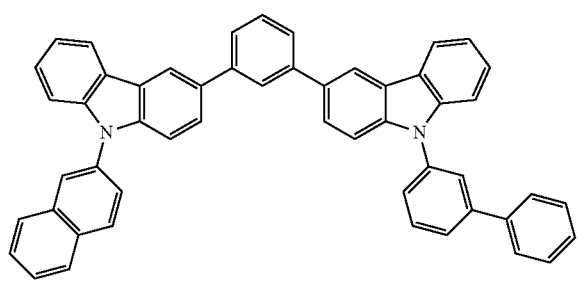
H-100
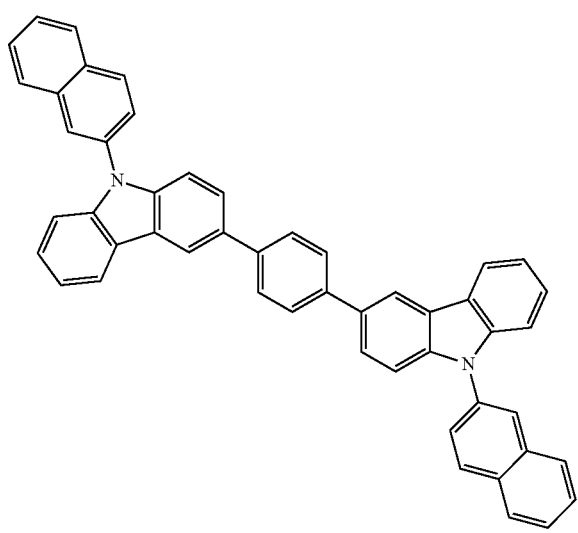
H-101
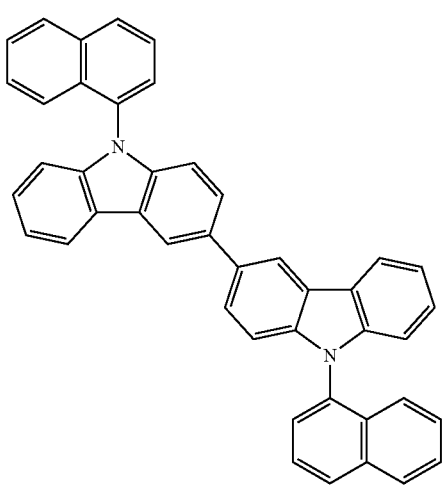
-continued
H-102
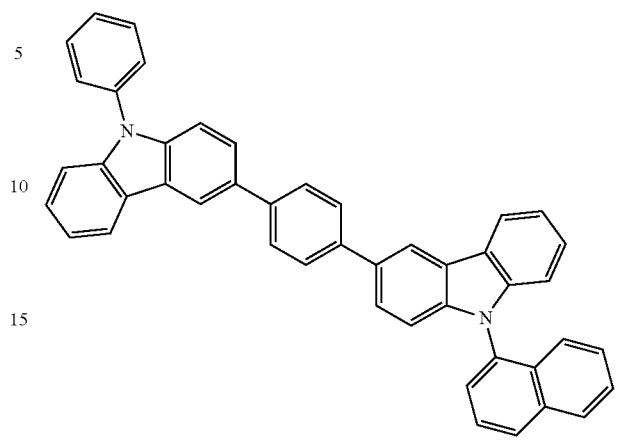
H-103
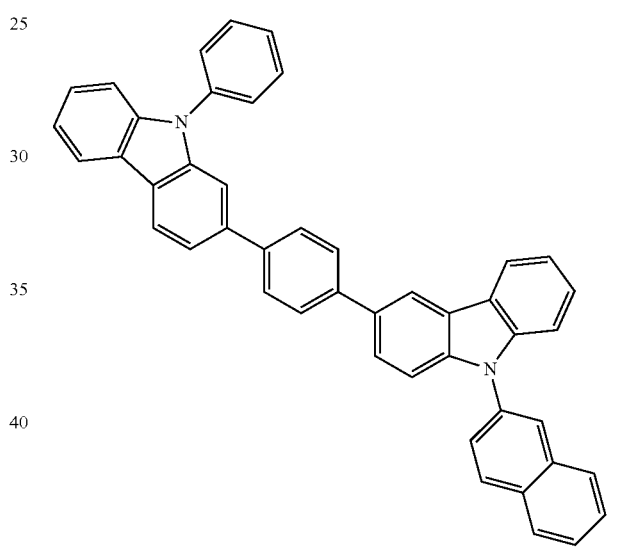
H-104
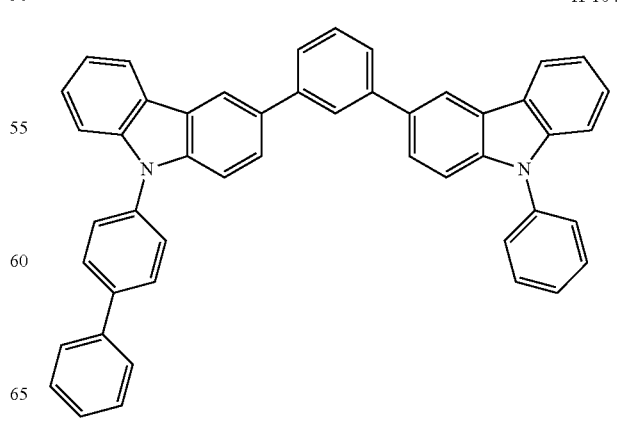

H-105
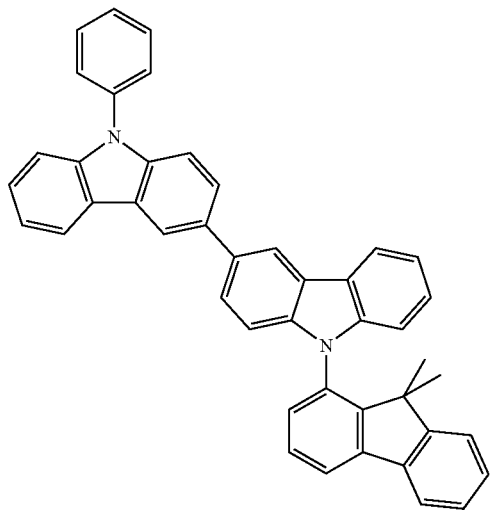
H-107
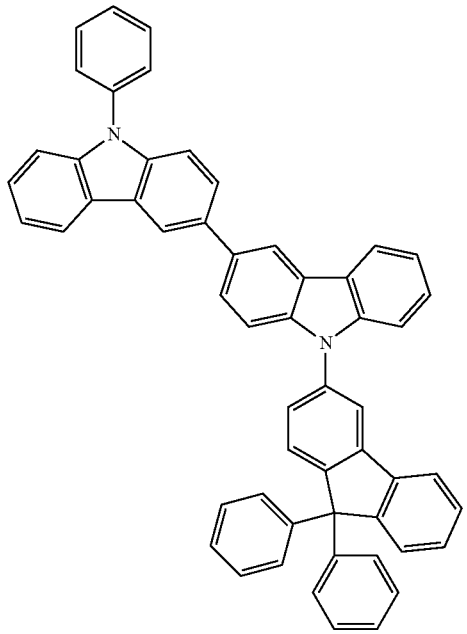
H-106
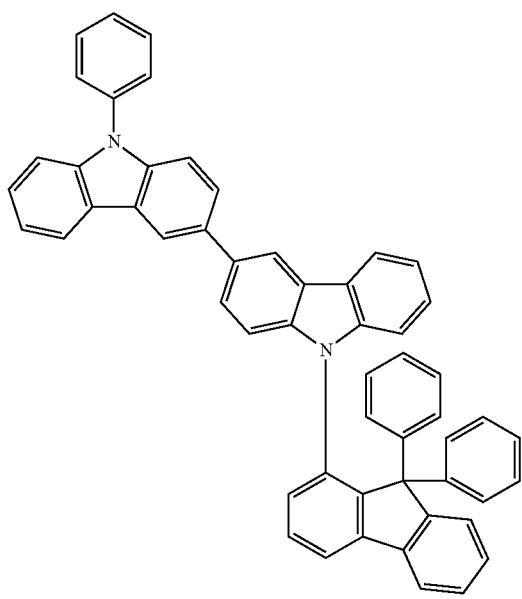
H-108
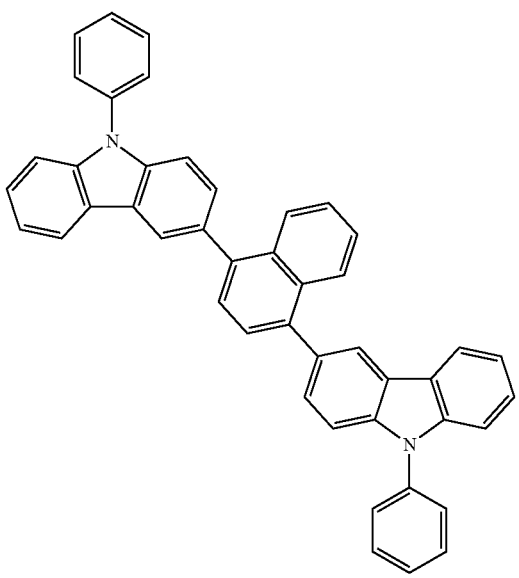

H-109
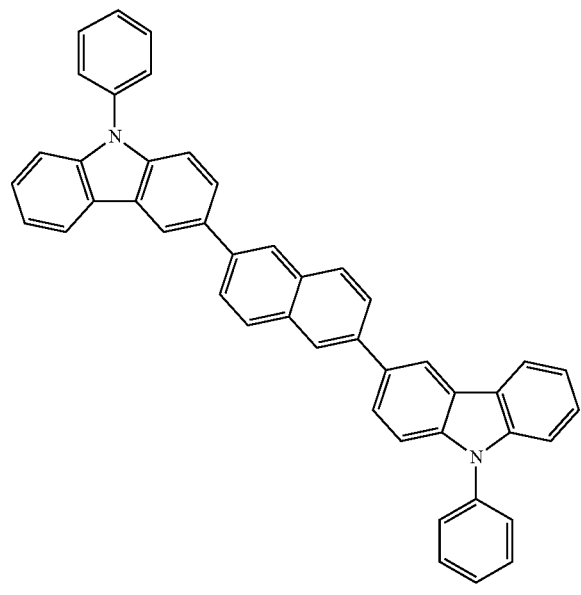
H-110
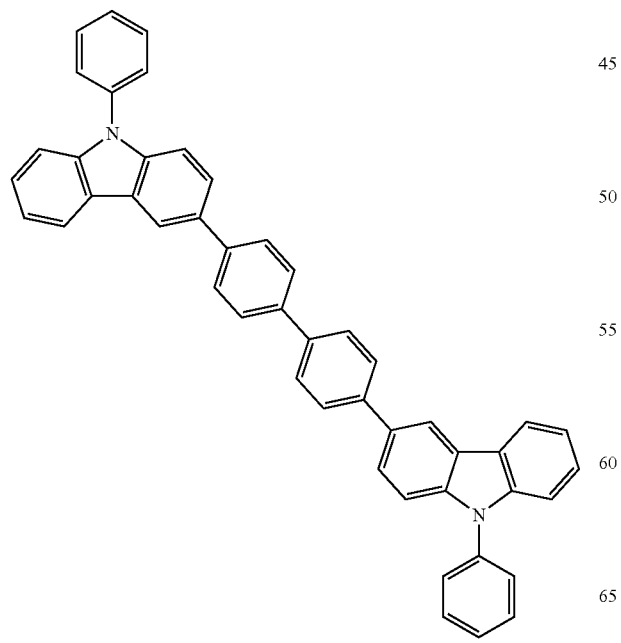
H-111
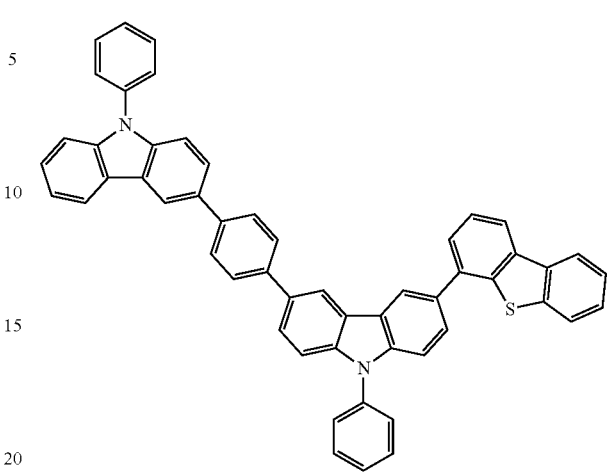
H-112
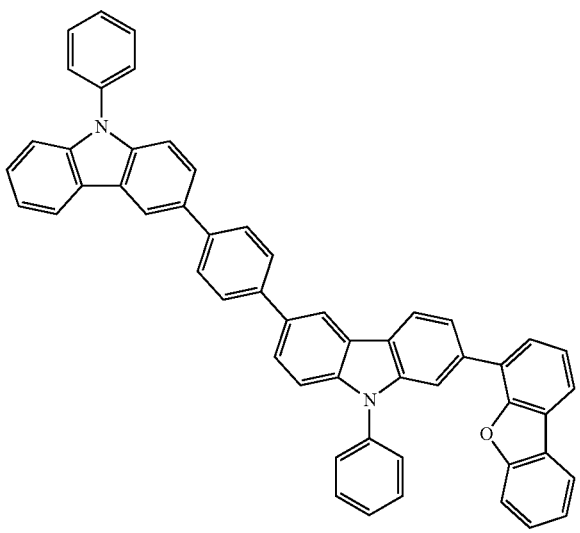

-continued
H-113
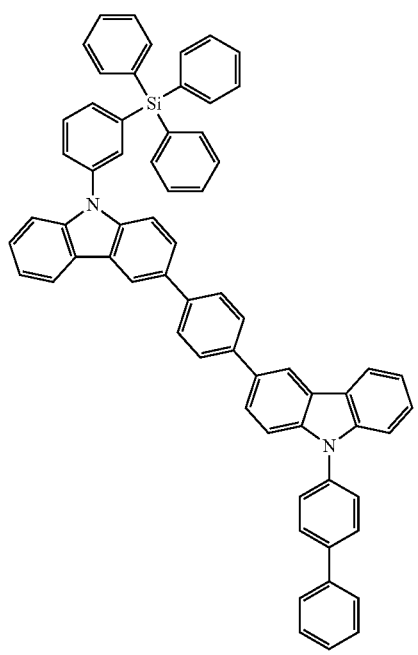
H-114
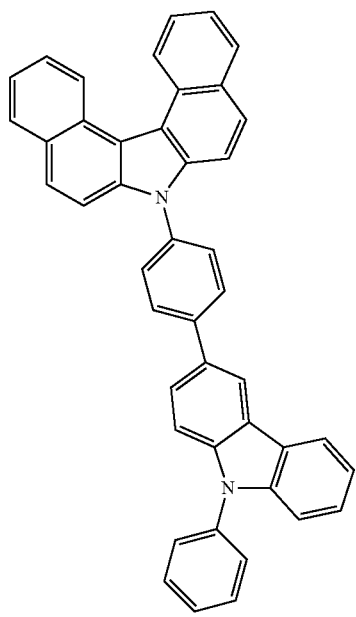
H-115
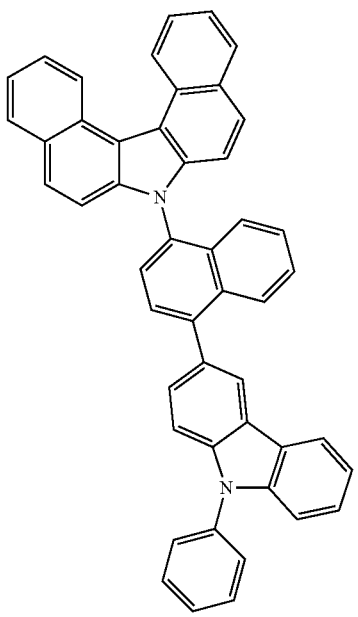
H-116
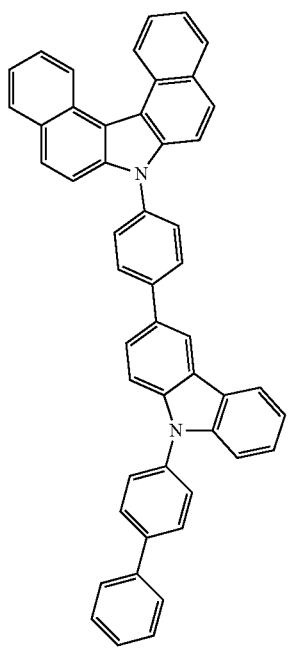

H-117
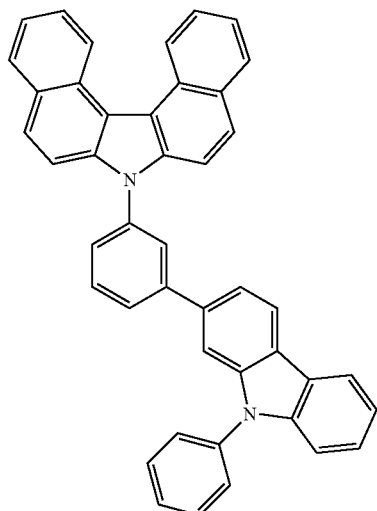
H-120
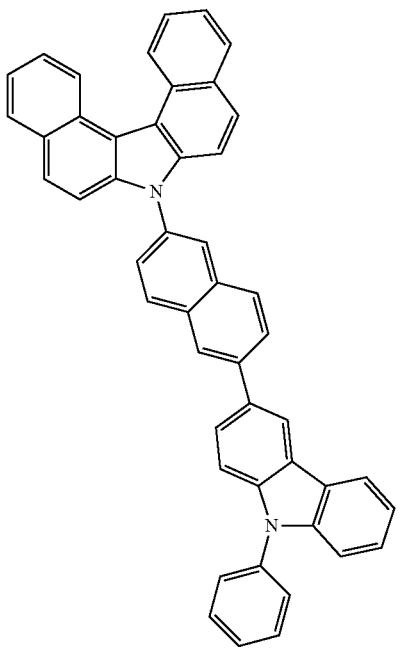
H-118
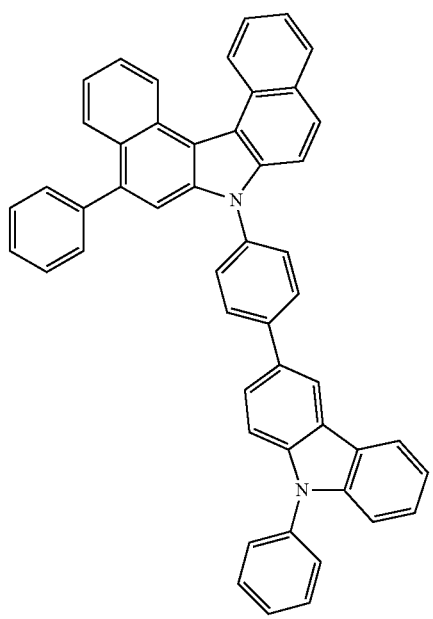
H-121
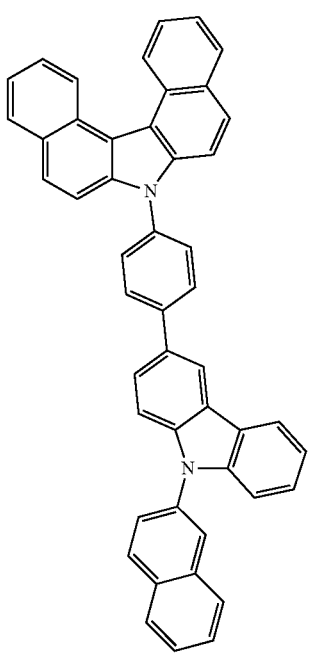

H-122
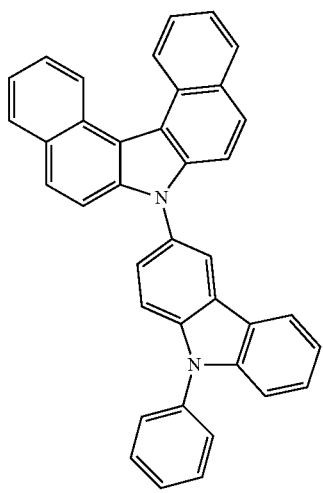
H-123
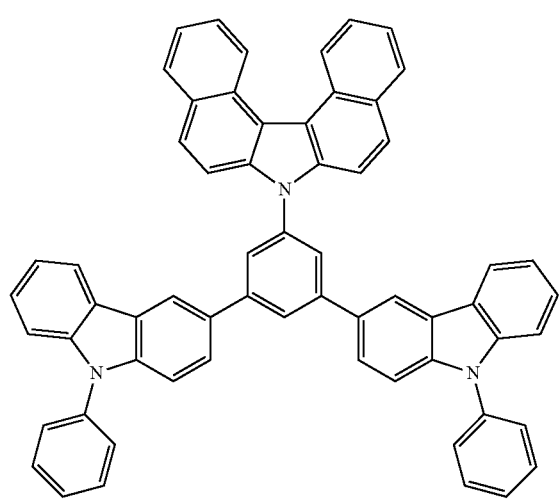
H-124
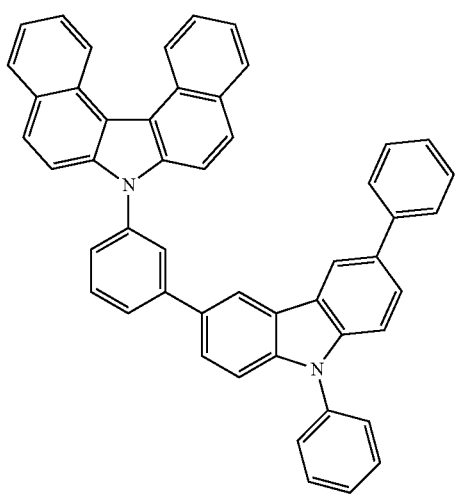
H-125
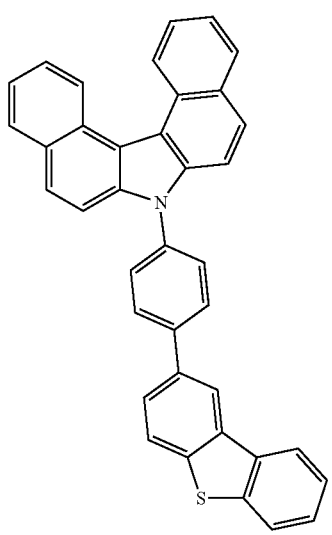
H-126
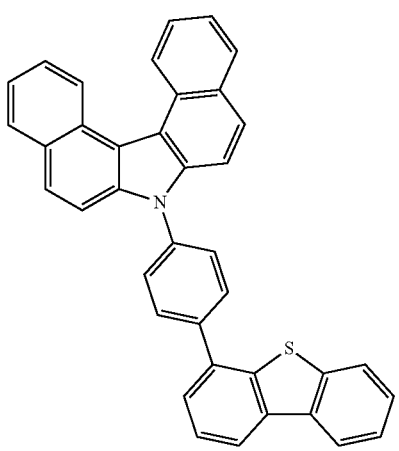
H-127
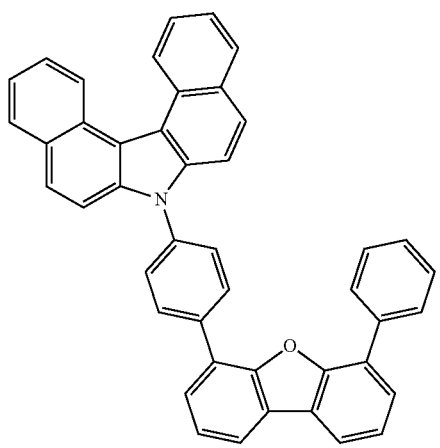

H-128
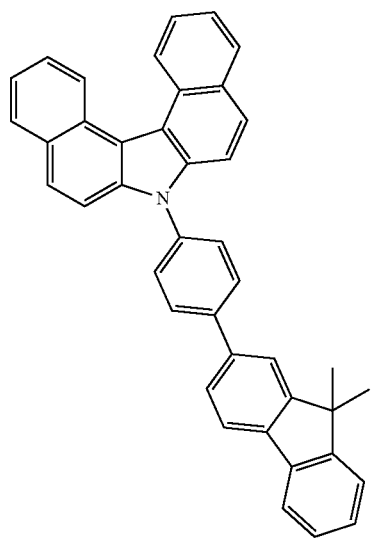
H-129
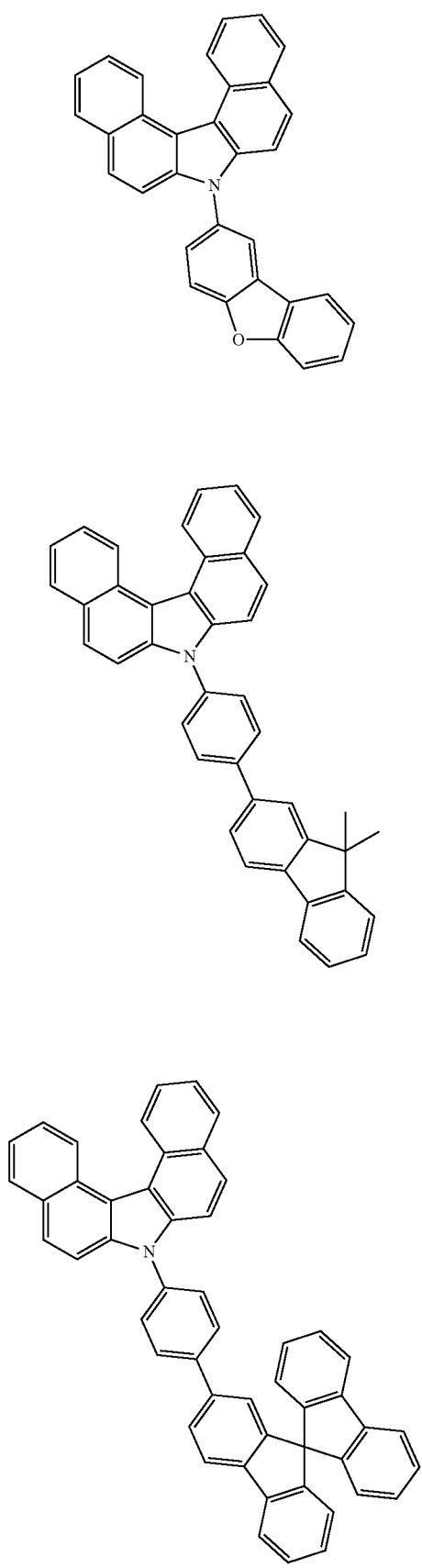
H-130
H-131
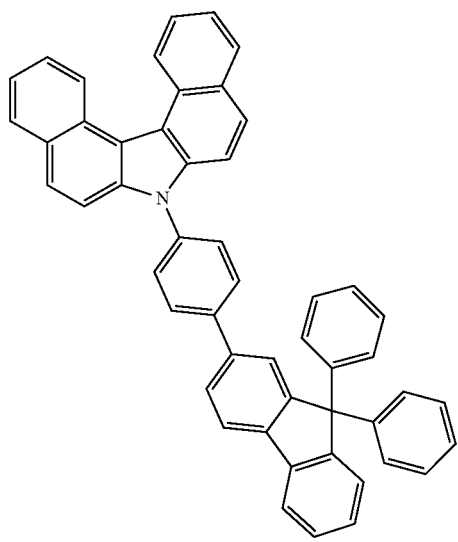
H-133
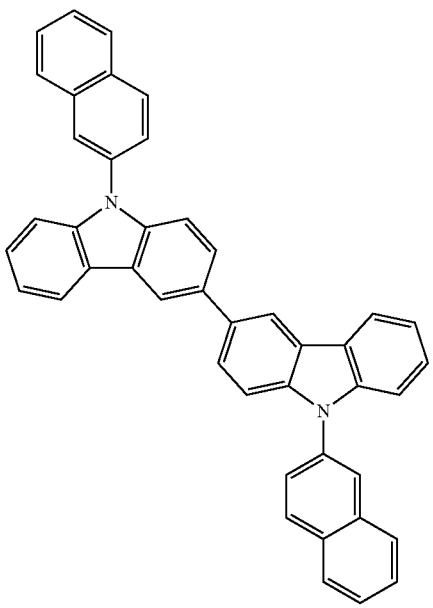

H-134
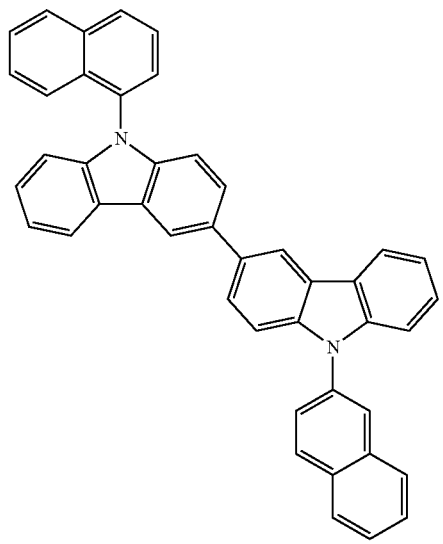
H-135
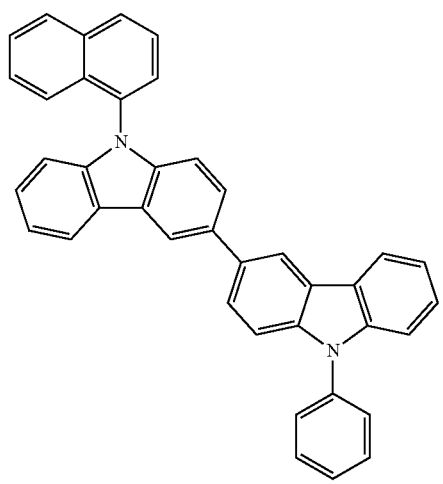
H-137
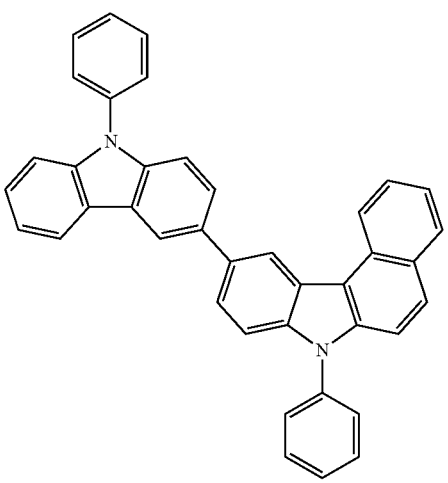
H-138
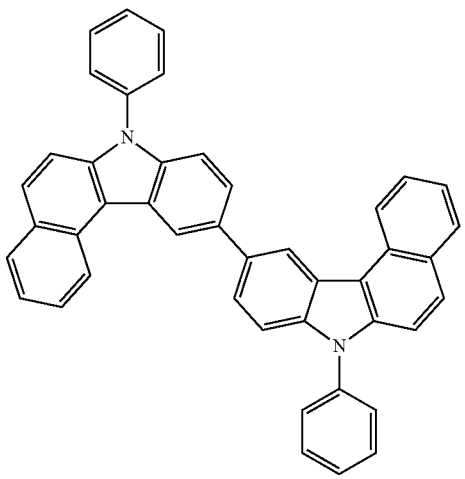
H-139
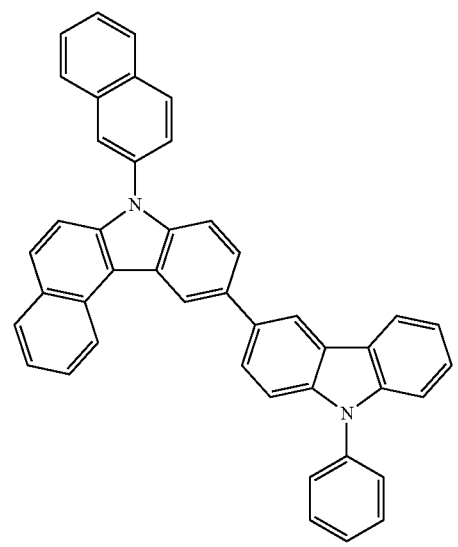
H-140
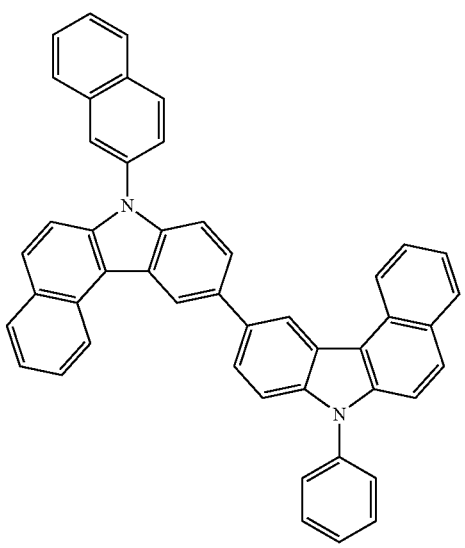

H-141
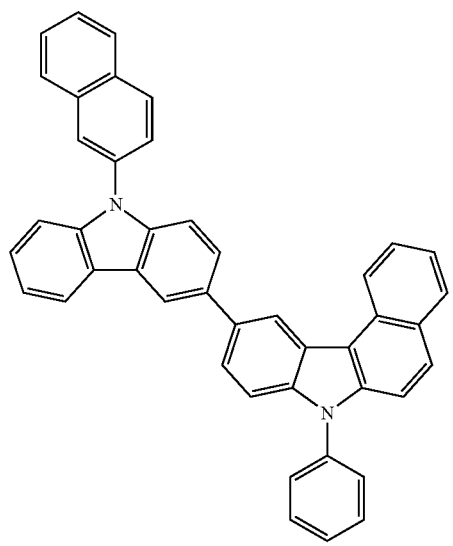
H-142
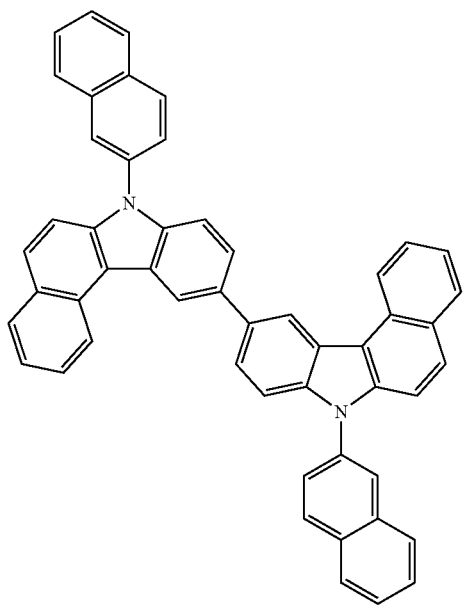
H-143
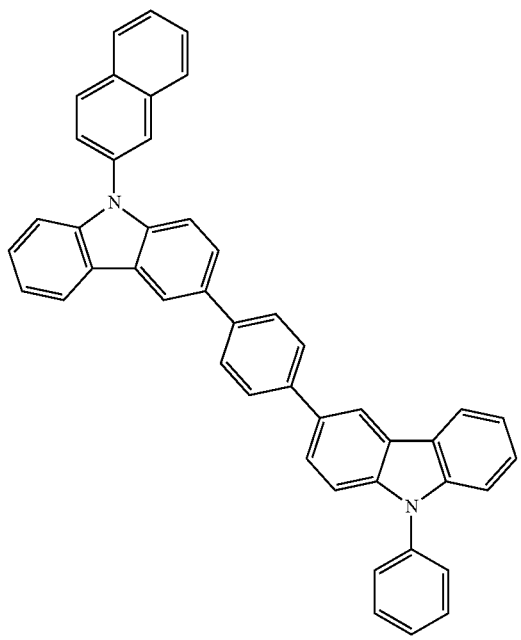
H-144
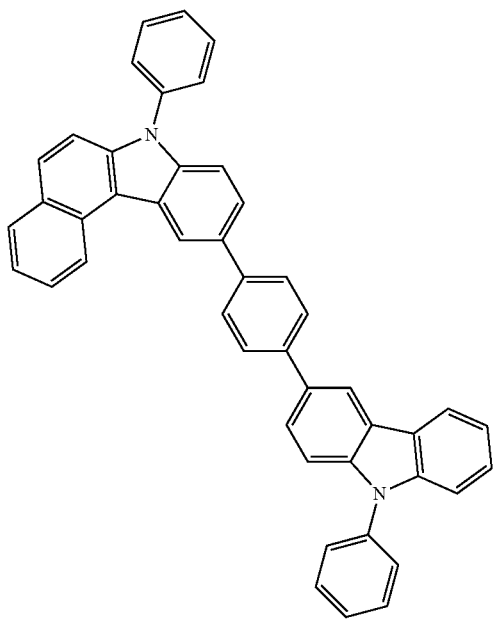

H-145
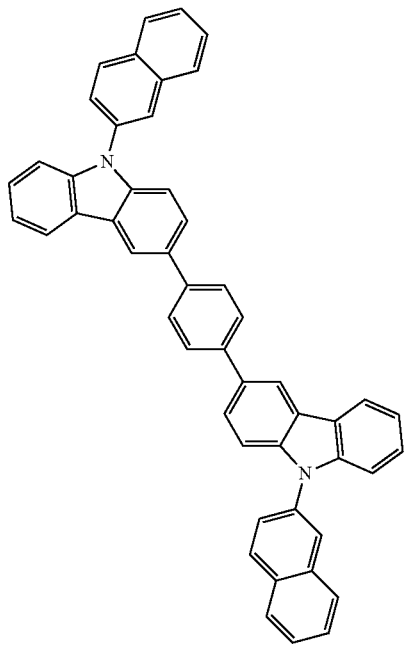
H-147
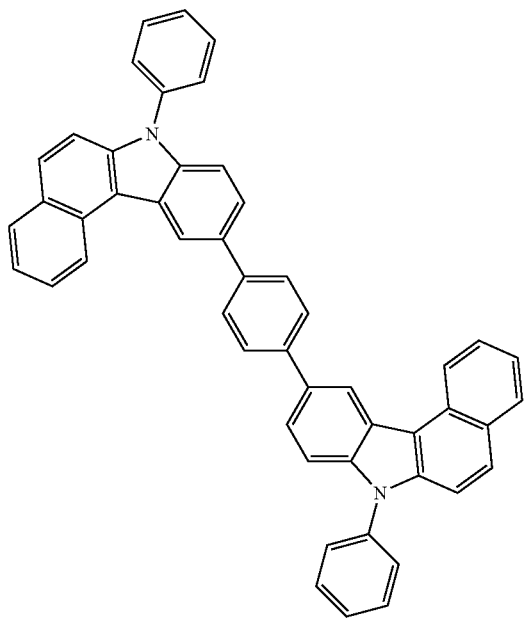
H-146
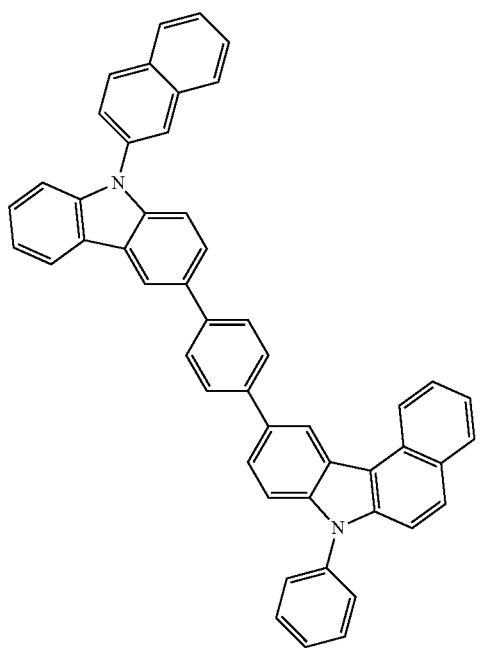
H-148
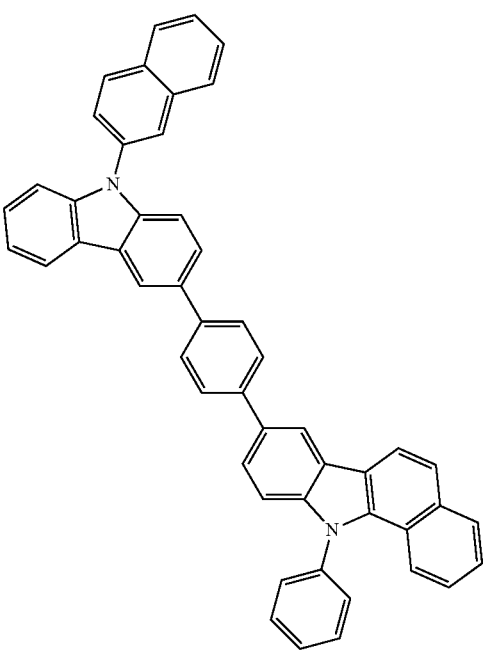

-continued
H-149
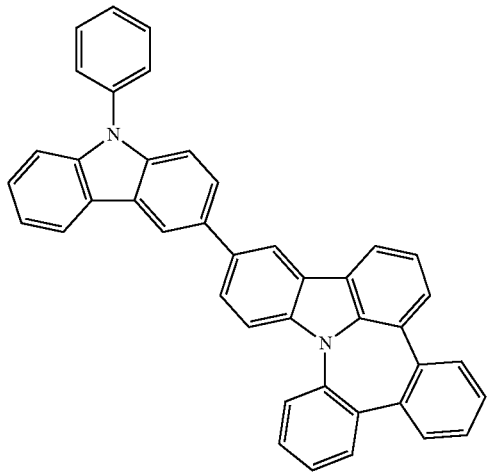
H-150
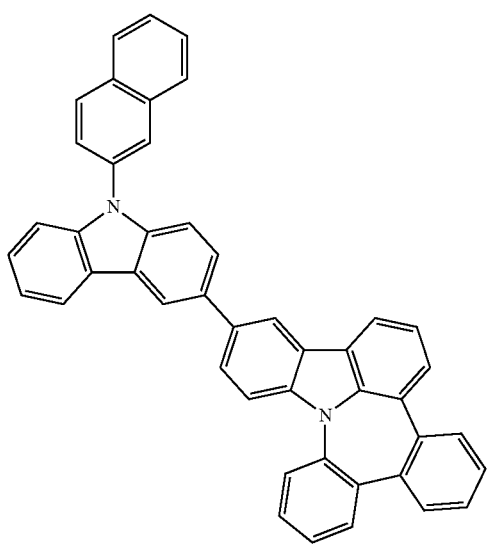
H-151
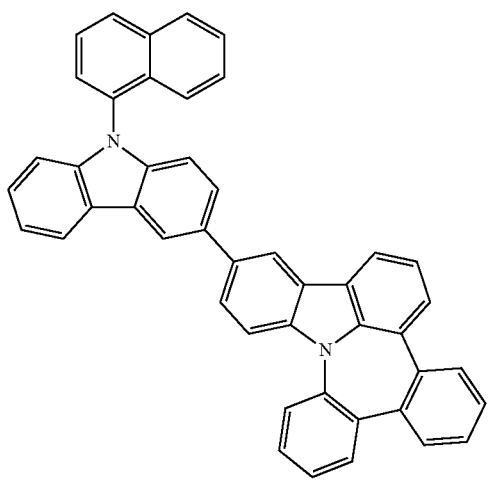
-continued
H-152
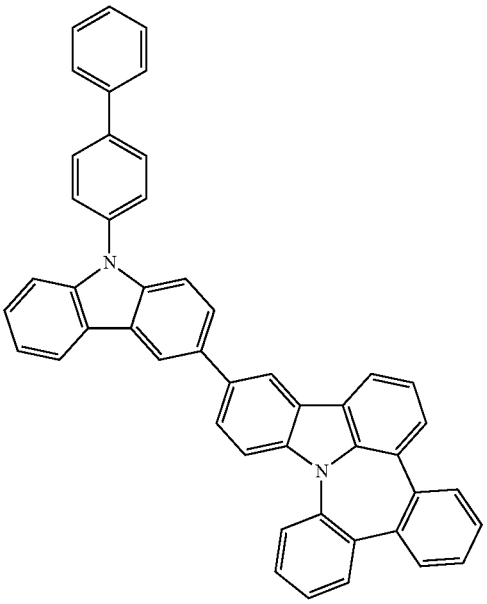
H-153
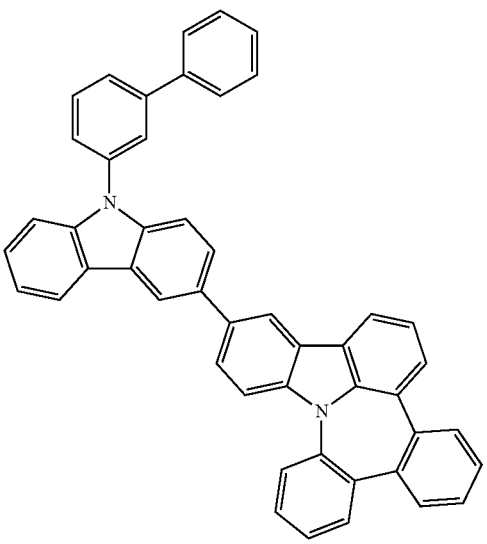

H-154
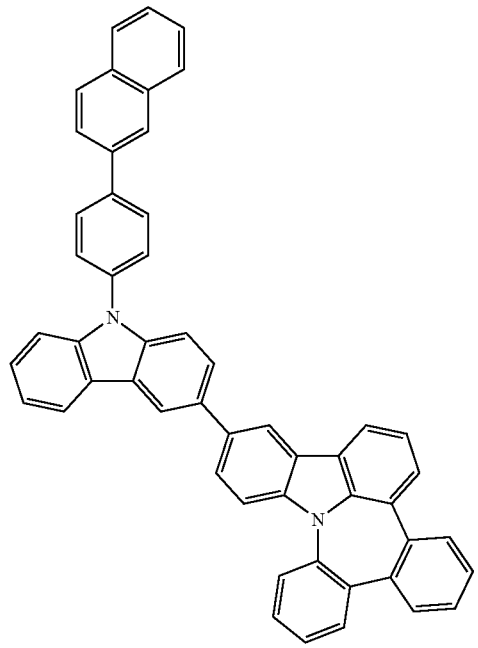
H-156
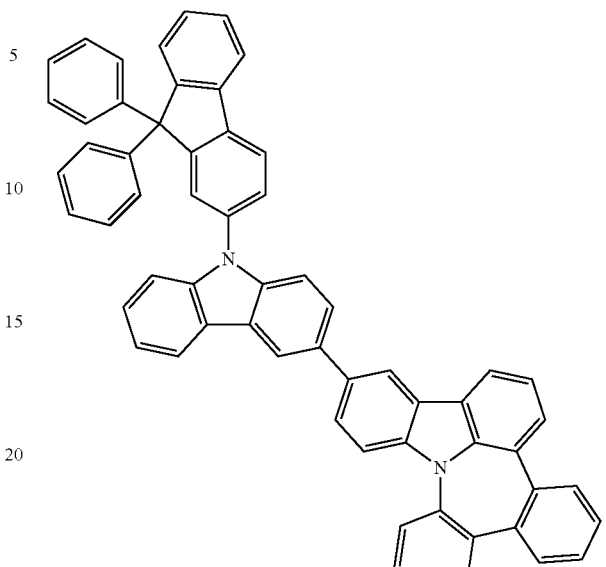
H-157
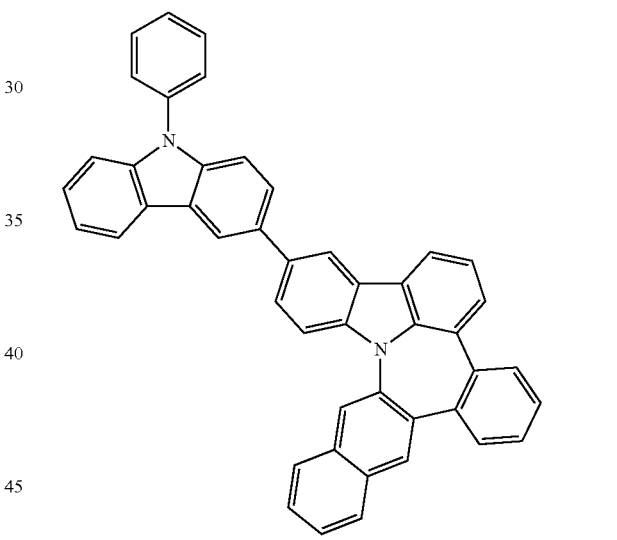
H-155
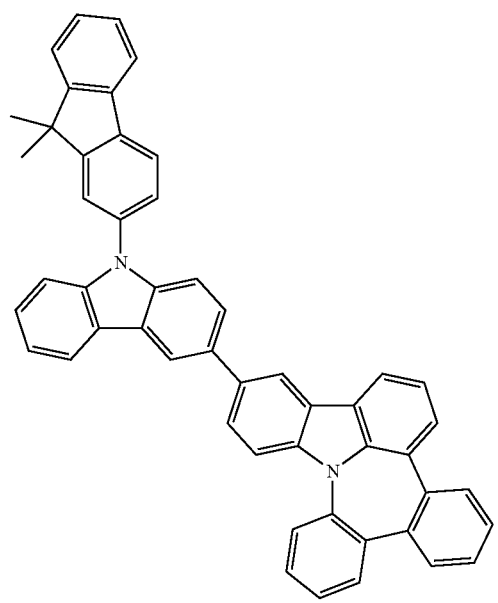
H-158
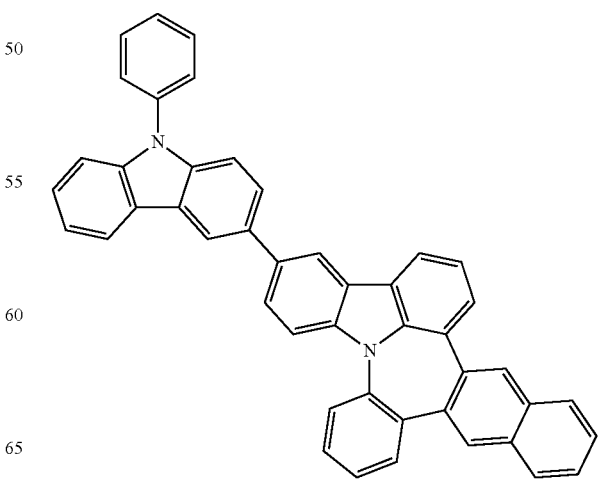

H-159
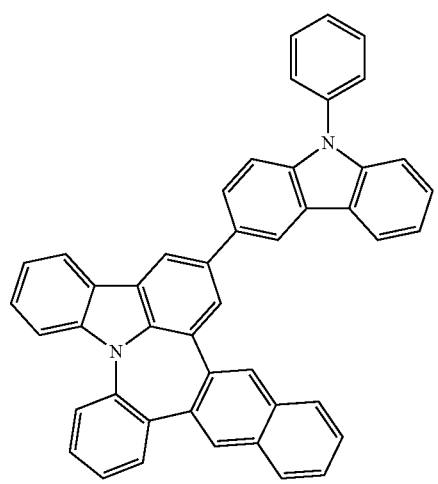
H-160
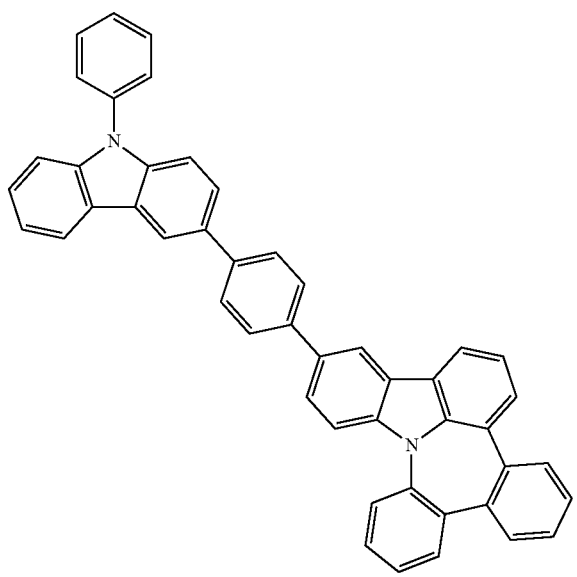
H-161
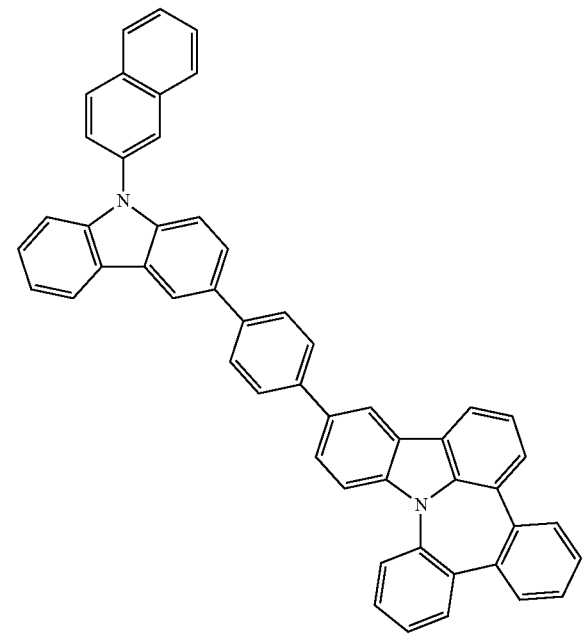
H-162
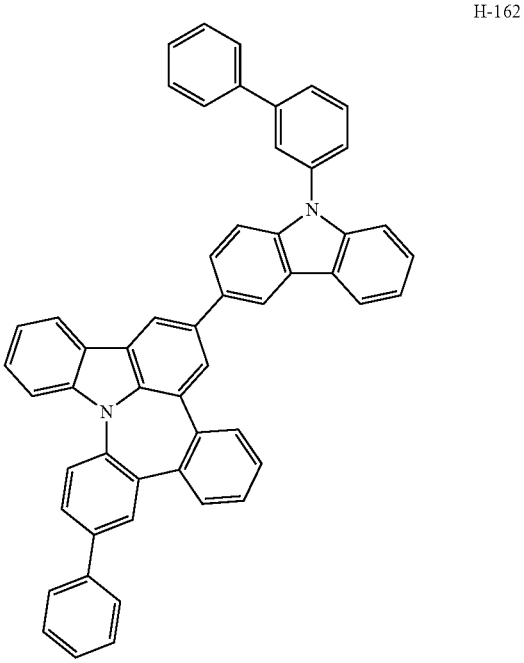

-continued
H-163
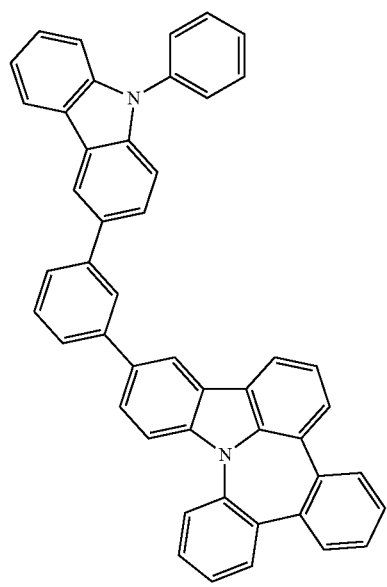
H-164
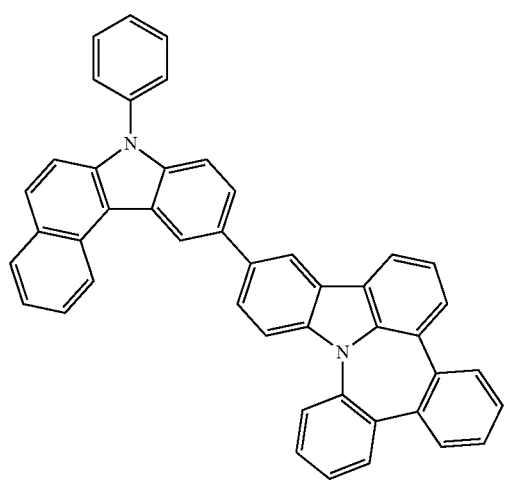
-continued
H-165
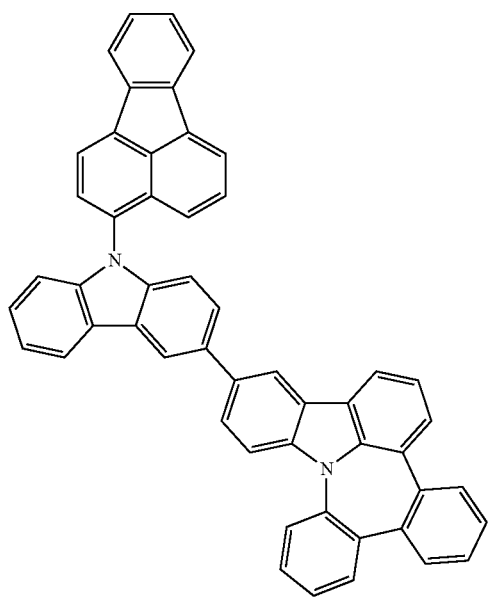
H-166
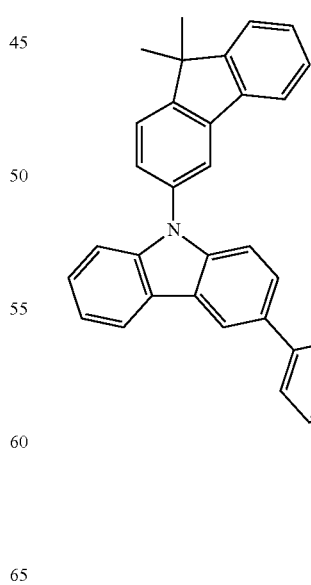

H-167
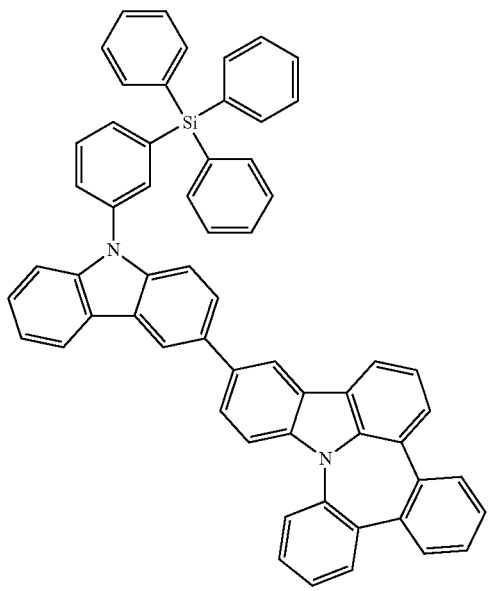
H-168
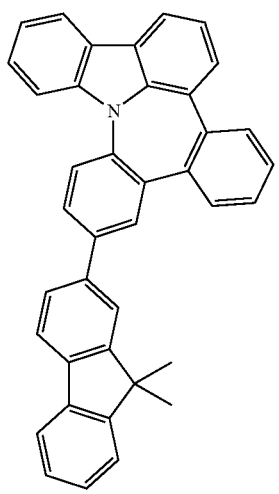
H-169
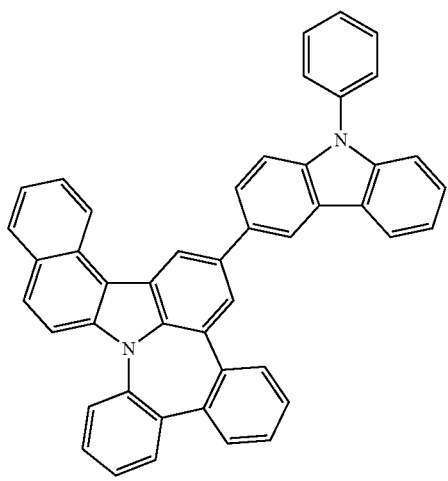
H-170
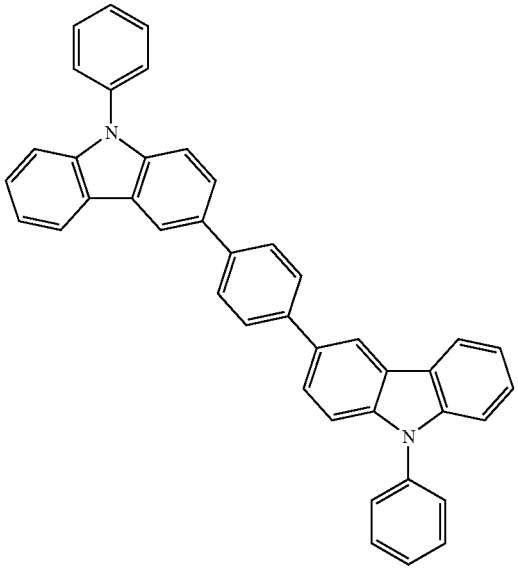
H-171
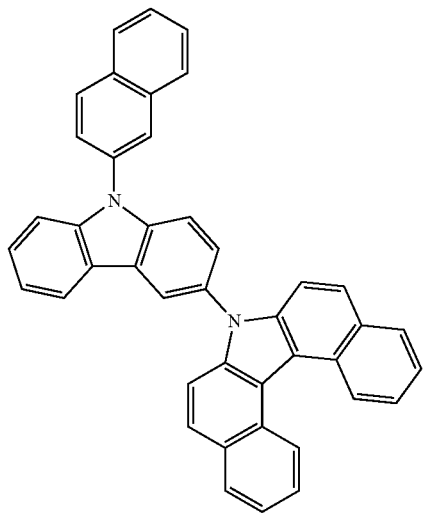
H-173
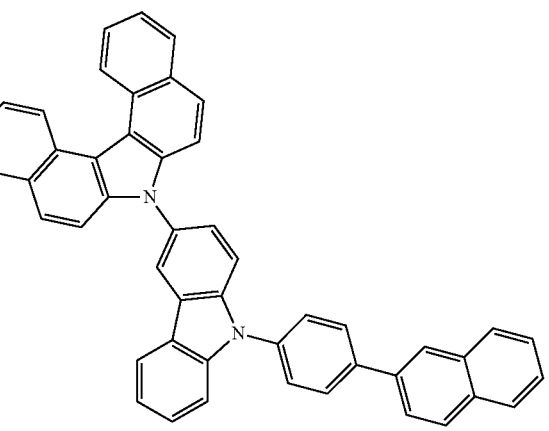

-continued
H-174
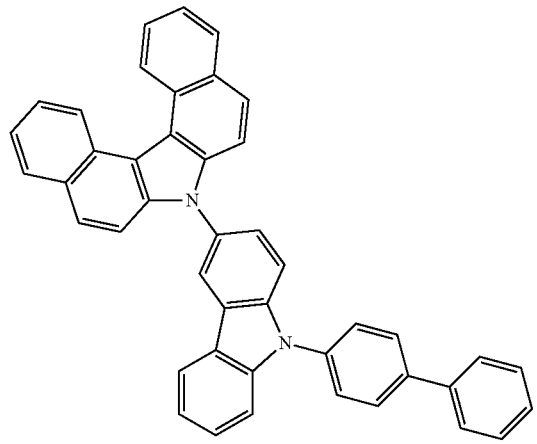
H-175
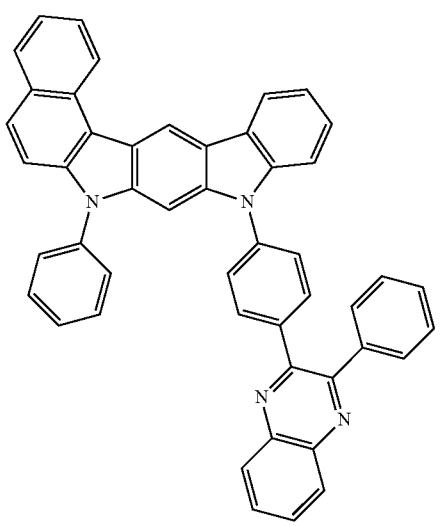
and
H-176
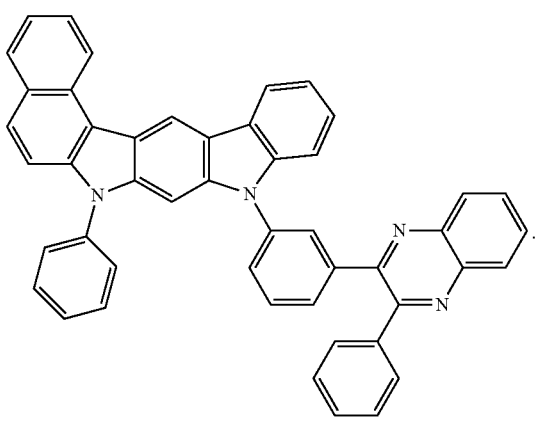
C-1
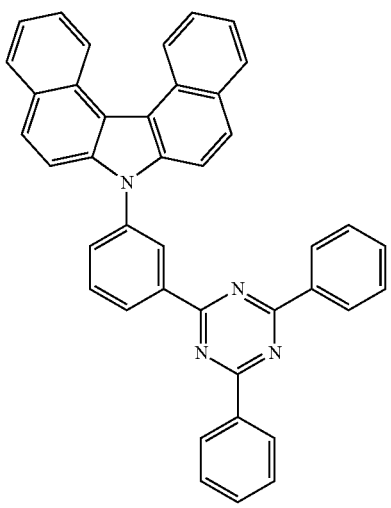
C-2
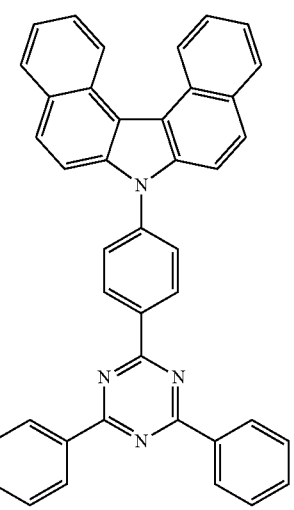
C-3
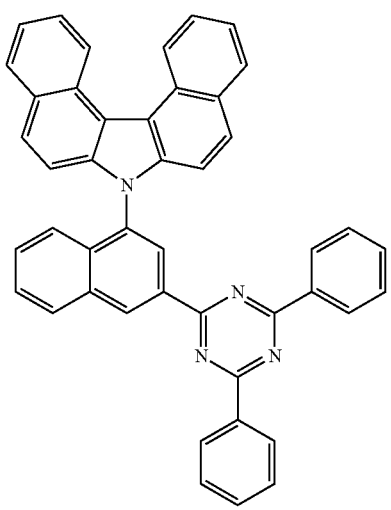
6. The organic electroluminescent device according to claim 1, wherein the compound represented by formula 2 is selected from the group consisting of:

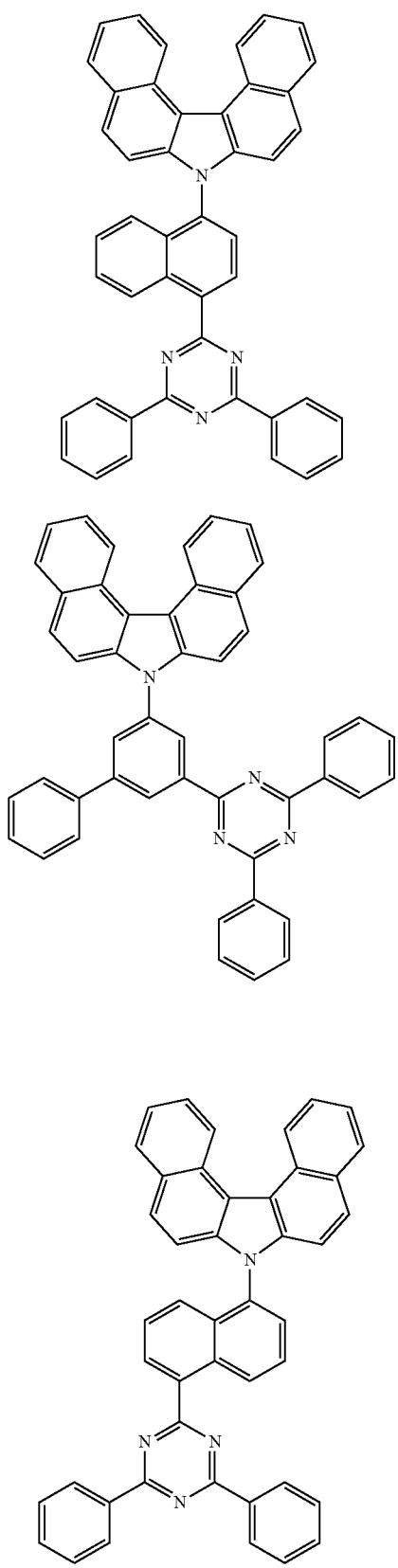
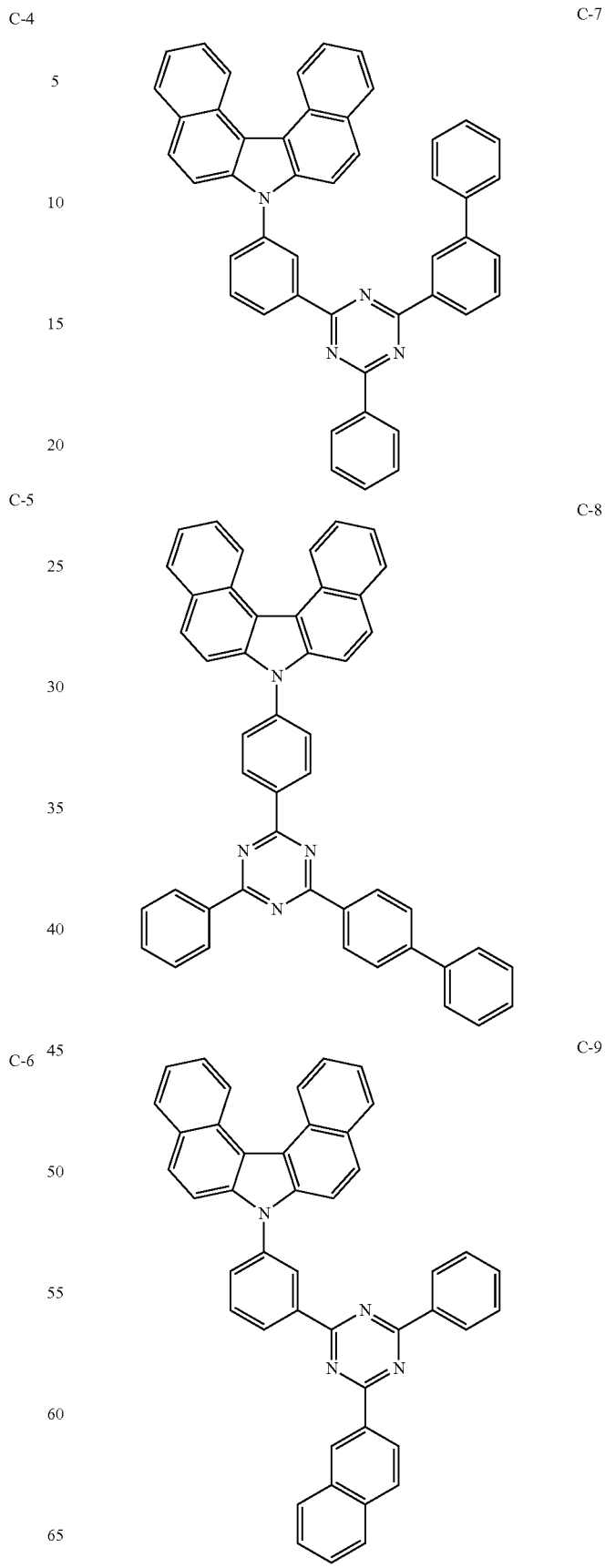

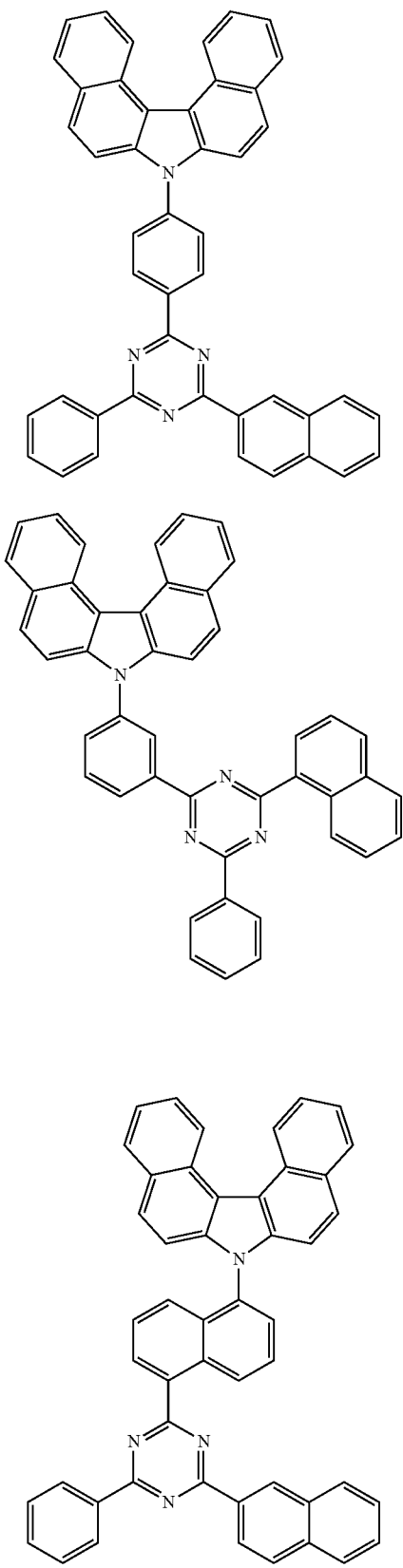
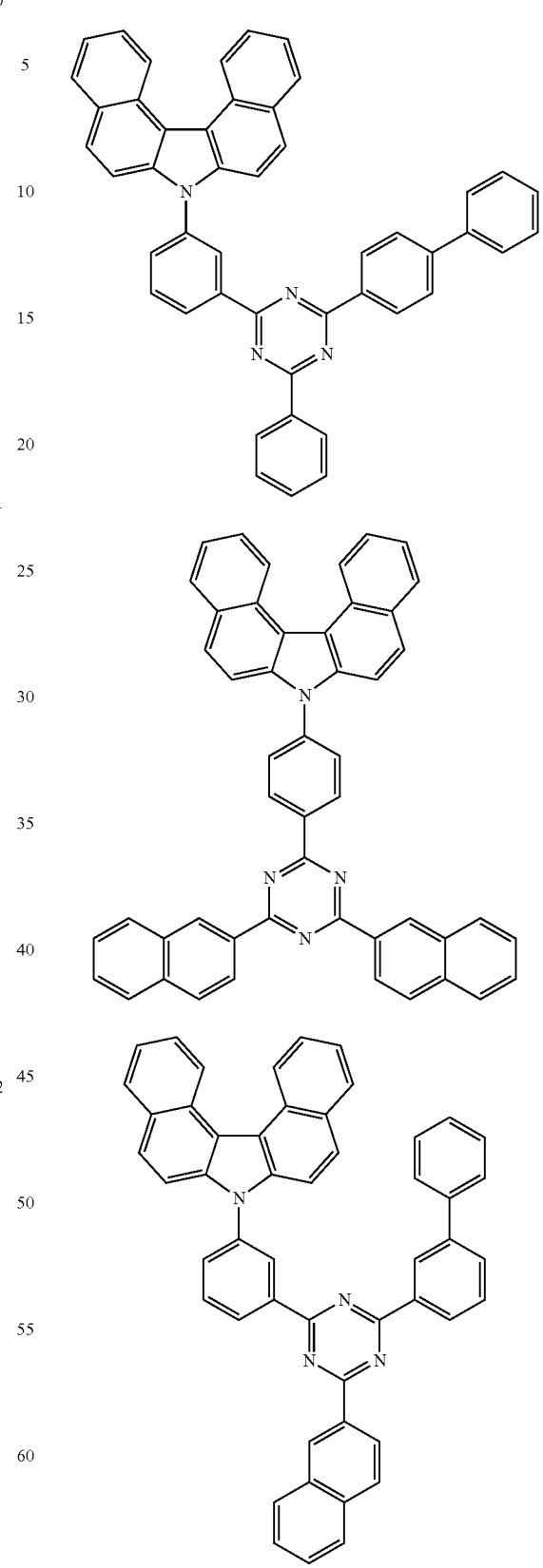

C-16
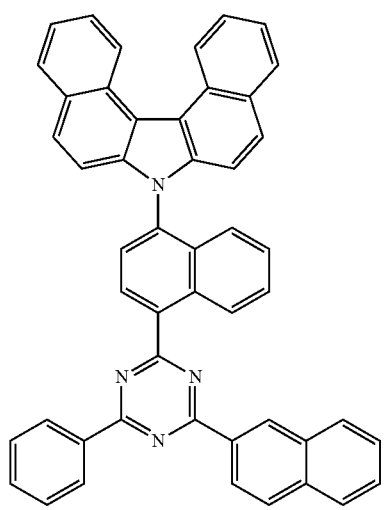
C-17
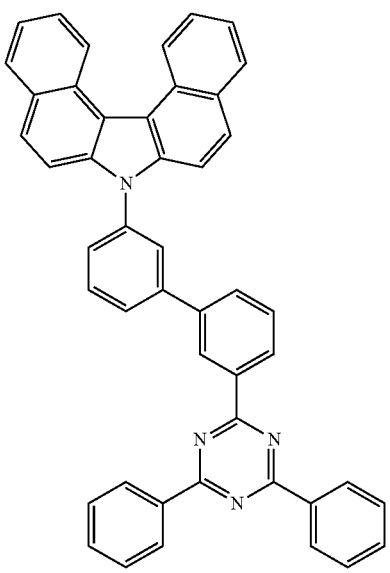
C-18
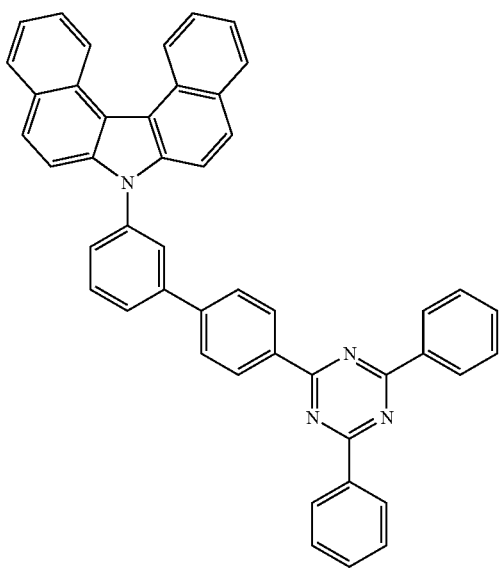
C-19
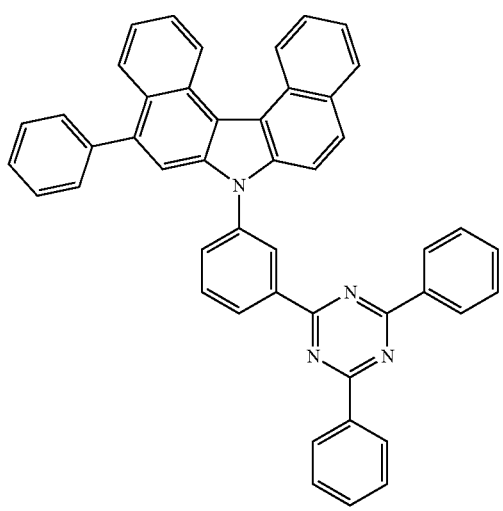
C-20
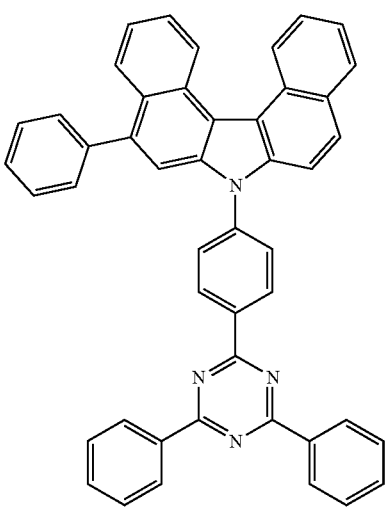
C-21
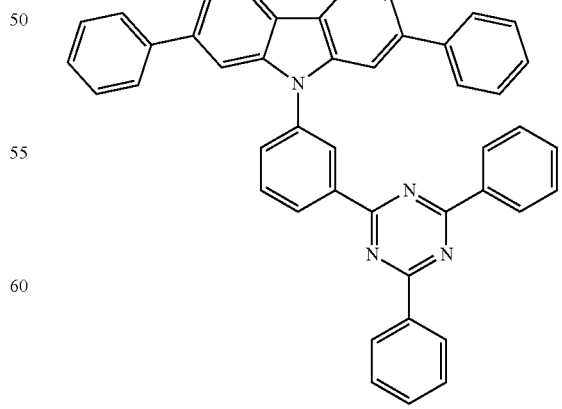

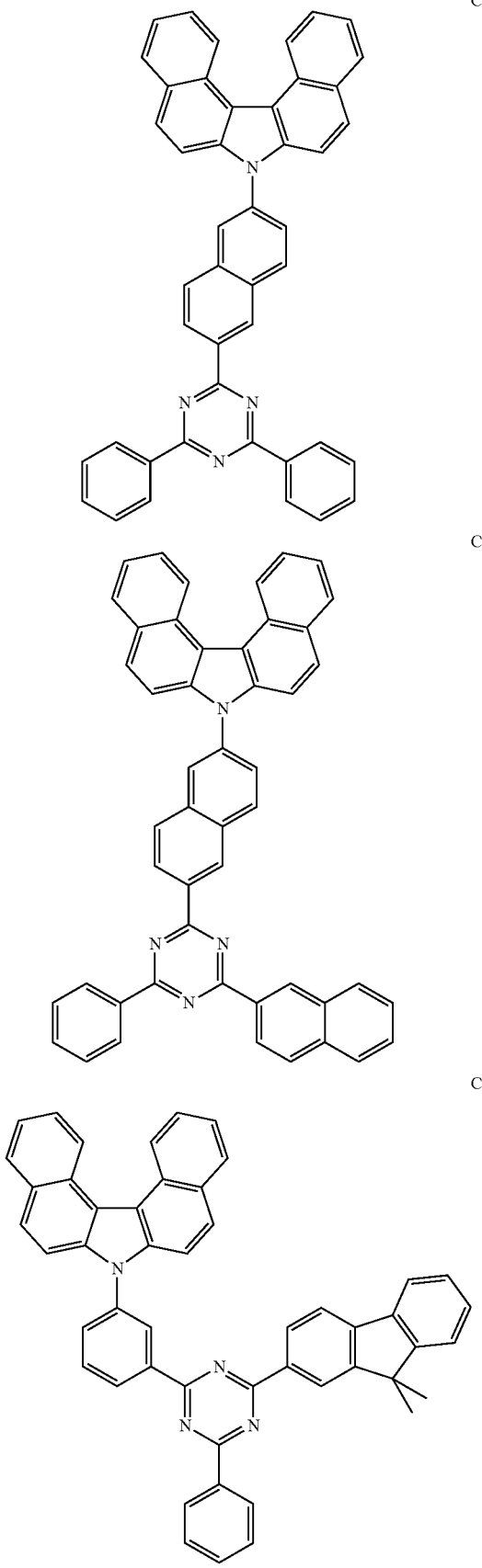
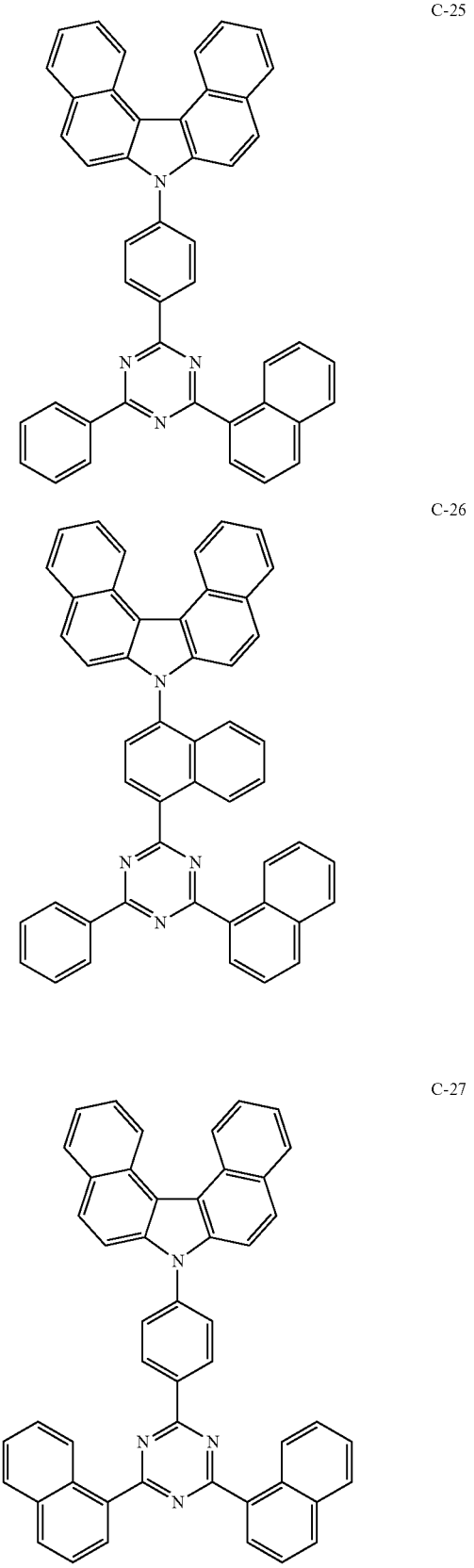

-continued
C-28
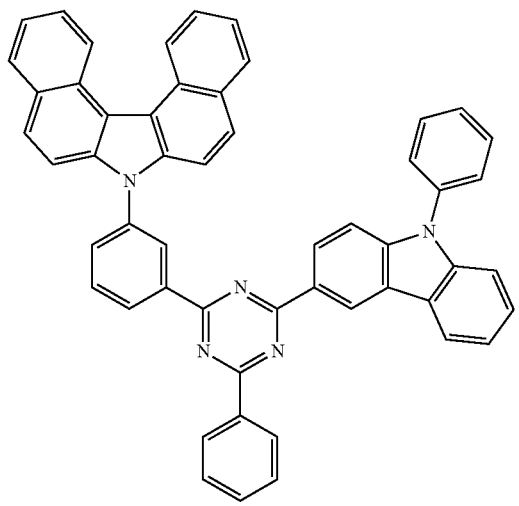
C-29
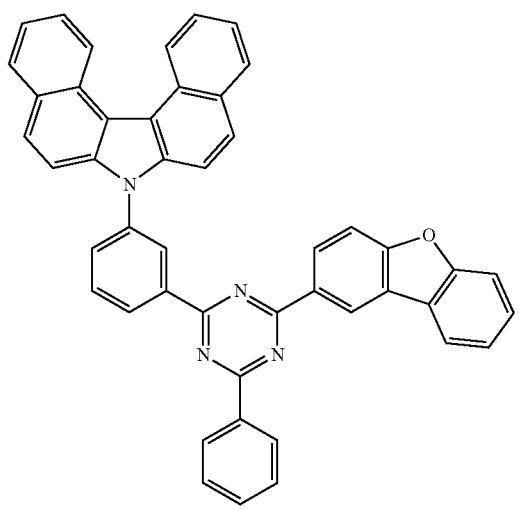
C-30
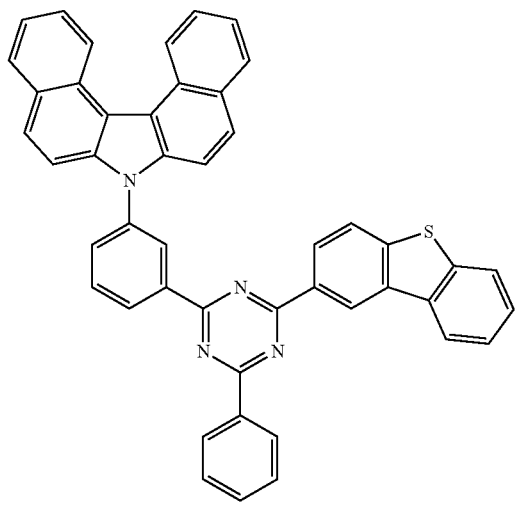
-continued
C-31
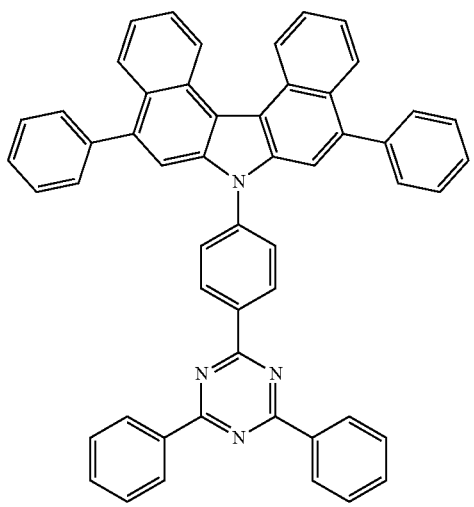
C-32
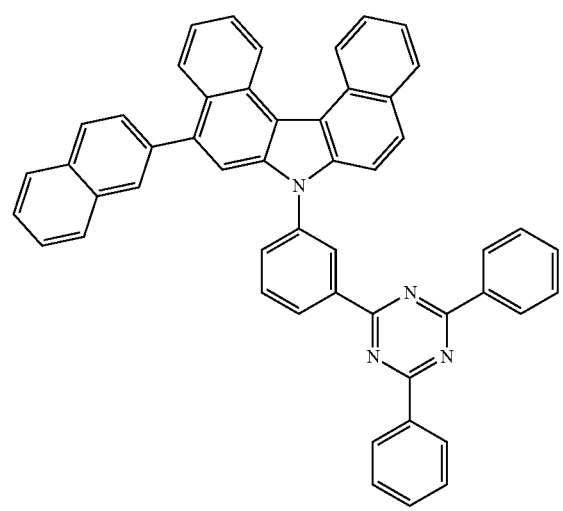
C-33
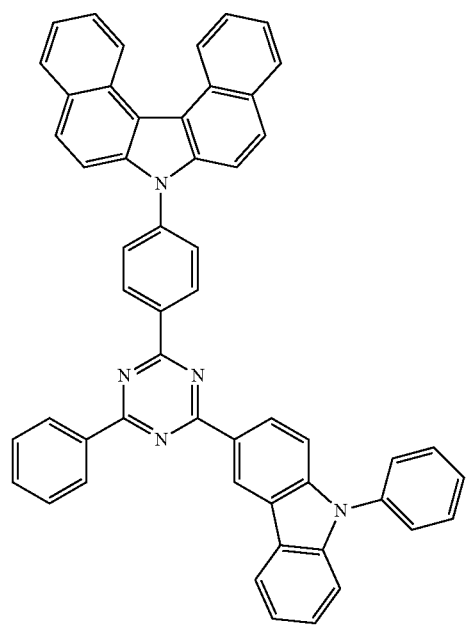

-continued
C-34
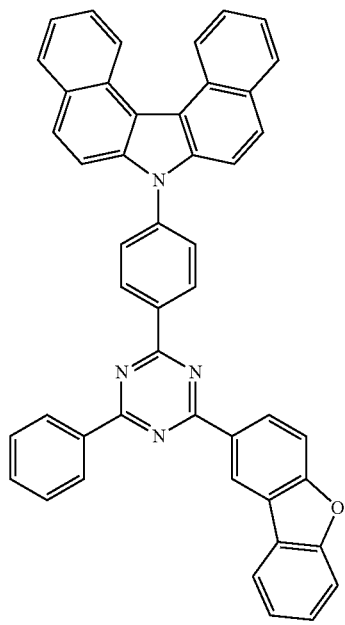
C-35
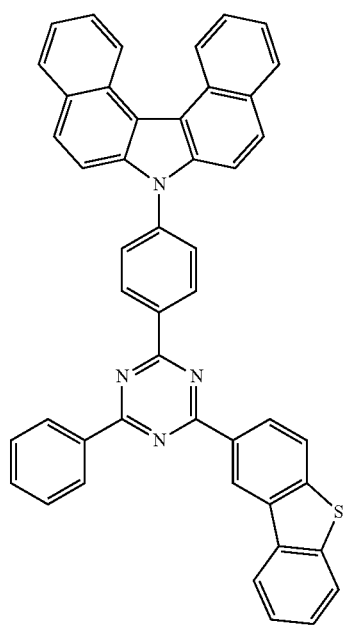
C-36
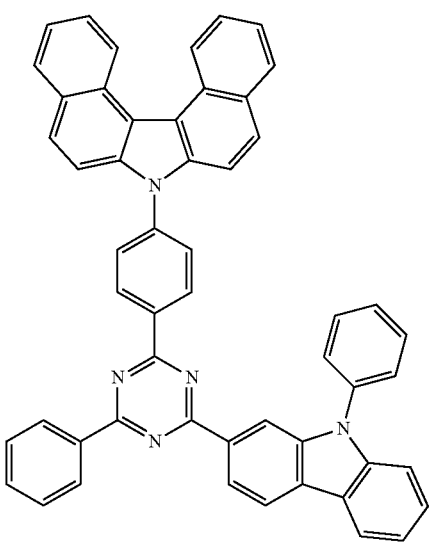
C-37
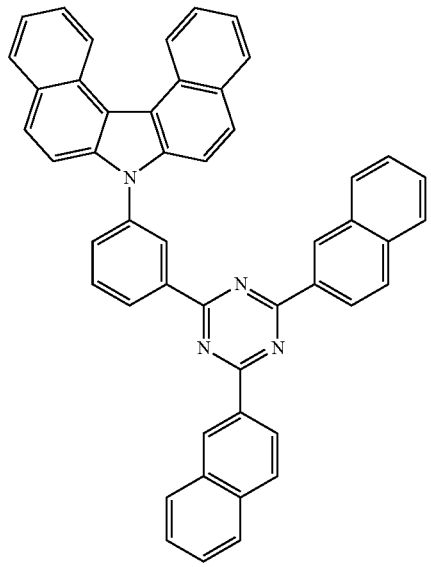
C-38
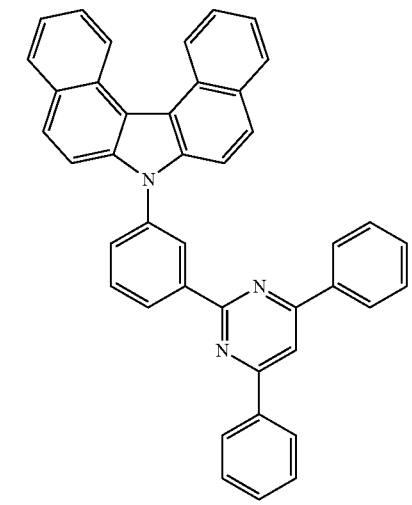

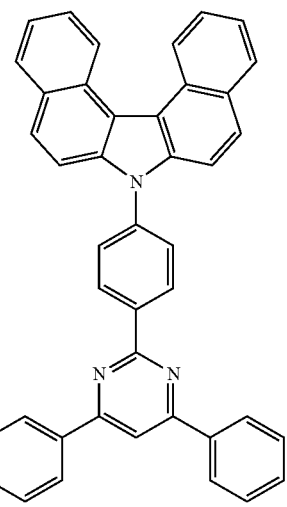
C-39
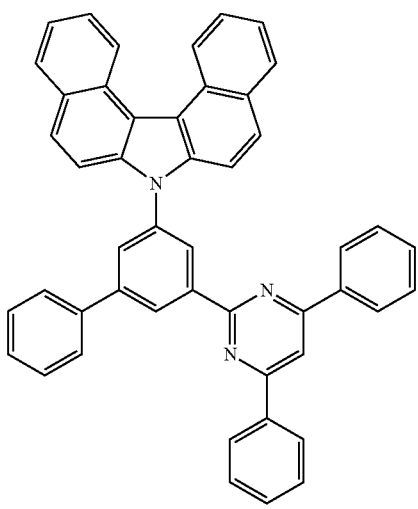
C-42
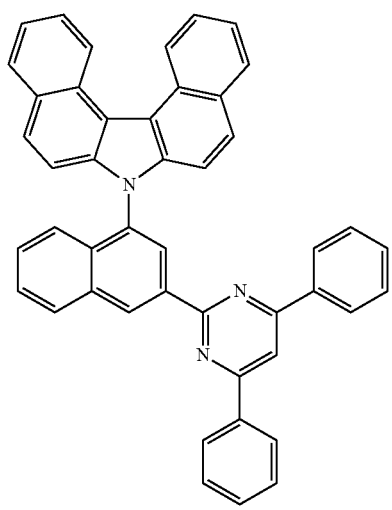
C-40
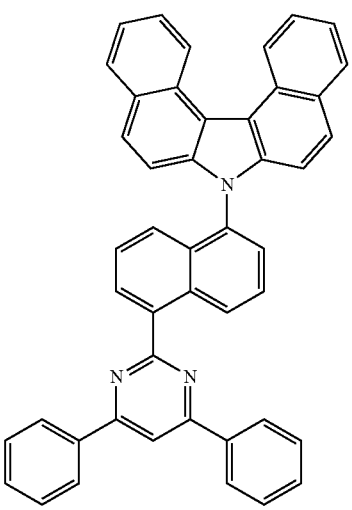
C-43
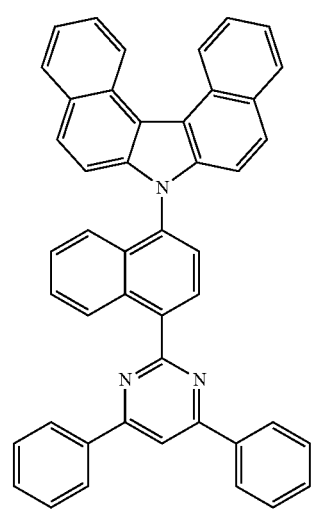
C-41
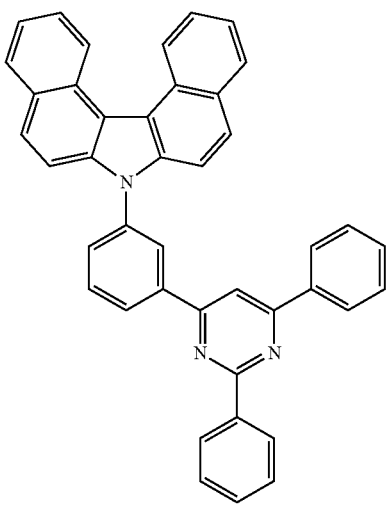
C-44

C-45
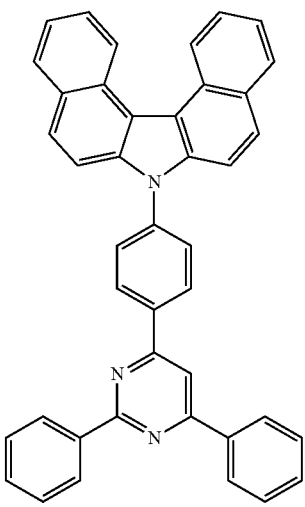
C-46
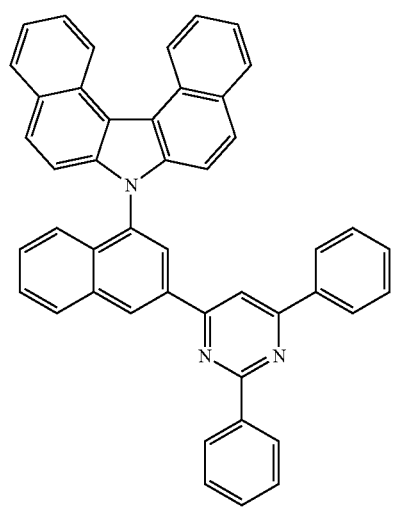
C-47
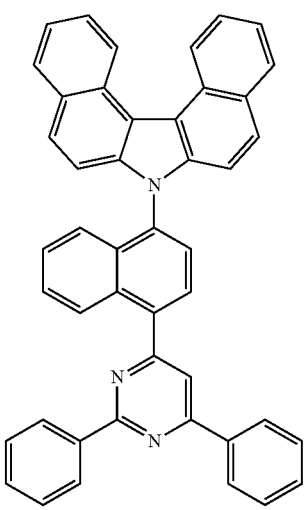
C-48
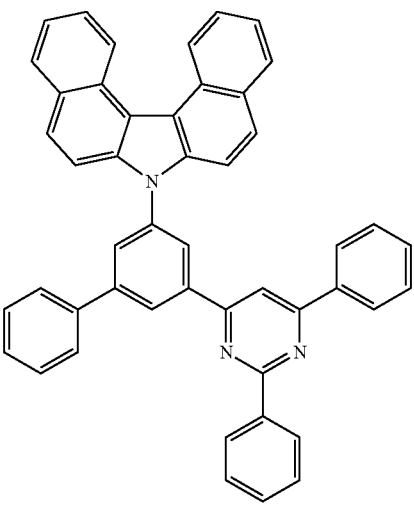
C-49
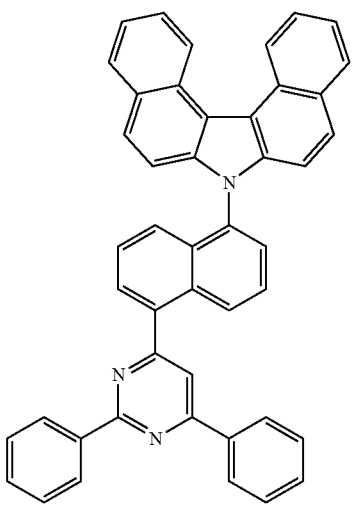
C-50
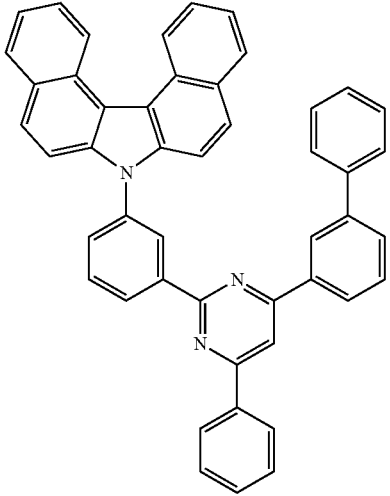

-continued
C-51
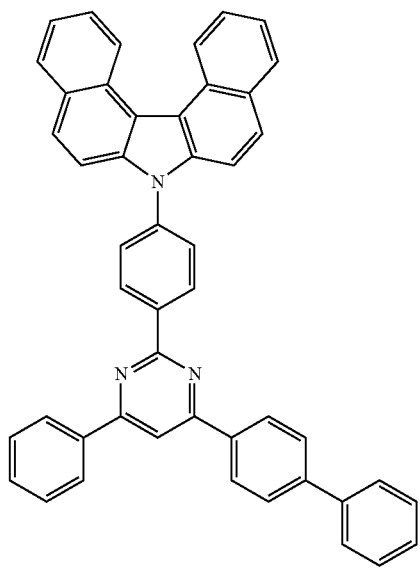
C-52
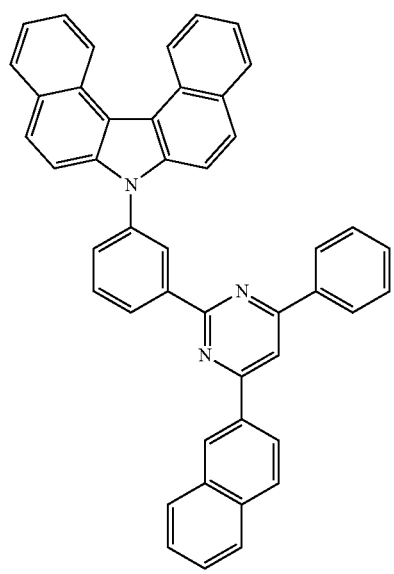
C-53
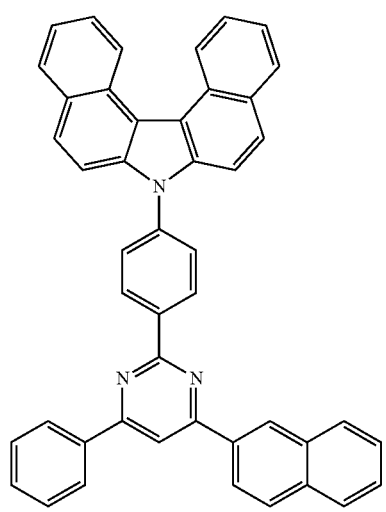
-continued
C-54
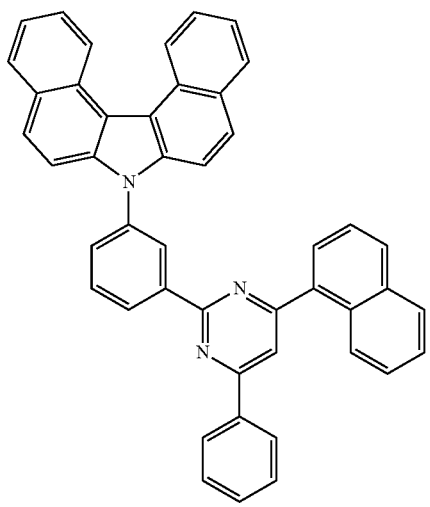
C-55
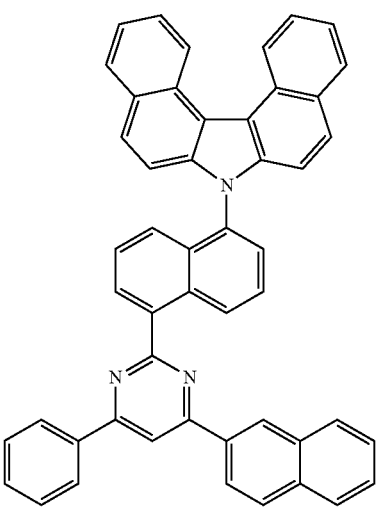
C-56
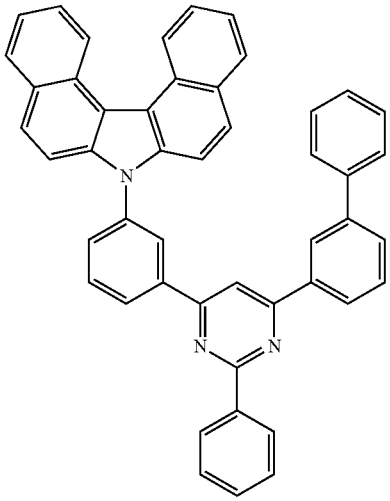

-continued
C-57
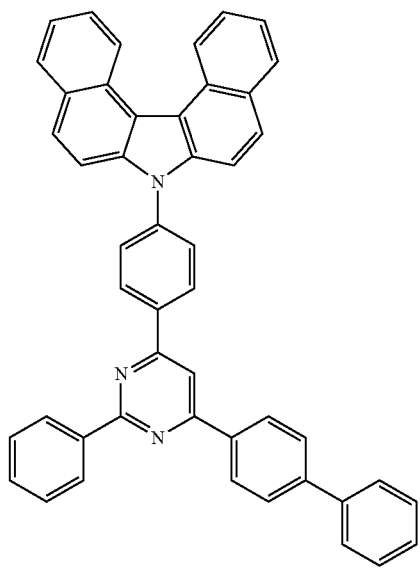
C-58
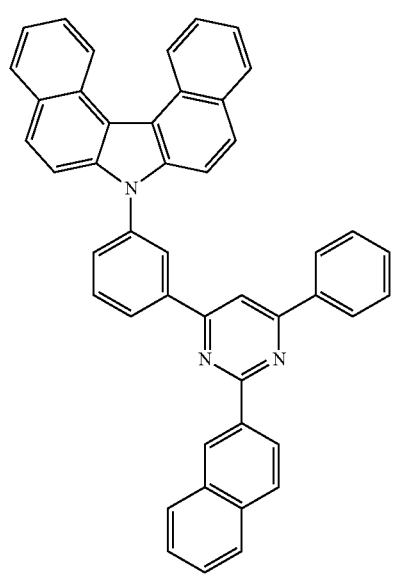
C-59
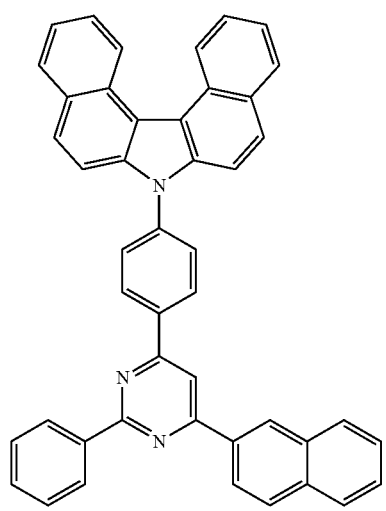
-continued
C-60
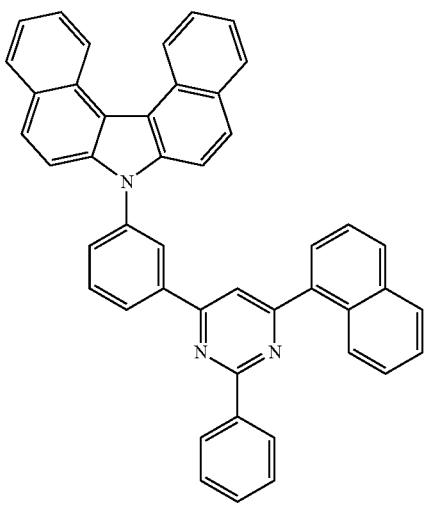
C-61
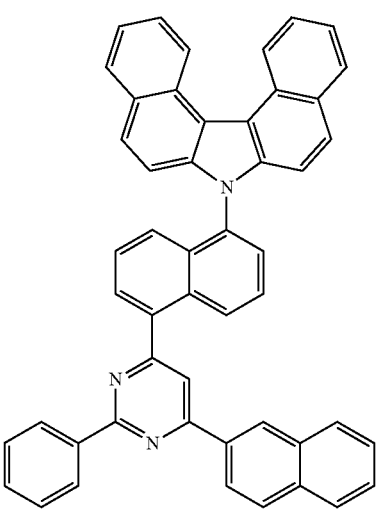
C-62
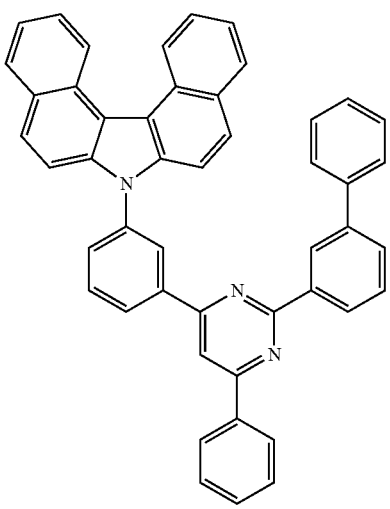

-continued
C-63
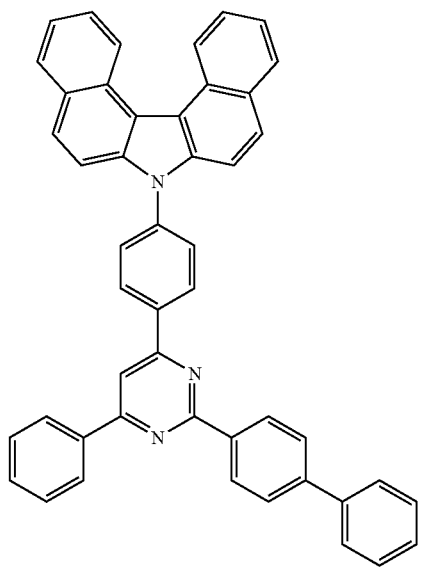
C-64
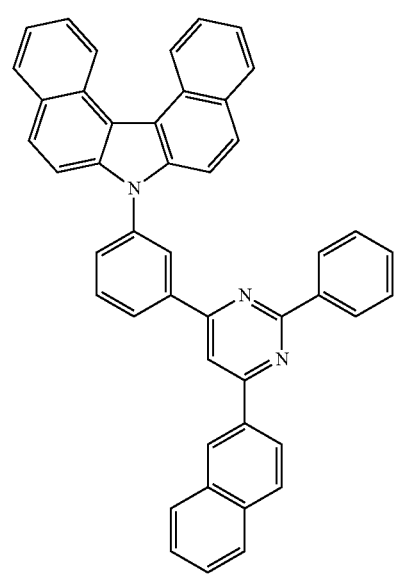
C-65
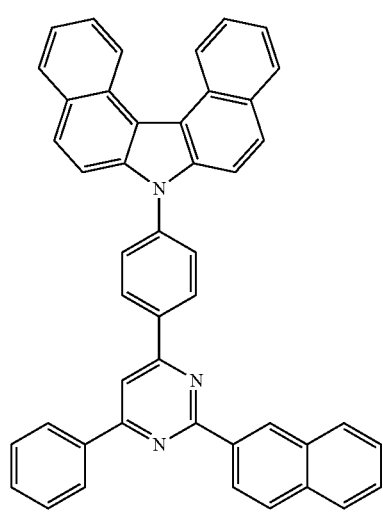
-continued
C-66
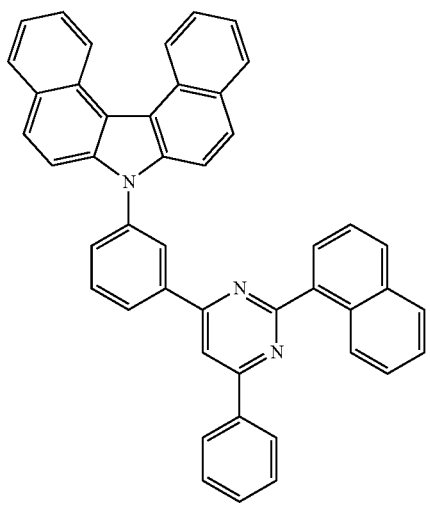
C-67
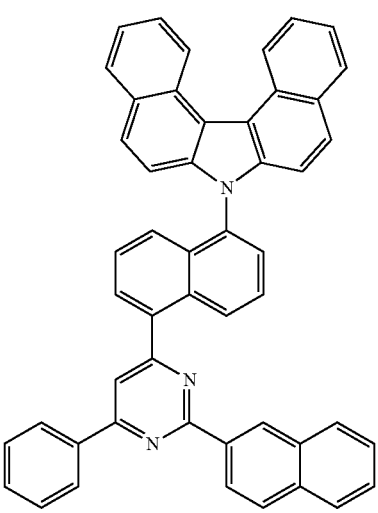
C-68
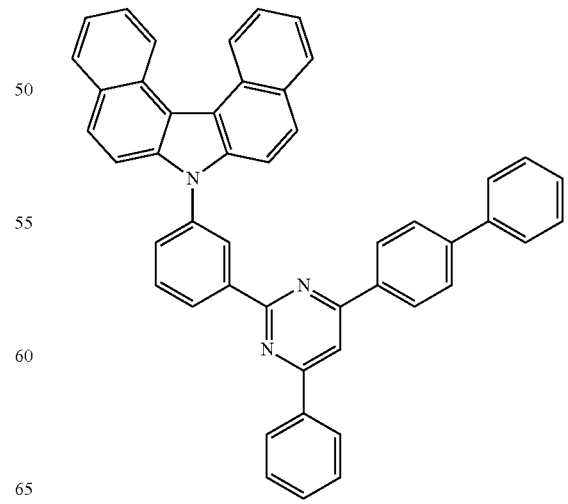

C-69
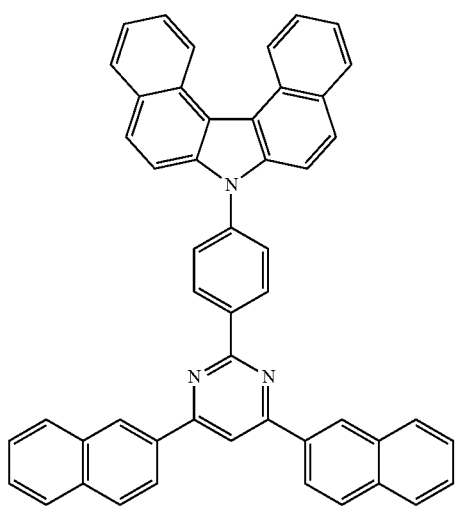
C-70
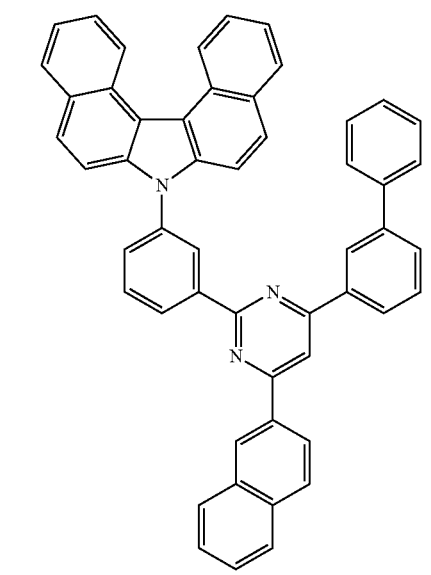
C-71
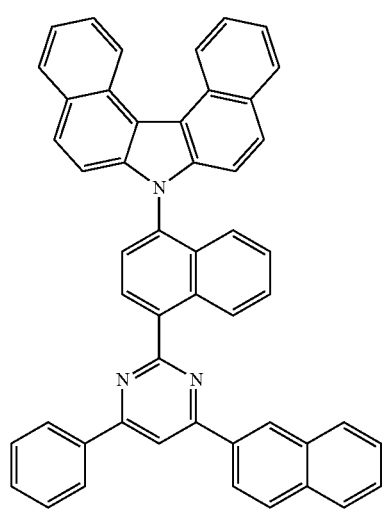
C-72
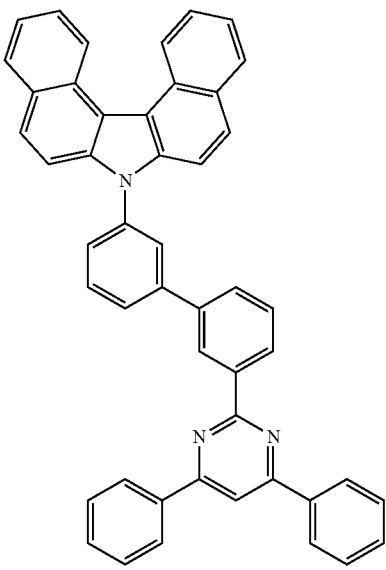
C-73
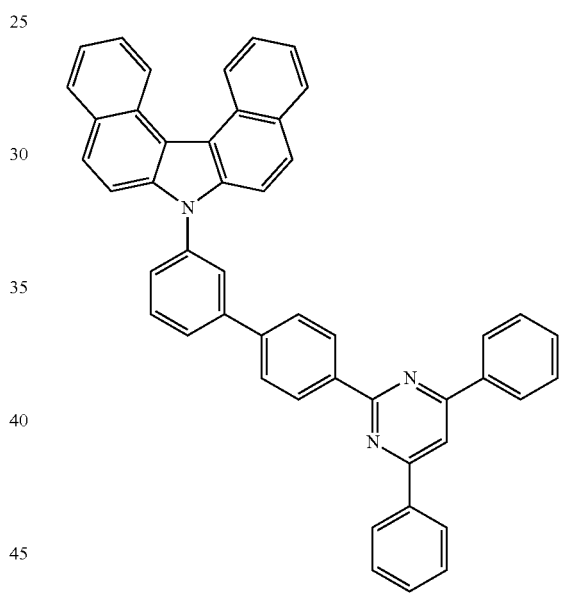
C-74
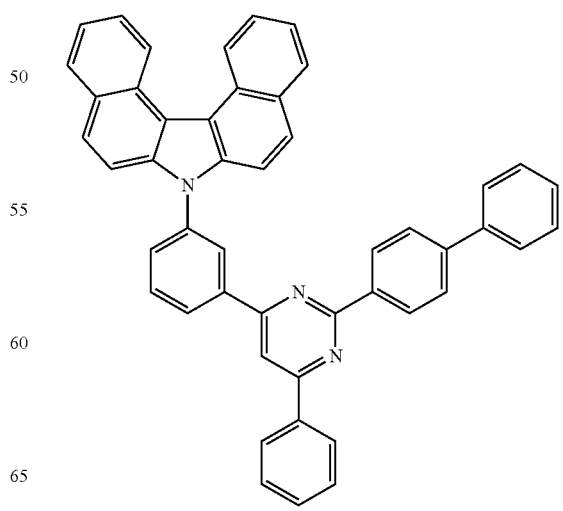

C-75
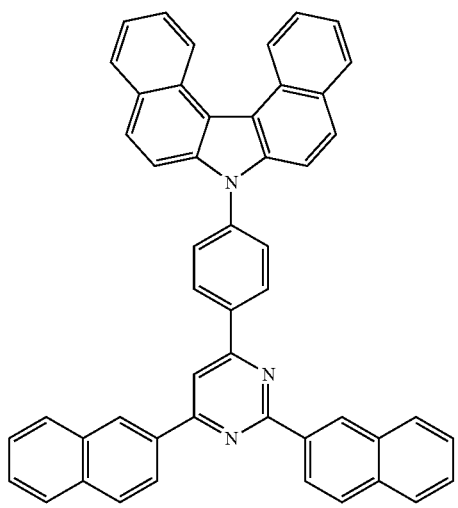
C-76
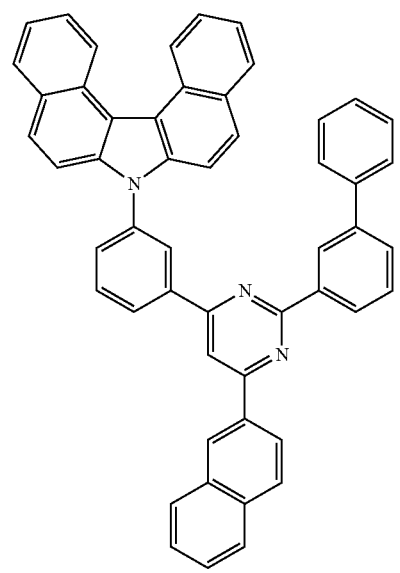
C-77
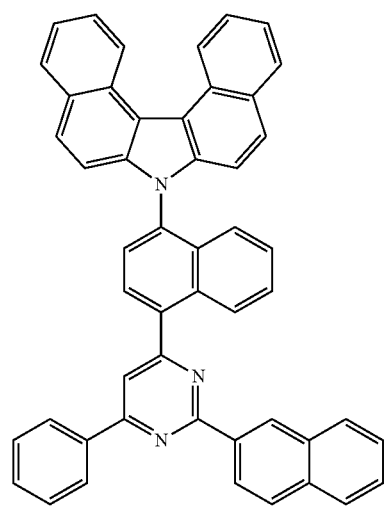
C-78
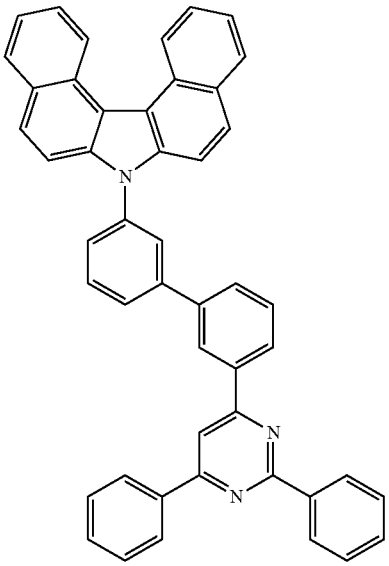
C-79
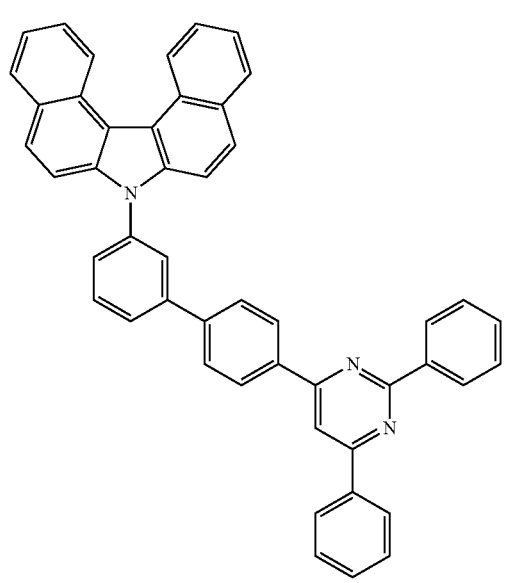
C-80
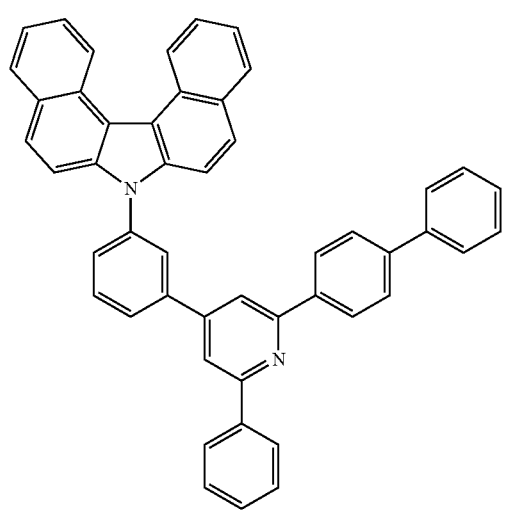

C-81
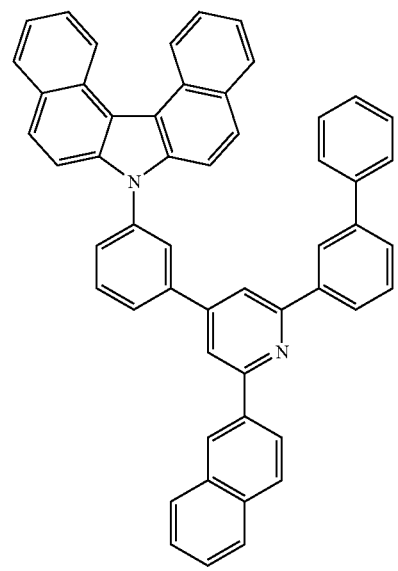
C-82
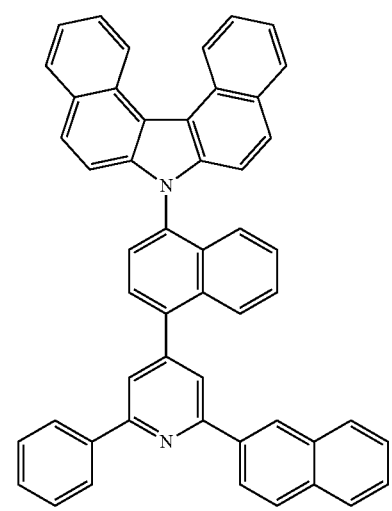
C-83
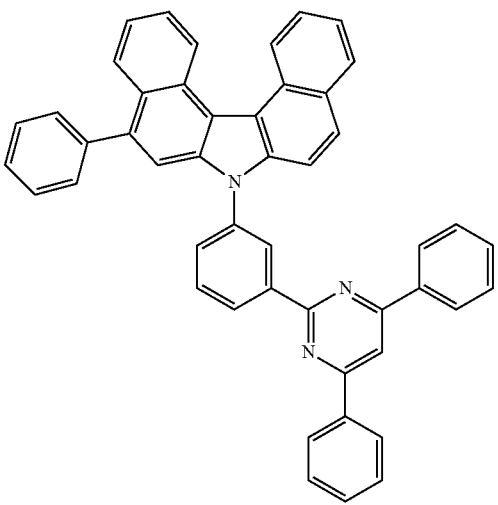
C-84
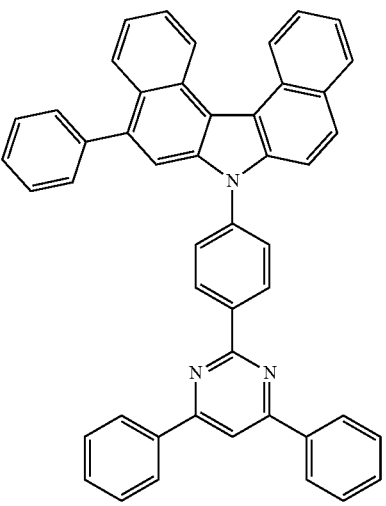
C-85
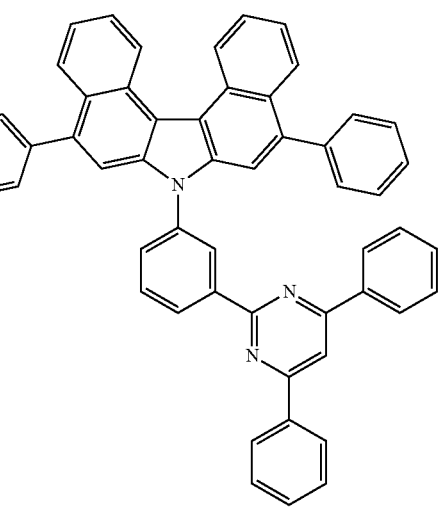
C-86
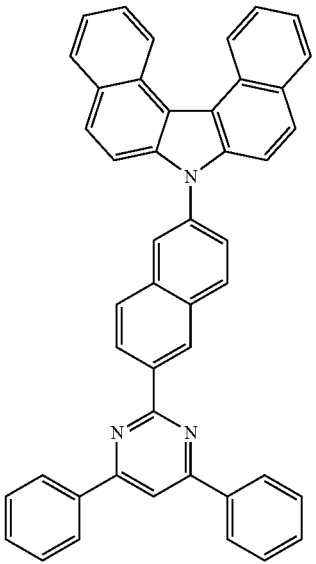

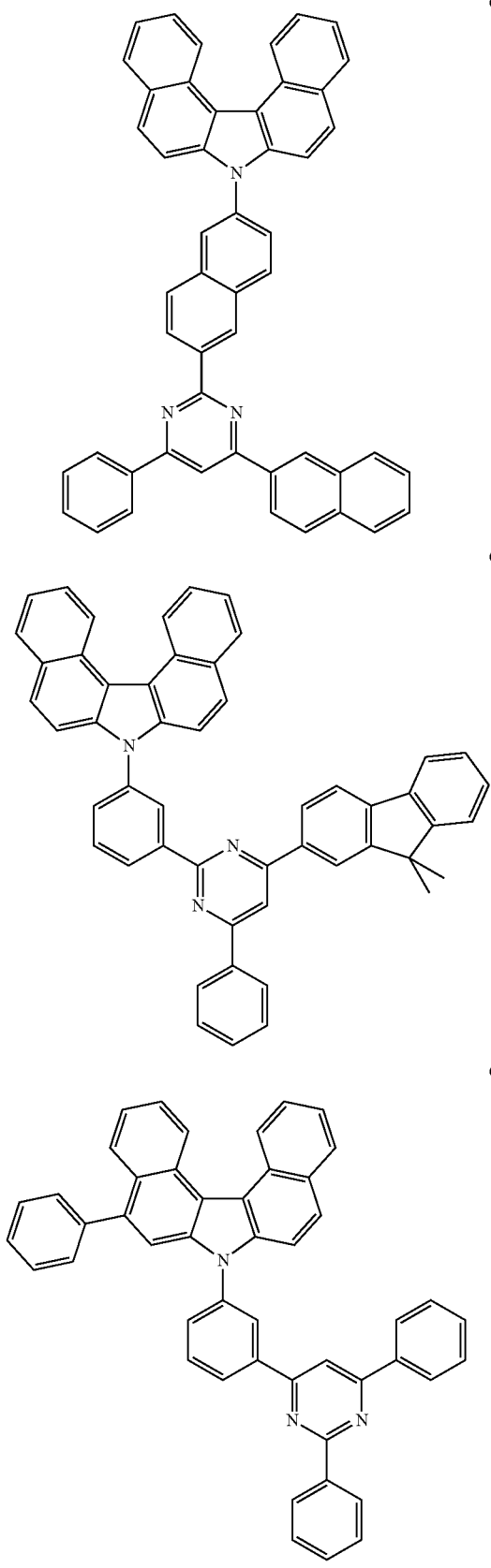
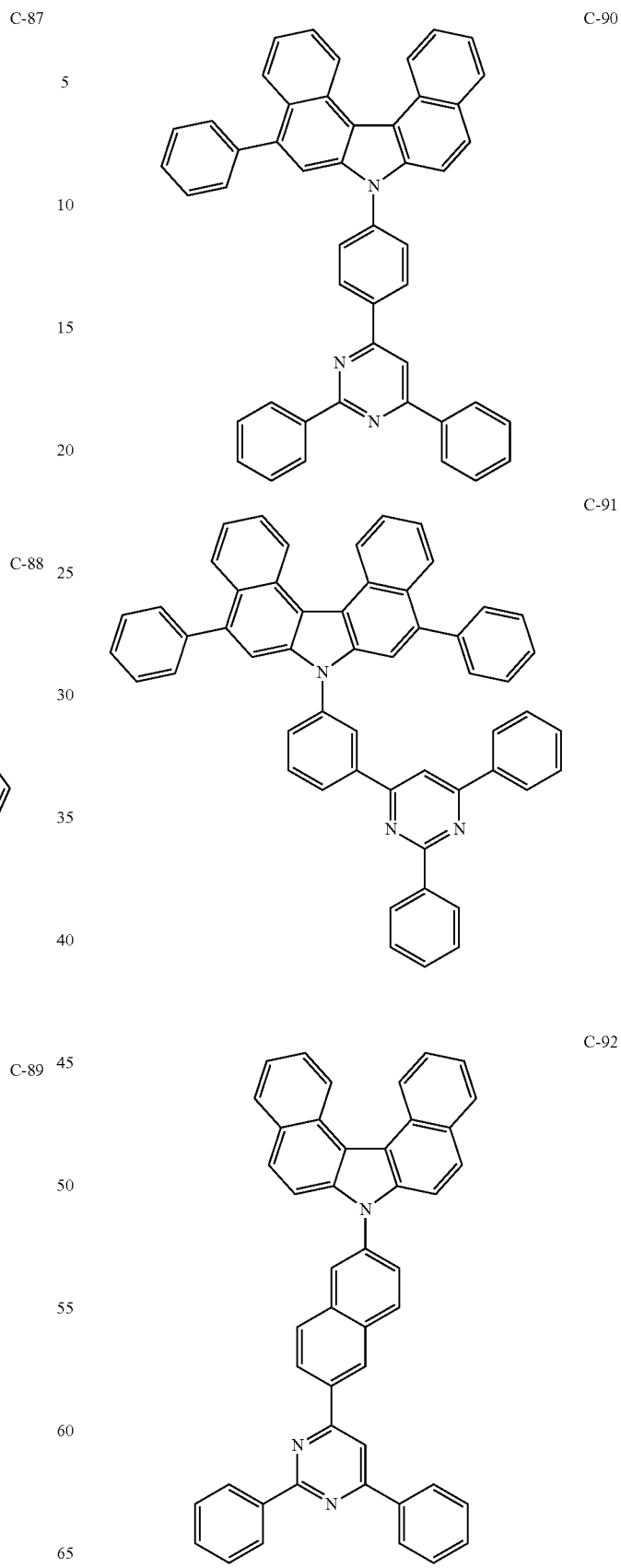

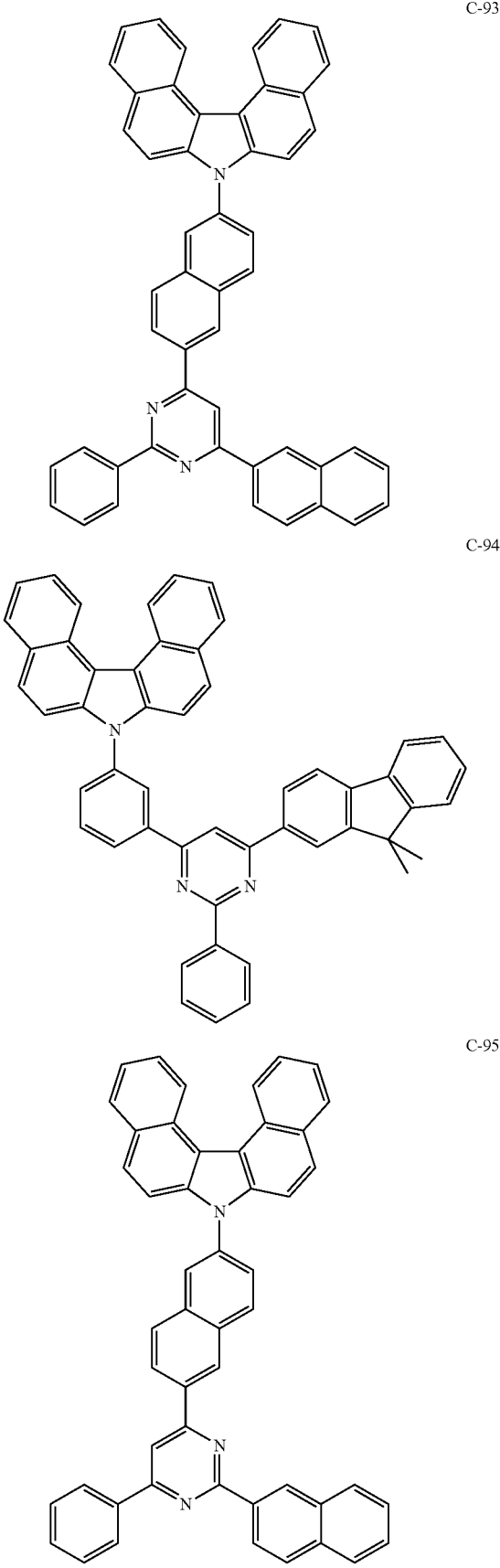
C-93
C-94
C-95
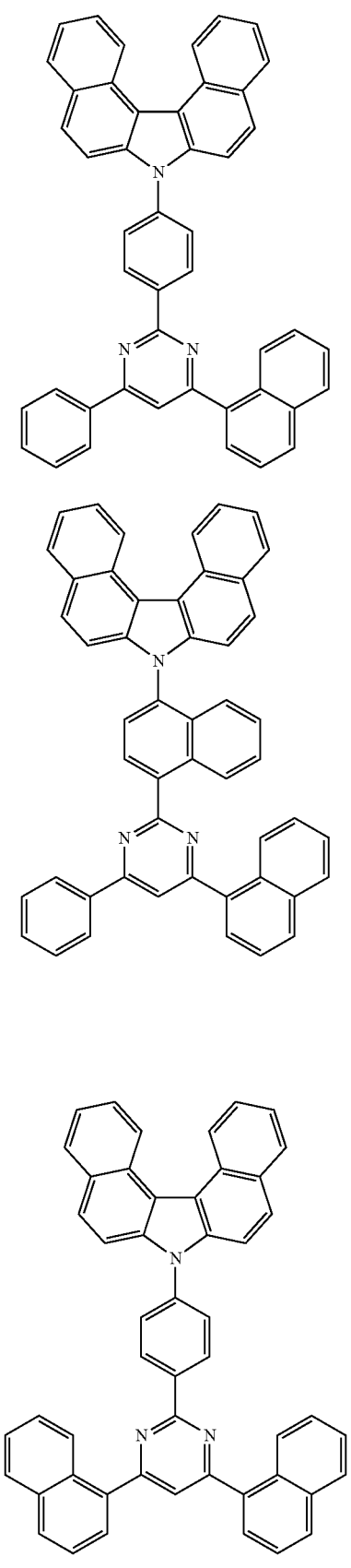
C-96
C-97
C-98

C-99
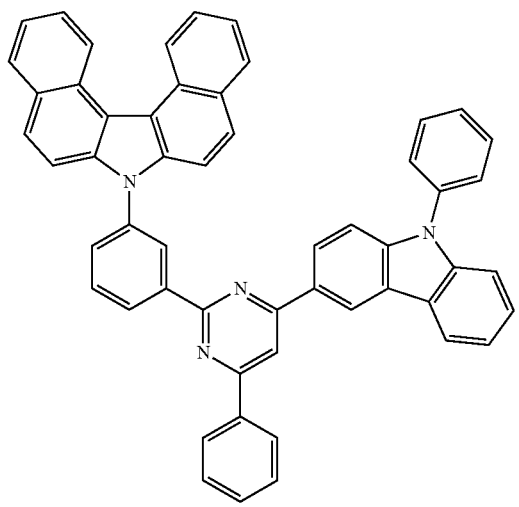
C-100
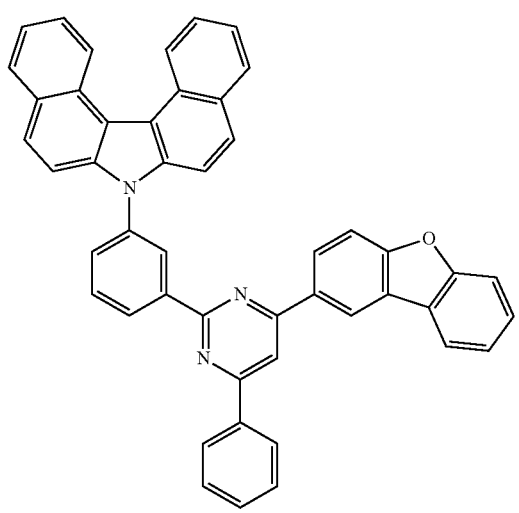
C-101
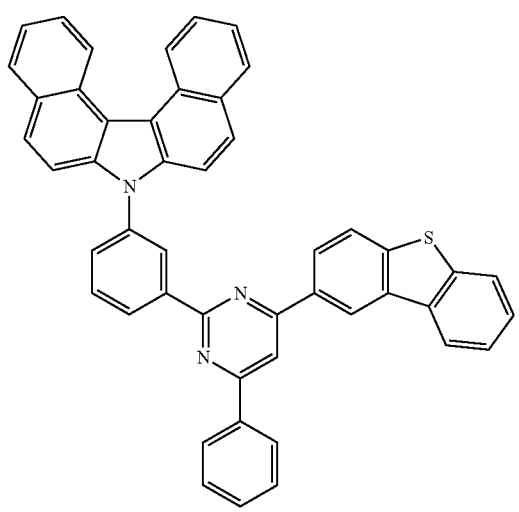
C-102
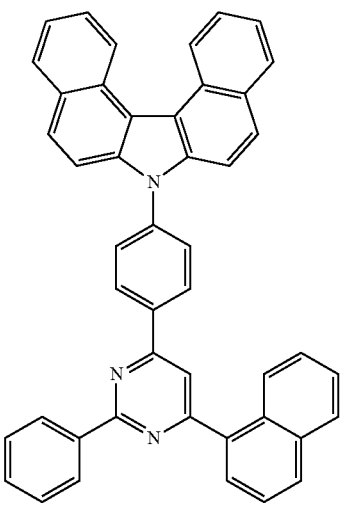
C-103
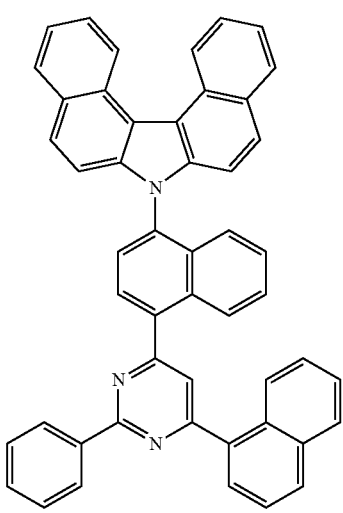
C-104
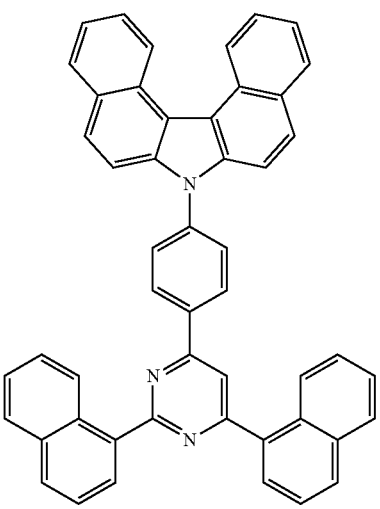

C-105
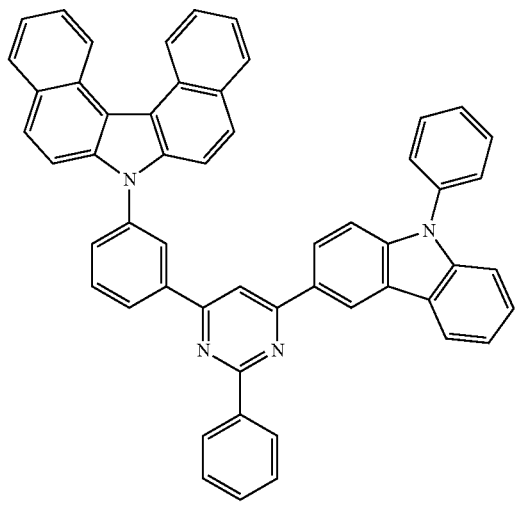
C-106
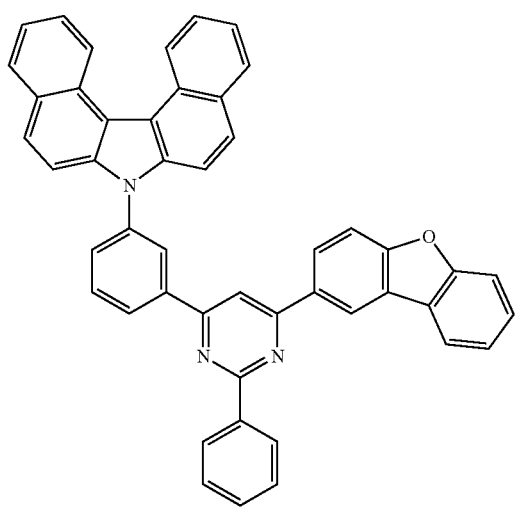
C-107
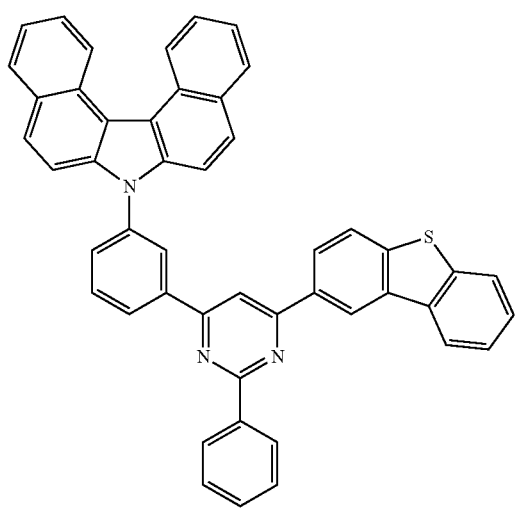
C-108
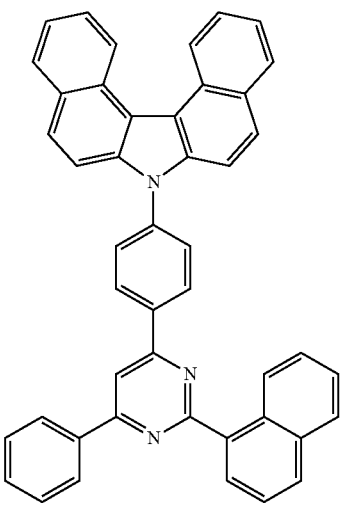
C-109
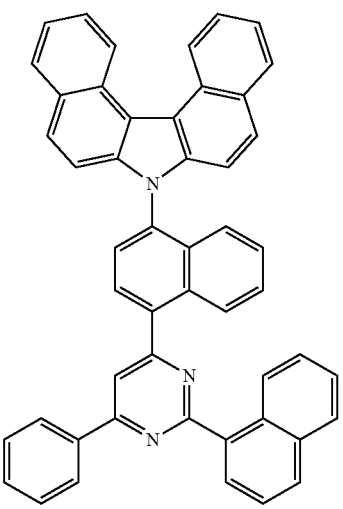
C-110
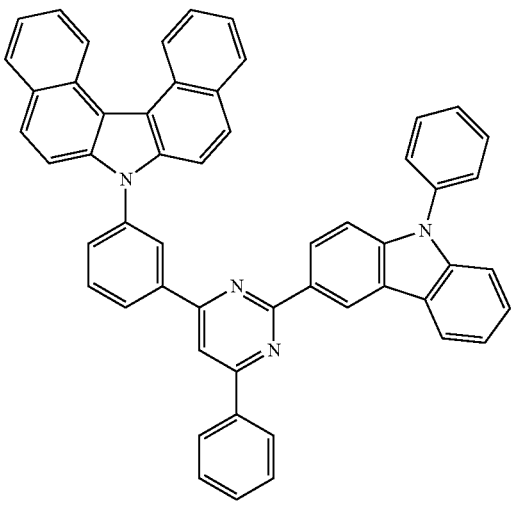

C-111
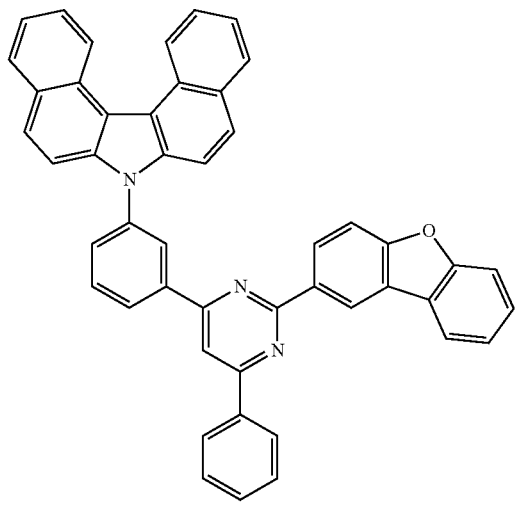
C-112
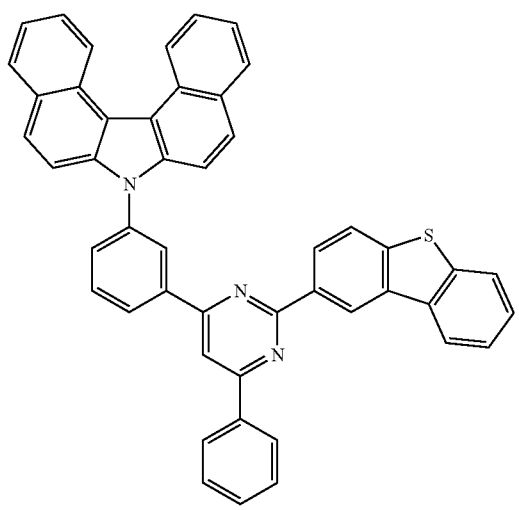
C-113
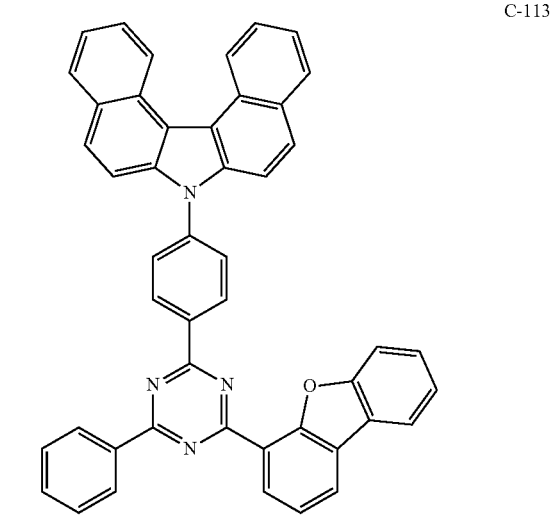
C-114
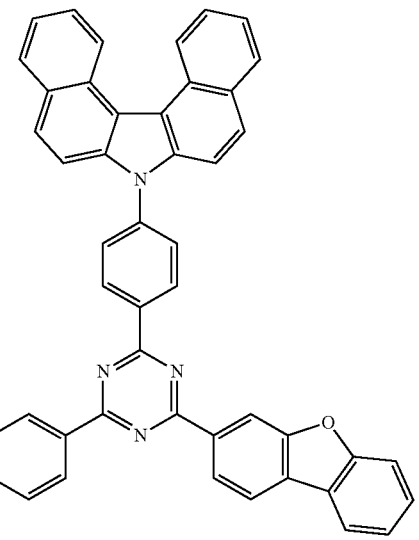
C-115
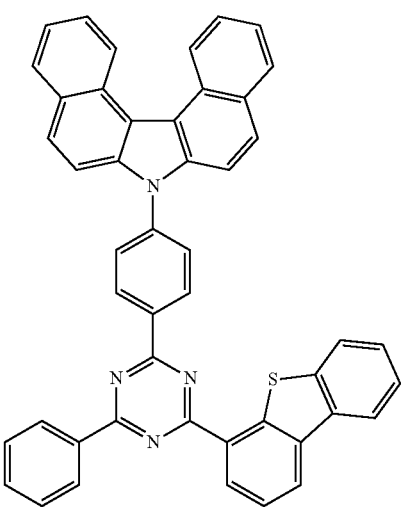
C-116
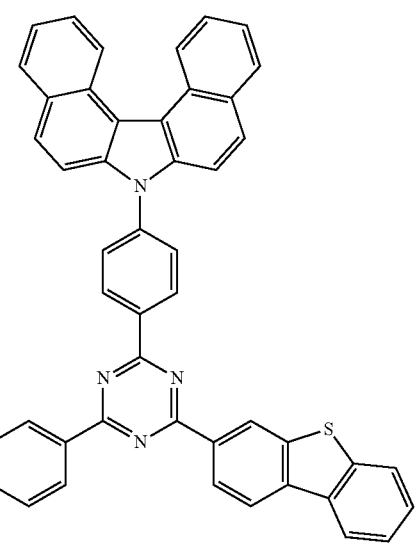

C-117
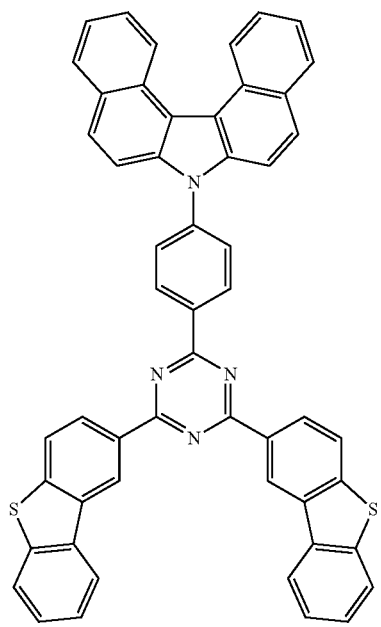
C-118
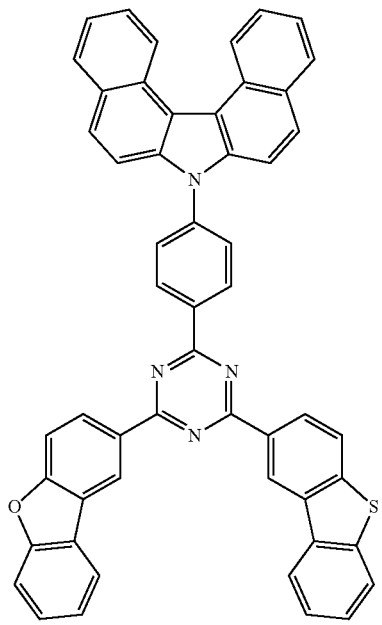
C-119
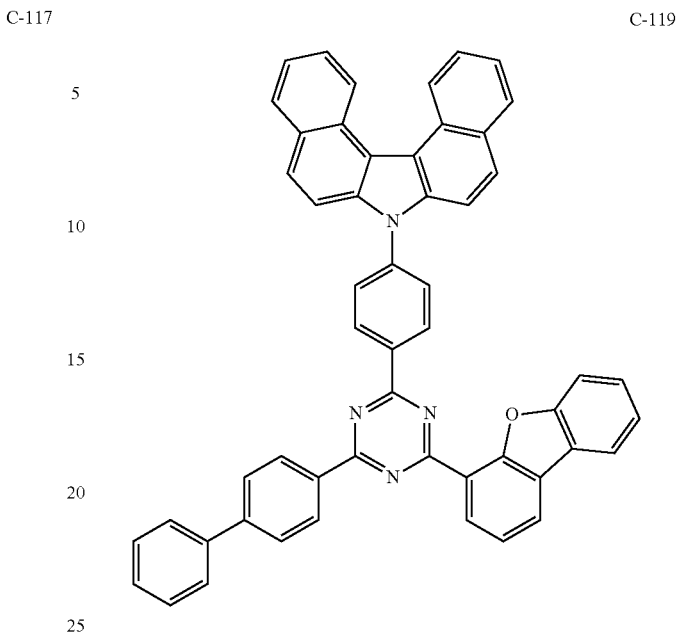
C-120
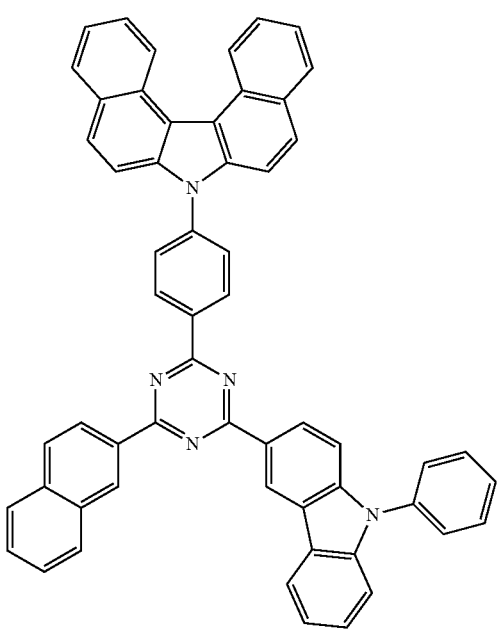

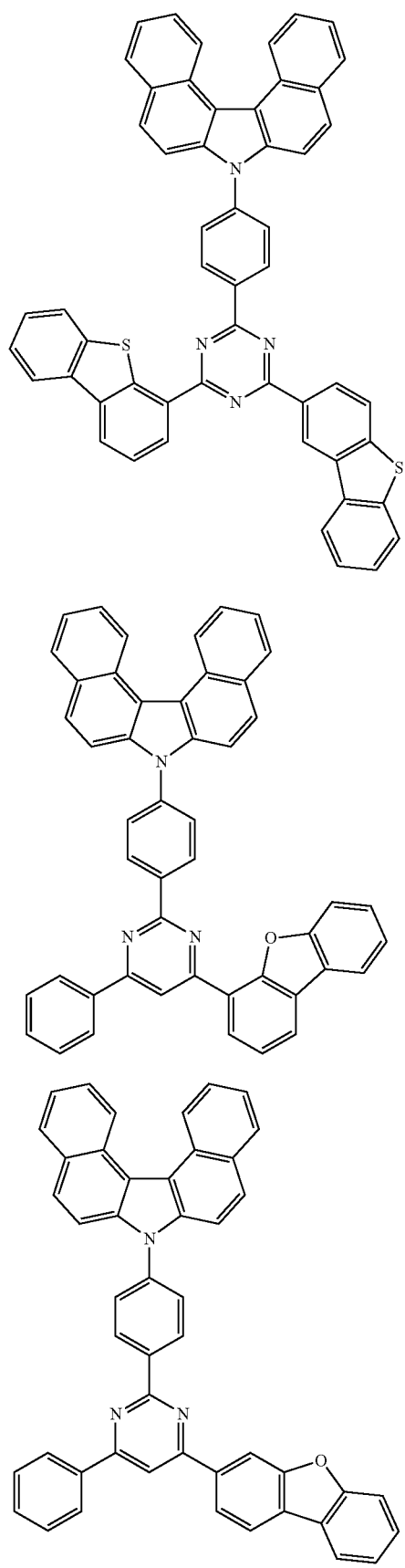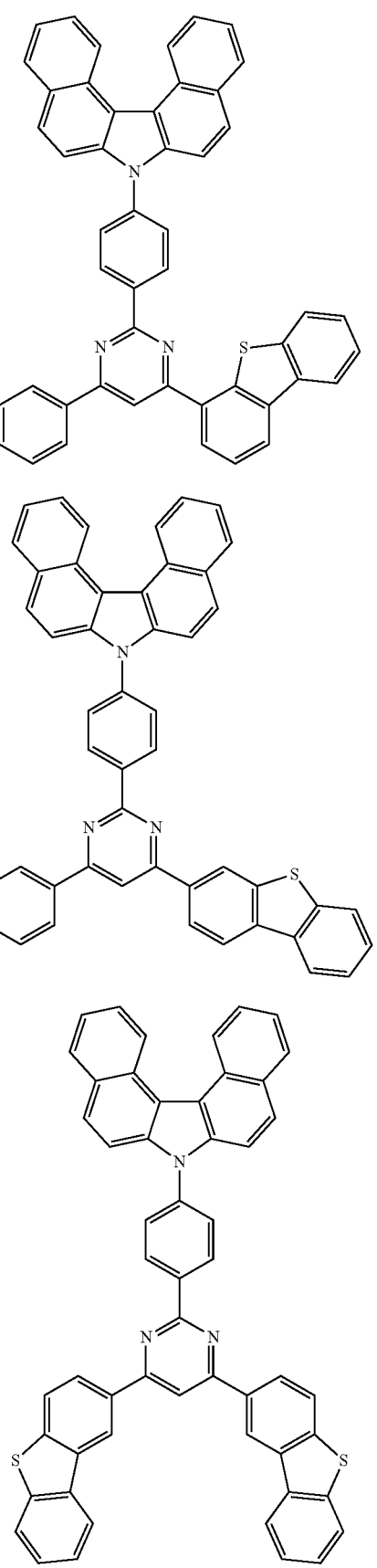

C-127
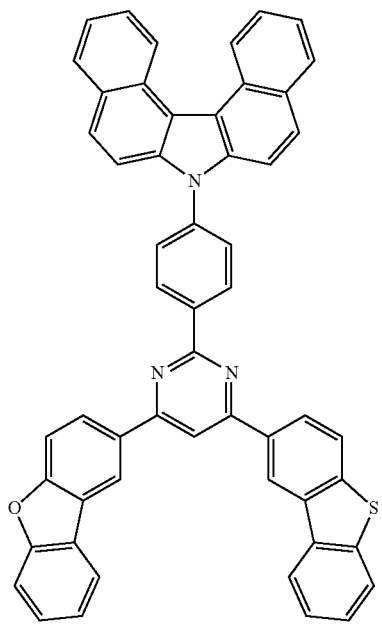
C-128
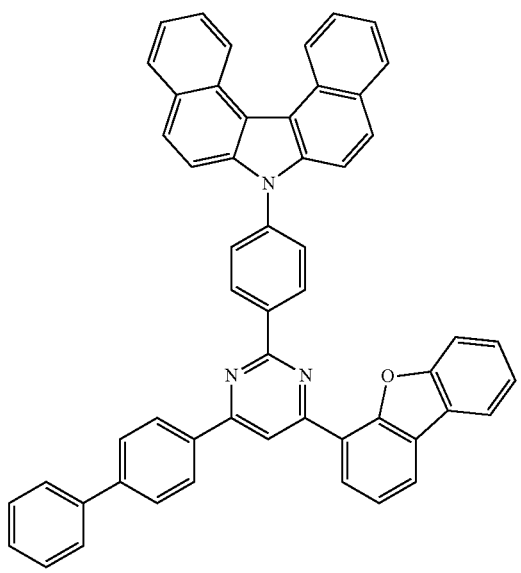
C-129
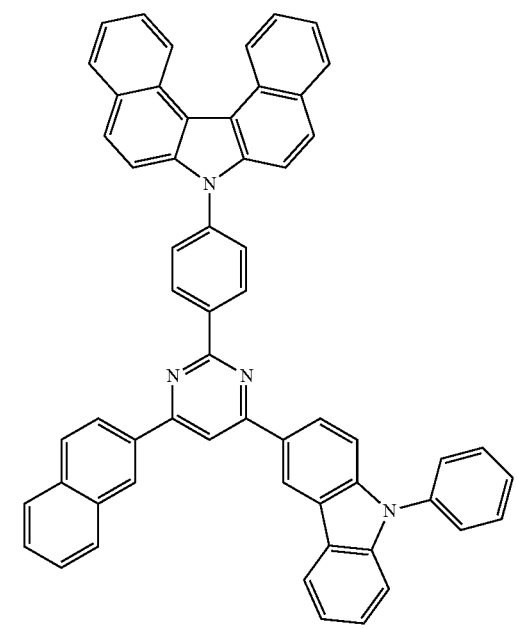
C-130
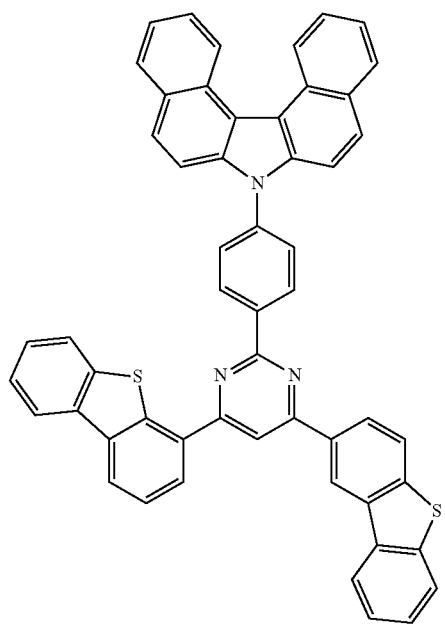

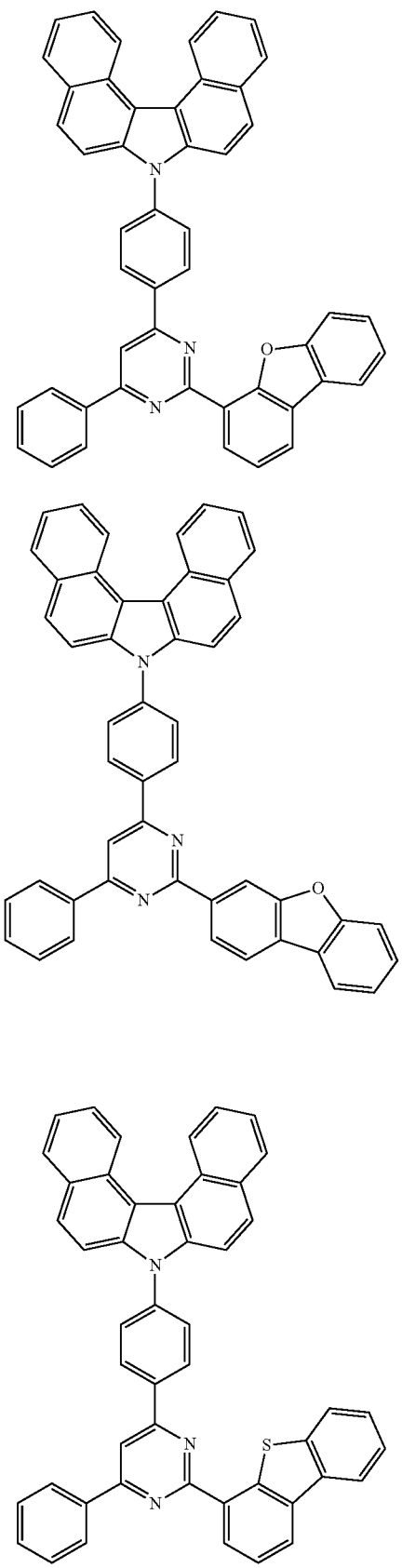

C-136
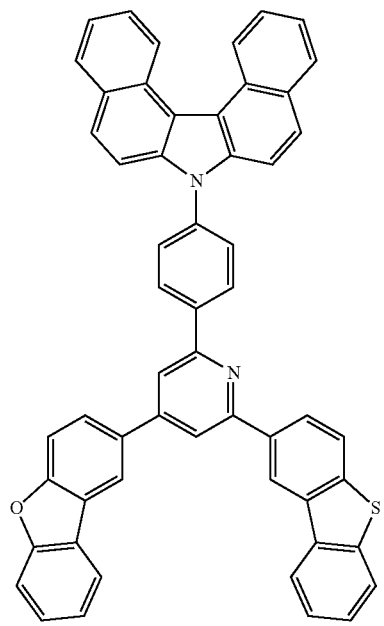
C-138
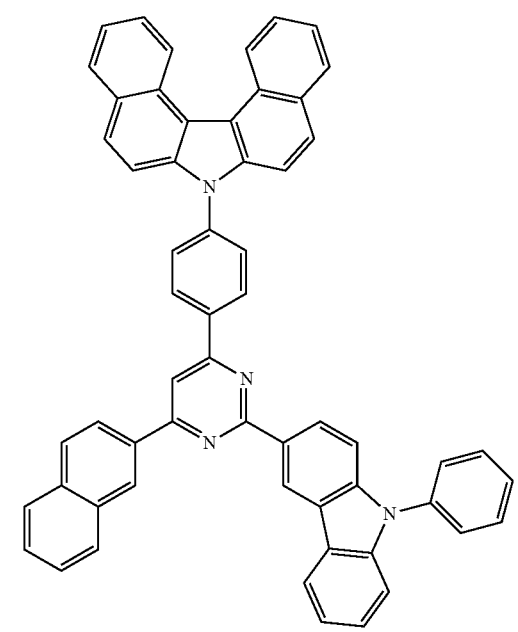
C-137
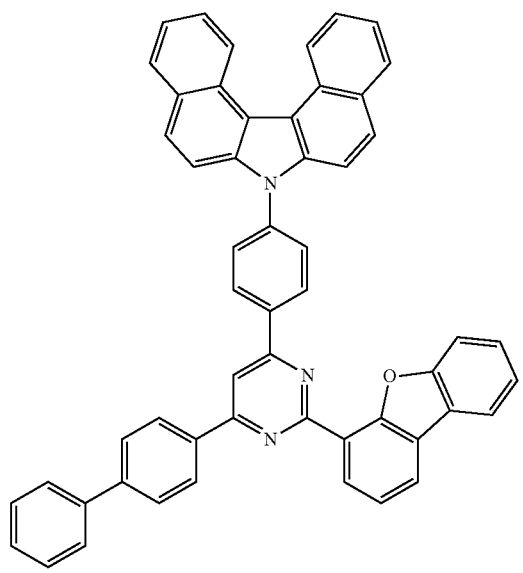
C-139
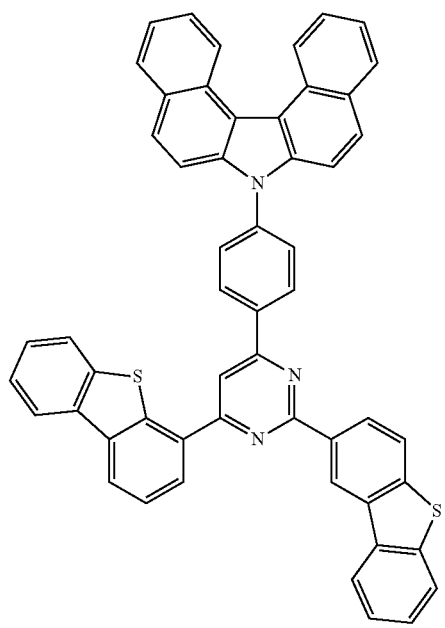

C-140
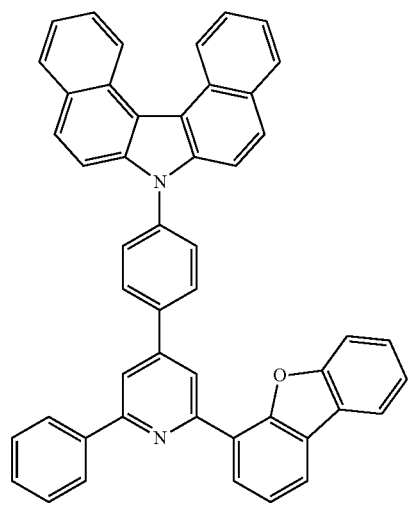
C-141
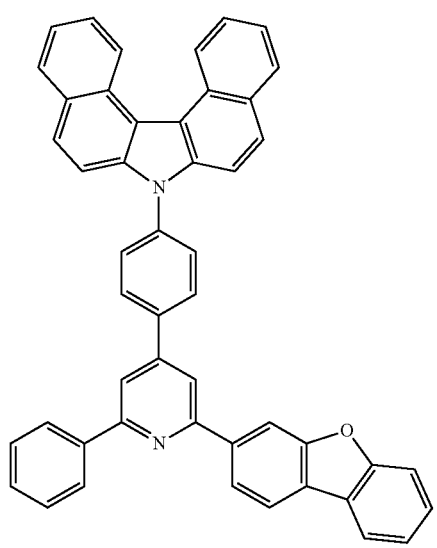
C-142
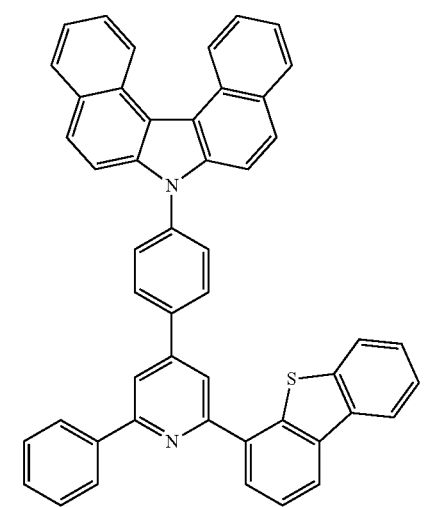
C-143
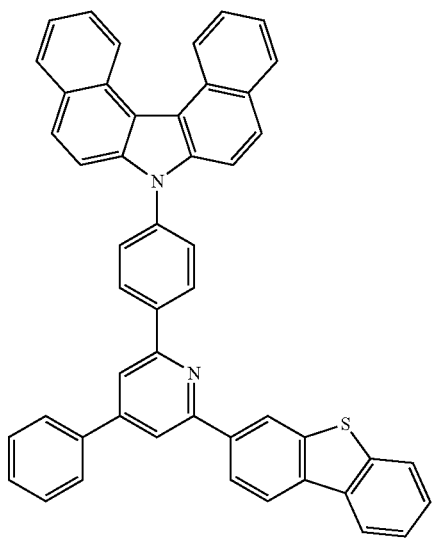
C-144
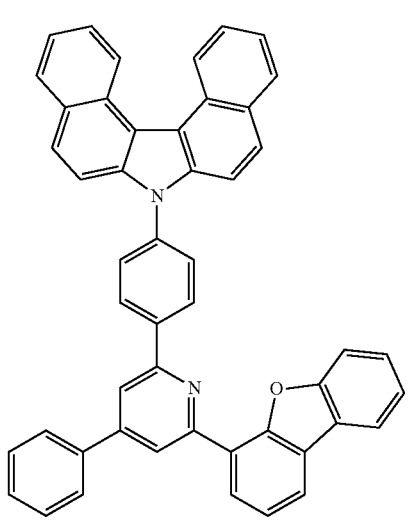
C-145
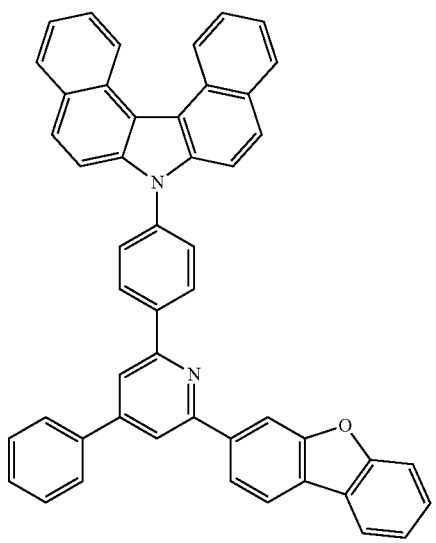

-continued
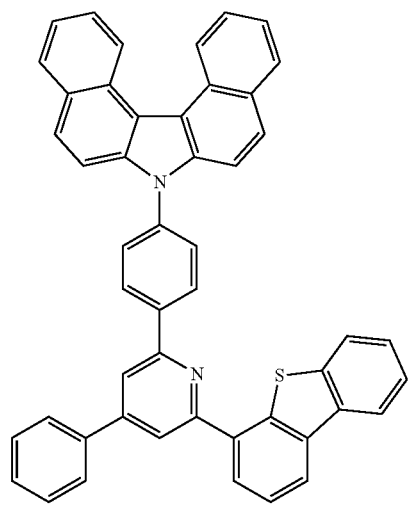
C-146
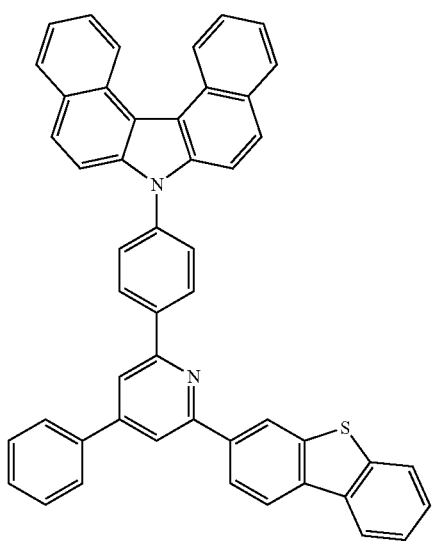
C-147
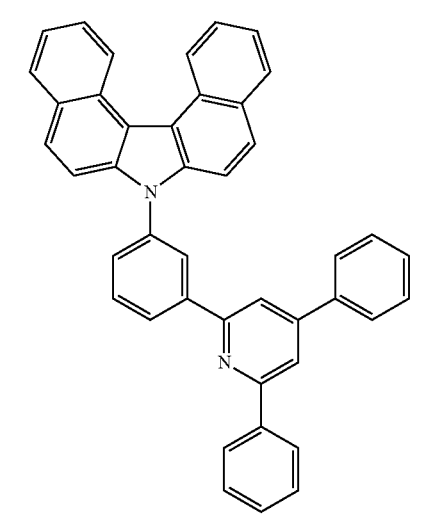
C-148
-continued
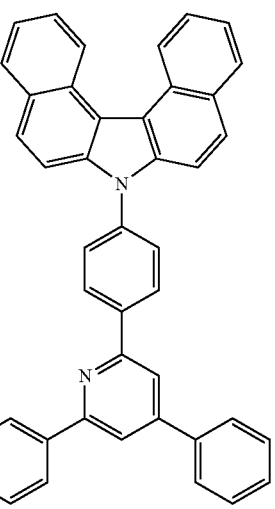
C-149
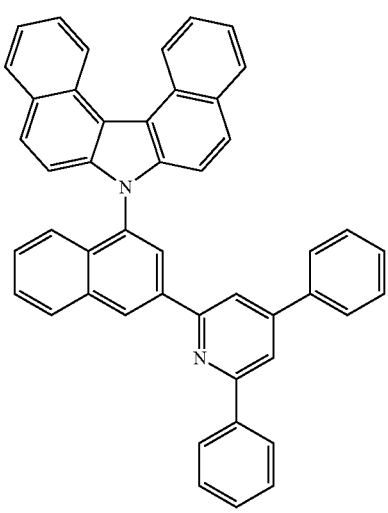
C-150
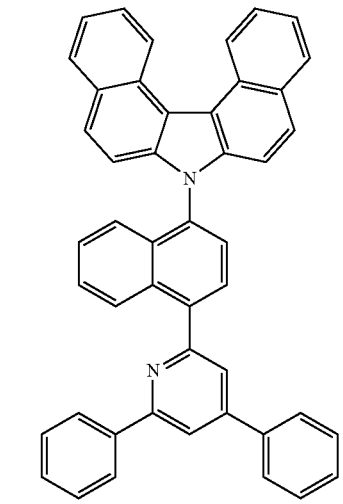
C-151

C-152
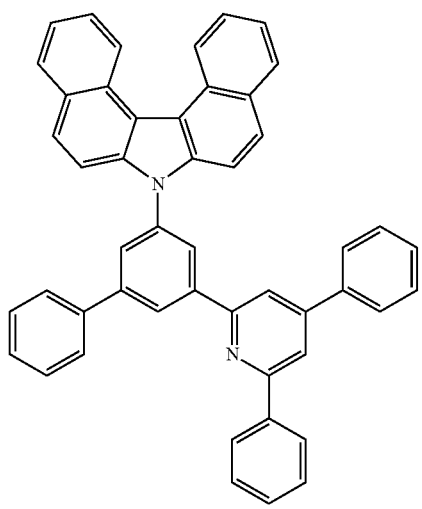
C-153
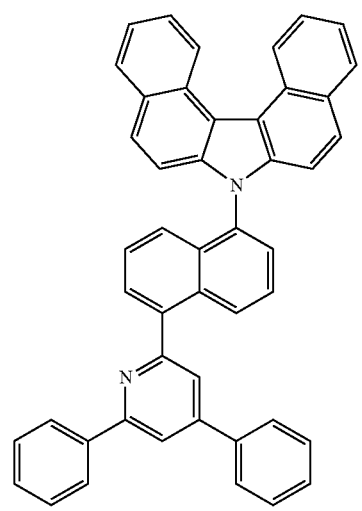
C-154
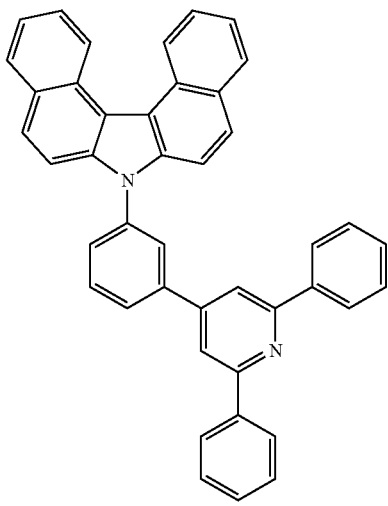
C-155
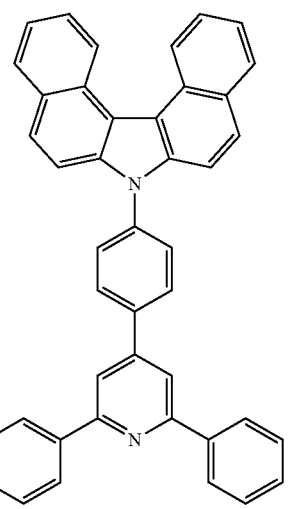
C-156
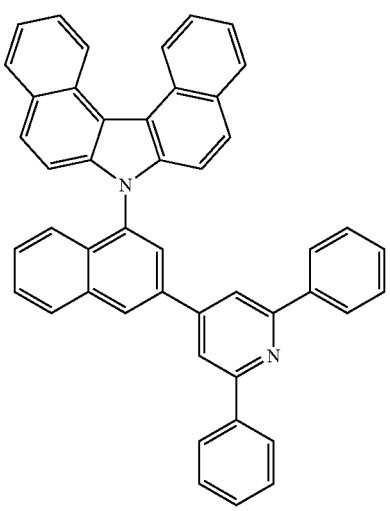
C-157
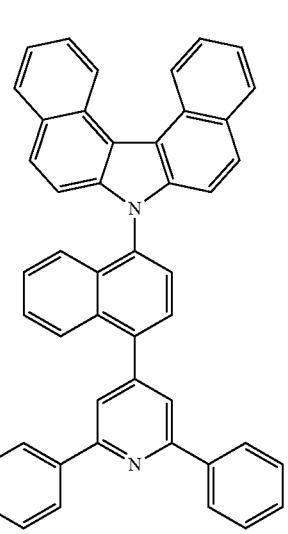

C-158
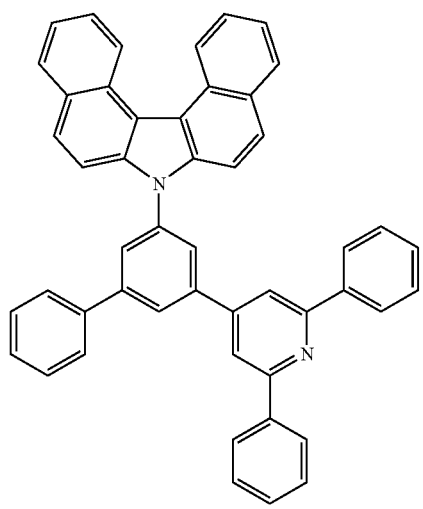
C-159
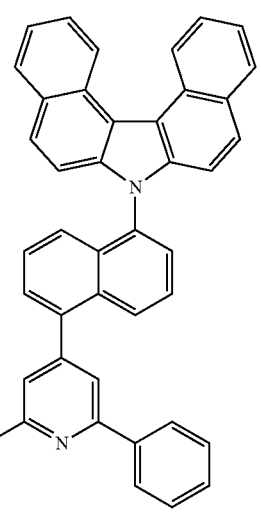
C-160
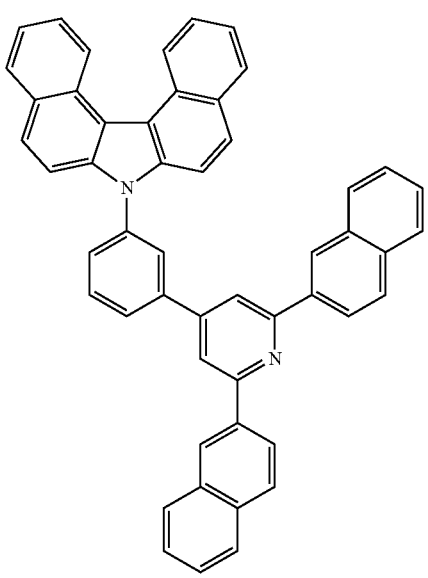
C-161
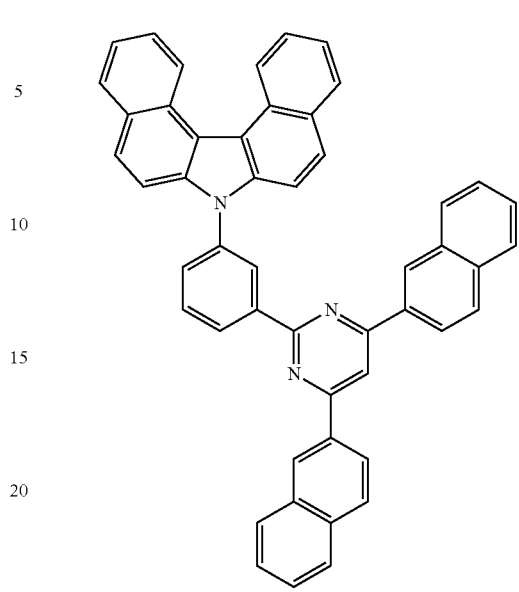
C-162
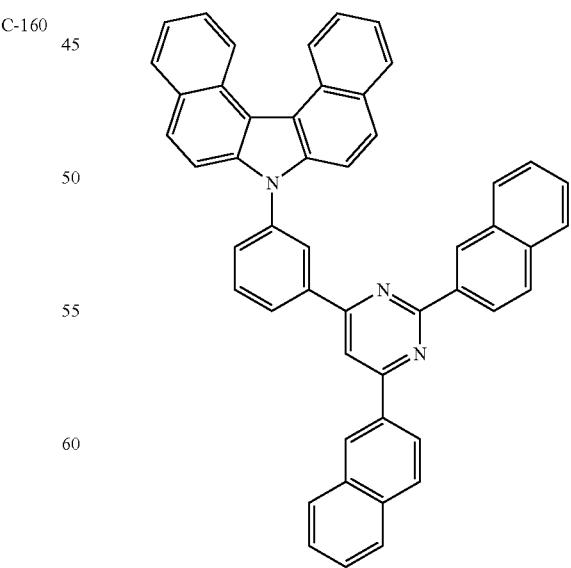

-continued
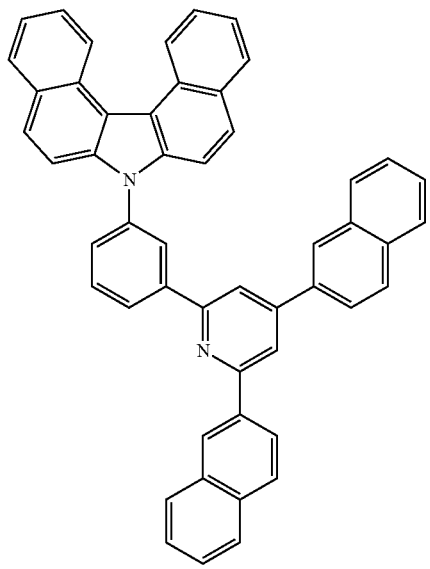
C-163
and
-continued
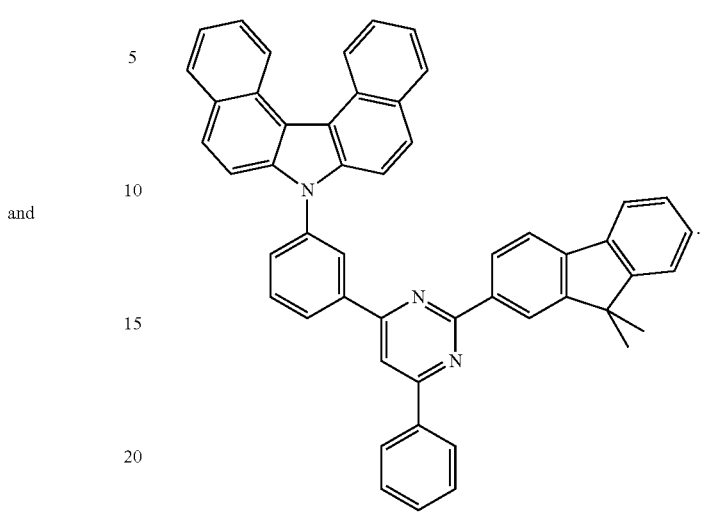
C-164
* * * * *